(12) United States Patent
Frost et al.

(10) Patent No.: US 12,187,801 B2
(45) Date of Patent: *Jan. 7, 2025

(54) CHIMERIC ANTIGEN RECEPTORS AGAINST AXL OR ROR2 AND METHODS OF USE THEREOF

(71) Applicants: Exuma Biotech Corp., West Palm Beach, FL (US); BioAtla. Inc., San Diego, CA (US)

(72) Inventors: Gregory Ian Frost, West Palm Beach, FL (US); James Joseph Onuffer, Jr., Alameda, CA (US); Jay M. Short, Jackson, WY (US); Gerhard Frey, San Diego, CA (US); Hwai Wen Chang, San Marcos, CA (US)

(73) Assignees: Exuma Biotech Corp., West Palm Beach, FL (US); BioAtla. Inc., San Diego, CA (US)

( * ) Notice: Subject to any disclaimer, the term of this patent is extended or adjusted under 35 U.S.C. 154(b) by 1252 days.

This patent is subject to a terminal disclaimer.

(21) Appl. No.: 16/478,360

(22) PCT Filed: Jan. 17, 2018

(86) PCT No.: PCT/US2018/014122
§ 371 (c)(1),
(2) Date: Jul. 16, 2019

(87) PCT Pub. No.: WO2018/136570
PCT Pub. Date: Jul. 26, 2018

(65) Prior Publication Data
US 2019/0367621 A1    Dec. 5, 2019

Related U.S. Application Data

(60) Provisional application No. 62/447,898, filed on Jan. 18, 2017, provisional application No. 62/467,059, filed on Mar. 3, 2017, provisional application No. 62/530,193, filed on Jul. 8, 2017.

(51) Int. Cl.
| | | |
|---|---|---|
| *C07K 16/28* | (2006.01) | |
| *A61K 39/00* | (2006.01) | |
| *A61P 35/00* | (2006.01) | |
| *C07K 14/705* | (2006.01) | |
| *C07K 14/71* | (2006.01) | |
| *C07K 14/725* | (2006.01) | |
| *C12N 5/0783* | (2010.01) | |

(52) U.S. Cl.
CPC ...... *C07K 16/2863* (2013.01); *A61K 39/4611* (2023.05); *A61K 39/4631* (2023.05); *A61K 39/464402* (2023.05); *A61P 35/00* (2018.01); *C07K 14/7051* (2013.01); *C07K 14/70517* (2013.01); *C07K 14/70521* (2013.01); *C07K 14/70578* (2013.01); *C07K 14/71* (2013.01); *C07K 16/2803* (2013.01); *C12N 5/0636* (2013.01); *C12N 5/0646* (2013.01); *A61K 2239/31* (2023.05); *A61K 2239/38* (2023.05); *A61K 2239/59* (2023.05); *C07K 2317/622* (2013.01); *C07K 2317/73* (2013.01); *C07K 2319/03* (2013.01)

(58) Field of Classification Search
CPC ........ C07K 16/00–468; C07K 16/2863; C07K 14/7051; A61K 35/17; A61K 39/46–46484
See application file for complete search history.

(56) References Cited

U.S. PATENT DOCUMENTS

| | | | |
|---|---|---|---|
| 10,023,648 B2 * | 7/2018 | Hombach | A61K 48/00 |
| 11,111,288 B2 * | 9/2021 | Short | C12N 5/0636 |
| 11,149,088 B2 | 10/2021 | Short et al. | |
| 11,279,924 B2 * | 3/2022 | Short | C07K 16/2863 |
| 11,897,959 B2 * | 2/2024 | Short | A61P 35/00 |
| 2016/0207989 A1 * | 7/2016 | Short | C07K 14/705 |

FOREIGN PATENT DOCUMENTS

| | | |
|---|---|---|
| WO | 2014186469 A2 | 11/2014 |
| WO | 2016033331 A1 | 3/2016 |
| WO | 2016142768 A1 | 9/2016 |
| WO | 2017078839 A1 | 5/2017 |
| WO | 2018044619 A1 | 3/2018 |
| WO | 2018136570 A1 | 7/2018 |

OTHER PUBLICATIONS

Philip et al., Blood 124:1277-1287 (Year: 2014).*
Gross & Eshhar, Annu Rev Pharmacol Toxicol 56:59-83 (Year: 2016).*
International Search Report and Written Opinion in International Appln. No. PCT/US2018/014122, mailed Apr. 4, 2018, 9 pages.
International Search Report and Written Opinion in International Appln. No. PCT/US2018/014122, mailed Apr. 4, 2018, 9 pages.

(Continued)

*Primary Examiner* — Jessica H Roark

(74) *Attorney, Agent, or Firm* — Double Helix Law; Emanuel Vacchiano; Michael Mand

(57) ABSTRACT

The present disclosure provides chimeric antigen receptors that bind to Axl and Ror2, and conditionally active chimeric antigen receptors (CARs) that recognize Axl and Ror2. Furthermore, provided herein are nucleic acids encoding these CARs and methods of making and using the CARs, including methods of treating cancer, especially cancers that express Axl and/or Ror2, such as renal cell carcinoma. The present disclosure provides cells genetically modified to produce the CARs.

22 Claims, 21 Drawing Sheets
Specification includes a Sequence Listing.

(56) References Cited

OTHER PUBLICATIONS

Intisar et al., "Adoptive T cell immunotherapy using chimeric antigen receptor against a novel cancer target Axl (VAC11P.1007)" The Journal of Immunology, vol. 192, Issue 1 Supplement 1 205.8, May 1, 2014.

Lucchi et al., "The Masking Game: Design of Activatable Antibodies and Mimetics for Selective Therapeutics and Cell Control", ACS Central Science, vol. 7, Issue 5, May 26, 2021, pp. 724-738, 10.1021/acscentsci.0c01448.

Cribbs et al., "Simplified production and concentration of lentiviral vectors to achieve high transduction in primary human T cells", BMC Biotechnology, vol. 13, Issue 98, Nov. 12, 2013, 8 pages, doi: 10.1186/1472-6750-13-98.

Holdorf et al., "Proline residues in CD28 and the Src homology (SH)3 domain of Lck are required for T cell costimulation.", J Exp Med. Aug. 2, 1999;190(3):375-84.

Kofler et al., "CD28 costimulation Impairs the efficacy of a redirected t-cell antitumor attack in the presence of regulatory t cells which can be overcome by preventing Lck activation", Mol Ther. Apr. 2011;19(4):760-7.

\* cited by examiner

F1-2-20

F1-2-13

F1-2-15

F1-1-1

F1-1-11

F1-1-12

F1-1-15

F1-1-17

F1-1-19

F1-1-20

F1-1-23

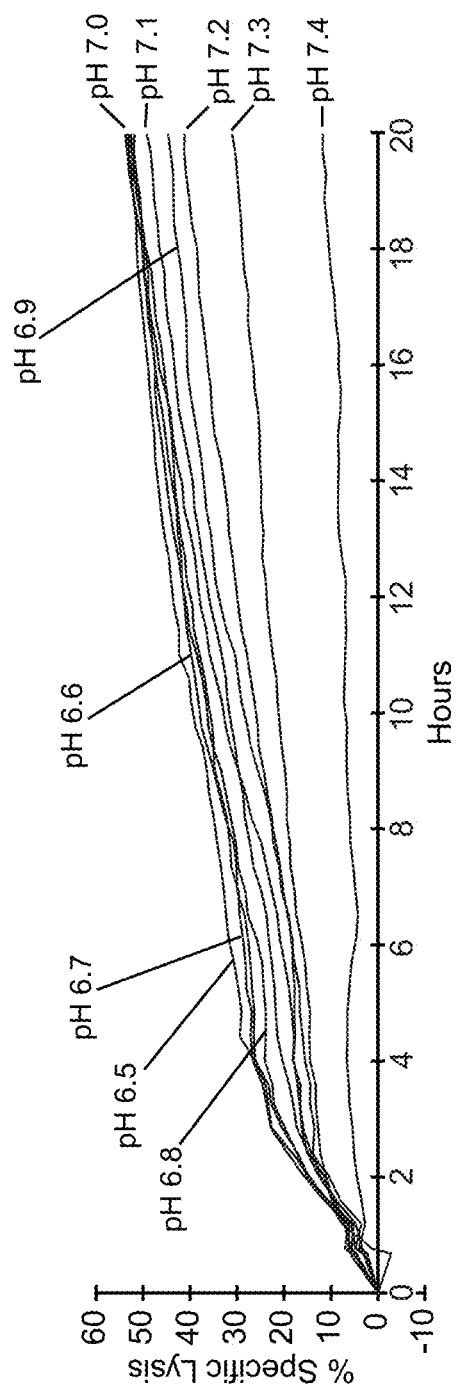

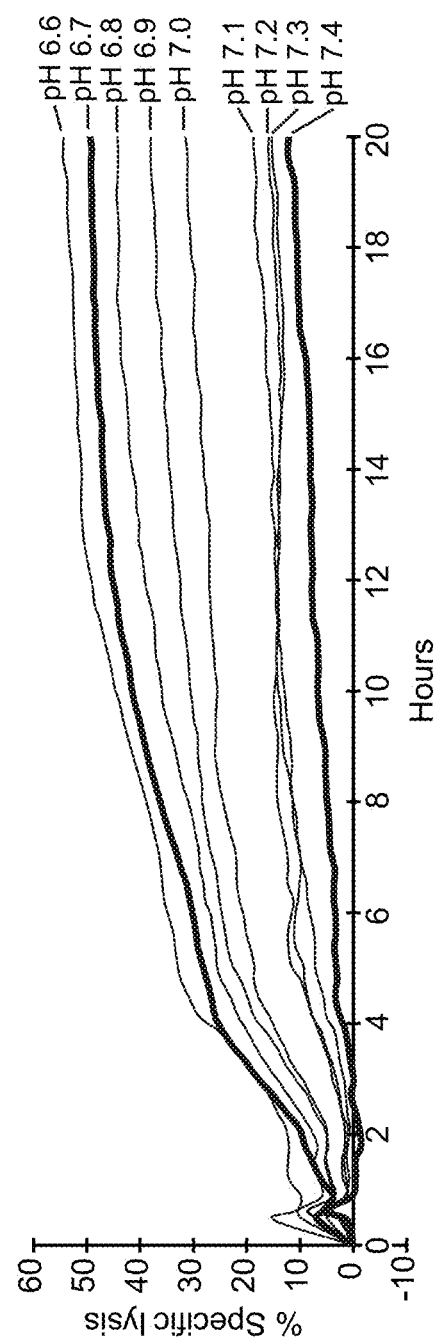

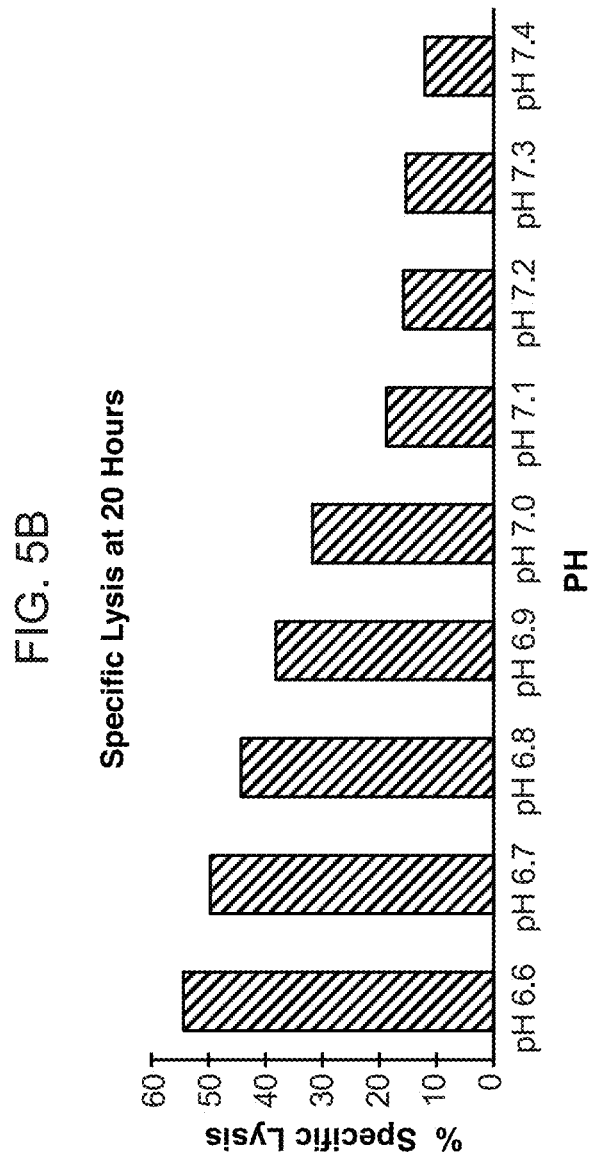

CAB-CAR to AXL

CAB-CAR to ROR2

IL-2 production of F1-1-15

IFN-γ production of F1-1-15

CHO Xenograft Volume (Mean +/-STD)
n=6/group

CHO-Axl Xenograft Volume (Mean +/-STD)
n=6/group

CHO Xenograft Volume (Mean +/-STD)
n=6/group

CHO-Axl Xenograft Volume (Mean +/-STD)
n=6/group

SEQUENCE LISTING

<160> NUMBER OF SEQ ID NOS: 161

<210> SEQ ID NO 1
<211> LENGTH: 42
<212> TYPE: PRT
<213> ORGANISM: Artificial Sequence
<220> FEATURE:
<223> OTHER INFORMATION: synthetic CD137 Co-stimulatory domain

<400> SEQUENCE: 1

Lys Arg Gly Arg Lys Lys Leu Leu Tyr Ile Phe Lys Gln Pro Phe Met
1               5                   10                  15

Arg Pro Val Gln Thr Thr Gln Glu Glu Asp Gly Cys Ser Cys Arg Phe
            20                  25                  30

Pro Glu Glu Glu Glu Gly Gly Cys Glu Leu
        35                  40

<210> SEQ ID NO 2
<211> LENGTH: 41
<212> TYPE: PRT
<213> ORGANISM: Artificial Sequence
<220> FEATURE:
<223> OTHER INFORMATION: synthetic CD28 Co-stimulatory domain

<400> SEQUENCE: 2

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Pro Tyr Ala Pro
            20                  25                  30

Pro Arg Asp Phe Ala Ala Tyr Arg Ser
        35                  40

<210> SEQ ID NO 3
<211> LENGTH: 41
<212> TYPE: PRT
<213> ORGANISM: Artificial Sequence
<220> FEATURE:
<223> OTHER INFORMATION: synthetic IC-delta Co-stimulatory domain

<400> SEQUENCE: 3

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Ala Tyr Ala Ala
            20                  25                  30

Ala Arg Asp Phe Ala Ala Tyr Arg Ser

<210> SEQ ID NO 4
<211> LENGTH: 35
<212> TYPE: PRT
<213> ORGANISM: Artificial Sequence
<220> FEATURE:
<223> OTHER INFORMATION: synthetic ICOS Co-stimulatory domain

<400> SEQUENCE: 4

```
Thr Lys Lys Lys Tyr Ser Ser Ser Val His Asp Pro Asn Gly Glu Tyr
1               5                   10                  15

Met Phe Met Arg Ala Val Asn Thr Ala Lys Lys Ser Arg Leu Thr Asp
            20                  25                  30

Val Thr Leu
        35
```

<210> SEQ ID NO 5
<211> LENGTH: 37
<212> TYPE: PRT
<213> ORGANISM: Artificial Sequence
<220> FEATURE:
<223> OTHER INFORMATION: synthetic OX40 Co-stimulatory domain

<400> SEQUENCE: 5

```
Arg Arg Asp Gln Arg Leu Pro Pro Asp Ala His Lys Pro Pro Gly Gly
1               5                   10                  15

Gly Ser Phe Arg Thr Pro Ile Gln Glu Glu Gln Ala Asp Ala His Ser
            20                  25                  30

Thr Leu Ala Lys Ile
        35
```

<210> SEQ ID NO 6
<211> LENGTH: 49
<212> TYPE: PRT
<213> ORGANISM: Artificial Sequence
<220> FEATURE:
<223> OTHER INFORMATION: synthetic CD27 Co-stimulatory domain

<400> SEQUENCE: 6

```
His Gln Arg Arg Lys Tyr Arg Ser Asn Lys Gly Glu Ser Pro Val Glu
1               5                   10                  15

Pro Ala Glu Pro Cys Arg Tyr Ser Cys Pro Arg Glu Glu Glu Gly Ser
            20                  25                  30

Thr Ile Pro Ile Gln Glu Asp Tyr Arg Lys Pro Glu Pro Ala Cys Ser
        35                  40                  45

Pro
```

<210> SEQ ID NO 7
<211> LENGTH: 114
<212> TYPE: PRT
<213> ORGANISM: Artificial Sequence
<220> FEATURE:
<223> OTHER INFORMATION: synthetic BLTA Co-stimulatory domain

<400> SEQUENCE: 7

```
Cys Cys Leu Arg Arg His Gln Gly Lys Gln Asn Glu Leu Ser Asp Thr
1               5                   10                  15

Ala Gly Arg Glu Ile Asn Leu Val Asp Ala His Leu Lys Ser Glu Gln
            20                  25                  30

Thr Glu Ala Ser Thr Arg Gln Asn Ser Gln Val Leu Leu Ser Glu Thr
        35                  40                  45
```

```
Gly Ile Tyr Asp Asn Asp Pro Asp Leu Cys Phe Arg Met Gln Glu Gly
            50                  55                  60

Ser Glu Val Tyr Ser Asn Pro Cys Leu Glu Glu Asn Lys Pro Gly Ile
 65                  70                  75                  80

Val Tyr Ala Ser Leu Asn His Ser Val Ile Gly Pro Asn Ser Arg Leu
                 85                  90                  95

Ala Arg Asn Val Lys Glu Ala Pro Thr Glu Tyr Ala Ser Ile Cys Val
            100                 105                 110

Arg Ser

<210> SEQ ID NO 8
<211> LENGTH: 187
<212> TYPE: PRT
<213> ORGANISM: Artificial Sequence
<220> FEATURE:
<223> OTHER INFORMATION: synthetic CD30 Co-stimulatory domain

<400> SEQUENCE: 8

Arg Arg Ala Cys Arg Lys Arg Ile Arg Gln Lys Leu His Leu Cys Tyr
 1               5                  10                  15

Pro Val Gln Thr Ser Gln Pro Lys Leu Glu Leu Val Asp Ser Arg Pro
                20                  25                  30

Arg Arg Ser Ser Thr Gln Leu Arg Ser Gly Ala Ser Val Thr Glu Pro
            35                  40                  45

Val Ala Glu Glu Arg Gly Leu Met Ser Gln Pro Leu Met Glu Thr Cys
 50                  55                  60

His Ser Val Gly Ala Ala Tyr Leu Glu Ser Leu Pro Leu Gln Asp Ala
 65                  70                  75                  80

Ser Pro Ala Gly Gly Pro Ser Ser Pro Arg Asp Leu Pro Glu Pro Arg
                 85                  90                  95

Val Ser Thr Glu His Thr Asn Asn Lys Ile Glu Lys Ile Tyr Ile Met
            100                 105                 110

Lys Ala Asp Thr Val Ile Val Gly Thr Val Lys Ala Glu Leu Pro Glu
            115                 120                 125

Gly Arg Gly Leu Ala Gly Pro Ala Glu Pro Glu Leu Glu Glu Glu Leu
        130                 135                 140

Glu Ala Asp His Thr Pro His Tyr Pro Glu Gln Glu Thr Glu Pro Pro
145                 150                 155                 160

Leu Gly Ser Cys Ser Asp Val Met Leu Ser Val Glu Glu Glu Gly Lys
                165                 170                 175

Glu Asp Pro Leu Pro Thr Ala Ala Ser Gly Lys
            180                 185

<210> SEQ ID NO 9
<211> LENGTH: 54
<212> TYPE: PRT
<213> ORGANISM: Artificial Sequence
<220> FEATURE:
<223> OTHER INFORMATION: synthetic GITR Co-stimulatory domain

<400> SEQUENCE: 9

His Ile Trp Gln Leu Arg Ser Gln Cys Met Trp Pro Arg Glu Thr Gln
 1               5                  10                  15

Leu Leu Leu Glu Val Pro Pro Ser Thr Glu Asp Ala Arg Ser Cys Gln
                20                  25                  30

Phe Pro Glu Glu Glu Arg Gly Glu Arg Ser Ala Glu Glu Lys Gly Arg
            35                  40                  45
```

Leu Gly Asp Leu Trp Val
    50

<210> SEQ ID NO 10
<211> LENGTH: 60
<212> TYPE: PRT
<213> ORGANISM: Artificial Sequence
<220> FEATURE:
<223> OTHER INFORMATION: synthetic HVEM Co-stimulatory domain

<400> SEQUENCE: 10

Cys Val Lys Arg Arg Lys Pro Arg Gly Asp Val Val Lys Val Ile Val
1               5                   10                  15

Ser Val Gln Arg Lys Arg Gln Glu Ala Glu Gly Glu Ala Thr Val Ile
            20                  25                  30

Glu Ala Leu Gln Ala Pro Pro Asp Val Thr Thr Val Ala Val Glu Glu
        35                  40                  45

Thr Ile Pro Ser Phe Thr Gly Arg Ser Pro Asn His
    50                  55                  60

<210> SEQ ID NO 11
<211> LENGTH: 163
<212> TYPE: PRT
<213> ORGANISM: Artificial Sequence
<220> FEATURE:
<223> OTHER INFORMATION: synthetic CD3Z isoform 1 Activating domain

<400> SEQUENCE: 11

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45

Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Arg Arg Lys Asn Pro Gln Glu Gly Leu Tyr Asn Glu
            100                 105                 110

Leu Gln Lys Asp Lys Met Ala Glu Ala Tyr Ser Glu Ile Gly Met Lys
        115                 120                 125

Gly Glu Arg Arg Arg Gly Lys Gly His Asp Gly Leu Tyr Gln Gly Leu
    130                 135                 140

Ser Thr Ala Thr Lys Asp Thr Tyr Asp Ala Leu His Met Gln Ala Leu
145                 150                 155                 160

Pro Pro Arg

<210> SEQ ID NO 12
<211> LENGTH: 164
<212> TYPE: PRT
<213> ORGANISM: Artificial Sequence
<220> FEATURE:
<223> OTHER INFORMATION: synthetic CD3Z isoform 2 Activating domain

<400> SEQUENCE: 12

Met Lys Trp Lys Ala Leu Phe Thr Ala Ala Ile Leu Gln Ala Gln Leu

```
                1               5                   10                  15
        Pro Ile Thr Glu Ala Gln Ser Phe Gly Leu Leu Asp Pro Lys Leu Cys
                        20                  25                  30

Tyr Leu Leu Asp Gly Ile Leu Phe Ile Tyr Gly Val Ile Leu Thr Ala
                        35                  40                  45

Leu Phe Leu Arg Val Lys Phe Ser Arg Ser Ala Asp Ala Pro Ala Tyr
                50                      55                  60

Gln Gln Gly Gln Asn Gln Leu Tyr Asn Glu Leu Asn Leu Gly Arg Arg
        65                      70                      75                      80

Glu Glu Tyr Asp Val Leu Asp Lys Arg Arg Gly Arg Asp Pro Glu Met
                        85                  90                  95

Gly Gly Lys Pro Gln Arg Arg Lys Asn Pro Gln Glu Gly Leu Tyr Asn
                        100                 105                 110

Glu Leu Gln Lys Asp Lys Met Ala Glu Ala Tyr Ser Glu Ile Gly Met
                        115                 120                 125

Lys Gly Glu Arg Arg Arg Gly Lys Gly His Asp Gly Leu Tyr Gln Gly
                        130                 135                 140

Leu Ser Thr Ala Thr Lys Asp Thr Tyr Asp Ala Leu His Met Gln Ala
        145                     150                     155                     160

Leu Pro Pro Arg
```

<210> SEQ ID NO 13
<211> LENGTH: 112
<212> TYPE: PRT
<213> ORGANISM: Artificial Sequence
<220> FEATURE:
<223> OTHER INFORMATION: synthetic CD3Z 3 Activating domain

<400> SEQUENCE: 13

```
        Arg Val Lys Phe Ser Arg Ser Ala Asp Ala Pro Ala Tyr Gln Gln Gly
        1                   5                   10                  15

Gln Asn Gln Leu Tyr Asn Glu Leu Asn Leu Gly Arg Arg Glu Glu Tyr
                        20                  25                  30

Asp Val Leu Asp Lys Arg Arg Gly Arg Asp Pro Glu Met Gly Gly Lys
                        35                  40                  45

Pro Arg Arg Lys Asn Pro Gln Glu Gly Leu Tyr Asn Glu Leu Gln Lys
                50                      55                  60

Asp Lys Met Ala Glu Ala Tyr Ser Glu Ile Gly Met Lys Gly Glu Arg
        65                      70                      75                      80

Arg Arg Gly Lys Gly His Asp Gly Leu Tyr Gln Gly Leu Ser Thr Ala
                        85                  90                  95

Thr Lys Asp Thr Tyr Asp Ala Leu His Met Gln Ala Leu Pro Pro Arg
                        100                 105                 110
```

<210> SEQ ID NO 14
<211> LENGTH: 21
<212> TYPE: PRT
<213> ORGANISM: Artificial Sequence
<220> FEATURE:
<223> OTHER INFORMATION: synthetic CD3Z 4 Activating domain

<400> SEQUENCE: 14

```
        Asn Gln Leu Tyr Asn Glu Leu Asn Leu Gly Arg Arg Glu Glu Tyr Asp
        1                   5                   10                  15

Val Leu Asp Lys Arg
                        20
```

-continued

<210> SEQ ID NO 15
<211> LENGTH: 22
<212> TYPE: PRT
<213> ORGANISM: Artificial Sequence
<220> FEATURE:
<223> OTHER INFORMATION: synthetic CD3Z 5 Activating domain

<400> SEQUENCE: 15

Glu Gly Leu Tyr Asn Glu Leu Gln Lys Asp Lys Met Ala Glu Ala Tyr
1               5                   10                  15

Ser Glu Ile Gly Met Lys
            20

<210> SEQ ID NO 16
<211> LENGTH: 21
<212> TYPE: PRT
<213> ORGANISM: Artificial Sequence
<220> FEATURE:
<223> OTHER INFORMATION: synthetic CD3Z 6 Activating domain

<400> SEQUENCE: 16

Asp Gly Leu Tyr Gln Gly Leu Ser Thr Ala Thr Lys Asp Thr Tyr Asp
1               5                   10                  15

Ala Leu His Met Gln
            20

<210> SEQ ID NO 17
<211> LENGTH: 171
<212> TYPE: PRT
<213> ORGANISM: Artificial Sequence
<220> FEATURE:
<223> OTHER INFORMATION: synthetic CD3D 1 Activating domain

<400> SEQUENCE: 17

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Met Cys Gln Ser Cys
                85                  90                  95

Val Glu Leu Asp Pro Ala Thr Val Ala Gly Ile Ile Val Thr Asp Val
            100                 105                 110

Ile Ala Thr Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170

<210> SEQ ID NO 18
<211> LENGTH: 127
<212> TYPE: PRT
<213> ORGANISM: Artificial Sequence

```
<220> FEATURE:
<223> OTHER INFORMATION: synthetic CD3D 2 Activating domain

<400> SEQUENCE: 18

Met Glu His Ser Thr Phe Leu Ser Gly Leu Val Leu Ala Thr Leu Leu
1               5                   10                  15

Ser Gln Val Ser Pro Phe Lys Ile Pro Ile Glu Glu Leu Glu Asp Arg
            20                  25                  30

Val Phe Val Asn Cys Asn Thr Ser Ile Thr Trp Val Glu Gly Thr Val
        35                  40                  45

Gly Thr Leu Leu Ser Asp Ile Thr Arg Leu Asp Leu Gly Lys Arg Ile
    50                  55                  60

Leu Asp Pro Arg Gly Ile Tyr Arg Cys Asn Gly Thr Asp Ile Tyr Lys
65                  70                  75                  80

Asp Lys Glu Ser Thr Val Gln Val His Tyr Arg Thr Ala Asp Thr Gln
                85                  90                  95

Ala Leu Leu Arg Asn Asp Gln Val Tyr Gln Pro Leu Arg Asp Arg Asp
            100                 105                 110

Asp Ala Gln Tyr Ser His Leu Gly Gly Asn Trp Ala Arg Asn Lys
        115                 120                 125

<210> SEQ ID NO 19
<211> LENGTH: 21
<212> TYPE: PRT
<213> ORGANISM: Artificial Sequence
<220> FEATURE:
<223> OTHER INFORMATION: synthetic CD3D 3 Activating domain

<400> SEQUENCE: 19

Asp Gln Val Tyr Gln Pro Leu Arg Asp Arg Asp Asp Ala Gln Tyr Ser
1               5                   10                  15

His Leu Gly Gly Asn
            20

<210> SEQ ID NO 20
<211> LENGTH: 206
<212> TYPE: PRT
<213> ORGANISM: Artificial Sequence
<220> FEATURE:
<223> OTHER INFORMATION: synthetic CD3E 1 Activating domain

<400> SEQUENCE: 20

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Met Ser
        115                 120                 125
```

```
Val Ala Thr Ile Val Ile Val Asp Ile Cys Ile Thr Gly Gly Leu Leu
            130                 135                 140

Leu Leu Val Tyr Tyr Trp Ser Lys Asn Arg Lys Ala Lys Ala Lys Pro
145                 150                 155                 160

Val Thr Arg Gly Ala Gly Ala Gly Gly Arg Gln Arg Gly Gln Asn Lys
                165                 170                 175

Glu Arg Pro Pro Pro Val Pro Asn Pro Asp Tyr Glu Pro Ile Arg Lys
            180                 185                 190

Gly Gln Arg Asp Leu Tyr Ser Gly Leu Asn Gln Arg Arg Ile
            195                 200                 205

<210> SEQ ID NO 21
<211> LENGTH: 21
<212> TYPE: PRT
<213> ORGANISM: Artificial Sequence
<220> FEATURE:
<223> OTHER INFORMATION: synthetic CD3E 2 Activating domain

<400> SEQUENCE: 21

Asn Pro Asp Tyr Glu Pro Ile Arg Lys Gly Gln Arg Asp Leu Tyr Ser
1               5                   10                  15

Gly Leu Asn Gln Arg
            20

<210> SEQ ID NO 22
<211> LENGTH: 182
<212> TYPE: PRT
<213> ORGANISM: Artificial Sequence
<220> FEATURE:
<223> OTHER INFORMATION: synthetic CD3G 1 Activating domain

<400> SEQUENCE: 22

Met Glu Gln Gly Lys Gly Leu Ala Val Leu Ile Leu Ala Ile Ile Leu
1               5                   10                  15

Leu Gln Gly Thr Leu Ala Gln Ser Ile Lys Gly Asn His Leu Val Lys
            20                  25                  30

Val Tyr Asp Tyr Gln Glu Asp Gly Ser Val Leu Leu Thr Cys Asp Ala
        35                  40                  45

Glu Ala Lys Asn Ile Thr Trp Phe Lys Asp Gly Lys Met Ile Gly Phe
    50                  55                  60

Leu Thr Glu Asp Lys Lys Lys Trp Asn Leu Gly Ser Asn Ala Lys Asp
65                  70                  75                  80

Pro Arg Gly Met Tyr Gln Cys Lys Gly Ser Gln Asn Lys Ser Lys Pro
                85                  90                  95

Leu Gln Val Tyr Tyr Arg Met Cys Gln Asn Cys Ile Glu Leu Asn Ala
            100                 105                 110

Ala Thr Ile Ser Gly Phe Leu Phe Ala Glu Ile Val Ser Ile Phe Val
        115                 120                 125

Leu Ala Val Gly Val Tyr Phe Ile Ala Gly Gln Asp Gly Val Arg Gln
    130                 135                 140

Ser Arg Ala Ser Asp Lys Gln Thr Leu Leu Pro Asn Asp Gln Leu Tyr
145                 150                 155                 160

Gln Pro Leu Lys Asp Arg Glu Asp Asp Gln Tyr Ser His Leu Gln Gly
                165                 170                 175

Asn Gln Leu Arg Arg Asn
            180

<210> SEQ ID NO 23
```

```
<211> LENGTH: 21
<212> TYPE: PRT
<213> ORGANISM: Artificial Sequence
<220> FEATURE:
<223> OTHER INFORMATION: synthetic CD3G 2 Activating domain

<400> SEQUENCE: 23

Asp Gln Leu Tyr Gln Pro Leu Lys Asp Arg Glu Asp Asp Gln Tyr Ser
1               5                   10                  15

His Leu Gln Gly Asn
            20

<210> SEQ ID NO 24
<211> LENGTH: 226
<212> TYPE: PRT
<213> ORGANISM: Artificial Sequence
<220> FEATURE:
<223> OTHER INFORMATION: synthetic CD79A 1 Activating domain

<400> SEQUENCE: 24

Met Pro Gly Gly Pro Gly Val Leu Gln Ala Leu Pro Ala Thr Ile Phe
1               5                   10                  15

Leu Leu Phe Leu Leu Ser Ala Val Tyr Leu Gly Pro Gly Cys Gln Ala
            20                  25                  30

Leu Trp Met His Lys Val Pro Ala Ser Leu Met Val Ser Leu Gly Glu
        35                  40                  45

Asp Ala His Phe Gln Cys Pro His Asn Ser Ser Asn Ala Asn Val
    50                  55                  60

Thr Trp Trp Arg Val Leu His Gly Asn Tyr Thr Trp Pro Pro Glu Phe
65                  70                  75                  80

Leu Gly Pro Gly Glu Asp Pro Asn Gly Thr Leu Ile Ile Gln Asn Val
                85                  90                  95

Asn Lys Ser His Gly Gly Ile Tyr Val Cys Arg Val Gln Glu Gly Asn
            100                 105                 110

Glu Ser Tyr Gln Gln Ser Cys Gly Thr Tyr Leu Arg Val Arg Gln Pro
        115                 120                 125

Pro Pro Arg Pro Phe Leu Asp Met Gly Glu Gly Thr Lys Asn Arg Ile
130                 135                 140

Ile Thr Ala Glu Gly Ile Ile Leu Leu Phe Cys Ala Val Val Pro Gly
145                 150                 155                 160

Thr Leu Leu Leu Phe Arg Lys Arg Trp Gln Asn Glu Lys Leu Gly Leu
                165                 170                 175

Asp Ala Gly Asp Glu Tyr Glu Asp Glu Asn Leu Tyr Glu Gly Leu Asn
            180                 185                 190

Leu Asp Asp Cys Ser Met Tyr Glu Asp Ile Ser Arg Gly Leu Gln Gly
        195                 200                 205

Thr Tyr Gln Asp Val Gly Ser Leu Asn Ile Gly Asp Val Gln Leu Glu
    210                 215                 220

Lys Pro
225

<210> SEQ ID NO 25
<211> LENGTH: 188
<212> TYPE: PRT
<213> ORGANISM: Artificial Sequence
<220> FEATURE:
<223> OTHER INFORMATION: synthetic CD79A 2 Activating domain

<400> SEQUENCE: 25
```

```
Met Pro Gly Gly Pro Gly Val Leu Gln Ala Leu Pro Thr Ile Phe
1               5                   10                  15

Leu Leu Phe Leu Leu Ser Ala Val Tyr Leu Gly Pro Gly Cys Gln Ala
            20                  25                  30

Leu Trp Met His Lys Val Pro Ala Ser Leu Met Val Ser Leu Gly Glu
        35                  40                  45

Asp Ala His Phe Gln Cys Pro His Asn Ser Ser Asn Ala Asn Val
    50                  55                  60

Thr Trp Trp Arg Val Leu His Gly Asn Tyr Thr Trp Pro Pro Glu Phe
65                  70                  75                  80

Leu Gly Pro Gly Glu Asp Pro Asn Glu Pro Pro Arg Pro Phe Leu
                85                  90                  95

Asp Met Gly Glu Gly Thr Lys Asn Arg Ile Ile Thr Ala Glu Gly Ile
            100                 105                 110

Ile Leu Leu Phe Cys Ala Val Val Pro Gly Thr Leu Leu Leu Phe Arg
            115                 120                 125

Lys Arg Trp Gln Asn Glu Lys Leu Gly Leu Asp Ala Gly Asp Glu Tyr
            130                 135                 140

Glu Asp Glu Asn Leu Tyr Glu Gly Leu Asn Leu Asp Asp Cys Ser Met
145                 150                 155                 160

Tyr Glu Asp Ile Ser Arg Gly Leu Gln Gly Thr Tyr Gln Asp Val Gly
                165                 170                 175

Ser Leu Asn Ile Gly Asp Val Gln Leu Glu Lys Pro
            180                 185

<210> SEQ ID NO 26
<211> LENGTH: 21
<212> TYPE: PRT
<213> ORGANISM: Artificial Sequence
<220> FEATURE:
<223> OTHER INFORMATION: synthetic CD79A 3 Activating domain

<400> SEQUENCE: 26

Glu Asn Leu Tyr Glu Gly Leu Asn Leu Asp Asp Cys Ser Met Tyr Glu
1               5                   10                  15

Asp Ile Ser Arg Gly
            20

<210> SEQ ID NO 27
<211> LENGTH: 113
<212> TYPE: PRT
<213> ORGANISM: Artificial Sequence
<220> FEATURE:
<223> OTHER INFORMATION: synthetic DAP12 1 Activating domain

<400> SEQUENCE: 27

Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
            35                  40                  45

Gly Asp Leu Val Leu Thr Val Leu Ile Ala Leu Ala Val Tyr Phe Leu
            50                  55                  60

Gly Arg Leu Val Pro Arg Gly Arg Gly Ala Ala Glu Ala Ala Thr Arg
65                  70                  75                  80

Lys Gln Arg Ile Thr Glu Thr Glu Ser Pro Tyr Gln Glu Leu Gln Gly
            85                  90                  95
```

-continued

```
Gln Arg Ser Asp Val Tyr Ser Asp Leu Asn Thr Gln Arg Pro Tyr Tyr
                100                 105                 110
Lys

<210> SEQ ID NO 28
<211> LENGTH: 107
<212> TYPE: PRT
<213> ORGANISM: Artificial Sequence
<220> FEATURE:
<223> OTHER INFORMATION: synthetic DAP12 2 Activating domain

<400> SEQUENCE: 28

Met Gly Gly Leu Glu Pro Cys Ser Arg Leu Leu Leu Leu Pro Leu Leu
1               5                   10                  15

Leu Ala Val Ser Gly Leu Arg Pro Val Gln Ala Gln Ala Gln Ser Asp
            20                  25                  30

Cys Ser Cys Ser Thr Val Ser Pro Gly Val Leu Ala Gly Ile Val Met
        35                  40                  45

Gly Asp Leu Val Leu Thr Val Leu Ile Ala Leu Ala Val Tyr Phe Leu
    50                  55                  60

Gly Arg Leu Val Pro Arg Gly Arg Gly Ala Ala Glu Ala Thr Arg Lys
65                  70                  75                  80

Gln Arg Ile Thr Glu Thr Glu Ser Pro Tyr Gln Glu Leu Gln Gly Gln
                85                  90                  95

Arg Ser Asp Val Tyr Ser Asp Leu Asn Thr Gln
                100                 105

<210> SEQ ID NO 29
<211> LENGTH: 102
<212> TYPE: PRT
<213> ORGANISM: Artificial Sequence
<220> FEATURE:
<223> OTHER INFORMATION: synthetic DAP12 3 Activating domain

<400> SEQUENCE: 29

Met Gly Gly Leu Glu Pro Cys Ser Arg Leu Leu Leu Leu Pro Leu Leu
1               5                   10                  15

Leu Ala Val Ser Asp Cys Ser Cys Ser Thr Val Ser Pro Gly Val Leu
            20                  25                  30

Ala Gly Ile Val Met Gly Asp Leu Val Leu Thr Val Leu Ile Ala Leu
        35                  40                  45

Ala Val Tyr Phe Leu Gly Arg Leu Val Pro Arg Gly Arg Gly Ala Ala
    50                  55                  60

Glu Ala Ala Thr Arg Lys Gln Arg Ile Thr Glu Thr Glu Ser Pro Tyr
65                  70                  75                  80

Gln Glu Leu Gln Gly Gln Arg Ser Asp Val Tyr Ser Asp Leu Asn Thr
                85                  90                  95

Gln Arg Pro Tyr Tyr Lys
                100

<210> SEQ ID NO 30
<211> LENGTH: 101
<212> TYPE: PRT
<213> ORGANISM: Artificial Sequence
<220> FEATURE:
<223> OTHER INFORMATION: synthetic DAP12 4 Activating domain

<400> SEQUENCE: 30

Met Gly Gly Leu Glu Pro Cys Ser Arg Leu Leu Leu Leu Pro Leu Leu
```

```
                1               5                  10                  15
Leu Ala Val Ser Asp Cys Ser Cys Ser Thr Val Ser Pro Gly Val Leu
                20                  25                  30

Ala Gly Ile Val Met Gly Asp Leu Val Leu Thr Val Leu Ile Ala Leu
                35                  40                  45

Ala Val Tyr Phe Leu Gly Arg Leu Val Pro Arg Gly Arg Gly Ala Ala
            50                  55                  60

Glu Ala Thr Arg Lys Gln Arg Ile Thr Glu Thr Glu Ser Pro Tyr Gln
 65                  70                  75                  80

Glu Leu Gln Gly Gln Arg Ser Asp Val Tyr Ser Asp Leu Asn Thr Gln
                85                  90                  95

Arg Pro Tyr Tyr Lys
            100

<210> SEQ ID NO 31
<211> LENGTH: 21
<212> TYPE: PRT
<213> ORGANISM: Artificial Sequence
<220> FEATURE:
<223> OTHER INFORMATION: synthetic DAP12 5 Activating domain

<400> SEQUENCE: 31

Glu Ser Pro Tyr Gln Glu Leu Gln Gly Gln Arg Ser Asp Val Tyr Ser
 1               5                  10                  15

Asp Leu Asn Thr Gln
            20

<210> SEQ ID NO 32
<211> LENGTH: 86
<212> TYPE: PRT
<213> ORGANISM: Artificial Sequence
<220> FEATURE:
<223> OTHER INFORMATION: synthetic FCER1G 1 Activating domain

<400> SEQUENCE: 32

Met Ile Pro Ala Val Val Leu Leu Leu Leu Leu Val Glu Gln Ala
 1               5                  10                  15

Ala Ala Leu Gly Glu Pro Gln Leu Cys Tyr Ile Leu Asp Ala Ile Leu
                20                  25                  30

Phe Leu Tyr Gly Ile Val Leu Thr Leu Leu Tyr Cys Arg Leu Lys Ile
            35                  40                  45

Gln Val Arg Lys Ala Ala Ile Thr Ser Tyr Glu Lys Ser Asp Gly Val
     50                  55                  60

Tyr Thr Gly Leu Ser Thr Arg Asn Gln Glu Thr Tyr Glu Thr Leu Lys
 65                  70                  75                  80

His Glu Lys Pro Pro Gln
            85

<210> SEQ ID NO 33
<211> LENGTH: 21
<212> TYPE: PRT
<213> ORGANISM: Artificial Sequence
<220> FEATURE:
<223> OTHER INFORMATION: synthetic FCER1G 2 Activating domain

<400> SEQUENCE: 33

Asp Gly Val Tyr Thr Gly Leu Ser Thr Arg Asn Gln Glu Thr Tyr Glu
 1               5                  10                  15

Thr Leu Lys His Glu
            20
```

-continued

<210> SEQ ID NO 34
<211> LENGTH: 20
<212> TYPE: PRT
<213> ORGANISM: Artificial Sequence
<220> FEATURE:
<223> OTHER INFORMATION: synthetic DAP10 Activating domain

<400> SEQUENCE: 34

Arg Pro Arg Arg Ser Pro Ala Gln Asp Gly Lys Val Tyr Ile Asn Met
1               5                   10                  15

Pro Gly Arg Gly
            20

<210> SEQ ID NO 35
<211> LENGTH: 68
<212> TYPE: PRT
<213> ORGANISM: Artificial Sequence
<220> FEATURE:
<223> OTHER INFORMATION: synthetic CD28 Activating domain

<400> SEQUENCE: 35

Phe Trp Val Leu Val Val Val Gly Gly Val Leu Ala Cys Tyr Ser Leu
1               5                   10                  15

Leu Val Thr Val Ala Phe Ile Ile Phe Trp Val Arg Ser Lys Arg Ser
            20                  25                  30

Arg Leu Leu His Ser Asp Tyr Met Asn Met Thr Pro Arg Arg Pro Gly
        35                  40                  45

Pro Thr Arg Lys His Tyr Gln Pro Tyr Ala Pro Pro Arg Asp Phe Ala
    50                  55                  60

Ala Tyr Arg Ser
65

<210> SEQ ID NO 36
<211> LENGTH: 619
<212> TYPE: PRT
<213> ORGANISM: Artificial Sequence
<220> FEATURE:
<223> OTHER INFORMATION: synthetic ZAP70 Activating domain

<400> SEQUENCE: 36

Met Pro Asp Pro Ala Ala His Leu Pro Phe Phe Tyr Gly Ser Ile Ser
1               5                   10                  15

Arg Ala Glu Ala Glu Glu His Leu Lys Leu Ala Gly Met Ala Asp Gly
            20                  25                  30

Leu Phe Leu Leu Arg Gln Cys Leu Arg Ser Leu Gly Gly Tyr Val Leu
        35                  40                  45

Ser Leu Val His Asp Val Arg Phe His His Phe Pro Ile Glu Arg Gln
    50                  55                  60

Leu Asn Gly Thr Tyr Ala Ile Ala Gly Gly Lys Ala His Cys Gly Pro
65                  70                  75                  80

Ala Glu Leu Cys Glu Phe Tyr Ser Arg Asp Pro Asp Gly Leu Pro Cys
                85                  90                  95

Asn Leu Arg Lys Pro Cys Asn Arg Pro Ser Gly Leu Glu Pro Gln Pro
            100                 105                 110

Gly Val Phe Asp Cys Leu Arg Asp Ala Met Val Arg Asp Tyr Val Arg
        115                 120                 125

Gln Thr Trp Lys Leu Glu Gly Glu Ala Leu Glu Gln Ala Ile Ile Ser
    130                 135                 140

```
Gln Ala Pro Gln Val Glu Lys Leu Ile Ala Thr Ala His Glu Arg
145                 150                 155                 160

Met Pro Trp Tyr His Ser Ser Leu Thr Arg Glu Glu Ala Glu Arg Lys
                165                 170                 175

Leu Tyr Ser Gly Ala Gln Thr Asp Gly Lys Phe Leu Leu Arg Pro Arg
                180                 185                 190

Lys Glu Gln Gly Thr Tyr Ala Leu Ser Leu Ile Tyr Gly Lys Thr Val
            195                 200                 205

Tyr His Tyr Leu Ile Ser Gln Asp Lys Ala Gly Lys Tyr Cys Ile Pro
        210                 215                 220

Glu Gly Thr Lys Phe Asp Thr Leu Trp Gln Leu Val Glu Tyr Leu Lys
225                 230                 235                 240

Leu Lys Ala Asp Gly Leu Ile Tyr Cys Leu Lys Glu Ala Cys Pro Asn
                245                 250                 255

Ser Ser Ala Ser Asn Ala Ser Gly Ala Ala Ala Pro Thr Leu Pro Ala
                260                 265                 270

His Pro Ser Thr Leu Thr His Pro Gln Arg Arg Ile Asp Thr Leu Asn
            275                 280                 285

Ser Asp Gly Tyr Thr Pro Glu Pro Ala Arg Ile Thr Ser Pro Asp Lys
        290                 295                 300

Pro Arg Pro Met Pro Met Asp Thr Ser Val Tyr Glu Ser Pro Tyr Ser
305                 310                 315                 320

Asp Pro Glu Glu Leu Lys Asp Lys Lys Leu Phe Leu Lys Arg Asp Asn
                325                 330                 335

Leu Leu Ile Ala Asp Ile Glu Leu Gly Cys Gly Asn Phe Gly Ser Val
            340                 345                 350

Arg Gln Gly Val Tyr Arg Met Arg Lys Lys Gln Ile Asp Val Ala Ile
        355                 360                 365

Lys Val Leu Lys Gln Gly Thr Glu Lys Ala Asp Thr Glu Glu Met Met
370                 375                 380

Arg Glu Ala Gln Ile Met His Gln Leu Asp Asn Pro Tyr Ile Val Arg
385                 390                 395                 400

Leu Ile Gly Val Cys Gln Ala Glu Ala Leu Met Leu Val Met Glu Met
                405                 410                 415

Ala Gly Gly Gly Pro Leu His Lys Phe Leu Val Gly Lys Arg Glu Glu
            420                 425                 430

Ile Pro Val Ser Asn Val Ala Glu Leu Leu His Gln Val Ser Met Gly
        435                 440                 445

Met Lys Tyr Leu Glu Glu Lys Asn Phe Val His Arg Asp Leu Ala Ala
    450                 455                 460

Arg Asn Val Leu Leu Val Asn Arg His Tyr Ala Lys Ile Ser Asp Phe
465                 470                 475                 480

Gly Leu Ser Lys Ala Leu Gly Ala Asp Asp Ser Tyr Tyr Thr Ala Arg
                485                 490                 495

Ser Ala Gly Lys Trp Pro Leu Lys Trp Tyr Ala Pro Glu Cys Ile Asn
            500                 505                 510

Phe Arg Lys Phe Ser Ser Arg Ser Asp Val Trp Ser Tyr Gly Val Thr
        515                 520                 525

Met Trp Glu Ala Leu Ser Tyr Gly Gln Lys Pro Tyr Lys Lys Met Lys
    530                 535                 540

Gly Pro Glu Val Met Ala Phe Ile Glu Gln Gly Lys Arg Met Glu Cys
545                 550                 555                 560

Pro Pro Glu Cys Pro Pro Glu Leu Tyr Ala Leu Met Ser Asp Cys Trp
```

565                 570                 575
Ile Tyr Lys Trp Glu Asp Arg Pro Asp Phe Leu Thr Val Glu Gln Arg
            580                 585                 590

Met Arg Ala Cys Tyr Tyr Ser Leu Ala Ser Lys Val Glu Gly Pro Pro
        595                 600                 605

Gly Ser Thr Gln Lys Ala Glu Ala Ala Cys Ala
    610                 615

<210> SEQ ID NO 37
<211> LENGTH: 9
<212> TYPE: PRT
<213> ORGANISM: Artificial Sequence
<220> FEATURE:
<223> OTHER INFORMATION: synthetic HA Epitope

<400> SEQUENCE: 37

Tyr Pro Tyr Asp Val Pro Asp Tyr Ala
1               5

<210> SEQ ID NO 38
<211> LENGTH: 8
<212> TYPE: PRT
<213> ORGANISM: Artificial Sequence
<220> FEATURE:
<223> OTHER INFORMATION: synthetic FLAG Epitope

<400> SEQUENCE: 38

Asp Tyr Lys Asp Asp Asp Asp Lys
1               5

<210> SEQ ID NO 39
<211> LENGTH: 10
<212> TYPE: PRT
<213> ORGANISM: Artificial Sequence
<220> FEATURE:
<223> OTHER INFORMATION: synthetic c-myc Epitope

<400> SEQUENCE: 39

Glu Gln Lys Leu Ile Ser Glu Glu Asp Leu
1               5                   10

<210> SEQ ID NO 40
<211> LENGTH: 5
<212> TYPE: PRT
<213> ORGANISM: Artificial Sequence
<220> FEATURE:
<223> OTHER INFORMATION: synthetic His5 Affinity

<400> SEQUENCE: 40

His His His His His
1               5

<210> SEQ ID NO 41
<211> LENGTH: 6
<212> TYPE: PRT
<213> ORGANISM: Artificial Sequence
<220> FEATURE:
<223> OTHER INFORMATION: synthetic HisX6 Affinity

<400> SEQUENCE: 41

His His His His His His
1               5

<210> SEQ ID NO 42
<211> LENGTH: 8

```
<212> TYPE: PRT
<213> ORGANISM: Artificial Sequence
<220> FEATURE:
<223> OTHER INFORMATION: synthetic Strep Tag Affinity

<400> SEQUENCE: 42

Trp Ser His Pro Gln Phe Glu Lys
1               5

<210> SEQ ID NO 43
<211> LENGTH: 5
<212> TYPE: PRT
<213> ORGANISM: Artificial Sequence
<220> FEATURE:
<223> OTHER INFORMATION: synthetic RYIRS Affinity

<400> SEQUENCE: 43

Arg Tyr Ile Arg Ser
1               5

<210> SEQ ID NO 44
<211> LENGTH: 4
<212> TYPE: PRT
<213> ORGANISM: Artificial Sequence
<220> FEATURE:
<223> OTHER INFORMATION: synthetic FHHT Affinity

<400> SEQUENCE: 44

Phe His His Thr
1

<210> SEQ ID NO 45
<211> LENGTH: 17
<212> TYPE: PRT
<213> ORGANISM: Artificial Sequence
<220> FEATURE:
<223> OTHER INFORMATION: synthetic Affinity

<400> SEQUENCE: 45

Trp Glu Ala Ala Ala Arg Glu Ala Cys Cys Arg Glu Cys Cys Ala Arg
1               5                   10                  15

Ala

<210> SEQ ID NO 46
<211> LENGTH: 24
<212> TYPE: PRT
<213> ORGANISM: Artificial Sequence
<220> FEATURE:
<223> OTHER INFORMATION: synthetic CD8 alpha Transmembrane domain

<400> SEQUENCE: 46

Ile Tyr Ile Trp Ala Pro Leu Ala Gly Thr Cys Gly Val Leu Leu Leu
1               5                   10                  15

Ser Leu Val Ile Thr Leu Tyr Cys
            20

<210> SEQ ID NO 47
<211> LENGTH: 23
<212> TYPE: PRT
<213> ORGANISM: Artificial Sequence
<220> FEATURE:
<223> OTHER INFORMATION: synthetic CD8 beta Transmembrane domain

<400> SEQUENCE: 47

Leu Gly Leu Leu Val Ala Gly Val Leu Val Leu Leu Val Ser Leu Gly
1               5                   10                  15
```

Val Ala Ile His Leu Cys Cys
            20

<210> SEQ ID NO 48
<211> LENGTH: 25
<212> TYPE: PRT
<213> ORGANISM: Artificial Sequence
<220> FEATURE:
<223> OTHER INFORMATION: synthetic CD4 Transmembrane domain

<400> SEQUENCE: 48

Ala Leu Ile Val Leu Gly Gly Val Ala Gly Leu Leu Leu Phe Ile Gly
1               5                   10                  15

Leu Gly Ile Phe Phe Cys Val Arg Cys
            20                  25

<210> SEQ ID NO 49
<211> LENGTH: 23
<212> TYPE: PRT
<213> ORGANISM: Artificial Sequence
<220> FEATURE:
<223> OTHER INFORMATION: synthetic CD3 zeta  Transmembrane domain

<400> SEQUENCE: 49

Leu Cys Tyr Leu Leu Asp Gly Ile Leu Phe Ile Tyr Gly Val Ile Leu
1               5                   10                  15

Thr Ala Leu Phe Leu Arg Val
            20

<210> SEQ ID NO 50
<211> LENGTH: 27
<212> TYPE: PRT
<213> ORGANISM: Artificial Sequence
<220> FEATURE:
<223> OTHER INFORMATION: synthetic CD28 Transmembrane domain

<400> SEQUENCE: 50

Phe Trp Val Leu Val Val Val Gly Gly Val Leu Ala Cys Tyr Ser Leu
1               5                   10                  15

Leu Val Thr Val Ala Phe Ile Ile Phe Trp Val
            20                  25

<210> SEQ ID NO 51
<211> LENGTH: 26
<212> TYPE: PRT
<213> ORGANISM: Artificial Sequence
<220> FEATURE:
<223> OTHER INFORMATION: synthetic OX40 Transmembrane domain

<400> SEQUENCE: 51

Val Ala Ala Ile Leu Gly Leu Gly Leu Val Leu Gly Leu Leu Gly Pro
1               5                   10                  15

Leu Ala Ile Leu Leu Ala Leu Tyr Leu Leu
            20                  25

<210> SEQ ID NO 52
<211> LENGTH: 24
<212> TYPE: PRT
<213> ORGANISM: Artificial Sequence
<220> FEATURE:
<223> OTHER INFORMATION: synthetic CD7  Transmembrane domain

<400> SEQUENCE: 52

Ala Leu Pro Ala Ala Leu Ala Val Ile Ser Phe Leu Leu Gly Leu Gly

-continued

```
                 1               5                  10                 15
Leu Gly Val Ala Cys Val Leu Ala
                20

<210> SEQ ID NO 53
<211> LENGTH: 15
<212> TYPE: PRT
<213> ORGANISM: Artificial Sequence
<220> FEATURE:
<223> OTHER INFORMATION: synthetic Linker 1

<400> SEQUENCE: 53

Gly Gly Gly Gly Ser Gly Gly Gly Gly Ser Gly Gly Gly Gly Ser
 1               5                  10                  15

<210> SEQ ID NO 54
<211> LENGTH: 30
<212> TYPE: PRT
<213> ORGANISM: Artificial Sequence
<220> FEATURE:
<223> OTHER INFORMATION: synthetic Linker 2

<400> SEQUENCE: 54

Gly Gly Gly Gly Ser Gly Gly Gly Gly Ser Gly Gly Gly Gly Ser Gly
 1               5                  10                  15
Gly Gly Gly Ser Gly Gly Gly Gly Ser Gly Gly Gly Gly Ser
            20                  25                  30

<210> SEQ ID NO 55
<211> LENGTH: 14
<212> TYPE: PRT
<213> ORGANISM: Artificial Sequence
<220> FEATURE:
<223> OTHER INFORMATION: synthetic Linker 3

<400> SEQUENCE: 55

Gly Gly Gly Gly Ser Gly Gly Gly Ser Gly Gly Gly Gly Ser
 1               5                  10

<210> SEQ ID NO 56
<211> LENGTH: 4
<212> TYPE: PRT
<213> ORGANISM: Artificial Sequence
<220> FEATURE:
<223> OTHER INFORMATION: synthetic Linker 4

<400> SEQUENCE: 56

Gly Gly Ser Gly
 1

<210> SEQ ID NO 57
<211> LENGTH: 5
<212> TYPE: PRT
<213> ORGANISM: Artificial Sequence
<220> FEATURE:
<223> OTHER INFORMATION: synthetic Linker 5

<400> SEQUENCE: 57

Gly Gly Ser Gly Gly
 1               5

<210> SEQ ID NO 58
<211> LENGTH: 5
<212> TYPE: PRT
<213> ORGANISM: Artificial Sequence
<220> FEATURE:
```

```
<223> OTHER INFORMATION: synthetic Linker 6

<400> SEQUENCE: 58

Gly Ser Gly Ser Gly
1               5

<210> SEQ ID NO 59
<211> LENGTH: 5
<212> TYPE: PRT
<213> ORGANISM: Artificial Sequence
<220> FEATURE:
<223> OTHER INFORMATION: synthetic Linker 7

<400> SEQUENCE: 59

Gly Ser Gly Gly Gly
1               5

<210> SEQ ID NO 60
<211> LENGTH: 5
<212> TYPE: PRT
<213> ORGANISM: Artificial Sequence
<220> FEATURE:
<223> OTHER INFORMATION: synthetic Linker 8

<400> SEQUENCE: 60

Gly Gly Gly Ser Gly
1               5

<210> SEQ ID NO 61
<211> LENGTH: 5
<212> TYPE: PRT
<213> ORGANISM: Artificial Sequence
<220> FEATURE:
<223> OTHER INFORMATION: synthetic Linker 9

<400> SEQUENCE: 61

Gly Ser Ser Ser Gly
1               5

<210> SEQ ID NO 62
<211> LENGTH: 4
<212> TYPE: PRT
<213> ORGANISM: Artificial Sequence
<220> FEATURE:
<223> OTHER INFORMATION: synthetic Hinge 1

<400> SEQUENCE: 62

Cys Pro Pro Cys
1

<210> SEQ ID NO 63
<211> LENGTH: 5
<212> TYPE: PRT
<213> ORGANISM: Artificial Sequence
<220> FEATURE:
<223> OTHER INFORMATION: synthetic Hinge 2

<400> SEQUENCE: 63

Asp Lys Thr His Thr
1               5

<210> SEQ ID NO 64
<211> LENGTH: 15
<212> TYPE: PRT
<213> ORGANISM: Artificial Sequence
<220> FEATURE:
<223> OTHER INFORMATION: synthetic Hinge 3
```

```
<400> SEQUENCE: 64

Cys Pro Glu Pro Lys Ser Cys Asp Thr Pro Pro Pro Cys Pro Arg
1               5                   10                  15

<210> SEQ ID NO 65
<211> LENGTH: 12
<212> TYPE: PRT
<213> ORGANISM: Artificial Sequence
<220> FEATURE:
<223> OTHER INFORMATION: synthetic Hinge 4

<400> SEQUENCE: 65

Glu Leu Lys Thr Pro Leu Gly Asp Thr Thr His Thr
1               5                   10

<210> SEQ ID NO 66
<211> LENGTH: 10
<212> TYPE: PRT
<213> ORGANISM: Artificial Sequence
<220> FEATURE:
<223> OTHER INFORMATION: synthetic Hinge 5

<400> SEQUENCE: 66

Lys Ser Cys Asp Lys Thr His Thr Cys Pro
1               5                   10

<210> SEQ ID NO 67
<211> LENGTH: 7
<212> TYPE: PRT
<213> ORGANISM: Artificial Sequence
<220> FEATURE:
<223> OTHER INFORMATION: synthetic Hinge 6

<400> SEQUENCE: 67

Lys Cys Cys Val Asp Cys Pro
1               5

<210> SEQ ID NO 68
<211> LENGTH: 7
<212> TYPE: PRT
<213> ORGANISM: Artificial Sequence
<220> FEATURE:
<223> OTHER INFORMATION: synthetic Hinge 7

<400> SEQUENCE: 68

Lys Tyr Gly Pro Pro Cys Pro
1               5

<210> SEQ ID NO 69
<211> LENGTH: 15
<212> TYPE: PRT
<213> ORGANISM: Artificial Sequence
<220> FEATURE:
<223> OTHER INFORMATION: synthetic Hinge 8

<400> SEQUENCE: 69

Glu Pro Lys Ser Cys Asp Lys Thr His Thr Cys Pro Pro Cys Pro
1               5                   10                  15

<210> SEQ ID NO 70
<211> LENGTH: 12
<212> TYPE: PRT
<213> ORGANISM: Artificial Sequence
<220> FEATURE:
<223> OTHER INFORMATION: synthetic Hinge 9
```

```
<400> SEQUENCE: 70

Glu Arg Lys Cys Cys Val Glu Cys Pro Pro Cys Pro
1               5                   10

<210> SEQ ID NO 71
<211> LENGTH: 17
<212> TYPE: PRT
<213> ORGANISM: Artificial Sequence
<220> FEATURE:
<223> OTHER INFORMATION: synthetic Hinge 10

<400> SEQUENCE: 71

Glu Leu Lys Thr Pro Leu Gly Asp Thr Thr His Thr Cys Pro Arg Cys
1               5                   10                  15

Pro

<210> SEQ ID NO 72
<211> LENGTH: 12
<212> TYPE: PRT
<213> ORGANISM: Artificial Sequence
<220> FEATURE:
<223> OTHER INFORMATION: synthetic Hinge 11

<400> SEQUENCE: 72

Ser Pro Asn Met Val Pro His Ala His His Ala Gln
1               5                   10

<210> SEQ ID NO 73
<211> LENGTH: 45
<212> TYPE: PRT
<213> ORGANISM: Artificial Sequence
<220> FEATURE:
<223> OTHER INFORMATION: synthetic Hinge 12

<400> SEQUENCE: 73

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala Cys Asp
            35                  40                  45

<210> SEQ ID NO 74
<211> LENGTH: 21
<212> TYPE: PRT
<213> ORGANISM: Artificial Sequence
<220> FEATURE:
<223> OTHER INFORMATION: synthetic CD8 Signal peptide

<400> SEQUENCE: 74

Met Ala Leu Pro Val Thr Ala Leu Leu Leu Pro Leu Ala Leu Leu Leu
1               5                   10                  15

His Ala Ala Arg Pro
            20

<210> SEQ ID NO 75
<211> LENGTH: 69
<212> TYPE: PRT
<213> ORGANISM: Artificial Sequence
<220> FEATURE:
<223> OTHER INFORMATION: synthetic CD8 Stalk-TM

<400> SEQUENCE: 75

Thr Thr Thr Pro Ala Pro Arg Pro Pro Thr Pro Ala Pro Thr Ile Ala
```

```
1               5                   10                  15
Ser Gln Pro Leu Ser Leu Arg Pro Glu Ala Cys Arg Pro Ala Ala Gly
            20                  25                  30

Gly Ala Val His Thr Arg Gly Leu Asp Phe Ala Cys Asp Ile Tyr Ile
        35                  40                  45

Trp Ala Pro Leu Ala Gly Thr Cys Gly Val Leu Leu Leu Ser Leu Val
    50                  55                  60

Ile Thr Leu Tyr Cys
65

<210> SEQ ID NO 76
<211> LENGTH: 66
<212> TYPE: PRT
<213> ORGANISM: Artificial Sequence
<220> FEATURE:
<223> OTHER INFORMATION: synthetic CD28 Stalk-TM

<400> SEQUENCE: 76

Ile Glu Val Met Tyr Pro Pro Pro Tyr Leu Asp Asn Glu Lys Ser Asn
1               5                   10                  15

Gly Thr Ile Ile His Val Lys Gly Lys His Leu Cys Pro Ser Pro Leu
            20                  25                  30

Phe Pro Gly Pro Ser Lys Pro Phe Trp Val Leu Val Val Val Gly Gly
        35                  40                  45

Val Leu Ala Cys Tyr Ser Leu Leu Val Thr Val Ala Phe Ile Ile Phe
    50                  55                  60

Trp Val
65

<210> SEQ ID NO 77
<211> LENGTH: 21
<212> TYPE: PRT
<213> ORGANISM: Artificial Sequence
<220> FEATURE:
<223> OTHER INFORMATION: synthetic 2A-1 Cleavage signal

<400> SEQUENCE: 77

Gly Ser Gly Glu Gly Arg Gly Ser Leu Leu Thr Cys Gly Asp Val Glu
1               5                   10                  15

Glu Asn Pro Gly Pro
            20

<210> SEQ ID NO 78
<211> LENGTH: 357
<212> TYPE: PRT
<213> ORGANISM: Artificial Sequence
<220> FEATURE:
<223> OTHER INFORMATION: synthetic eTAG Elimination domain

<400> SEQUENCE: 78

Met Leu Leu Leu Val Thr Ser Leu Leu Leu Cys Glu Leu Pro His Pro
1               5                   10                  15

Ala Phe Leu Leu Ile Pro Arg Lys Val Cys Asn Gly Ile Gly Ile Gly
            20                  25                  30

Glu Phe Lys Asp Ser Leu Ser Ile Asn Ala Thr Asn Ile Lys His Phe
        35                  40                  45

Lys Asn Cys Thr Ser Ile Ser Gly Asp Leu His Ile Leu Pro Val Ala
    50                  55                  60

Phe Arg Gly Asp Ser Phe Thr His Thr Pro Pro Leu Asp Pro Gln Glu
65                  70                  75                  80
```

```
Leu Asp Ile Leu Lys Thr Val Lys Glu Ile Thr Gly Phe Leu Leu Ile
                85                  90                  95

Gln Ala Trp Pro Glu Asn Arg Thr Asp Leu His Ala Phe Glu Asn Leu
            100                 105                 110

Glu Ile Ile Arg Gly Arg Thr Lys Gln His Gly Gln Phe Ser Leu Ala
        115                 120                 125

Val Val Ser Leu Asn Ile Thr Ser Leu Gly Leu Arg Ser Leu Lys Glu
130                 135                 140

Ile Ser Asp Gly Asp Val Ile Ile Ser Gly Asn Lys Asn Leu Cys Tyr
145                 150                 155                 160

Ala Asn Thr Ile Asn Trp Lys Lys Leu Phe Gly Thr Ser Gly Gln Lys
                165                 170                 175

Thr Lys Ile Ile Ser Asn Arg Gly Glu Asn Ser Cys Lys Ala Thr Gly
            180                 185                 190

Gln Val Cys His Ala Leu Cys Ser Pro Glu Gly Cys Trp Gly Pro Glu
        195                 200                 205

Pro Arg Asp Cys Val Ser Cys Arg Asn Val Ser Arg Gly Arg Glu Cys
210                 215                 220

Val Asp Lys Cys Asn Leu Leu Glu Gly Glu Pro Arg Glu Phe Val Glu
225                 230                 235                 240

Asn Ser Glu Cys Ile Gln Cys His Pro Glu Cys Leu Pro Gln Ala Met
                245                 250                 255

Asn Ile Thr Cys Thr Gly Arg Gly Pro Asp Asn Cys Ile Gln Cys Ala
            260                 265                 270

His Tyr Ile Asp Gly Pro His Cys Val Lys Thr Cys Pro Ala Gly Val
        275                 280                 285

Met Gly Glu Asn Asn Thr Leu Val Trp Lys Tyr Ala Asp Ala Gly His
290                 295                 300

Val Cys His Leu Cys His Pro Asn Cys Thr Tyr Gly Cys Thr Gly Pro
305                 310                 315                 320

Gly Leu Glu Gly Cys Pro Thr Asn Gly Pro Lys Ile Pro Ser Ile Ala
                325                 330                 335

Thr Gly Met Val Gly Ala Leu Leu Leu Leu Val Val Ala Leu Gly
            340                 345                 350

Ile Gly Leu Phe Met
        355

<210> SEQ ID NO 79
<211> LENGTH: 120
<212> TYPE: PRT
<213> ORGANISM: Artificial Sequence
<220> FEATURE:
<223> OTHER INFORMATION: synthetic Axl 4007V VH  Conditionally active
      scFv

<400> SEQUENCE: 79

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ser Phe Trp Gly Ala
            20                  25                  30

Thr Met Asn Trp Ile Arg Gln Pro Pro Gly Lys Gly Leu Glu Trp Ile
        35                  40                  45

Gly Leu Ile Lys Pro Ser Asn Gly Gly Thr Ser Tyr Asn Gln Lys Phe
    50                  55                  60

Lys Gly Arg Val Thr Ile Ser Ala Asp Lys Ser Ile Ser Thr Ala Tyr
```

```
                65                  70                  75                  80
Leu Gln Trp Ser Ser Leu Lys Ala Ser Asp Thr Ala Met Tyr Tyr Cys
                    85                  90                  95

Ala His Gly His Tyr Glu Ser Tyr Glu Ala Met Asp Tyr Trp Gly Gln
                100                 105                 110

Gly Thr Leu Val Thr Val Ser Ser
                115                 120

<210> SEQ ID NO 80
<211> LENGTH: 107
<212> TYPE: PRT
<213> ORGANISM: Artificial Sequence
<220> FEATURE:
<223> OTHER INFORMATION: synthetic Axl 4007V VL  Conditionally active
      scFv

<400> SEQUENCE: 80

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Val Ser Ala
                20                  25                  30

Val Ala Trp Tyr Gln Gln Lys Pro Gly Gln Ala Pro Arg Leu Leu Ile
            35                  40                  45

Tyr Trp Gln Asp Thr Arg His Thr Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Glu His Phe Ser Pro Pro Leu
                85                  90                  95

Thr Phe Gly Gln Gly Thr Lys Val Glu Ile Lys
                100                 105

<210> SEQ ID NO 81
<211> LENGTH: 106
<212> TYPE: PRT
<213> ORGANISM: Artificial Sequence
<220> FEATURE:
<223> OTHER INFORMATION: synthetic Ror2 VL 4 Conditionally active scFv

<400> SEQUENCE: 81

Ala Ile Gln Leu Thr Gln Ser Pro Ser Ser Leu Ser Ala Ser Val Gly
1               5                   10                  15

Asp Arg Val Thr Ile Thr Cys Ser Ala Thr Ser Ser Val Ser Tyr Met
                20                  25                  30

His Trp Tyr Leu Gln Lys Pro Gly Gln Ser Pro Gln Leu Leu Ile Tyr
            35                  40                  45

Gly Thr Ser Asn Leu Ala Ser Gly Val Pro Asp Arg Phe Ser Gly Ser
        50                  55                  60

Gly Ser Gly Thr Asp Phe Thr Leu Lys Ile Ser Arg Val Glu Ala Glu
65                  70                  75                  80

Asp Val Gly Val Tyr Tyr Cys Gln Gln Arg Ser Ser Tyr Pro Phe Thr
                85                  90                  95

Phe Gly Gln Gly Thr Lys Val Glu Ile Lys
                100                 105

<210> SEQ ID NO 82
<211> LENGTH: 119
<212> TYPE: PRT
<213> ORGANISM: Artificial Sequence
```

```
<220> FEATURE:
<223> OTHER INFORMATION: synthetic Ror2 R98H VH Conditionally active
      scFv

<400> SEQUENCE: 82

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Thr Gly
            20                  25                  30

Tyr Tyr Trp Asn Trp Val Arg Gln Ala Arg Gly Gln Arg Leu Glu Trp
        35                  40                  45

Ile Gly Tyr Ile Thr Tyr Asp Gly Ser Lys Asn Tyr Asn Pro Ser Leu
50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ser His Phe Glu Gly Val Trp Tyr Gly Leu Asp Tyr Trp Gly Gln Gly
            100                 105                 110

Thr Leu Val Thr Val Ser Ser
            115

<210> SEQ ID NO 83
<211> LENGTH: 119
<212> TYPE: PRT
<213> ORGANISM: Artificial Sequence
<220> FEATURE:
<223> OTHER INFORMATION: synthetic Ror2 Y33E VH Conditionally active
      scFv

<400> SEQUENCE: 83

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Thr Gly
            20                  25                  30

Glu Tyr Trp Asn Trp Val Arg Gln Ala Arg Gly Gln Arg Leu Glu Trp
        35                  40                  45

Ile Gly Tyr Ile Thr Tyr Asp Gly Ser Lys Asn Tyr Asn Pro Ser Leu
50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ser Arg Phe Glu Gly Val Trp Tyr Gly Leu Asp Tyr Trp Gly Gln Gly
            100                 105                 110

Thr Leu Val Thr Val Ser Ser
            115

<210> SEQ ID NO 84
<211> LENGTH: 111
<212> TYPE: PRT
<213> ORGANISM: Artificial Sequence
<220> FEATURE:
<223> OTHER INFORMATION: synthetic Ror2 VL Conditionally active scFv

<400> SEQUENCE: 84

Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Arg Tyr
```

```
                    20                  25                  30

Gly Asn Ser Phe Ile His Trp Tyr Gln Gln Lys Pro Gly Lys Ala Pro
            35                  40                  45

Lys Leu Leu Ile Tyr Arg Thr Tyr Asn Leu Glu Ser Gly Ile Pro Ala
        50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln Gln Thr Asn
                85                  90                  95

Glu Asp Pro Trp Thr Phe Gly Gln Gly Thr Lys Val Glu Ile Lys
            100                 105                 110

<210> SEQ ID NO 85
<211> LENGTH: 10
<212> TYPE: PRT
<213> ORGANISM: Artificial Sequence
<220> FEATURE:
<223> OTHER INFORMATION: synthetic Ror2 L3 4 Conditionally active scFv
<220> FEATURE:
<221> NAME/KEY: X is T, I, or P
<222> LOCATION: (3)..(3)
<220> FEATURE:
<221> NAME/KEY: X is E or V
<222> LOCATION: (5)..(5)
<220> FEATURE:
<221> NAME/KEY: X is F or T
<222> LOCATION: (8)..(8)
<220> FEATURE:
<221> NAME/KEY: X is F or T
<222> LOCATION: (10)..(10)

<400> SEQUENCE: 85

Gln Gln Xaa Asn Xaa Asp Pro Xaa Thr Xaa
1               5                   10

<210> SEQ ID NO 86
<211> LENGTH: 111
<212> TYPE: PRT
<213> ORGANISM: Artificial Sequence
<220> FEATURE:
<223> OTHER INFORMATION: synthetic Ror2 VL 5 Conditionally active scFv

<400> SEQUENCE: 86

Asp Ile Val Leu Thr Gln Ser Pro Asp Ser Leu Ala Val Ser Leu Gly
1               5                   10                  15

Gln Arg Ala Thr Ile Ser Cys Arg Ala Ser Glu Ser Val Asp Arg Tyr
            20                  25                  30

Gly Asn Ser Phe Ile His Trp Tyr Leu Gln Lys Pro Gly Gln Pro Pro
        35                  40                  45

Lys Leu Leu Ile Tyr Arg Thr Tyr Asn Leu Glu Ser Gly Ile Pro Ala
    50                  55                  60

Arg Phe Ser Gly Thr Gly Ser Arg Thr Asp Phe Thr Leu Thr Ile Asn
65                  70                  75                  80

Pro Val Glu Ala Asp Asp Val Ala Thr Tyr Tyr Cys Gln Gln Thr Asn
                85                  90                  95

Glu Asp Pro Trp Thr Phe Gly Gln Gly Thr Lys Val Glu Ile Lys
            100                 105                 110

<210> SEQ ID NO 87
<211> LENGTH: 6
<212> TYPE: PRT
<213> ORGANISM: Artificial Sequence
<220> FEATURE:
```

```
<223> OTHER INFORMATION: synthetic Axl H1 1 Conditionally active scFv
<220> FEATURE:
<221> NAME/KEY: X is T or W
<222> LOCATION: (1)..(1)
<220> FEATURE:
<221> NAME/KEY: X is H or A
<222> LOCATION: (3)..(3)

<400> SEQUENCE: 87

Xaa Gly Xaa Thr Met Asn
1               5

<210> SEQ ID NO 88
<211> LENGTH: 17
<212> TYPE: PRT
<213> ORGANISM: Artificial Sequence
<220> FEATURE:
<223> OTHER INFORMATION: synthetic Axl H2 1 Conditionally active scFv

<400> SEQUENCE: 88

Leu Ile Lys Pro Ser Asn Gly Gly Thr Ser Tyr Asn Gln Lys Phe Lys
1               5                   10                  15

Gly

<210> SEQ ID NO 89
<211> LENGTH: 11
<212> TYPE: PRT
<213> ORGANISM: Artificial Sequence
<220> FEATURE:
<223> OTHER INFORMATION: synthetic Axl H31 Conditionally active scFv
<220> FEATURE:
<221> NAME/KEY: X is H or D
<222> LOCATION: (2)..(2)
<220> FEATURE:
<221> NAME/KEY: X is E or H
<222> LOCATION: (4)..(4)
<220> FEATURE:
<221> NAME/KEY: X is E or F
<222> LOCATION: (7)..(7)

<400> SEQUENCE: 89

Gly Xaa Tyr Xaa Ser Tyr Xaa Ala Met Asp Tyr
1               5                   10

<210> SEQ ID NO 90
<211> LENGTH: 11
<212> TYPE: PRT
<213> ORGANISM: Artificial Sequence
<220> FEATURE:
<223> OTHER INFORMATION: synthetic Axl L1 1 Conditionally active scFv
<220> FEATURE:
<221> NAME/KEY: X is S or V
<222> LOCATION: (7)..(7)

<400> SEQUENCE: 90

Lys Ala Ser Gln Asp Val Xaa Ser Ala Val Ala
1               5                   10

<210> SEQ ID NO 91
<211> LENGTH: 7
<212> TYPE: PRT
<213> ORGANISM: Artificial Sequence
<220> FEATURE:
<223> OTHER INFORMATION: synthetic Axl L2 1 Conditionally active scFv
<220> FEATURE:
<221> NAME/KEY: X is A or Q
<222> LOCATION: (2)..(2)
<220> FEATURE:
<221> NAME/KEY: X is S or D
<222> LOCATION: (3)..(3)
```

```
<220> FEATURE:
<221> NAME/KEY: X is H or D
<222> LOCATION: (6)..(6)

<400> SEQUENCE: 91

Trp Xaa Xaa Thr Arg Xaa Thr
1               5

<210> SEQ ID NO 92
<211> LENGTH: 9
<212> TYPE: PRT
<213> ORGANISM: Artificial Sequence
<220> FEATURE:
<223> OTHER INFORMATION: synthetic Axl L3 1 Conditionally active scFv
<220> FEATURE:
<221> NAME/KEY: X is T or P
<222> LOCATION: (6)..(6)
<220> FEATURE:
<221> NAME/KEY: X is T or R
<222> LOCATION: (9)..(9)

<400> SEQUENCE: 92

Gln Glu His Phe Ser Xaa Pro Leu Xaa
1               5

<210> SEQ ID NO 93
<211> LENGTH: 120
<212> TYPE: PRT
<213> ORGANISM: Artificial Sequence
<220> FEATURE:
<223> OTHER INFORMATION: synthetic Axl WT VH Conditionally active scFv

<400> SEQUENCE: 93

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ser Phe Thr Gly His
            20                  25                  30

Thr Met Asn Trp Ile Arg Gln Pro Pro Gly Lys Gly Leu Glu Trp Ile
        35                  40                  45

Gly Leu Ile Lys Pro Ser Asn Gly Gly Thr Ser Tyr Asn Gln Lys Phe
    50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala His Gly His Tyr Glu Ser Tyr Phe Ala Met Asp Tyr Trp Gly Gln
            100                 105                 110

Gly Thr Leu Val Thr Val Ser Ser
        115                 120

<210> SEQ ID NO 94
<211> LENGTH: 107
<212> TYPE: PRT
<213> ORGANISM: Artificial Sequence
<220> FEATURE:
<223> OTHER INFORMATION: synthetic Axl WT VL Conditionally active scFv

<400> SEQUENCE: 94

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ser Ala
            20                  25                  30

Val Ala Trp Tyr Gln Gln Lys Pro Gly Gln Ala Pro Arg Leu Leu Ile
```

```
                    35                  40                  45
Tyr Trp Ala Ser Thr Arg His Thr Gly Val Pro Ser Arg Phe Ser Gly
         50                  55                  60

Ser Gly Ser Gly Thr Glu Phe Thr Leu Thr Ile Ser Ser Leu Gln Pro
 65                  70                  75                  80

Asp Asp Phe Ala Thr Tyr Tyr Cys Gln Glu His Phe Ser Thr Pro Leu
                 85                  90                  95

Thr Phe Gly Gln Gly Thr Lys Val Glu Ile Lys
            100                 105

<210> SEQ ID NO 95
<211> LENGTH: 10
<212> TYPE: PRT
<213> ORGANISM: Artificial Sequence
<220> FEATURE:
<223> OTHER INFORMATION: synthetic Ror2 H1 1 Conditionally active scFv
<220> FEATURE:
<221> NAME/KEY: X is F or E
<222> LOCATION: (4)..(4)
<220> FEATURE:
<221> NAME/KEY: X is Y or D
<222> LOCATION: (7)..(7)
<220> FEATURE:
<221> NAME/KEY: X is M or D
<222> LOCATION: (9)..(9)

<400> SEQUENCE: 95

Gly Tyr Thr Xaa Thr Glu Xaa Thr Xaa His
1               5                   10

<210> SEQ ID NO 96
<211> LENGTH: 12
<212> TYPE: PRT
<213> ORGANISM: Artificial Sequence
<220> FEATURE:
<223> OTHER INFORMATION: synthetic Ror2 H1 2 Conditionally active scFv
<220> FEATURE:
<221> NAME/KEY: X is T or S
<222> LOCATION: (1)..(1)

<400> SEQUENCE: 96

Xaa Gly Tyr Ser Ile Thr Thr Gly Tyr Tyr Trp Asn
1               5                   10

<210> SEQ ID NO 97
<211> LENGTH: 17
<212> TYPE: PRT
<213> ORGANISM: Artificial Sequence
<220> FEATURE:
<223> OTHER INFORMATION: synthetic Ror2 H1 2 Conditionally active scFv
<220> FEATURE:
<221> NAME/KEY: X is E or I
<222> LOCATION: (2)..(2)
<220> FEATURE:
<221> NAME/KEY: X is T or D
<222> LOCATION: (4)..(4)

<400> SEQUENCE: 97

Gly Xaa Asn Xaa Asn Asn Gly Gly Thr Gly Tyr Asn Gln Lys Phe Lys
1               5                   10                  15

Gly

<210> SEQ ID NO 98
<211> LENGTH: 16
<212> TYPE: PRT
<213> ORGANISM: Artificial Sequence
<220> FEATURE:
```

```
<223> OTHER INFORMATION: synthetic Ror2 H2 2 Conditionally active scFv

<400> SEQUENCE: 98

Tyr Ile Thr Tyr Asp Gly Ser Lys Asn Tyr Asn Pro Ser Leu Lys Asn
1               5                   10                  15

<210> SEQ ID NO 99
<211> LENGTH: 13
<212> TYPE: PRT
<213> ORGANISM: Artificial Sequence
<220> FEATURE:
<223> OTHER INFORMATION: synthetic Ror2 H3 1 Conditionally active scFv

<400> SEQUENCE: 99

Gly Ser Leu Tyr Ser Tyr Gly Asn Ser Tyr Phe Asp Tyr
1               5                   10

<210> SEQ ID NO 100
<211> LENGTH: 10
<212> TYPE: PRT
<213> ORGANISM: Artificial Sequence
<220> FEATURE:
<223> OTHER INFORMATION: synthetic Ror2 H3 2 Conditionally active scFv
<220> FEATURE:
<221> NAME/KEY: X is Y or G
<222> LOCATION: (6)..(6)

<400> SEQUENCE: 100

Phe Glu Gly Val Trp Xaa Gly Leu Asp Tyr
1               5                   10

<210> SEQ ID NO 101
<211> LENGTH: 10
<212> TYPE: PRT
<213> ORGANISM: Artificial Sequence
<220> FEATURE:
<223> OTHER INFORMATION: synthetic Ror2 L1 1 Conditionally active scFv
<220> FEATURE:
<221> NAME/KEY: X is E or V
<222> LOCATION: (6)..(6)

<400> SEQUENCE: 101

Ser Ala Thr Ser Ser Xaa Ser Tyr Met His
1               5                   10

<210> SEQ ID NO 102
<211> LENGTH: 15
<212> TYPE: PRT
<213> ORGANISM: Artificial Sequence
<220> FEATURE:
<223> OTHER INFORMATION: synthetic Ror2 L1 2 Conditionally active scFv

<400> SEQUENCE: 102

Arg Ala Ser Glu Ser Val Asp Arg Tyr Gly Asn Ser Phe Ile His
1               5                   10                  15

<210> SEQ ID NO 103
<211> LENGTH: 7
<212> TYPE: PRT
<213> ORGANISM: Artificial Sequence
<220> FEATURE:
<223> OTHER INFORMATION: synthetic Ror2 L2 1 Conditionally active scFv
<220> FEATURE:
<221> NAME/KEY: X is G or H
<222> LOCATION: (1)..(1)

<400> SEQUENCE: 103

Xaa Thr Ser Asn Leu Ala Ser
```

```
<210> SEQ ID NO 104
<211> LENGTH: 7
<212> TYPE: PRT
<213> ORGANISM: Artificial Sequence
<220> FEATURE:
<223> OTHER INFORMATION: synthetic Ror2 L2 2 Conditionally active scFv

<400> SEQUENCE: 104

Arg Thr Tyr Asn Leu Glu Ser
1               5

<210> SEQ ID NO 105
<211> LENGTH: 9
<212> TYPE: PRT
<213> ORGANISM: Artificial Sequence
<220> FEATURE:
<223> OTHER INFORMATION: synthetic Ror2 L3 1 Conditionally active scFv

<400> SEQUENCE: 105

Gln Gln Arg Ser Ser Tyr Pro Phe Thr
1               5

<210> SEQ ID NO 106
<211> LENGTH: 9
<212> TYPE: PRT
<213> ORGANISM: Artificial Sequence
<220> FEATURE:
<223> OTHER INFORMATION: synthetic Ror2 L3 2 Conditionally active scFv

<400> SEQUENCE: 106

Gln Gln Thr Asn Glu Asp Pro Trp Thr
1               5

<210> SEQ ID NO 107
<211> LENGTH: 119
<212> TYPE: PRT
<213> ORGANISM: Artificial Sequence
<220> FEATURE:
<223> OTHER INFORMATION: synthetic Ror2 WT VH Conditionally active scFv

<400> SEQUENCE: 107

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Thr Gly
            20                  25                  30

Tyr Tyr Trp Asn Trp Val Arg Gln Ala Arg Gly Gln Arg Leu Glu Trp
        35                  40                  45

Ile Gly Tyr Ile Thr Tyr Asp Gly Ser Lys Asn Tyr Asn Pro Ser Leu
    50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ser Arg Phe Glu Gly Val Trp Tyr Gly Leu Asp Tyr Trp Gly Gln Gly
            100                 105                 110

Thr Leu Val Thr Val Ser Ser
        115

<210> SEQ ID NO 108
<211> LENGTH: 60
<212> TYPE: PRT
```

<213> ORGANISM: Artificial Sequence
<220> FEATURE:
<223> OTHER INFORMATION: synthetic Axl VL 1 Conditionally active scFv

<400> SEQUENCE: 108

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Val Ser Ala
            20                  25                  30

Val Ala Trp Tyr Gln Gln Lys Pro Gly Gln Ala Pro Arg Leu Leu Ile
        35                  40                  45

Tyr Trp Gln Asp Thr Arg His Thr Gly Val Pro Ser
    50                  55                  60

<210> SEQ ID NO 109
<211> LENGTH: 60
<212> TYPE: PRT
<213> ORGANISM: Artificial Sequence
<220> FEATURE:
<223> OTHER INFORMATION: synthetic Axl VL 2 Conditionally active scFv

<400> SEQUENCE: 109

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Ser Ser Ala
            20                  25                  30

Val Ala Trp Tyr Gln Gln Lys Pro Gly Gln Ala Pro Arg Leu Leu Ile
        35                  40                  45

Tyr Trp Gln Asp Thr Arg His Thr Gly Val Pro Ser
    50                  55                  60

<210> SEQ ID NO 110
<211> LENGTH: 60
<212> TYPE: PRT
<213> ORGANISM: Artificial Sequence
<220> FEATURE:
<223> OTHER INFORMATION: synthetic Axl VL 3 Conditionally active scFv

<400> SEQUENCE: 110

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Val Ser Ala
            20                  25                  30

Val Ala Trp Tyr Gln Gln Lys Pro Gly Gln Ala Pro Arg Leu Leu Ile
        35                  40                  45

Tyr Trp Gln Asp Thr Arg His Thr Gly Val Pro Ser
    50                  55                  60

<210> SEQ ID NO 111
<211> LENGTH: 60
<212> TYPE: PRT
<213> ORGANISM: Artificial Sequence
<220> FEATURE:
<223> OTHER INFORMATION: synthetic Axl VL 4 Conditionally active scFv

<400> SEQUENCE: 111

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Val Ser Ala
            20                  25                  30

Val Ala Trp Tyr Gln Gln Lys Pro Gly Gln Ala Pro Arg Leu Leu Ile

```
                35                  40                  45
Tyr Trp Gln Asp Thr Arg His Thr Gly Val Pro Ser
        50                  55                  60

<210> SEQ ID NO 112
<211> LENGTH: 120
<212> TYPE: PRT
<213> ORGANISM: Artificial Sequence
<220> FEATURE:
<223> OTHER INFORMATION: synthetic Axl VH 1 Conditionally active scFv

<400> SEQUENCE: 112

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ser Phe Thr Gly Ala
            20                  25                  30

Thr Met Asn Trp Ile Arg Gln Pro Pro Gly Lys Gly Leu Glu Trp Ile
        35                  40                  45

Gly Leu Ile Lys Pro Ser Asn Gly Gly Thr Ser Tyr Asn Gln Lys Phe
    50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala His Gly His Tyr Glu Ser Tyr Glu Ala Met Asp Tyr Trp Gly Gln
            100                 105                 110

Gly Thr Leu Val Thr Val Ser Ser
        115                 120

<210> SEQ ID NO 113
<211> LENGTH: 120
<212> TYPE: PRT
<213> ORGANISM: Artificial Sequence
<220> FEATURE:
<223> OTHER INFORMATION: synthetic Axl VH 2 Conditionally active scFv

<400> SEQUENCE: 113

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ser Phe Trp Gly Ala
            20                  25                  30

Thr Met Asn Trp Ile Arg Gln Pro Pro Gly Lys Gly Leu Glu Trp Ile
        35                  40                  45

Gly Leu Ile Lys Pro Ser Asn Gly Gly Thr Ser Tyr Asn Gln Lys Phe
    50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala His Gly His Tyr Glu Ser Tyr Glu Ala Met Asp Tyr Trp Gly Gln
            100                 105                 110

Gly Thr Leu Val Thr Val Ser Ser
        115                 120

<210> SEQ ID NO 114
<211> LENGTH: 120
<212> TYPE: PRT
<213> ORGANISM: Artificial Sequence
<220> FEATURE:
```

<223> OTHER INFORMATION: synthetic Axl VH 3 Conditionally active scFv

<400> SEQUENCE: 114

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ser Phe Thr Gly His
            20                  25                  30

Thr Met Asn Trp Ile Arg Gln Pro Pro Gly Lys Gly Leu Glu Trp Ile
        35                  40                  45

Gly Leu Ile Lys Pro Ser Asn Gly Gly Thr Ser Tyr Asn Gln Lys Phe
    50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala His Gly His Tyr Glu Ser Tyr Glu Ala Met Asp Tyr Trp Gly Gln
            100                 105                 110

Gly Thr Leu Val Thr Val Ser Ser
        115                 120

<210> SEQ ID NO 115
<211> LENGTH: 122
<212> TYPE: PRT
<213> ORGANISM: Artificial Sequence
<220> FEATURE:
<223> OTHER INFORMATION: synthetic Ror2 VH 1 Conditionally active scFv

<400> SEQUENCE: 115

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Phe Thr Glu Tyr
            20                  25                  30

Thr Met His Trp Met Lys Gln Ser His Arg Lys Ser Leu Glu Trp Ile
        35                  40                  45

Gly Gly Ile Asn Thr Asn Asn Gly Gly Thr Gly Tyr Asn Gln Lys Phe
    50                  55                  60

Lys Gly Lys Ala Thr Leu Thr Val Asp Lys Ser Ser Ser Thr Ala Tyr
65                  70                  75                  80

Met Glu Leu Arg Ser Leu Thr Ser Glu Asp Ser Ala Val Tyr Phe Cys
                85                  90                  95

Ala Arg Gly Ser Leu Tyr Ser Tyr Gly Asn Ser Tyr Phe Asp Tyr Trp
            100                 105                 110

Gly Gln Gly Thr Leu Val Thr Val Ser Ser
        115                 120

<210> SEQ ID NO 116
<211> LENGTH: 122
<212> TYPE: PRT
<213> ORGANISM: Artificial Sequence
<220> FEATURE:
<223> OTHER INFORMATION: synthetic Ror2 VH 1 Conditionally active scFv

<400> SEQUENCE: 116

Glu Val Gln Leu Gln Gln Ser Gly Pro Glu Leu Val Lys Pro Gly Ala
1               5                   10                  15

Ser Val Lys Ile Ser Cys Lys Thr Ser Gly Tyr Thr Glu Thr Glu Asp
            20                  25                  30

Thr Asp His Trp Met Lys Gln Ser His Arg Lys Ser Leu Glu Trp Ile

```
            35                  40                  45

Gly Gly Glu Asn Asp Asn Gly Gly Thr Gly Tyr Asn Gln Lys Phe
        50                  55                  60

Lys Gly Lys Ala Thr Leu Thr Val Asp Lys Ser Ser Thr Ala Tyr
 65                  70                  75                  80

Met Glu Leu Arg Ser Leu Thr Ser Glu Asp Ser Ala Val Tyr Phe Cys
                85                  90                  95

Ala His Gly Ser Leu Tyr Ser Tyr Gly Asn Ser Tyr Phe Asp Tyr Trp
                100                 105                 110

Gly Gln Gly Thr Leu Val Thr Val Ser Ser
            115                 120

<210> SEQ ID NO 117
<211> LENGTH: 122
<212> TYPE: PRT
<213> ORGANISM: Artificial Sequence
<220> FEATURE:
<223> OTHER INFORMATION: synthetic Ror2 VH 3 Conditionally active scFv

<400> SEQUENCE: 117

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
                20                  25                  30

Thr Met His Trp Val Arg Gln Ala Arg Gly Gln Arg Leu Glu Trp Ile
            35                  40                  45

Gly Gly Ile Asn Thr Asn Asn Gly Gly Thr Gly Tyr Asn Gln Lys Phe
        50                  55                  60

Lys Gly Arg Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95

Ala His Gly Ser Leu Tyr Ser Tyr Gly Asn Ser Tyr Phe Asp Tyr Trp
                100                 105                 110

Gly Gln Gly Thr Leu Val Thr Val Ser Ser
            115                 120

<210> SEQ ID NO 118
<211> LENGTH: 122
<212> TYPE: PRT
<213> ORGANISM: Artificial Sequence
<220> FEATURE:
<223> OTHER INFORMATION: synthetic Ror2 VH 4 Conditionally active scFv

<400> SEQUENCE: 118

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Glu Tyr
                20                  25                  30

Thr Met His Trp Val Arg Gln Ala Pro Gly Gln Gly Leu Glu Trp Met
            35                  40                  45

Gly Gly Ile Asn Thr Asn Asn Gly Gly Thr Gly Tyr Asn Gln Lys Phe
        50                  55                  60

Lys Gly Arg Val Thr Ile Ser Ala Asp Lys Ser Ile Ser Thr Ala Tyr
 65                  70                  75                  80

Leu Gln Trp Ser Ser Leu Lys Ala Ser Asp Thr Ala Met Tyr Tyr Cys
                85                  90                  95
```

Ala His Gly Ser Leu Tyr Ser Tyr Gly Asn Ser Tyr Phe Asp Tyr Trp
            100                 105                 110

Gly Gln Gly Thr Leu Val Thr Val Ser Ser
        115                 120

<210> SEQ ID NO 119
<211> LENGTH: 122
<212> TYPE: PRT
<213> ORGANISM: Artificial Sequence
<220> FEATURE:
<223> OTHER INFORMATION: synthetic Ror2 VH 5 Conditionally active scFv

<400> SEQUENCE: 119

Glu Val Gln Leu Val Gln Ser Gly Ala Glu Val Lys Lys Pro Gly Glu
1               5                   10                  15

Ser Leu Arg Ile Ser Cys Lys Gly Ser Gly Tyr Thr Phe Thr Glu Tyr
            20                  25                  30

Thr Met His Trp Ile Arg Gln Ser Pro Ser Arg Gly Leu Glu Trp Leu
        35                  40                  45

Gly Gly Ile Asn Thr Asn Asn Gly Thr Gly Tyr Asn Gln Lys Phe
    50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala His Gly Ser Leu Tyr Ser Tyr Gly Asn Ser Tyr Phe Asp Tyr Trp
            100                 105                 110

Gly Gln Gly Thr Leu Val Thr Val Ser Ser
        115                 120

<210> SEQ ID NO 120
<211> LENGTH: 119
<212> TYPE: PRT
<213> ORGANISM: Artificial Sequence
<220> FEATURE:
<223> OTHER INFORMATION: synthetic Ror2 VH 6 Conditionally active scFv

<400> SEQUENCE: 120

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Thr Gly
            20                  25                  30

Tyr Tyr Trp Asn Trp Ile Arg Gln Phe Pro Gly Asn Lys Leu Glu Trp
        35                  40                  45

Met Ala Tyr Ile Thr Tyr Asp Gly Ser Lys Asn Tyr Asn Pro Ser Leu
    50                  55                  60

Lys Asn Arg Ile Ser Ile Thr Arg Asp Thr Ser Lys Asn Lys Phe Phe
65                  70                  75                  80

Leu Lys Leu Asn Ser Val Thr Ser Glu Asp Thr Ala Thr Tyr Tyr Cys
                85                  90                  95

Ser Arg Phe Glu Gly Val Trp Tyr Gly Leu Asp Tyr Trp Gly Gln Gly
            100                 105                 110

Thr Leu Val Thr Val Ser Ser
        115

<210> SEQ ID NO 121
<211> LENGTH: 119
<212> TYPE: PRT
<213> ORGANISM: Artificial Sequence

```
<220> FEATURE:
<223> OTHER INFORMATION: synthetic Ror2 VH 7 Conditionally active scFv

<400> SEQUENCE: 121

Asp Val Gln Leu Gln Glu Ser Gly Pro Gly Leu Val Lys Pro Ser Gln
1               5                   10                  15

Ser Leu Ser Leu Thr Cys Ser Val Thr Gly Tyr Ser Ile Thr Thr Gly
            20                  25                  30

Tyr Tyr Trp Asn Trp Ile Arg Gln Phe Pro Gly Asn Lys Leu Glu Trp
        35                  40                  45

Met Ala Tyr Ile Thr Tyr Asp Gly Ser Lys Asn Tyr Asn Pro Ser Leu
    50                  55                  60

Lys Asn Arg Ile Ser Ile Thr Arg Asp Thr Ser Lys Asn Lys Phe Phe
65                  70                  75                  80

Leu Lys Leu Asn Ser Val Thr Ser Glu Asp Thr Ala Thr Tyr Tyr Cys
                85                  90                  95

Ser His Phe Glu Gly Val Trp Gly Gly Leu Asp Tyr Trp Gly Gln Gly
            100                 105                 110

Thr Leu Val Thr Val Ser Ser
        115

<210> SEQ ID NO 122
<211> LENGTH: 106
<212> TYPE: PRT
<213> ORGANISM: Artificial Sequence
<220> FEATURE:
<223> OTHER INFORMATION: synthetic Ror2 VL 1 Conditionally active scFv

<400> SEQUENCE: 122

Gln Ile Val Leu Thr Gln Ser Pro Ala Ile Met Ser Ala Ser Pro Gly
1               5                   10                  15

Glu Lys Val Thr Ile Thr Cys Ser Ala Thr Ser Ser Val Ser Tyr Met
            20                  25                  30

His Trp Phe Gln Gln Lys Pro Gly Thr Ser Pro Lys Leu Trp Ile Tyr
        35                  40                  45

Gly Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Gln Gly Thr Lys Val Glu Ile Lys
            100                 105

<210> SEQ ID NO 123
<211> LENGTH: 106
<212> TYPE: PRT
<213> ORGANISM: Artificial Sequence
<220> FEATURE:
<223> OTHER INFORMATION: synthetic Ror2 VL 2 Conditionally active scFv

<400> SEQUENCE: 123

Gln Ile Val Leu Thr Gln Ser Pro Ala Ile Met Ser Ala Ser Pro Gly
1               5                   10                  15

Glu Lys Val Thr Ile Thr Cys Ser Ala Thr Ser Ser Glu Ser Tyr Met
            20                  25                  30

His Trp Phe Gln Gln Lys Pro Gly Thr Ser Pro Lys Leu Trp Ile Tyr
        35                  40                  45
```

```
His Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Met Glu Ala Glu
65                  70                  75                  80

Asp Ala Ala Thr Tyr Tyr Cys Gln Gln Arg Ser Ser Tyr Pro Phe Thr
                85                  90                  95

Phe Gly Gln Gly Thr Lys Val Glu Ile Lys
                100                 105

<210> SEQ ID NO 124
<211> LENGTH: 106
<212> TYPE: PRT
<213> ORGANISM: Artificial Sequence
<220> FEATURE:
<223> OTHER INFORMATION: synthetic Ror2 VL 3 Conditionally active scFv

<400> SEQUENCE: 124

Ala Ile Gln Leu Thr Gln Ser Pro Ser Ser Leu Ser Ala Ser Val Gly
1               5                   10                  15

Asp Arg Val Thr Ile Thr Cys Ser Ala Thr Ser Ser Val Ser Tyr Met
                20                  25                  30

His Trp Tyr Gln Gln Lys Pro Gly Gln Ala Pro Arg Leu Leu Ile Tyr
            35                  40                  45

Gly Thr Ser Asn Leu Ala Ser Gly Val Pro Asp Arg Phe Ser Gly Ser
    50                  55                  60

Gly Ser Gly Thr Asp Phe Thr Leu Lys Ile Ser Arg Val Glu Ala Glu
65                  70                  75                  80

Asp Val Gly Val Tyr Tyr Cys Gln Gln Arg Ser Ser Tyr Pro Phe Thr
                85                  90                  95

Phe Gly Gln Gly Thr Lys Val Glu Ile Lys
                100                 105

<210> SEQ ID NO 125
<211> LENGTH: 43
<212> TYPE: PRT
<213> ORGANISM: Artificial Sequence
<220> FEATURE:
<223> OTHER INFORMATION: synthetic wild-type CD8 Stalk

<400> SEQUENCE: 125

Thr Thr Thr Pro Ala Pro Arg Pro Pro Thr Pro Ala Pro Thr Ile Ala
1               5                   10                  15

Ser Gln Pro Leu Ser Leu Arg Pro Glu Ala Cys Arg Pro Ala Ala Gly
                20                  25                  30

Gly Ala Val His Thr Arg Gly Leu Asp Phe Ala
            35                  40

<210> SEQ ID NO 126
<211> LENGTH: 42
<212> TYPE: PRT
<213> ORGANISM: Artificial Sequence
<220> FEATURE:
<223> OTHER INFORMATION: synthetic wild-type CD28 Stalk

<400> SEQUENCE: 126

Phe Cys Lys Ile Glu Val Met Tyr Pro Pro Pro Tyr Leu Asp Asn Glu
1               5                   10                  15

Lys Ser Asn Gly Thr Ile Ile His Val Lys Gly Lys His Leu Cys Pro
                20                  25                  30

Ser Pro Leu Phe Pro Gly Pro Ser Lys Pro
```

<210> SEQ ID NO 127
<211> LENGTH: 113
<212> TYPE: PRT
<213> ORGANISM: Artificial Sequence
<220> FEATURE:
<223> OTHER INFORMATION: synthetic CD3Z 7 Activating domain

<400> SEQUENCE: 127

Arg Val Lys Phe Ser Arg Ser Ala Asp Ala Pro Ala Tyr Gln Gln Gly
1               5                   10                  15

Gln Asn Gln Leu Tyr Asn Glu Leu Asn Leu Gly Arg Arg Glu Glu Tyr
            20                  25                  30

Asp Val Leu Asp Lys Arg Arg Gly Arg Asp Pro Glu Met Gly Gly Lys
        35                  40                  45

Pro Gln Arg Arg Lys Asn Pro Gln Glu Gly Leu Tyr Asn Glu Leu Gln
    50                  55                  60

Lys Asp Lys Met Ala Glu Ala Tyr Ser Glu Ile Gly Met Lys Gly Glu
65                  70                  75                  80

Arg Arg Arg Gly Lys Gly His Asp Gly Leu Tyr Gln Gly Leu Ser Thr
                85                  90                  95

Ala Thr Lys Asp Thr Tyr Asp Ala Leu His Met Gln Ala Leu Pro Pro
            100                 105                 110

Arg

<210> SEQ ID NO 128
<211> LENGTH: 241
<212> TYPE: PRT
<213> ORGANISM: Artificial Sequence
<220> FEATURE:
<223> OTHER INFORMATION: synthetic scFv from F1-2-15

<400> SEQUENCE: 128

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ser Phe Trp Gly Ala
            20                  25                  30

Thr Met Asn Trp Ile Arg Gln Pro Pro Gly Lys Gly Leu Glu Trp Ile
        35                  40                  45

Gly Leu Ile Lys Pro Ser Asn Gly Gly Thr Ser Tyr Asn Gln Lys Phe
    50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala His Gly His Tyr Glu Ser Tyr Glu Ala Met Asp Tyr Trp Gly Gln
            100                 105                 110

Gly Thr Leu Val Thr Val Ser Gly Gly Gly Gly Ser Gly Gly Gly Gly
        115                 120                 125

Ser Gly Gly Gly Gly Ser Asp Ile Gln Met Thr Gln Ser Pro Ser Ser
    130                 135                 140

Leu Ser Ala Ser Val Gly Asp Arg Val Thr Ile Thr Cys Lys Ala Ser
145                 150                 155                 160

Gln Asp Val Val Ser Ala Val Ala Trp Tyr Gln Gln Lys Pro Gly Gln
                165                 170                 175

Ala Pro Arg Leu Leu Ile Tyr Trp Gln Asp Thr Arg His Thr Gly Val

```
                180             185             190
Pro Ser Arg Phe Ser Gly Ser Gly Ser Gly Thr Glu Phe Thr Leu Thr
            195                 200                 205

Ile Ser Ser Leu Gln Pro Asp Asp Phe Ala Thr Tyr Tyr Cys Gln Glu
    210                 215                 220

His Phe Ser Pro Pro Leu Thr Phe Gly Gln Gly Thr Lys Val Glu Ile
225                 230                 235                 240

Lys

<210> SEQ ID NO 129
<211> LENGTH: 242
<212> TYPE: PRT
<213> ORGANISM: Artificial Sequence
<220> FEATURE:
<223> OTHER INFORMATION: synthetic scFv from F1-2-13

<400> SEQUENCE: 129

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ser Phe Trp Gly Ala
            20                  25                  30

Thr Met Asn Trp Ile Arg Gln Pro Gly Lys Gly Leu Glu Trp Ile
        35                  40                  45

Gly Leu Ile Lys Pro Ser Asn Gly Gly Thr Ser Tyr Asn Gln Lys Phe
    50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala His Gly His Tyr Glu Ser Tyr Glu Ala Met Asp Tyr Trp Gly Gln
            100                 105                 110

Gly Thr Leu Val Thr Val Ser Ser Gly Gly Gly Ser Gly Gly Gly
            115                 120                 125

Gly Ser Gly Gly Gly Ser Asp Ile Gln Met Thr Gln Ser Pro Ser
130                 135                 140

Ser Leu Ser Ala Ser Val Gly Asp Arg Val Thr Ile Thr Cys Lys Ala
145                 150                 155                 160

Ser Gln Asp Val Val Ser Ala Val Ala Trp Tyr Gln Gln Lys Pro Gly
            165                 170                 175

Gln Ala Pro Arg Leu Leu Ile Tyr Trp Gln Asp Thr Arg His Thr Gly
            180                 185                 190

Val Pro Ser Arg Phe Ser Gly Ser Gly Ser Gly Thr Glu Phe Thr Leu
            195                 200                 205

Thr Ile Ser Ser Leu Gln Pro Asp Asp Phe Ala Thr Tyr Tyr Cys Gln
        210                 215                 220

Glu His Phe Ser Pro Pro Leu Thr Phe Gly Gln Gly Thr Lys Val Glu
225                 230                 235                 240

Ile Lys

<210> SEQ ID NO 130
<211> LENGTH: 260
<212> TYPE: PRT
<213> ORGANISM: Artificial Sequence
<220> FEATURE:
<223> OTHER INFORMATION: synthetic scFv from F1-1-19

<400> SEQUENCE: 130
```

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Thr Gly
            20                  25                  30

Glu Tyr Trp Asn Trp Val Arg Gln Ala Arg Gly Gln Arg Leu Glu Trp
            35                  40                  45

Ile Gly Tyr Ile Thr Tyr Asp Gly Ser Lys Asn Tyr Asn Pro Ser Leu
        50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ser Arg Phe Glu Gly Val Trp Tyr Gly Leu Asp Tyr Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Gly Gly Gly Ser Gly Gly Gly Ser
    130                 135                 140

Gly Gly Gly Gly Ser Ala Ile Gln Leu Thr Gln Ser Pro Ser Ser Leu
145                 150                 155                 160

Ser Ala Ser Val Gly Asp Arg Val Thr Ile Thr Cys Arg Ala Ser Glu
                165                 170                 175

Ser Val Asp Arg Tyr Gly Asn Ser Phe Ile His Trp Tyr Gln Gln Lys
            180                 185                 190

Pro Gly Lys Ala Pro Lys Leu Leu Ile Tyr Arg Thr Tyr Asn Leu Glu
            195                 200                 205

Ser Gly Ile Pro Ala Arg Phe Ser Gly Ser Gly Ser Gly Thr Glu Phe
        210                 215                 220

Thr Leu Thr Ile Ser Ser Leu Gln Ser Glu Asp Phe Ala Val Tyr Tyr
225                 230                 235                 240

Cys Gln Gln Thr Asn Glu Asp Pro Trp Thr Phe Gly Gln Gly Thr Lys
                245                 250                 255

Val Glu Ile Lys
            260

<210> SEQ ID NO 131
<211> LENGTH: 260
<212> TYPE: PRT
<213> ORGANISM: Artificial Sequence
<220> FEATURE:
<223> OTHER INFORMATION: synthetic scFv from F1-1-23

<400> SEQUENCE: 131

Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Arg Tyr
            20                  25                  30

Gly Asn Ser Phe Ile His Trp Tyr Gln Gln Lys Pro Gly Lys Ala Pro
            35                  40                  45

Lys Leu Leu Ile Tyr Arg Thr Tyr Asn Leu Glu Ser Gly Ile Pro Ala
        50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln Gln Thr Asn
                85                  90                  95

Glu Asp Pro Trp Thr Phe Gly Gln Gly Thr Lys Val Glu Ile Lys Gly
            100                 105                 110

Gly Gly Gly Ser Gly Gly Gly Gly Ser Gly Gly Gly Ser Gly Gly
            115                 120                 125

Gly Gly Ser Gly Gly Gly Ser Gly Gly Gly Ser Gln Val Gln
            130                 135                 140

Leu Gln Glu Ser Gly Pro Gly Leu Val Lys Pro Ser Gln Thr Leu Ser
145                 150                 155                 160

Leu Thr Cys Thr Val Ser Gly Tyr Ser Ile Thr Thr Gly Glu Tyr Trp
                    165                 170                 175

Asn Trp Val Arg Gln Ala Arg Gly Gln Arg Leu Glu Trp Ile Gly Tyr
                180                 185                 190

Ile Thr Tyr Asp Gly Ser Lys Asn Tyr Asn Pro Ser Leu Lys Asn Arg
            195                 200                 205

Val Thr Ile Ser Val Asp Thr Ser Lys Asn Gln Phe Ser Leu Lys Leu
            210                 215                 220

Ser Ser Val Thr Ala Ala Asp Thr Ala Val Tyr Tyr Cys Ser Arg Phe
225                 230                 235                 240

Glu Gly Val Trp Tyr Gly Leu Asp Tyr Trp Gly Gln Gly Thr Leu Val
                245                 250                 255

Thr Val Ser Ser
            260

<210> SEQ ID NO 132
<211> LENGTH: 260
<212> TYPE: PRT
<213> ORGANISM: Artificial Sequence
<220> FEATURE:
<223> OTHER INFORMATION: synthetic scFV from F1-1-15

<400> SEQUENCE: 132

Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Arg Tyr
            20                  25                  30

Gly Asn Ser Phe Ile His Trp Tyr Gln Gln Lys Pro Gly Lys Ala Pro
        35                  40                  45

Lys Leu Leu Ile Tyr Arg Thr Tyr Asn Leu Glu Ser Gly Ile Pro Ala
50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln Gln Thr Asn
                85                  90                  95

Glu Asp Pro Trp Thr Phe Gly Gln Gly Thr Lys Val Glu Ile Lys Gly
            100                 105                 110

Gly Gly Gly Ser Gly Gly Gly Gly Ser Gly Gly Gly Ser Gly Gly
            115                 120                 125

Gly Gly Ser Gly Gly Gly Ser Gly Gly Gly Ser Gln Val Gln
            130                 135                 140

Leu Gln Glu Ser Gly Pro Gly Leu Val Lys Pro Ser Gln Thr Leu Ser
145                 150                 155                 160

Leu Thr Cys Thr Val Ser Gly Tyr Ser Ile Thr Thr Gly Tyr Tyr Trp
                    165                 170                 175

Asn Trp Val Arg Gln Ala Arg Gly Gln Arg Leu Glu Trp Ile Gly Tyr
                180                 185                 190

```
Ile Thr Tyr Asp Gly Ser Lys Asn Tyr Asn Pro Ser Leu Lys Asn Arg
        195                 200                 205

Val Thr Ile Ser Val Asp Thr Ser Lys Asn Gln Phe Ser Leu Lys Leu
    210                 215                 220

Ser Ser Val Thr Ala Ala Asp Thr Ala Val Tyr Tyr Cys Ser His Phe
225                 230                 235                 240

Glu Gly Val Trp Tyr Gly Leu Asp Tyr Trp Gly Gln Gly Thr Leu Val
                245                 250                 255

Thr Val Ser Ser
            260

<210> SEQ ID NO 133
<211> LENGTH: 83
<212> TYPE: PRT
<213> ORGANISM: Artificial Sequence
<220> FEATURE:
<223> OTHER INFORMATION: synthetic IC-delta CD137 Dual Co-stimulatory
      domain

<400> SEQUENCE: 133

Arg Ser Lys Arg Ser Arg Leu Leu His Ser Asp Tyr Met Asn Met Thr
1               5                   10                  15

Pro Arg Arg Pro Gly Pro Thr Arg Lys His Tyr Gln Ala Tyr Ala Ala
            20                  25                  30

Ala Arg Asp Phe Ala Ala Tyr Arg Ser Lys Arg Gly Arg Lys Lys Leu
        35                  40                  45

Leu Tyr Ile Phe Lys Gln Pro Phe Met Arg Pro Val Gln Thr Thr Gln
50                  55                  60

Glu Glu Asp Gly Cys Ser Cys Arg Phe Pro Glu Glu Glu Glu Gly Gly
65                  70                  75                  80

Cys Glu Leu

<210> SEQ ID NO 134
<211> LENGTH: 6
<212> TYPE: PRT
<213> ORGANISM: Artificial Sequence
<220> FEATURE:
<223> OTHER INFORMATION: synthetic Axl H1 2 Conditionally active scFv
<220> FEATURE:
<221> NAME/KEY: X is T, A, or W
<222> LOCATION: (1)..(1)
<220> FEATURE:
<221> NAME/KEY: X is H or A
<222> LOCATION: (3)..(3)
<220> FEATURE:
<221> NAME/KEY: X is T or I
<222> LOCATION: (4)..(4)
<220> FEATURE:
<221> NAME/KEY: X is N or I
<222> LOCATION: (6)..(6)

<400> SEQUENCE: 134

Xaa Gly Xaa Xaa Met Xaa
1               5

<210> SEQ ID NO 135
<211> LENGTH: 17
<212> TYPE: PRT
<213> ORGANISM: Artificial Sequence
<220> FEATURE:
<223> OTHER INFORMATION: synthetic Axl H1 2 Conditionally active scFv
<220> FEATURE:
<221> NAME/KEY: X is P or N
<222> LOCATION: (4)..(4)
```

```
<220> FEATURE:
<221> NAME/KEY: X is S, I, or T
<222> LOCATION: (10)..(10)

<400> SEQUENCE: 135

Leu Ile Lys Xaa Ser Asn Gly Gly Thr Xaa Tyr Asn Gln Lys Phe Lys
1               5                   10                  15

Gly

<210> SEQ ID NO 136
<211> LENGTH: 13
<212> TYPE: PRT
<213> ORGANISM: Artificial Sequence
<220> FEATURE:
<223> OTHER INFORMATION: synthetic Axl H3 2 Conditionally active scFv
<220> FEATURE:
<221> NAME/KEY: X is H, D, E, P, R, or W
<222> LOCATION: (2)..(2)
<220> FEATURE:
<221> NAME/KEY: X is Y or N
<222> LOCATION: (3)..(3)
<220> FEATURE:
<221> NAME/KEY: X is E, A, D, F, G, H, I, L, M, N, R, V, or Y
<222> LOCATION: (4)..(4)
<220> FEATURE:
<221> NAME/KEY: X is S, D, M, N, or Q
<222> LOCATION: (5)..(5)
<220> FEATURE:
<221> NAME/KEY: X is Y, C, E, or P
<222> LOCATION: (6)..(6)
<220> FEATURE:
<221> NAME/KEY: X is F, E, N, S, T, or V
<222> LOCATION: (7)..(7)
<220> FEATURE:
<221> NAME/KEY: X is A, D, G, L, or Y
<222> LOCATION: (8)..(8)
<220> FEATURE:
<221> NAME/KEY: X is M, E, or F
<222> LOCATION: (9)..(9)
<220> FEATURE:
<221> NAME/KEY: X is W, A, D, H, L, N, P, R, or T
<222> LOCATION: (12)..(12)
<220> FEATURE:
<221> NAME/KEY: X is G or H
<222> LOCATION: (13)..(13)

<400> SEQUENCE: 136

Gly Xaa Xaa Xaa Xaa Xaa Xaa Xaa Xaa Asp Tyr Xaa Xaa
1               5                   10

<210> SEQ ID NO 137
<211> LENGTH: 11
<212> TYPE: PRT
<213> ORGANISM: Artificial Sequence
<220> FEATURE:
<223> OTHER INFORMATION: synthetic Axl L1 2 Conditionally active scFv
<220> FEATURE:
<221> NAME/KEY: X is V, D, G, N, or W
<222> LOCATION: (6)..(6)
<220> FEATURE:
<221> NAME/KEY: X is S or V
<222> LOCATION: (7)..(7)
<220> FEATURE:
<221> NAME/KEY: X is A, L, or M
<222> LOCATION: (9)..(9)
<220> FEATURE:
<221> NAME/KEY: X is A, D, N, or Q
<222> LOCATION: (11)..(11)

<400> SEQUENCE: 137

Lys Ala Ser Gln Asp Xaa Xaa Ser Xaa Val Xaa
1               5                   10
```

```
<210> SEQ ID NO 138
<211> LENGTH: 7
<212> TYPE: PRT
<213> ORGANISM: Artificial Sequence
<220> FEATURE:
<223> OTHER INFORMATION: synthetic Axl L2 2 Conditionally active scFv
<220> FEATURE:
<221> NAME/KEY: X is W or F
<222> LOCATION: (1)..(1)
<220> FEATURE:
<221> NAME/KEY: X is A, I, N, P, or Q
<222> LOCATION: (2)..(2)
<220> FEATURE:
<221> NAME/KEY: X is S or D
<222> LOCATION: (3)..(3)
<220> FEATURE:
<221> NAME/KEY: X is H or D
<222> LOCATION: (6)..(6)

<400> SEQUENCE: 138

Xaa Xaa Xaa Thr Arg Xaa Thr
1               5

<210> SEQ ID NO 139
<211> LENGTH: 9
<212> TYPE: PRT
<213> ORGANISM: Artificial Sequence
<220> FEATURE:
<223> OTHER INFORMATION: synthetic Axl L2 2 Conditionally active scFv
<220> FEATURE:
<221> NAME/KEY: X is H, C, F, I, L, Q, S, T, V, or Y
<222> LOCATION: (3)..(3)
<220> FEATURE:
<221> NAME/KEY: X is F, C, D, E, G, N, or S
<222> LOCATION: (4)..(4)
<220> FEATURE:
<221> NAME/KEY: X is T, C, or P
<222> LOCATION: (6)..(6)
<220> FEATURE:
<221> NAME/KEY: X is P, A, C, D, E, H, K, S, T, V, or W
<222> LOCATION: (7)..(7)
<220> FEATURE:
<221> NAME/KEY: X is L, G, or R
<222> LOCATION: (8)..(8)
<220> FEATURE:
<221> NAME/KEY: X is T, I, or R
<222> LOCATION: (9)..(9)

<400> SEQUENCE: 139

Gln Glu Xaa Xaa Ser Xaa Xaa Xaa Xaa
1               5

<210> SEQ ID NO 140
<211> LENGTH: 10
<212> TYPE: PRT
<213> ORGANISM: Artificial Sequence
<220> FEATURE:
<223> OTHER INFORMATION: synthetic Ror2 H1 3 Conditionally active scFv
<220> FEATURE:
<221> NAME/KEY: X is F or E
<222> LOCATION: (4)..(4)
<220> FEATURE:
<221> NAME/KEY: X is Y or D
<222> LOCATION: (7)..(7)
<220> FEATURE:
<221> NAME/KEY: X is T or C
<222> LOCATION: (8)..(8)
<220> FEATURE:
<221> NAME/KEY: X is M, D, E, or Y
<222> LOCATION: (9)..(9)

<400> SEQUENCE: 140

Gly Tyr Thr Xaa Thr Glu Xaa Xaa Xaa His
```

-continued

```
1               5                   10
```

<210> SEQ ID NO 141
<211> LENGTH: 11
<212> TYPE: PRT
<213> ORGANISM: Artificial Sequence
<220> FEATURE:
<223> OTHER INFORMATION: synthetic Ror2 H1 4 Conditionally active scFv
<220> FEATURE:
<221> NAME/KEY: X is Y, E, R, or T
<222> LOCATION: (8)..(8)

<400> SEQUENCE: 141

```
Gly Tyr Ser Ile Thr Thr Gly Xaa Tyr Trp Asn
1               5                   10
```

<210> SEQ ID NO 142
<211> LENGTH: 17
<212> TYPE: PRT
<213> ORGANISM: Artificial Sequence
<220> FEATURE:
<223> OTHER INFORMATION: synthetic Ror2 H2 3 Conditionally active scFv
<220> FEATURE:
<221> NAME/KEY: X is G or S
<222> LOCATION: (1)..(1)
<220> FEATURE:
<221> NAME/KEY: X is I or E
<222> LOCATION: (2)..(2)
<220> FEATURE:
<221> NAME/KEY: X is N, C, L, or V
<222> LOCATION: (3)..(3)
<220> FEATURE:
<221> NAME/KEY: X is D or E
<222> LOCATION: (4)..(4)
<220> FEATURE:
<221> NAME/KEY: X is T, D, or E
<222> LOCATION: (4)..(4)

<400> SEQUENCE: 142

```
Xaa Xaa Xaa Xaa Asn Asn Gly Gly Thr Gly Tyr Asn Gln Lys Phe Lys
1               5                   10                  15

Gly
```

<210> SEQ ID NO 143
<211> LENGTH: 16
<212> TYPE: PRT
<213> ORGANISM: Artificial Sequence
<220> FEATURE:
<223> OTHER INFORMATION: synthetic Ror2 H2 4 Conditionally active scFv
<220> FEATURE:
<221> NAME/KEY: X is K or N
<222> LOCATION: (8)..(8)

<400> SEQUENCE: 143

```
Tyr Ile Thr Tyr Asp Gly Ser Xaa Asn Tyr Asn Pro Ser Leu Lys Asn
1               5                   10                  15
```

<210> SEQ ID NO 144
<211> LENGTH: 16
<212> TYPE: PRT
<213> ORGANISM: Artificial Sequence
<220> FEATURE:
<223> OTHER INFORMATION: synthetic Ror2 H3 3 Conditionally active scFv
<220> FEATURE:
<221> NAME/KEY: X is A, M, or T
<222> LOCATION: (1)..(1)
<220> FEATURE:
<221> NAME/KEY: X is R or H
<222> LOCATION: (2)..(2)
<220> FEATURE:
<221> NAME/KEY: X is G or E

```
<222> LOCATION: (3)..(3)
<220> FEATURE:
<221> NAME/KEY: X is L or F
<222> LOCATION: (5)..(5)
<220> FEATURE:
<221> NAME/KEY: X is S or G
<222> LOCATION: (7)..(7)
<220> FEATURE:
<221> NAME/KEY: X is G or D
<222> LOCATION: (9)..(9)
<220> FEATURE:
<221> NAME/KEY: X is N or E
<222> LOCATION: (10)..(10)
<220> FEATURE:
<221> NAME/KEY: X is D or L
<222> LOCATION: (14)..(14)
<220> FEATURE:
<221> NAME/KEY: X is Y, C, or T
<222> LOCATION: (15)..(15)
<220> FEATURE:
<221> NAME/KEY: X is W or L
<222> LOCATION: (16)..(16)

<400> SEQUENCE: 144

Xaa Xaa Xaa Ser Xaa Tyr Xaa Tyr Xaa Xaa Ser Tyr Phe Xaa Xaa Xaa
1               5                   10                  15

<210> SEQ ID NO 145
<211> LENGTH: 13
<212> TYPE: PRT
<213> ORGANISM: Artificial Sequence
<220> FEATURE:
<223> OTHER INFORMATION: synthetic Ror2 H3 4 Conditionally active scFv
<220> FEATURE:
<221> NAME/KEY: X is R, G, H, W, or Y
<222> LOCATION: (3)..(3)
<220> FEATURE:
<221> NAME/KEY: X is F, C, N, or Q
<222> LOCATION: (4)..(4)
<220> FEATURE:
<221> NAME/KEY: X is E or S
<222> LOCATION: (5)..(5)
<220> FEATURE:
<221> NAME/KEY: X is G, E, F, H, M, Q, or S
<222> LOCATION: (6)..(6)
<220> FEATURE:
<221> NAME/KEY: X is W, A, I, P, Q, T, or V
<222> LOCATION: (8)..(8)
<220> FEATURE:
<221> NAME/KEY: X is Y, G, N, or Q
<222> LOCATION: (9)..(9)
<220> FEATURE:
<221> NAME/KEY: X is G, S, or T
<222> LOCATION: (10)..(10)
<220> FEATURE:
<221> NAME/KEY: X is Y or I
<222> LOCATION: (13)..(13)

<400> SEQUENCE: 145

Cys Ser Xaa Xaa Xaa Xaa Val Xaa Xaa Xaa Leu Asp Xaa
1               5                   10

<210> SEQ ID NO 146
<211> LENGTH: 10
<212> TYPE: PRT
<213> ORGANISM: Artificial Sequence
<220> FEATURE:
<223> OTHER INFORMATION: synthetic Ror2 L1 3 Conditionally active scFv
<220> FEATURE:
<221> NAME/KEY: X is V or E
<222> LOCATION: (6)..(6)
<220> FEATURE:
<221> NAME/KEY: X is S or D
<222> LOCATION: (7)..(7)
<220> FEATURE:
```

```
<221> NAME/KEY: X is Y, C, or D
<222> LOCATION: (8)..(8)
<220> FEATURE:
<221> NAME/KEY: X is H, G, or L
<222> LOCATION: (10)..(10)

<400> SEQUENCE: 146

Ser Ala Thr Ser Ser Xaa Xaa Xaa Met Xaa
1               5                   10

<210> SEQ ID NO 147
<211> LENGTH: 15
<212> TYPE: PRT
<213> ORGANISM: Artificial Sequence
<220> FEATURE:
<223> OTHER INFORMATION: synthetic Ror2 L1 4 Conditionally active scFv
<220> FEATURE:
<221> NAME/KEY: X is F, S, or T
<222> LOCATION: (13)..(13)

<400> SEQUENCE: 147

Arg Ala Ser Glu Ser Val Asp Arg Tyr Gly Asn Ser Xaa Ile His
1               5                   10                  15

<210> SEQ ID NO 148
<211> LENGTH: 7
<212> TYPE: PRT
<213> ORGANISM: Artificial Sequence
<220> FEATURE:
<223> OTHER INFORMATION: synthetic Ror2 L2 3 Conditionally active scFv
<220> FEATURE:
<221> NAME/KEY: X is G, C, H, or P
<222> LOCATION: (1)..(1)

<400> SEQUENCE: 148

Xaa Thr Ser Asn Leu Ala Ser
1               5

<210> SEQ ID NO 149
<211> LENGTH: 7
<212> TYPE: PRT
<213> ORGANISM: Artificial Sequence
<220> FEATURE:
<223> OTHER INFORMATION: synthetic Ror2 L2 4 Conditionally active scFv
<220> FEATURE:
<221> NAME/KEY: X is R, C, D, E, or W
<222> LOCATION: (1)..(1)
<220> FEATURE:
<221> NAME/KEY: X is N or D
<222> LOCATION: (4)..(4)

<400> SEQUENCE: 149

Xaa Thr Tyr Xaa Leu Glu Ser
1               5

<210> SEQ ID NO 150
<211> LENGTH: 10
<212> TYPE: PRT
<213> ORGANISM: Artificial Sequence
<220> FEATURE:
<223> OTHER INFORMATION: synthetic Ror2 L3 3 Conditionally active scFv
<220> FEATURE:
<221> NAME/KEY: X is Q or E
<222> LOCATION: (2)..(2)
<220> FEATURE:
<221> NAME/KEY: X is R or H
<222> LOCATION: (3)..(3)
<220> FEATURE:
<221> NAME/KEY: X is S, D, G, I, Q, or V
<222> LOCATION: (5)..(5)
<220> FEATURE:
```

```
<221> NAME/KEY: X is T or D
<222> LOCATION: (9)..(9)
<220> FEATURE:
<221> NAME/KEY: X is F, D, or E
<222> LOCATION: (10)..(10)

<400> SEQUENCE: 150

Gln Xaa Xaa Ser Xaa Tyr Pro Phe Xaa Xaa
1               5                   10

<210> SEQ ID NO 151
<211> LENGTH: 122
<212> TYPE: PRT
<213> ORGANISM: Artificial Sequence
<220> FEATURE:
<223> OTHER INFORMATION: synthetic Ror2 CAB3 VH

<400> SEQUENCE: 151

Gln Val Gln Leu Val Gln Ser Gly Ala Glu Val Lys Lys Pro Gly Ala
1               5                   10                  15

Ser Val Lys Val Ser Cys Lys Ala Ser Gly Tyr Thr Phe Thr Glu Tyr
            20                  25                  30

Thr Met His Trp Ile Arg Gln Ser Pro Ser Arg Gly Leu Glu Trp Leu
        35                  40                  45

Gly Gly Ile Asn Asp Asn Asn Gly Thr Gly Tyr Asn Gln Lys Phe
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Arg Gly Ser Leu Tyr Ser Tyr Gly Asn Ser Tyr Phe Asp Tyr Trp
            100                 105                 110

Gly Gln Gly Thr Leu Val Thr Val Ser Ser
        115                 120

<210> SEQ ID NO 152
<211> LENGTH: 60
<212> TYPE: PRT
<213> ORGANISM: Artificial Sequence
<220> FEATURE:
<223> OTHER INFORMATION: synthetic Ror2 CAB VL

<400> SEQUENCE: 152

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Arg Pro Gly Gln Ser Pro Arg Arg Leu Ile Tyr
        35                  40                  45

His Thr Ser Asn Leu Ala Ser Gly Val Pro Asp Arg
    50                  55                  60

<210> SEQ ID NO 153
<211> LENGTH: 260
<212> TYPE: PRT
<213> ORGANISM: Artificial Sequence
<220> FEATURE:
<223> OTHER INFORMATION: synthetic scFV from F1-1-11

<400> SEQUENCE: 153

Gln Val Gln Leu Gln Glu Ser Gly Pro Gly Leu Val Lys Pro Ser Gln
1               5                   10                  15
```

```
Thr Leu Ser Leu Thr Cys Thr Val Ser Gly Tyr Ser Ile Thr Thr Gly
            20                  25                  30

Tyr Tyr Trp Asn Trp Val Arg Gln Ala Arg Gly Gln Arg Leu Glu Trp
            35                  40                  45

Ile Gly Tyr Ile Thr Tyr Asp Gly Ser Lys Asn Tyr Asn Pro Ser Leu
 50                      55                  60

Lys Asn Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ser His Phe Glu Gly Val Trp Tyr Gly Leu Asp Tyr Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Gly Gly Gly Ser Gly Gly Gly Gly Ser
 130                     135                 140

Gly Gly Gly Gly Ser Ala Ile Gln Leu Thr Gln Ser Pro Ser Ser Leu
145                     150                 155                 160

Ser Ala Ser Val Gly Asp Arg Val Thr Ile Thr Cys Arg Ala Ser Glu
            165                 170                 175

Ser Val Asp Arg Tyr Gly Asn Ser Phe Ile His Trp Tyr Gln Gln Lys
            180                 185                 190

Pro Gly Lys Ala Pro Lys Leu Leu Ile Tyr Arg Thr Tyr Asn Leu Glu
            195                 200                 205

Ser Gly Ile Pro Ala Arg Phe Ser Gly Ser Gly Ser Gly Thr Glu Phe
 210                     215                 220

Thr Leu Thr Ile Ser Ser Leu Gln Ser Glu Asp Phe Ala Val Tyr Tyr
225                 230                 235                 240

Cys Gln Gln Thr Asn Glu Asp Pro Trp Thr Phe Gly Gln Gly Thr Lys
                245                 250                 255

Val Glu Ile Lys
            260

<210> SEQ ID NO 154
<211> LENGTH: 245
<212> TYPE: PRT
<213> ORGANISM: Artificial Sequence
<220> FEATURE:
<223> OTHER INFORMATION: synthetic scFV from F1-1-17

<400> SEQUENCE: 154

Gln Val Gln Leu Gln Glu Ser Gly Pro Gly Leu Val Lys Pro Ser Gln
 1               5                  10                  15

Thr Leu Ser Leu Thr Cys Thr Val Ser Gly Tyr Ser Ile Thr Thr Gly
            20                  25                  30

Glu Tyr Trp Asn Trp Val Arg Gln Ala Arg Gly Gln Arg Leu Glu Trp
            35                  40                  45

Ile Gly Tyr Ile Thr Tyr Asp Gly Ser Lys Asn Tyr Asn Pro Ser Leu
 50                      55                  60

Lys Asn Arg Val Thr Ile Ser Val Asp Thr Ser Lys Asn Gln Phe Ser
 65                  70                  75                  80

Leu Lys Leu Ser Ser Val Thr Ala Ala Asp Thr Ala Val Tyr Tyr Cys
                85                  90                  95

Ser Arg Phe Glu Gly Val Trp Tyr Gly Leu Asp Tyr Trp Gly Gln Gly
            100                 105                 110
```

```
Thr Leu Val Thr Val Ser Ser Gly Gly Gly Ser Gly Gly Gly
            115                 120                 125

Ser Gly Gly Gly Ser Ala Ile Gln Leu Thr Gln Ser Pro Ser Ser
    130                 135                 140

Leu Ser Ala Ser Val Gly Asp Arg Val Thr Ile Thr Cys Arg Ala Ser
145                 150                 155                 160

Glu Ser Val Asp Arg Tyr Gly Asn Ser Phe Ile His Trp Tyr Gln Gln
                165                 170                 175

Lys Pro Gly Lys Ala Pro Lys Leu Leu Ile Tyr Arg Thr Tyr Asn Leu
            180                 185                 190

Glu Ser Gly Ile Pro Ala Arg Phe Ser Gly Ser Gly Ser Gly Thr Glu
            195                 200                 205

Phe Thr Leu Thr Ile Ser Ser Leu Gln Ser Glu Asp Phe Ala Val Tyr
    210                 215                 220

Tyr Cys Gln Gln Thr Asn Glu Asp Pro Trp Thr Phe Gly Gly Gly Thr
225                 230                 235                 240

Lys Val Glu Ile Lys
            245

<210> SEQ ID NO 155
<211> LENGTH: 243
<212> TYPE: PRT
<213> ORGANISM: Artificial Sequence
<220> FEATURE:
<223> OTHER INFORMATION: synthetic scFV from F1-1-25

<400> SEQUENCE: 155

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Arg Pro Gly Gln Ser Pro Arg Arg Leu Ile Tyr
        35                  40                  45

His Thr Ser Asn Leu Ala Ser Gly Val Pro Asp Arg Phe Ser Gly Ser
    50                  55                  60

Gly Ser Gly Thr Asp Phe Thr Leu Lys Ile Ser Arg Val Glu Ala Glu
65                  70                  75                  80

Asp Val Gly Val Tyr Tyr Cys Gln Gln Arg Ser Ser Tyr Pro Phe Thr
                85                  90                  95

Phe Gly Gln Gly Thr Lys Val Glu Ile Lys Gly Gly Gly Gly Ser Gly
            100                 105                 110

Gly Gly Gly Ser Gly Gly Gly Ser Gln Val Gln Leu Val Gln Ser
        115                 120                 125

Gly Ala Glu Val Lys Lys Pro Gly Ala Ser Val Lys Val Ser Cys Lys
    130                 135                 140

Ala Ser Gly Tyr Thr Phe Thr Glu Tyr Thr Met His Trp Ile Arg Gln
145                 150                 155                 160

Ser Pro Ser Arg Gly Leu Glu Trp Leu Gly Gly Ile Asn Asp Asn Asn
                165                 170                 175

Gly Gly Thr Gly Tyr Asn Gln Lys Phe Lys Gly Arg Phe Thr Ile Ser
            180                 185                 190

Arg Asp Asn Ser Lys Asn Thr Leu Tyr Leu Gln Met Asn Ser Leu Arg
        195                 200                 205

Ala Glu Asp Thr Ala Val Tyr Tyr Cys Ala Arg Gly Ser Leu Tyr Ser
    210                 215                 220
```

Tyr Gly Asn Ser Tyr Phe Asp Tyr Trp Gly Gln Gly Thr Leu Val Thr
225                 230                 235                 240

Val Ser Ser

<210> SEQ ID NO 156
<211> LENGTH: 258
<212> TYPE: PRT
<213> ORGANISM: Artificial Sequence
<220> FEATURE:
<223> OTHER INFORMATION: synthetic scFv from F1-1-26

<400> SEQUENCE: 156

Glu Ile Val Leu Thr Gln Ser Pro Ala Thr Leu Ser Leu Ser Pro Gly
1               5                   10                  15

Glu Arg Ala Thr Leu Ser Cys Ser Ala Thr Ser Ser Val Ser Tyr Met
            20                  25                  30

His Trp Phe Gln Gln Arg Pro Gly Gln Ser Pro Arg Arg Leu Ile Tyr
        35                  40                  45

His Thr Ser Asn Leu Ala Ser Gly Val Pro Asp Arg Phe Ser Gly Ser
    50                  55                  60

Gly Ser Gly Thr Asp Phe Thr Leu Lys Ile Ser Arg Val Glu Ala Glu
65                  70                  75                  80

Asp Val Gly Val Tyr Tyr Cys Gln Gln Arg Ser Ser Tyr Pro Phe Thr
                85                  90                  95

Phe Gly Gln Gly Thr Lys Val Glu Ile Lys Gly Gly Gly Gly Ser Gly
            100                 105                 110

Gly Gly Gly Ser Gly Gly Gly Ser Gly Gly Gly Ser Gly Gly
        115                 120                 125

Gly Gly Ser Gly Gly Gly Ser Gln Val Gln Leu Val Gln Ser Gly
    130                 135                 140

Ala Glu Val Lys Lys Pro Gly Ala Ser Val Lys Val Ser Cys Lys Ala
145                 150                 155                 160

Ser Gly Tyr Thr Phe Thr Glu Tyr Thr Met His Trp Ile Arg Gln Ser
                165                 170                 175

Pro Ser Arg Gly Leu Glu Trp Leu Gly Gly Ile Asn Asp Asn Asn Gly
            180                 185                 190

Gly Thr Gly Tyr Asn Gln Lys Phe Lys Gly Arg Phe Thr Ile Ser Arg
        195                 200                 205

Asp Asn Ser Lys Asn Thr Leu Tyr Leu Gln Met Asn Ser Leu Arg Ala
    210                 215                 220

Glu Asp Thr Ala Val Tyr Tyr Cys Ala Arg Gly Ser Leu Tyr Ser Tyr
225                 230                 235                 240

Gly Asn Ser Tyr Phe Asp Tyr Trp Gly Gln Gly Thr Leu Val Thr Val
                245                 250                 255

Ser Ser

<210> SEQ ID NO 157
<211> LENGTH: 245
<212> TYPE: PRT
<213> ORGANISM: Artificial Sequence
<220> FEATURE:
<223> OTHER INFORMATION: synthetic scFV from F1-1-9

<400> SEQUENCE: 157

Gln Val Gln Leu Gln Glu Ser Gly Pro Gly Leu Val Lys Pro Ser Gln
1               5                   10                  15

Thr Leu Ser Leu Thr Cys Thr Val Ser Gly Tyr Ser Ile Thr Thr Gly
            20                  25                  30

Tyr Tyr Trp Asn Trp Val Arg Gln Ala Arg Gly Gln Arg Leu Glu Trp
            35                  40                  45

Ile Gly Tyr Ile Thr Tyr Asp Gly Ser Lys Asn Tyr Asn Pro Ser Leu
50                  55                  60

Lys Asn Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ser His Phe Glu Gly Val Trp Tyr Gly Leu Asp Tyr Trp Gly Gln Gly
            100                 105                 110

Thr Leu Val Thr Val Ser Ser Gly Gly Gly Ser Gly Gly Gly Gly
            115                 120                 125

Ser Gly Gly Gly Gly Ser Ala Ile Gln Leu Thr Gln Ser Pro Ser Ser
        130                 135                 140

Leu Ser Ala Ser Val Gly Asp Arg Val Thr Ile Thr Cys Arg Ala Ser
145                 150                 155                 160

Glu Ser Val Asp Arg Tyr Gly Asn Ser Phe Ile His Trp Tyr Gln Gln
                165                 170                 175

Lys Pro Gly Lys Ala Pro Lys Leu Leu Ile Tyr Arg Thr Tyr Asn Leu
            180                 185                 190

Glu Ser Gly Ile Pro Ala Arg Phe Ser Gly Ser Gly Ser Gly Thr Glu
            195                 200                 205

Phe Thr Leu Thr Ile Ser Ser Leu Gln Ser Glu Asp Phe Ala Val Tyr
        210                 215                 220

Tyr Cys Gln Gln Thr Asn Glu Asp Pro Trp Thr Phe Gly Gln Gly Thr
225                 230                 235                 240

Lys Val Glu Ile Lys
                245

<210> SEQ ID NO 158
<211> LENGTH: 245
<212> TYPE: PRT
<213> ORGANISM: Artificial Sequence
<220> FEATURE:
<223> OTHER INFORMATION: synthetic scFV from F1-1-21

<400> SEQUENCE: 158

Ala Ile Gln Leu Thr Gln Ser Pro Ser Ser Leu Ser Ala Ser Val Gly
1               5                   10                  15

Asp Arg Val Thr Ile Thr Cys Arg Ala Ser Glu Ser Val Asp Arg Tyr
            20                  25                  30

Gly Asn Ser Phe Ile His Trp Tyr Gln Gln Lys Pro Gly Lys Ala Pro
        35                  40                  45

Lys Leu Leu Ile Tyr Arg Thr Tyr Asn Leu Glu Ser Gly Ile Pro Ala
    50                  55                  60

Arg Phe Ser Gly Ser Gly Ser Gly Thr Glu Phe Thr Leu Thr Ile Ser
65                  70                  75                  80

Ser Leu Gln Ser Glu Asp Phe Ala Val Tyr Tyr Cys Gln Gln Thr Asn
                85                  90                  95

Glu Asp Pro Trp Thr Phe Gly Gln Gly Thr Lys Val Glu Ile Lys Gly
            100                 105                 110

Gly Gly Gly Ser Gly Gly Gly Gly Ser Gly Gly Gly Gly Ser Gln Val
        115                 120                 125

Gln Leu Gln Glu Ser Gly Pro Gly Leu Val Lys Pro Ser Gln Thr Leu
130                 135                 140

Ser Leu Thr Cys Thr Val Ser Gly Tyr Ser Ile Thr Thr Gly Glu Tyr
145                 150                 155                 160

Trp Asn Trp Val Arg Gln Ala Arg Gly Gln Arg Leu Glu Trp Ile Gly
                165                 170                 175

Tyr Ile Thr Tyr Asp Gly Ser Lys Asn Tyr Asn Pro Ser Leu Lys Asn
            180                 185                 190

Arg Val Thr Ile Ser Val Asp Thr Ser Lys Asn Gln Phe Ser Leu Lys
        195                 200                 205

Leu Ser Ser Val Thr Ala Ala Asp Thr Ala Val Tyr Tyr Cys Ser Arg
210                 215                 220

Phe Glu Gly Val Trp Tyr Gly Leu Asp Tyr Trp Gly Gln Gly Thr Leu
225                 230                 235                 240

Val Thr Val Ser Ser
            245

<210> SEQ ID NO 159
<211> LENGTH: 257
<212> TYPE: PRT
<213> ORGANISM: Artificial Sequence
<220> FEATURE:
<223> OTHER INFORMATION: synthetic scFV from F1-2-3

<400> SEQUENCE: 159

Glu Val Gln Leu Val Gln Ser Gly Ala Glu Val Lys Lys Pro Gly Ala
1               5                   10                  15

Thr Val Lys Ile Ser Cys Lys Val Ser Gly Tyr Ser Phe Trp Gly Ala
                20                  25                  30

Thr Met Asn Trp Ile Arg Gln Pro Pro Gly Lys Gly Leu Glu Trp Ile
            35                  40                  45

Gly Leu Ile Lys Pro Ser Asn Gly Gly Thr Ser Tyr Asn Gln Lys Phe
50                  55                  60

Lys Gly Arg Val Thr Ile Ser Ala Asp Lys Ser Ile Ser Thr Ala Tyr
65                  70                  75                  80

Leu Gln Trp Ser Ser Leu Lys Ala Ser Asp Thr Ala Met Tyr Tyr Cys
                85                  90                  95

Ala His Gly His Tyr Glu Ser Tyr Glu Ala Met Asp Tyr Trp Gly Gln
            100                 105                 110

Gly Thr Leu Val Thr Val Ser Ser Gly Gly Gly Gly Ser Gly Gly Gly
        115                 120                 125

Gly Ser Gly Gly Gly Gly Ser Gly Gly Gly Gly Ser Gly Gly Gly Gly
130                 135                 140

Ser Gly Gly Gly Gly Ser Asp Ile Gln Met Thr Gln Ser Pro Ser Ser
145                 150                 155                 160

Leu Ser Ala Ser Val Gly Asp Arg Val Thr Ile Thr Cys Lys Ala Ser
                165                 170                 175

Gln Asp Val Val Ser Ala Val Ala Trp Tyr Gln Gln Lys Pro Gly Gln
            180                 185                 190

Ala Pro Arg Leu Leu Ile Tyr Trp Gln Asp Thr Arg His Thr Gly Val
        195                 200                 205

Pro Ser Arg Phe Ser Gly Ser Gly Ser Gly Thr Glu Phe Thr Leu Thr
210                 215                 220

Ile Ser Ser Leu Gln Pro Asp Asp Phe Ala Thr Tyr Tyr Cys Gln Glu
225                 230                 235                 240

```
His Phe Ser Pro Pro Leu Thr Phe Gly Gln Gly Thr Lys Val Glu Ile
            245                 250                 255
Lys

<210> SEQ ID NO 160
<211> LENGTH: 242
<212> TYPE: PRT
<213> ORGANISM: Artificial Sequence
<220> FEATURE:
<223> OTHER INFORMATION: synthetic scFV from F1-2-8

<400> SEQUENCE: 160

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Val Ser Ala
            20                  25                  30

Val Ala Trp Tyr Gln Gln Lys Pro Gly Gln Ala Pro Arg Leu Leu Ile
        35                  40                  45

Tyr Trp Gln Asp Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Glu His Phe Ser Pro Pro Leu
                85                  90                  95

Thr Phe Gly Gln Gly Thr Lys Val Glu Ile Lys Gly Gly Gly Gly Ser
            100                 105                 110

Gly Gly Gly Gly Ser Gly Gly Gly Ser Glu Val Gln Leu Val Gln
        115                 120                 125

Ser Gly Ala Glu Val Lys Lys Pro Gly Ala Thr Val Lys Ile Ser Cys
130                 135                 140

Lys Val Ser Gly Tyr Ser Phe Trp Gly Ala Thr Met Asn Trp Ile Arg
145                 150                 155                 160

Gln Pro Pro Gly Lys Gly Leu Glu Trp Ile Gly Leu Ile Lys Pro Ser
            165                 170                 175

Asn Gly Gly Thr Ser Tyr Asn Gln Lys Phe Lys Gly Arg Val Thr Ile
            180                 185                 190

Ser Ala Asp Lys Ser Ile Ser Thr Ala Tyr Leu Gln Trp Ser Ser Leu
        195                 200                 205

Lys Ala Ser Asp Thr Ala Met Tyr Tyr Cys Ala His Gly His Tyr Glu
    210                 215                 220

Ser Tyr Glu Ala Met Asp Tyr Trp Gly Gln Gly Thr Leu Val Thr Val
225                 230                 235                 240

Ser Ser

<210> SEQ ID NO 161
<211> LENGTH: 257
<212> TYPE: PRT
<213> ORGANISM: Artificial Sequence
<220> FEATURE:
<223> OTHER INFORMATION: synthetic scFV from F1-2-10

<400> SEQUENCE: 161

Asp Ile Gln Met Thr Gln Ser Pro Ser Ser Leu Ser Ala Ser Val Gly
1               5                   10                  15

Asp Arg Val Thr Ile Thr Cys Lys Ala Ser Gln Asp Val Val Ser Ala
            20                  25                  30

Val Ala Trp Tyr Gln Gln Lys Pro Gly Gln Ala Pro Arg Leu Leu Ile
```

```
                35                  40                  45
Tyr Trp Gln Asp Thr Arg His Thr Gly Val Pro Ser Arg Phe Ser Gly
    50                  55                  60

Ser Gly Ser Gly Thr Glu Phe Thr Leu Thr Ile Ser Ser Leu Gln Pro
65                  70                  75                  80

Asp Asp Phe Ala Thr Tyr Tyr Cys Gln Glu His Phe Ser Pro Pro Leu
                85                  90                  95

Thr Phe Gly Gln Gly Thr Lys Val Glu Ile Lys Gly Gly Gly Gly Ser
                100                 105                 110

Gly Gly Gly Gly Ser Gly Gly Gly Ser Gly Gly Gly Gly Ser Gly
            115                 120                 125

Gly Gly Gly Ser Gly Gly Gly Ser Glu Val Gln Leu Val Gln Ser
            130                 135                 140

Gly Ala Glu Val Lys Lys Pro Gly Ala Thr Val Lys Ile Ser Cys Lys
145                 150                 155                 160

Val Ser Gly Tyr Ser Phe Trp Gly Ala Thr Met Asn Trp Ile Arg Gln
                165                 170                 175

Pro Pro Gly Lys Gly Leu Glu Trp Ile Gly Leu Ile Lys Pro Ser Asn
                180                 185                 190

Gly Gly Thr Ser Tyr Asn Gln Lys Phe Lys Gly Arg Val Thr Ile Ser
            195                 200                 205

Ala Asp Lys Ser Ile Ser Thr Ala Tyr Leu Gln Trp Ser Ser Leu Lys
210                 215                 220

Ala Ser Asp Thr Ala Met Tyr Tyr Cys Ala His Gly His Tyr Glu Ser
225                 230                 235                 240

Tyr Glu Ala Met Asp Tyr Trp Gly Gln Gly Thr Leu Val Thr Val Ser
                245                 250                 255

Ser
```

CHIMERIC ANTIGEN RECEPTORS AGAINST AXL OR ROR2 AND METHODS OF USE THEREOF

CROSS-REFERENCE TO RELATED APPLICATIONS

This application is claims the benefit of U.S. Provisional Application No. 62/447,898, filed Jan. 18, 2017, U.S. Provisional Application No. 62/467,059, filed Mar. 3, 2017, and U.S. Provisional Application No. 62/530,193, filed Jul. 8, 2017. These applications cited in this paragraph are incorporated by reference herein in their entirety.

SEQUENCE LISTING

This application hereby incorporates by reference the material of the electronic Sequencing Listing filed concurrently herewith. The materials in the electronic Sequence Listing is submitted as a text (.txt) file entitled "F1.002.WO.01_Seqlist.txt" created on Jan. 17, 2018, which has a file size of 126 KB, and is herein incorporated by reference in its entirety.

JOINT RESEARCH AGREEMENT

Exuma Biotech Corp., formerly F1 Oncology, Inc., and BioAtla, Inc., formerly BioAtla, LLC, are parties to a joint research agreement that relates to the subject matter disclosed herein.

FIELD OF DISCLOSURE

This disclosure relates to chimeric antigen receptors and uses of the chimeric antigen receptors in diagnostic and therapeutic methods.

BACKGROUND OF THE DISCLOSURE

In cell-based adoptive immunotherapy, immune cells isolated from a patient can be modified to express synthetic proteins that enable the cells to perform new therapeutic functions after they are subsequently transferred back into the patient. An example of such a synthetic protein is a chimeric antigen receptor (CAR). An example of a currently used CAR is a fusion of an extracellular recognition domain (e.g., an antigen-specific targeting region or ASTR), a transmembrane domain, and one or more intracellular signaling domains. Upon antigen engagement, the intracellular signaling portion of the CAR can initiate an activation-related response in an immune cell, such as release of cytolytic molecules to induce tumor cell death, etc. Although CARs and CAR-T therapy has been very effective for certain types of blood cancers, there remains a need for CARs and CAR-T therapy against solid tumors, which have proven thus far to be much more elusive.

While CARs represent an impressive method to treat various diseases, the safety of CARs has recently come into question through adverse events during clinical trials. One method to decrease these adverse events is by reducing the on-target off-tumor binding of the ASTRs. CARs with conditionally active ASTRs only bind to antigen under certain conditions, such as those that exist in the tumor microenvironment, and provide a reduction in on-target off-tumor binding such that the CARs do not bind the antigen in normal physiological conditions. Thus, the side effects of these CARs are reduced and treatment can proceed more safely.

Receptor tyrosine kinases (RTKs) are a family of cell surface receptors that regulate a range of normal cellular processes through ligand-controlled tyrosine kinase activity. Over the past 20 years, deregulation of RTKs has been shown to play a critical role in cancer development and progression. RTKs are now recognized as prognostic molecular biomarkers and as targets of oncology therapeutics.

Axl protein (also known as Ark, UFO, Tyro-7) is an RTK in the Tyro-3 family of kinases. The Tyro-3 receptor kinases are characterized by a combination of two immunoglobin-like domains and dual fibronectin type III repeats in the extracellular region and a cytoplasmic kinase domain. The ligands for Tyro-3 receptor kinases are Gas6 (growth-arrest-specific 6) and protein S, two vitamin-K dependent proteins that show 43% amino acid sequence identity and share similar domain structures. Each protein has an N-terminal Gla domain containing 11 g-carboxyglutamic acid residues, followed by four epidermal growth factor (EGF)-like modules, and a C-terminal sex hormone-binding globulin (SHBG)-like structure consisting of two tandem laminin G domains. The SHBG domain is both necessary and sufficient for Tyro-3 receptor kinase binding and activation, whereas the Gla domain binds the negatively charged membrane phospholipids and plays an important role in Tyro-3 kinase-mediated phagocytosis of apoptotic cells.

Axl activation leads to signaling through PI-3-kinase/Akt and other major pathways like Ras/Erk and β-catenin/TCF. Axl is weakly expressed in a range of normal tissues, including brain, heart, skeletal muscle, the organ capsules and connective tissues of several other organs, and in monocytes, but not lymphocytes. Akt phosphorylation induced by Axl has been described in survival of fibroblasts, endothelial cells, vascular smooth muscle cells and neurons. Furthermore, Axl plays a role in cell-adhesion and chemotaxis because Axl knockout animals display impaired platelet aggregate stabilization and thrombus formation as a result of reduced activation of the platelet integrin IIb3.

Dysregulation of Axl or its ligand Gas6 is implicated in the pathogenesis of a variety of human cancers. Axl overexpression has been demonstrated in various cancer types, e.g. breast (Meric et al., *Clin. Cancer Res.*, vol. 8, pp. 361-367, 2002; Berclaz et al., *Ann. Oncol.*, vol. 12, pp. 819-824, 2001), colon (Chen et al., *Int. J. Cancer*, vol. 83, pp. 579-584, 1999; Craven et al., *Int. J. Cancer*, vol. 60, pp. 791-797, 1995), prostate (Jacob et al., *Cancer Detect. Prev.*, vol. 23, pp. 325-332, 1999), lung (Wimmel et al., *Eur J Cancer*, vol. 37, pp. 2264-2274, 2001), gastric (Wu et al., *Anticancer Res.*, vol. 22, pp. 1071-1078, 2002), ovarian (Sun et al., *Oncology*, vol. 66, pp. 450-457, 2004), endometrial (Sun et al., *Ann. Oncol.*, vol. 14, pp. 898-906, 2003), renal (Chung et al., *DNA Cell Biol.*, vol. 22, pp. 533-540, 2003), hepatocellular (Tsou et al., *Genomics*, vol. 50, pp. 331-340, 1998), thyroid (Ito et al., *Thyroid*, vol. 12, pp. 971-975, 2002; Ito et al., *Thyroid*, vol. 9, pp. 563-567, 1999), osteosarcoma (Nakano et al., *J. Biol. Chem.*, vol. 270, pp. 5702-5705, 2003), melanoma (van Ginkel et al., *Cancer Res.*, vol. 64, pp. 128-134, 2004), in head and neck squamous cell carcinoma (Green et al., *Br J. Cancer.*, vol. 94, pp. 1446-51, 2006), ovarian cancer, renal cancer, glioma, endocrine, pancreas, lymphoma, brain, liver, renal cell carcinoma, renal clear cell, bladder, rectum, cervical squamous cell carcinoma, and furthermore in lymphoma and various leukemias, including chronic myelogenous leukemia (Janssen et al., *Oncogene*, vol. 6, pp. 2113-2120, 1991; Braunger et al., *Oncogene*, vol. 14, pp. 2619-2631 1997; O'Bryan et al., *Mol. Cell. Biol.*, vol. 11, pp. 5016-5031, 1991), and acute myeloid leukemia (Rochlitz et al., *Leukemia*, vol. 13, pp. 1352-1358, 1999).

Axl expression is induced by targeted chemotherapy drugs and drug-induced Axl expression confers resistance to chemotherapy in acute myeloid leukemia (Hong et al, *Cancer Letters*, vol. 268, pp. 314-324, 2008), as well as resistance to imatinib and Lapatinib/Herceptin in gastrointestinal stromal tumors (Mehadevan, et al, *Oncogene*, vol. 26, pp. 3909-3919, 2007) and breast cancer (Liu et al, Cancer Research, vol. 281, pp. 6871-6878, 2009), respectively.

Moreover, Axl has been identified to be related to tumor metastasis because Axl is upregulated in aggressive breast cancer cell lines compared to non-invasive cells. In vitro, Axl activity was found to be required for migration and invasion, and this activity could be inhibited by antibody treatment (WO 04/008147). Similarly, abrogation of Axl activity in vivo, either via expression of a dominant negative version of Axl (Vajkoczy, P., et al., *Proc. Natl. Acad. Science U.S.A.*, vol. 103, pp. 5799-5804, 2005) or by siRNA mediated downregulation of Axl (Holland et al., *Cancer Res.*, vol. 65, pp. 9294-9303, 2005) prevented subcutaneous and orthotopic cell growth in murine xenograft experiments.

Accordingly, anti-Axl monoclonal antibodies have been suggested for use in the treatment of cancers. For example, publications relating to anti-Axl antibodies include WO 2009/063965, WO 2009/062690, WO 2011/014457, US 2014/0227283, and U.S. Pat. No. 8,853,369. US 2014/0227283 discloses monoclonal anti-Axl antibodies and uses thereof in diagnostic and therapeutic methods. WO 2009/062690 discloses antibodies that bind to the extracellular domain of the Axl protein and can at least partially inhibit Axl activity. However, even for targets such as Axl, where monoclonal antibodies have been identified and are available as reagents, many challenges exist that make it very difficult to create a conditionally active CAR against Axl or Ror2.

Another RTK, Ror2, also called receptor tyrosine kinase-like orphan receptor 2, is a membrane-bound that is activated by non-canonical Wnt signaling through its association with the Wnt5A glycoprotein during normal bone and cartilage development. Ror2 has only one transmembrane domain, which separates its extracellular and intracellular domains. Ror2 is known to play crucial roles in the normal development of various organs and tissues. In mammals, Ror2- and Wnt5A-deficient mice exhibit similar abnormalities during developmental morphogenesis, reflecting their defects in convergent extension movements and planar cell polarity. Furthermore, mutations of the human Ror2 gene are responsible for the genetic skeletal disorders dominant brachydactyly type B and recessive Robinow syndrome. Ror2 has been found to mediate polarized cell migration and malfunction of Ror2 results in heritable skeletal disorders and tumor invasion (Minami et al., "Ror-family receptor tyrosine kinases in noncanonical Wnt signaling: their implications in developmental morphogenesis and human diseases," *Dev Dyn.*, vol. 239, pp. 1-15, 2010). Further, Debebe et al., ("Ror2 as a therapeutic target in cancer," *Pharmacol. Ther.*, vol. 50, pp. 143-148, 2015) discloses that Ror2 mediates both canonical and non-canonical signaling pathways.

Ror2 has also been reported to have pro-tumorigenic effects. US 2014/0322234 discloses that the expression and activity of Ror2 in various cancers is different from normal tissues. Thus, it is suggested that dysregulation of Ror2 plays a role in the pathogenesis of a variety of human cancers. US 2014/0322234 also contemplates that antibodies against Ror2 may be used in diagnosis of cancers and inhibition of cancer cell growth. For example, such antibodies may be conjugated to a cytotoxic agent that has a high degree of cytotoxicity for cancer cells expressing Ror2, such that the cytotoxic agent can effectively kill the cancer cells. The Ror2 gene may also be used in classification of cancers according to the Ror2 expression pattern in the cancers.

Ror2 is involved in the development and progression of cancers ("The dual role of the novel Wnt receptor tyrosine kinase, Ror2, in human carcinogenesis," *International Journal of Cancer*, vol. 133, pp. 779-787, 2013). Specifically, Ror2 has been found to play a pivotal role in carcinogenesis of numerous cancers including colon cancer, hepatocellular carcinoma, metastatic melanoma, and renal cell carcinoma. For example, Ror2 is over-expressed in osteosarcoma, melanoma, renal cell carcinoma, prostate carcinoma, squamous cell carcinomas of the head and neck, colon cancer, breast cancer, lymphoma, leukemia, thyroid, endocrine pancreas, brain, ovarian, renal papillary, lung, pancreas, liver, renal clear cell, bladder, endometrial, rectum, cervical squamous cell carcinoma, and stromal tumors. In the majority of these cancer types, Ror2 expression is associated with more aggressive cancer states. Ror2 thus has the potential of being a drug target for cancer treatments by inhibition of the Wnt signaling pathway.

There remains a need for an effective treatment that harnesses the power of the immune system to fight cancer, but that has reduced or eliminated on-target off-tumor as well as off-target effects. Though monoclonal antibodies against Ror2 and Axl are commercially available, there is a need for CARs that include antibody fragments targeting Ror2 or Axl that are conditionally active, that effectively target cells expressing Ror2 or Axl only in certain environments, such as a cancer microenvironment. Creating such conditionally active CARs presents numerous challenges. For example, antibody fragments must be created and identified, that not only bind Axl or Ror2 when they are expressed on the surface of T cells or NK cells as part of CARs, but that additionally have the ability to recognize an epitope that is exposed on cancer cells. Furthermore, such CARs much bind to their targets in a conditionally active manner, especially under the acidic pH of a tumor compared to a normal physiological pH. Additionally, such candidate CARs, when bound to their target, must activate a T cell or NK cell expressing the CAR to express a cytotoxic function. Thus, there are many requirements for a CAR containing such an antibody fragment, to help solve problems posed by current CAR-T methods. Such a conditionally active CAR against Axl or Ror2 would hold promise for treating solid cancers using CAR-T therapy, thus overcoming a major limitation of current CAR-T therapies.

SUMMARY OF THE DISCLOSURE

The present disclosure provides chimeric antigen receptors (CARs), and nucleic acids comprising nucleotide sequences encoding the CARs, that bind to Axl and/or Ror2, and conditionally active biologic (CAB) CARs that bind to Axl and Ror2. The present disclosure provides cells genetically modified to produce the CARs, and methods for making such cells. The CARs of the present disclosure can be used in various methods, which are also provided, including methods for activating immune cells under certain conditions, such as a pH below a threshold value, methods for performing adoptive cell therapy such as CAR therapy, for example CAR therapy against cancer, for example renal cell carcinoma.

Details of aspects and embodiments provided herein are provided throughout this disclosure. For the sake of clarity, this Summary section is not intended to be, and should not be construed to limit the scope of the disclosure provided herein.

BRIEF DESCRIPTION OF THE DRAWINGS

FIG. 4A shows representative results from a real-time killing assay of CHO-Axl cells by T cells expressing one of the conditionally active CARs against Axl provided herein, at various pHs.

FIG. 5A shows representative results from a real-time killing assay of CHO-Ror2 cells by T cells expressing one of the conditionally active CAB-CARs against Ror2 provided herein, at various pHs. FIG. 5B provides lysis results at the 20 hour time point at various pHs as noted, for the same CAB-CAR as FIG. 5A.

FIG. 8A shows the levels of IL-2 in media from F1-0-01 or F1-2-15 T cells alone or when co-incubated with CHO or CHO-Axl. FIG. 8B shows the levels of IFN-γ in media from F1-0-01 or F1-2-15 T cells alone or when co-incubated with CHO or CHO-Axl. Cytokine levels in media when CHO or CHO-Axl cells are incubated in the absence of effector T cells are also shown as a control in FIGS. 8A and 8B. FIG. 8C shows the levels of IL-2 in media from F1-0-01 or F1-1-15 T cells alone or when co-incubated with CHO or CHO-Ror2. FIG. 8D shows the levels of IFN-γ in media from F1-0-01 or F1-1-15 T cells alone or when co-incubated with CHO or CHO-Ror2. Cytokine levels in media when CHO or CHO-Ror2 cells are incubated in the absence of effector T cells are also shown as a control in FIGS. 8C and 8D.

In FIG. 9A, the media was initially at pH 6.7 and experimental wells (solid line) and control cells (dashed line) were treated with or without NaHCO$_3$, respectively, at the time indicated by the arrow. In FIG. 9B, the media was initially at pH 6.7 and experimental wells (solid line) and control cells (dashed line) were treated with or without NaOH, respectively, at the time indicated by the arrow. In FIG. 9C, the media was initially at pH 7.4 and experimental wells (solid line) and control cells (dashed line) were treated with or without HCl, respectively.

DEFINITIONS

Figure 1:
FIG. 1 provides a bar graph showing percent transduction of CD3$^+$ cells based on FACS analysis of eTag expression.

The terms "chimeric antigen receptor" or "CAR" or "CARs" as used herein refer to engineered receptors, which graft an antigen specificity onto cells, for example T cells, NK cells, macrophages, and stem cells. The CARs of the invention may include at least one antigen-specific targeting region (ASTR), a hinge or stalk domain (i e extracellular stalk domain (ESD)), a transmembrane domain (TM), one or more co-stimulatory domains (CSDs), and an intracellular activating domain (IAD). In certain embodiments, the ESD and/or CSD are optional. CARs provided herein in some embodiments have specifically recited domains (e.g. a CD3Z intracellular activating domain) For such specially recited domains, it is intended that the domain retains an activity of a wild-type domain such that it can be effectively employed in a CAR (i.e. the CAR retains the ability to bind a target and in response, transmit a signal through an intracellular activating domain found in the CAR), and has at least 80% sequence identity to a known human sequence for that specific domain, over the portion of the domain providing such activity. For example, a CD3Z intracellular domain has at least 80% sequence identity at the amino acid level, to a known human CD3Z sequence, and when found on a CAR retains the ability to transmit a signal upon binding of an ASTR of the CAR to it target. In another embodiment, the CAR is a bispecific CAR, which is specific to two different antigens or epitopes. After the ASTR binds specifically to a target antigen, the IAD activates intracellular signaling. For example, the IAD can redirect T cell specificity and reactivity toward a selected target in a non-MHC-restricted manner, exploiting the antigen-binding properties of antibodies. The non-MHC-restricted antigen recognition gives T cells expressing the CAR the ability to recognize an antigen independent of antigen processing, thus bypassing a major mechanism of tumor escape. Moreover, when expressed in T cells, CARs advantageously do not dimerize with endogenous T cell receptor (TCR) alpha and beta chains.

The term "conditionally active" as used herein with respect to a CAR or an ASTR refers to a CAR or an ASTR that has a lower binding affinity or, in illustrative embodiments, a higher binding affinity to one or more target antigens under a condition(s) in a target microenvironment than under a condition in a normal physiological environment. In illustrative embodiments, conditionally active CARs provided herein are more active under a condition in a tumor microenvironment or an in vitro tumor surrogate assay compared to under a condition in a non-tumor microenvironment or a normal condition. The conditions in the tumor microenvironment include lower pH, higher concentrations of lactate and pyruvate, hypoxia, lower concentration of glucose, and slightly higher temperature in comparison with non-tumor microenvironment. For example, a conditionally active CAR, in certain embodiments, is virtually inactive at normal body temperature, but is active at a higher temperature in a tumor microenvironment. In yet another embodiment, a conditionally active CAR is less active in normal oxygenated blood, but more active under a less oxygenated environment that exists in a tumor. In an illustrative embodiments provided herein, a conditionally active CAR is less active in normal physiological pH 7.2-7.8, but more active under an acidic pH 6.0-6.8 that exists in a tumor microenvironment. There are other conditions in the tumor microenvironment known to a person skilled in the field that may also be used as the condition in the present invention under which conditionally active CARs and ASTRs have different binding affinities. Conditionally active CARs can be referred to herein as "conditionally active biologic CARs" or "CAB-CARs" and "microenvironment restricted biologic CARs" or "MRB-CARs".

The term "microenvironment" as used herein means any portion or region of a tissue or body that has constant or temporal, physical or chemical differences from other regions of the tissue or regions of the body. For tumors, the term "tumor microenvironment" as used herein refers to the environment in which a tumor exists, which is the non-cellular area within the tumor and the area directly outside the tumorous tissue but does not pertain to the intracellular compartment of the cancer cell itself. The tumor and the tumor microenvironment are closely related and interact constantly. A tumor can change its microenvironment, and the microenvironment can affect how a tumor grows and spreads. Typically, the tumor microenvironment has a low pH in the range of 5.8 to 7.0, more commonly in the range of 6.0 to 6.8, in the range of 6.2-6.8. On the other hand, a normal physiological pH is in the range of 7.2-7.8. The tumor microenvironment is also known to have lower concentration of glucose and other nutrients, but higher concentration of lactic acid, in comparison with blood plasma. Furthermore, the tumor microenvironment can have a temperature that is 0.3 to 1° C. higher than the normal physiological temperature. The tumor microenvironment has been discussed in Gillies et al., "MRI of the Tumor Microenvironment," *Journal of Magnetic Resonance Imaging*, vol. 16, pp. 430-450, 2002, hereby incorporated by reference herein its entirety. The term "non-tumor microenvironment" refers to a microenvironment at a site other than a tumor.

The terms "polynucleotide" and "nucleic acid," used interchangeably herein, refer to a polymeric form of nucleotides of any length, either ribonucleotides or deoxyribonucleotides. Thus, this term includes, but is not limited to, single-, double-, or multi-stranded DNA or RNA, genomic DNA, cDNA, DNA-RNA hybrids, or a polymer comprising purine and pyrimidine bases or other natural, chemically or biochemically modified, non-natural, or derivatized nucleotide bases.

The terms "antibodies" and "immunoglobulin" include antibodies or immunoglobulins of any isotype, as well as fragments of antibodies which retain specific binding to an epitope, typically the same epitope as the full antibody when both a heavy and light chain of the antibody are present for the assay, including, but not limited to, Fab, Fab', Fab'-SH, $(Fab')_2$ Fv, scFv, divalent scFv, and Fd fragments, chimeric antibodies, humanized antibodies, single-chain antibodies, and fusion proteins comprising an antigen-specific targeting region of an antibody and a non-antibody protein.

"Antibody fragments" include a portion of an intact antibody, for example, the antigen binding or variable region of the intact antibody. Examples of antibody fragments include Fab, Fab', $F(ab')_2$, and Fv fragments; diabodies; linear antibodies (Zapata et al., Protein Eng. 8(10): 1057-1062 (1995)); single-chain antibody molecules; and multi-specific antibodies formed from antibody fragments. Papain digestion of antibodies produces two identical antigen-binding fragments, called "Fab" fragments, each with a single antigen-binding site, and a residual "Fe" fragment, a designation reflecting the ability to crystallize readily. Pepsin treatment yields an $F(ab')_2$ fragment that has two antigen combining sites and is still capable of cross-linking antigen.

"Single-chain Fv," "scFv," or "sFv" antibody fragments include the $V_H$ and $V_L$ domains of antibody, wherein these domains are present in a single polypeptide chain. In some embodiments, the Fv polypeptide further includes a polypeptide linker between the $V_H$ and $V_L$ domains, which enables the sFv to form the desired structure for antigen binding. For a review of sFv, see Pluckthun in *The Pharmacology of Monoclonal Antibodies*, vol. 113, Rosenburg and Moore eds., Springer-Verlag, New York, pp. 269-315 (1994).

As used herein, the term "affinity" refers to the equilibrium constant for the reversible binding of two agents and is expressed as a dissociation constant (Kd). Affinity can be at least 1-fold greater, at least 2-fold greater, at least 3-fold greater, at least 4-fold greater, at least 5-fold greater, at least 6-fold greater, at least 7-fold greater, at least 8-fold greater, at least 9-fold greater, at least 10-fold greater, at least 20-fold greater, at least 30-fold greater, at least 40-fold greater, at least 50-fold greater, at least 60-fold greater, at least 70-fold greater, at least 80-fold greater, at least 90-fold greater, at least 100-fold greater, or at least 1000-fold greater, or more, than the affinity of an antibody for unrelated amino acid sequences. Affinity of an antibody to a target protein can be, for example, from about 100 nanomolar (nM) to about 0.1 nM, from about 100 nM to about 1 picomolar (pM), or from about 100 nM to about 1 femtomolar (fM) or more. As used herein, the term "avidity" refers to the resistance of a complex of two or more agents to dissociation after dilution. The terms "immunoreactive" and "preferentially binds" are used interchangeably herein with respect to antibodies and/or antigen-binding fragments.

The term "binding" refers to a direct association between two molecules, due to, for example, covalent, electrostatic, hydrophobic, and ionic and/or hydrogen-bond interactions, including interactions such as salt bridges and water bridges. Non-specific binding would refer to binding with an affinity of less than about $10^{-7}$ M, e.g., binding with an affinity of $10^{-6}$ M, $10^{-5}$ M, $10^{-4}$ M, etc.

As used herein, the term "hinge region" refers to a flexible polypeptide connector region (also referred to herein as "hinge" or "spacer") providing structural flexibility and spacing to flanking polypeptide regions and can consist of natural or synthetic polypeptides. A "hinge region" derived from an immunoglobulin (e.g., IgG1) is generally defined as stretching from Glu216 to Pro230 of human IgG1 (Burton (1985) *Molec. Immunol.*, 22:161-206). Hinge regions of other IgG isotypes may be aligned with the IgG 1 sequence by placing the first and last cysteine residues forming inter-heavy chain disulfide (S—S) bonds in the same positions. The hinge region may be of natural occurrence or non-natural occurrence, including but not limited to an altered hinge region as described in U.S. Pat. No. 5,677,425. The hinge region can include a complete hinge region derived from an antibody of a different class or subclass from that of the CH1 domain. The term "hinge region" can also include regions derived from CD8, CD28, or other receptors that provide a similar function in providing flexibility and spacing to flanking regions.

An "isolated" polypeptide is one that has been identified and separated and/or recovered from a component of its natural environment. Contaminant components of its natural environment are materials that would interfere with diagnostic or therapeutic uses for the polypeptide, and may include enzymes, hormones, and other proteinaceous or nonproteinaceous solutes. In some embodiments, the polypeptide will be purified (1) to greater than 90%, greater than 95%, or greater than 98%, by weight of antibody as determined by the Lowry method, for example, more than 99% by weight, (2) to a degree sufficient to obtain at least 15 residues of N-terminal or internal amino acid sequence by use of a spinning cup sequenator, or (3) to homogeneity by sodium dodecyl sulfate-polyacrylamide gel electrophoresis (SDS-PAGE) under reducing or nonreducing conditions using Coomassie blue or silver stain. Isolated polypeptide includes the polypeptide in situ within recombinant cells since at least one component of the polypeptide's natural environment will not be present. In some instances, isolated polypeptide will be prepared by at least one purification step.

The term "immune cells" as used herein generally includes white blood cells (leukocytes) which are derived from hematopoietic stem cells (HSC) produced in the bone marrow "Immune cells" includes, e.g., lymphocytes (T cells (i.e. T lymphocytes), B cells, natural killer (NK) (CD3-CD56+) cells) and myeloid-derived cells (neutrophil, eosinophil, basophil, monocyte, macrophage, dendritic cells). "T cells" include all types of immune cells expressing CD3 including T-helper cells (CD4$^+$ cells), cytotoxic T-cells (CD8$^+$ cells), T-regulatory cells (Treg) and gamma-delta T cells, and NK T cells (CD3+ and CD56+). A skilled artisan will understand T cells and/or NK cells, as used throughout the disclosure, can include only T cells, only NK cells, or both T cells and NK cells. In certain illustrative embodiments and aspects provided herein, T cells are activated and transduced. Furthermore, T cells are provided in certain illustrative composition embodiments and aspects provided herein. A "cytotoxic cell" includes CD8$^+$ T cells, natural-killer (NK) cells, NK-T cells, γδ T cells, and neutrophils, which are cells capable of mediating cytotoxicity responses.

As used herein, the term "stem cell" generally includes pluripotent or multipotent stem cells. "Stem cells" includes, e.g., embryonic stem cells (ES); mesenchymal stem cells (MSC); induced-pluripotent stem cells (iPS); and committed progenitor cells (hematopoeitic stem cells (HSC); bone marrow derived cells, etc.).

The term "Axl" as used herein, refers to any native Axl from any vertebrate source, including mammals such as primates (e.g. humans) and rodents (e.g., mice and rats), unless otherwise indicated. The term encompasses "full-length," unprocessed Axl as well as any form of Axl that results from processing in the cell. The term also encompasses naturally occurring variants of Axl, e.g., splice variants or allelic variants. The amino acid sequence of human Axl is well-known in the art and available from public databases such as GenBank.

The term "Axl activation" as used herein refers to activation, or phosphorylation, of the Axl receptor. Generally, Axl activation results in signal transduction (e.g. that caused by an intracellular kinase domain of an Axl receptor phosphorylating tyrosine residues in Axl or a substrate polypeptide). Axl activation may be mediated by Axl ligand (Gas6) binding to an Axl receptor of interest. Gas6 binding to Axl may activate a kinase domain of Axl and thereby result in phosphorylation of tyrosine residues in the Axl and/or phosphorylation of tyrosine residues in additional substrate polypeptides(s).

The term "Axl mediated anti-apoptosis" as used herein refers to all Axl-involving processes that prevent human cells, preferably but not limited to human cancer cells from programmed cell death (apoptosis). In particular, it refers to processes that prevent human cells, preferably but not limited to human cancer cells from induction of apoptosis through growth factor withdrawal, hypoxia, exposure to chemotherapeutic agents or radiation, or initiation of the Fas/Apo-1 receptor-mediated signaling, and are stimulated or mediated by non-catalytic or catalytic activities of Axl, preferably including Axl phosphorylation and/or Axl-mediated signal transduction.

The term "Ror2" as used herein, refers to receptor tyrosine kinase-like orphan receptor 2, which is a predicted 943-amino acid protein with in vitro protein kinase activity, shown in Genbank accession number AAI30523. Many lineage-restricted receptor tyrosine kinases were initially identified as 'orphans' homologous to known receptors, and only subsequently used to identify their unknown growth factors. DeChiara et al. (2000) identified one such orphan, encoded by Ror2.

As used herein, the terms "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse effect attributable to the disease. "Treatment," as used herein, covers any treatment of a disease in a mammal, e.g., in a human, and includes: (a) preventing the disease from occurring in a subject which may be predisposed to the disease but has not yet been diagnosed as having it; (b) inhibiting the disease, i.e., arresting its development; and (c) relieving the disease, i.e., causing regression of the disease.

The terms "individual," "subject," "host," and "patient," used interchangeably herein, refer to a mammal, including, but not limited to, humans, murines (e.g., rats, mice), lagomorphs (e.g., rabbits), non-human primates, humans, canines, felines, ungulates (e.g., equines, bovines, ovines, porcines, caprines), etc.

A "therapeutically effective amount" or "efficacious amount" refers to the amount of an agent, or combined amounts of two agents, that, when administered to a mammal or other subject for treating a disease, is sufficient to affect such treatment for the disease. The "therapeutically effective amount" will vary depending on the agent(s), the disease and its severity and the age, weight, etc., of the subject to be treated.

As used herein, the term "evolution", or "evolving", refers to using one or more methods of mutagenesis to generate a different polynucleotide encoding a different polypeptide, which is itself an improved biological molecule and/or contributes to the generation of another improved biological molecule.

"Physiological" or "normal" or "normal physiological" conditions are conditions such as, but not limited to, temperature, pH, osmotic pressure, osmolality, oxidative stress and electrolyte concentration, as well as other parameters, that would be considered within a normal range at the site of administration, or at the tissue or organ at the site of action, to a subject.

It is to be understood that the present disclosure and the aspects and embodiments provided herein, are not limited to particular examples disclosed, as such may, of course, vary. It is also to be understood that the terminology used herein is for the purpose of disclosing particular examples and embodiments only, and is not intended to be limiting, since the scope of the present disclosure will be limited only by the appended claims.

Where a range of values is provided, it is understood that each intervening value, to the tenth of the unit of the lower limit unless the context clearly dictates otherwise, between the upper and lower limit of that range and any other stated or intervening value in that stated range, is encompassed within the invention. The upper and lower limits of these smaller ranges may independently be included in the smaller ranges, and are also encompassed within the invention, subject to any specifically excluded limit in the stated range. Where the stated range includes one or both of the limits, ranges excluding either or both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a," "an," and "the" include plural referents unless the context clearly dictates otherwise. Thus, for example, reference to "a chimeric antigen receptor" includes a plurality of such chimeric antigen receptors and equivalents thereof known to those skilled in the art, and so forth. It is further noted that the claims may be drafted to exclude any optional element. As such, this statement is intended to serve as antecedent basis for use of such exclusive terminology as "solely," "only" and the like in connection with the recitation of claim elements, or use of a "negative" limitation.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable sub-combination. All combinations of the embodiments pertaining to the invention are specifically embraced by the present invention and are disclosed herein just as if each and every combination was individually and explicitly disclosed. In addition, all sub-combinations of the various embodiments and elements thereof are also specifically embraced by the present invention and are disclosed herein just as if each and every such sub-combination was individually and explicitly disclosed herein.

DETAILED DESCRIPTION

The aspects and embodiments disclosure herein overcome the problem of off-tumor effects of current therapies by providing in one aspect, a conditionally active chimeric antigen receptor (CAR) for binding Axl and/or Ror2. The CARs for binding Axl and/or Ror2 are active in a tumor environment but not normal physiological tissue/organs. In addition to various embodiments of CARs that bind Axl and/or Ror2, provided herein are nucleic acid embodiments that include a nucleotide sequence encoding any of the CARs provided herein, as well as viral constructs for expressing any of the CARs, cells infected with at least one of the viral constructs, as well as recombinant cells expressing the CARs. A CAR of the present disclosure can be used in various methods, which are also provided, along with methods of infecting T-cells and other cytotoxic cells with expression vectors, such as recombinant viral vectors, that encode the CARs of the present disclosure.

Chimeric Antigen Receptors

The present disclosure provides a chimeric antigen receptor, which, for simplicity, is referred to herein as a "CAR." In illustrative embodiments, a CAR of the present disclosure binds to Axl or Ror2 and in further illustrative embodiments, the CAR binds to Axl or Ror2 in a conditionally active manner. In certain illustrative embodiments, a CAR provided herein includes: a) at least one conditionally active antigen-specific targeting region (ASTR) that exhibits an increased binding at pH 6.7 compared to a pH of 7.4; b) a transmembrane domain; and c) an intracellular activating domain. In illustrative embodiments, the antigen-specific targeting region of the CAR is a conditionally active scFv portion of an anti-Axl or anti-Ror2 antibody. Furthermore, in illustrative embodiments the ASTR exhibits an increase in activity in a tumor environment or an in vitro tumor surrogate assay condition compared to a normal physiological environment.

A CAR of the present disclosure can be present in the plasma membrane of a eukaryotic cell, e.g., a mammalian cell, where suitable mammalian cells include, but are not limited to, a cytotoxic cell, a T lymphocyte, a stem cell, a progeny of a stem cell, a progenitor cell, a progeny of a progenitor cell, and an NK cell, an NK-T cell, and a macrophage. When present in the plasma membrane of a eukaryotic cell, a CAR of the present disclosure is active in the presence of Axl and/or Ror2 that, in certain conditions, binds the ASTR. Axl and Ror2 are a second member of the specific binding pair. Axl and/or Ror2 of the specific binding pair can be a soluble (e.g., not bound to a cell) factor; a factor present on the surface of a cell such as a target cell; a factor presented on a solid surface; a factor present in a lipid bilayer; and the like. Where the ASTR is an antibody, and the second member of the specific binding pair is an antigen, the antigen can be a soluble (e.g., not bound to a cell) antigen; an antigen present on the surface of a cell such as a target cell; an antigen presented on a solid surface; an antigen present in a lipid bilayer; and the like.

In some instances, a CAR of the present disclosure, when present in the plasma membrane of a eukaryotic cell, and when activated by Axl and/or Ror2, increases expression of at least one nucleic acid in the cell. For example, in some cases, a CAR of the present disclosure, when present in the plasma membrane of a eukaryotic cell, and when activated by Axl and/or Ror2, increases expression of at least one nucleic acid in the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the level of transcription of the nucleic acid in the absence of Axl and/or Ror2.

As an example, the CAR of the present disclosure can include an immunoreceptor tyrosine-based activation motif (ITAM)-containing intracellular signaling polypeptide; in such cases, a CAR of the present disclosure, when present in the plasma membrane of a eukaryotic cell, and when activated by Axl and/or Ror2, increases nuclear factor of activated T cells (NFAT)-dependent transcription. NFAT-dependent transcription includes transcription induced by any member of the NFAT family, including, e.g., NFATe1, NFATc2, NFATc3, NFATc4, NFAT5; AP-1; Sp1; NKKB; and the like.

A CAR of the present disclosure, when present in the plasma membrane of a eukaryotic cell, and when activated by Axl or Ror2, can, in some instances, result in increased production of one or more cytokines by the cell. For example, a CAR of the present disclosure, when present in the plasma membrane of a eukaryotic cell, and when activated by Axl or Ror2, can increase production of a cytokine by the cell by at least 10%, at least 15%, at least 20%, at least 25%, at least 30%, at least 40%, at least 50%, at least 75%, at least 2-fold, at least 2.5-fold, at least 5-fold, at least 10-fold, or more than 10-fold, compared with the amount of cytokine produced by the cell in the absence of Axl and/or Ror2. In some embodiments, a CAR of the present disclosure, when present in the membrane of a eukaryotic cell, and when activated by Axl and/or Ror2, can increase secretion of a cytokine by the cell by at least 10%, at least 15%, at least 20%, at least 25%, at least 30%, at least 40%, at least 50%, at least 75%, at least 2-fold, at least 2.5-fold, at least 5-fold, at least 10-fold, or more than 10-fold, compared with the amount of cytokine secreted by the cell in the absence of Axl and/or Ror2. Cytokines whose production can be increased include, but are not limited to interferon gamma (IFN-γ), tumor necrosis factor-alpha (TNF-a), IL-2, IL-15, IL-12, IL-4, IL-5, IL-10; a chemokine; a growth factor; and the like.

In some cases, a CAR of the present disclosure, when present in the plasma membrane of a eukaryotic cell, and when activated by Axl and/or Ror2, can result in an increase in transcription of a nucleic acid in the cell, an increase in production of a cytokine, and an increase in secretion of the cytokine by the cell.

In some instances, a CAR of the present disclosure, when present in the plasma membrane of a eukaryotic cell, and when activated by Axl and/or Ror2, results in cytotoxic activity by the cell toward a target cell that expresses on its cell surface an antigen to which the antigen-binding domain of the first polypeptide of the CAR binds. For example, where the eukaryotic cell is a cytotoxic cell (e.g., an NK cell or a cytotoxic T lymphocyte), a CAR of the present disclosure, when present in the plasma membrane of the cell, and when activated by Axl and/or Ror2, increases cytotoxic activity of the cell toward a target cell that expresses on its cell surface Axl and/or Ror2. For example, where the eukaryotic cell is an NK cell or a T lymphocyte, a CAR of the present disclosure, when present in the plasma membrane of the cell, and when activated by Axl and/or Ror2, increases cytotoxic activity of the cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the cell in the absence of Axl and/or Ror2.

In some cases, a CAR of the present disclosure, when present in the plasma membrane of a eukaryotic cell, and when activated by Axl and/or Ror2, can result in other CAR activation related events such as proliferation and expansion (either due to increased cellular division or anti-apoptotic responses).

In some cases, a CAR of the present disclosure, when present in the plasma membrane of a eukaryotic cell, and when activated by Axl and/or Ror2, can result in other CAR activation related events such as intracellular signaling modulation, cellular differentiation, or cell death.

A CAR of the present disclosure can be present in a eukaryotic cell membrane, where the first and second polypeptides of the CAR are not covalently linked to one another. A CAR of the present disclosure can be present in a eukaryotic cell membrane as a single heterodimer that is not covalently linked to any other polypeptide in the membrane. Alternatively, a first CAR of the present disclosure can be present in a eukaryotic cell membrane as a heterodimer that is covalently or non-covalently linked to a second CAR of the present disclosure. In some cases, the first and the second CAR are covalently linked via a disulfide bond formed between cysteines present in a hinge region present in both the first polypeptide of the first CAR and the first polypeptide of the second CAR.

In some cases, a CAR of the present disclosure can be present in a eukaryotic cell membrane, where the first polypeptides of the CAR include an antibody fragment and the second polypeptides of the CAR include a signal transducing domain derived from a cytokine receptor, such that, upon dimerization, the CAR may represent a heterodimeric-signalobody CAR, e.g., a signalobody composed of at least two independent polypeptides. A "signalobody", as it is known in the art, is a single chimeric macromolecule composed of an antibody fragment and a signal transduction domain derived from a cytokine receptor. In certain instances, a heterodimeric-signalobody CAR of the present disclosure, when present in the cell membrane of a eukaryotic cell, dimerized by a dimerizer, and activated by an antigen, e.g., an oligomerized antigen, may induce the oligomerization of the heterodimeric-signalobody CAR. Such ligand-induced oligomerization of a heterodimeric-signalobody CAR may activate, e.g., increase, or perpetuate, e.g., maintain, signal transduction, e.g., ligand-induced oligomerization of a heterodimeric-signalobody CAR may transmit a signal eliciting a cellular response. In some instances, a plurality of heterodimeric-signalobody CARs may be utilized combinatorially to elicit a desired cellular response.

Antigen-Specific Targeting Regions

A CAR of the present disclosure includes a member of a specific binding pair, which is typically an ASTR. Specific binding pairs include, but are not limited to, antigen-antibody binding pairs; ligand-receptor binding pairs; and the like. Thus, a member of a specific binding pair suitable for use in a CAR of the present disclosure includes an ASTR that is an antibody, an antigen, a ligand, a receptor binding domain of a ligand, a receptor, a ligand binding domain of a receptor, and an affibody.

An ASTR suitable for use in a CAR of the present disclosure can be any antigen-binding polypeptide. In certain embodiments, the ASTR is an antibody such as a full-length antibody, a single-chain antibody, an Fab fragment, an Fab' fragment, an (Fab')2 fragment, an Fv fragment, and a divalent single-chain antibody or a diabody.

In some embodiments, the ASTR is a single chain Fv (scFv). In some embodiments, the heavy chain is positioned N-terminal of the light chain in the CAR. In other embodiments, the light chain is positioned N-terminal of the heavy chain in the CAR. In any of the disclosed embodiments, the heavy and light chains can be separated by a linker as discussed in more detail herein. In any of the disclosed embodiments, the heavy or light chain can be at the N-terminus of the CAR and is typically C-terminal of another domain, such as a signal sequence or peptide.

Other antibody-based recognition domains (cAb VHH (camelid antibody variable domains) and humanized versions, IgNAR VH (shark antibody variable domains) and humanized versions, sdAb VH (single domain antibody variable domains) and "camelized" antibody variable domains are suitable for use with the CARs and methods using the CARs of the present disclosure. In some instances, T-cell receptor (TCR) based recognition domains such as single chain TCR (scTv, single chain two-domain TCR containing VαVβ) are also suitable for use.

Conditionally Active Biologic CARs (CAB-CARs)

CARs of the present disclosure are typically conditionally active. This property is typically the result of the conditionally active nature of the ASTR domain of the CAR. In illustrative embodiments, CAB-CARs of the present disclosure have a higher binding affinity to Axl or Ror2 under a condition(s) in a tumor microenvironment than under a condition in a non-tumor microenvironment. In some embodiments, the condition in the tumor microenvironment and the condition in a non-tumor microenvironment are both pH. Thus, the CAB-CARs can selectively bind to Axl or Ror2 in a conditionally active manner typically because they have a higher binding affinity for Axl or Ror2 at a pH of about 6.0-6.8, a pH that is encountered in a tumor microenvironment, compared to a pH of 7.2-7.8, a pH that is encountered in a normal physiological environment. For example, CAB-CARs can have a higher binding affinity to Axl or Ror2 at pH 6.7 than at pH 7.4. Additionally, or alternatively, CAB-CARs can have a higher binding affinity to Axl or Ror2 at pH 6.0 than at pH 7.4. Such conditions can be tested in an in vitro tumor surrogate assay that for example, tests for antigen binding and/or CAR activity (e.g. cell lysis) under one or more conditions found in an in vivo tumor environment, as set out in more detail below, which differ from the corresponding condition(s) in normal physiological tissue. For example, an in vitro tumor surrogate assay condition can be a low pH (e.g. 6.0-6.8) compared to a physiological pH (7.2-7.8). In an illustrative example, a tumor surrogate assay condition is a pH of 6.7 whereas a corresponding physiological pH is 7.4.

In some embodiments, CAB-CARs can be obtained by identifying a VH and/or VL of an antibody that was identified under physiologic conditions (i.e. parent, "wild type" or "wt" antibody). Antibodies can then mutated and tested (evolved). A skilled artisan can utilize the method for identifying conditionally active antibodies disclosed in U.S. Pat. No. 8,709,755 to identify additional conditionally active antibodies and antibody fragments that can be used in ASTRs for CABCARs of the present disclosure. The complementarity determining region (CDR) is a 3-dimensional structure that is formed by the interaction of the VH and VL. To alter the binding specificity of a starting point ("wt" antibody), it is reasonable to expect that mutating either or both the VH/VL could lead to CAB activity in a CAB-CAR. To generate a conditionally active antibody, both the VH and the VL are typically identified under physiologic conditions, and then either the VH or the VL or more typically both the VH and VL are mutated and tested in non-physiologic conditions, such as a pH of 6.0 to 6.7 or another condition of a tumor microenvironment, to generate a conditionally active antibody.

Nucleic acid encoding VH and/or VL regions of wild-type antibodies can be cloned using known methods. Variants of such wild-type VH and VL regions can then be prepared by introducing modifications into the nucleotide sequence encoding the heavy and light chain variable regions. Such modifications include, for example, deletions from, and/or insertions into and/or substitutions of residues within the amino acid sequences of the antibody or antibody fragment. Any combination of deletion(s), insertion(s), and substitution(s) can be made to arrive at a conditionally active antibody fragment.

More detailed methods for making and/or isolating conditionally active ASTRs are provided in a separate section herein.

Conditionally Active ASTRs Targeting Axl

Illustrative embodiments of any of the various aspects provided herein, include a CAR with a conditionally active ASTR that specifically binds to an Axl protein at a pH of 6.7 compared to a pH of 7.4 Examples of such ASTRs and CARs containing such ASTRs, are provided in the Examples herein. In certain embodiments, the ASTR binds to the same epitope of Axl as an antibody that includes the heavy chain of SEQ ID NO:79 and the light chain of SEQ ID NO:80. In illustrative embodiments, the ASTR binds to the same epitope of Axl as a single-chain variable antibody |comprising an antibody heavy chain of SEQ ID NO:79 and an antibody light chain of SEQ ID NO:80.

The ASTR can be a single-chain antibody, an Fab fragment, an Fab' fragment, an (Fab')2 fragment, an Fv fragment, a divalent single-chain antibody, or a diabody. In illustrative embodiments, the conditionally active ASTR that binds Axl is a single-chain variable fragment comprising a heavy chain and a light chain.

In some embodiments where the ASTR binds to Axl, and in illustrative embodiments binds to the same epitope of Axl as a single-chain variable antibody fragment comprising an antibody heavy chain of SEQ ID NO:79 and an antibody light chain of SEQ ID NO:80, the heavy chain variable region can include three complementarity determining regions, said regions having sequences H1, H2, and H3, wherein:
  the H1 sequence is $X_1GX_2TMN$ (SEQ ID NO:87);
  the H2 sequence is LIKPSNGGTSYNQKFKG (SEQ ID NO:88); and
  the H3 sequence is $GX_3YX_4SYX_5AMDY$ (SEQ ID NO:89), wherein $X_1$ is T or W; $X_2$ is H or A, $X_3$ is H or D; $X_4$ is E or H; and $X_5$ is E or F.

In some embodiments where the ASTR binds to Axl, and in illustrative embodiments binds to the same epitope of Axl as a single-chain variable antibody fragment comprising an antibody heavy chain of SEQ ID NO:79 and an antibody light chain of SEQ ID NO:80, including the heavy chain embodiments immediately above, the ASTR can include a light chain variable region that includes three complementarity determining regions, said regions having sequences L1, L2, and L3, wherein:
  the L1 sequence is $KASQDVX_6SAVA$ (SEQ ID NO:90);
  the L2 sequence is $WX_7X_8TRX_9T$ (SEQ ID NO:91); and
  the L3 sequence is $QEHFSX_{10}PLX_{11}$ (SEQ ID NO:92), wherein $X_6$ is S or V; $X_7$ is A or Q; $X_8$ is S or D; $X_9$ is H or D; $X_{10}$ is T or P; and $X_{11}$ is T or R.

In some embodiments where the ASTR binds to Axl, and in illustrative embodiments binds to the same epitope of Axl as a single-chain variable antibody fragment comprising an antibody heavy chain of SEQ ID NO:79 and an antibody light chain of SEQ ID NO:80, the heavy chain variable region can include three complementarity determining regions, said regions having sequences H1, H2, and H3, wherein:
  the H1 sequence is $X_1GX_2X_3MX_4$ (SEQ ID NO:134);
  the H2 sequence is $LIKX_5SNGGTX_6YNQKFKG$ (SEQ ID NO:135); and
  the H3 sequence is $GX_7X_8X_9X_{10}X_{11}X_{12}X_{13}X_{14}DYX_{15}X_{16}$ (SEQ ID NO:136),
  wherein $X_1$ is T, A, or W; $X_2$ is H or A; $X_3$ is T or I; $X_4$ is N or I; $X_5$ is P or N; $X_6$ is 5, I, or T; $X_7$ is H, D, E, P, R, or W; $X_8$ is Y or N; $X_9$ is E, A, D, F, G, H, I, L, M, N, R, V, or Y; $X_{10}$ is S, D, M, N, or Q; $X_{11}$ is Y, C, E, or P; $X_{12}$ is F, E, N, S, T, or V; $X_{13}$ is A, D, G, L, or Y; $X_{14}$ is M, E, or F; $X_{15}$ is W, A, D, H, L, N, P, R, or T; and $X_{16}$ is G or H.

In some embodiments where the ASTR binds to Axl, and in illustrative embodiments binds to the same epitope of Axl as a single-chain variable antibody fragment comprising an antibody heavy chain of SEQ ID NO:79 and an antibody light chain of SEQ ID NO:80, including the heavy chain embodiments immediately above, the ASTR can include a light chain variable region that includes three complementarity determining regions, said regions having sequences L1, L2, and L3, wherein:
  the L1 sequence is $KASQDX_{17}X_{18}SX_{19}VX_{20}$ (SEQ ID NO:137);
  the L2 sequence is $X_{21}X_{22}X_{23}TRX_{24}T$ (SEQ ID NO:138); and
  the L3 sequence is $QEX_{25}X_{26}SX_{27}X_{28}X_{29}X_{30}$ (SEQ ID NO:139),
  wherein $X_{17}$ is V, D, G, N, or W; $X_{18}$ is S or V; $X_{19}$ is A, L, or M; $X_{20}$ is A, D, N, or Q; $X_{21}$ is W or F; $X_{22}$ is A, I, N, P, or Q; $X_{23}$ is S or D; $X_{24}$ is H or D; $X_{25}$ is H, C, F, I, L, Q, S, T, V, or Y; $X_{26}$ is F, C, D, E, G, N, or S; $X_{27}$ is T, C, or P; $X_{28}$ is P, A, C, D, E, H, K, S, T, V, or W; $X_{29}$ is L, G, or R; and $X_{30}$ is T, I, or R.

In certain illustrative embodiments, the ASTR includes the light chain variable region of SEQ ID NO:80 and/or the heavy chain variable region of SEQ ID NO:79. These illustrative embodiments can include the heavy chain N-terminal to the light chain or the light chain N-terminal to the heavy chain. In an illustrative embodiment, the anti-Axl ASTR can include the sequence of any of SEQ ID NO:128, SEQ ID NO:129, SEQ ID NO:159, SEQ ID NO:160, or SEQ ID NO:161.

The heavy and light chains of any of these anti-Axl embodiments that include two variable regions, the variable regions are typically separated by a linker. The linker can be between 6 and 100 amino acids in length. In some embodiments, the linker is linker 1 (SEQ ID NO:53), linker 2 (SEQ ID NO:54), or linker 3 (SEQ ID NO:55). In illustrative embodiments, the two variable regions are a heavy chain variable region and a light chain variable region. Either the heavy chain or light chain can be located N-terminal to the other on the ASTR. In certain illustrative embodiments, the heavy chain is N-terminal to the light chain.

Exemplary conditionally active CARs (CAB-CARs) that have increased binding to Axl at pH 6.7 compared to ph7.4 are found in Example 1 herein. In illustrative embodiments, the CAR or ASTR can bind to the same epitope of Axl as a single-chain variable antibody fragment comprising an antibody heavy chain of SEQ ID NO:79 and an antibody light chain of SEQ ID NO:80. In further embodiments of such illustrative embodiments, the anti-Axl CAR or ASTR comprises or is a single chain variable fragment (scFv). In further illustrative examples, the anti-Axl scFv comprises either a heavy chain that is N-terminal to a light chain or a light chain that is N-terminal to a heavy chain. In any of the embodiments herein that includes a CAR, and in illustrative embodiments binds to the same epitope of Axl as an antibody that includes the antibody heavy chain of SEQ ID NO:79 and the antibody light chain of SEQ ID NO:80, the ASTR can include any of SEQ ID NOs:128, 129, 159, 160, or 161. Furthermore, anti-Axl CARs of any of the embodiments herein can include any of the CAR components provided herein. In certain exemplary embodiments, the anti-Axl CARs can include the CAR components listed in Table 1 and can be any of the CARs in Table 1. More typically for any embodiments herein that include an anti-Axl CAR, the CAR is a CAB-CAR, and in non-limiting illustrative embodiments, can include, for example, any of the CAB-CAR components and CAB-CARs provided in Table 1 that demonstrated cytotoxic activity. For example, the anti-Axl CAB-CAR can include a CD8 signal peptide, a CD8 or CD28 stalk/transmembrane domain, a CD137, ICΔ, or both a ICΔ co-stimulatory domain and a CD137 co-stimulatory domain, and/or a CD3Z activation domain. Furthermore, illustrative CARs for any of the embodiments herein that includes an anti-Axl CAR, and especially an anti-Axl CAB-CAR, in non-limiting illustrative embodiments include any of the anti-Axl CAB-CARs that demonstrated conditional cytotoxic activity in Table 1. Such illustrative CAB-CARs include F1-2-1, F1-2-2, F1-2-3, F1-2-6, F1-2-8, F1-2-10, F1-2-13, F1-2-14, F1-2-15, F1-2-22, or F1-2-23 of Table 1. In any of the embodiments herein that includes an ASTR, the ASTR can include the ASTR of F1-2-1, F1-2-2, F1-2-3, F1-2-6, F1-2-8, F1- 2-10, F1-2-13, F1-2-14, F1-2-15, F1-2-22, or F1-2-23. Furthermore, illustrative CARs for any of the embodiments herein that includes an anti-Axl CAR, and especially an anti-Axl CAB-CAR, in non-limiting illustrative embodiments include any of the anti-Axl CAB-CARs that demonstrated high conditional cytotoxic activity in Table 1. Such illustrative CAB-CARs include F1-2-13, F1-2-15, F1-2-22, or F1-2-23. Accordingly, in any of the embodiments herein that includes an ASTR, the ASTR can include the ASTR of F1-2-1, F1-2-2, F1-2-3, F1-2-6, F1-2-8, F1-2-10, F1-2-13, F1-2-14, F1-2-15, F1-2-22, or F1-2-23.

The heavy chain variable region polypeptides and light chain variable region polypeptides disclosed herein were identified from a parent antibody heavy chain variable region (SEQ ID NO:93) and a parent antibody light chain variable region (SEQ ID NO:94) using a method disclosed in U.S. Pat. No. 8,709,755. A skilled artisan can utilize the method for identifying conditionally active antibodies disclosed in U.S. Pat. No. 8,709,755 to identify additional conditionally active antibodies and antibody fragments that can be used in ASTRs for CAB-CARs of the present disclosure.

In some embodiments, the heavy chain variable regions can be SEQ ID NOs:112-114. In some embodiments, the light chain variable regions can be SEQ ID NOs:108-111. These heavy and light chain variable regions can specifically bind to Axl. Antibodies comprising any one of these heavy and light chain variable regions have been found to have a higher binding affinity to Axl at a pH 6.7 than at a pH 7.4. A pH 6.7 is a pH found in the tumor microenvironment. A pH 7.4 is a pH found in a non-tumor, normal physiological microenvironment.

The CAR can also include variants of the heavy and light chain variable regions of the sequences of SEQ ID NOs: 108-114 that can specifically bind to Axl. In order to derive these variants, it was determined that the complementarity determining regions (CDRs) of the heavy chain variable regions (H1-H3) and the CDRs of the light chain variable regions (L1-L3) should remain intact. The variants of these heavy and light chain variable regions may be prepared by introducing appropriate modifications into the nucleotide sequence encoding the heavy and light chain variable regions, or by peptide synthesis. Such modifications include, for example, deletions from, and/or insertions into and/or substitutions of residues within the amino acid sequences of the antibody or antibody fragment. Any combination of deletion(s), insertion(s), and substitution(s) can be made to arrive at the final construct, provided that the final construct possesses at least one of the desired characteristics, e.g., antigen-binding.

Conditionally Active ASTRs Targeting Ror2

Illustrative embodiments of any of the various aspects provided herein, include a CAR with a conditionally active ASTR that specifically binds to a Ror2 protein at a pH of 6.7 compared to a pH of 7.4. Examples of such ASTRs and CARs containing such ASTRs, are provided in the Examples herein. In certain embodiments, the ASTR binds to the same epitope of Ror2 as an antibody that includes the heavy chain of SEQ ID NO:82 or SEQ ID NO:83 or the ASTR binds to the same epitope of Ror2 as an antibody that includes the heavy chain of SEQ ID NO:151. In illustrative embodiments, the ASTR binds to the same epitope of Ror2 as a single-chain variable antibody fragment comprising an antibody heavy chain of SEQ ID NO:82 or SEQ ID NO:83 or the ASTR binds to the same epitope of Ror2 as a single-chain variable antibody fragment comprising an antibody heavy chain of SEQ ID NO:151. In illustrative embodiments, the ASTR binds to the same epitope of Ror2 as a single-chain variable antibody fragment that includes the antibody heavy chain of SEQ ID NO:82 or SEQ ID NO:83 and an antibody light chain of SEQ ID NO:84 or the ASTR binds to the same epitope of Ror2 as a single-chain variable antibody fragment that includes the antibody heavy chain of SEQ ID NO:151 and the antibody light chain of SEQ ID NO:152.

The ASTR can be a single-chain antibody, an Fab fragment, an Fab' fragment, an (Fab')2 fragment, an Fv fragment, a divalent single-chain antibody, or a diabody. In illustrative embodiments, the conditionally active ASTR that binds Ror2 is a single-chain variable fragment comprising a heavy chain and a light chain.

In some embodiments where the ASTR binds to Ror2, the ASTR can include a heavy chain variable region with three complementarity determining regions, said regions having H1, H2, and H3 sequences, wherein:
the H1 sequence is GYTX$_1$TEX$_2$TX$_3$H (SEQ ID NO:95) or X$_4$GYSITTGYYWN (SEQ ID NO:96);
the H2 sequence is GX$_5$NX$_6$NNGGTGYNQKFKG (SEQ ID NO:97) or YITYDGSKNYNPSLKN (SEQ ID NO:98); and
the H3 sequence is GSLYSYGNSYFDY (SEQ ID NO:99) or FEGVWX$_7$GLDY (SEQ ID NO:100),
wherein X$_1$ is F or E; X$_2$ is Y or D, X$_3$ is M or D; X$_4$ is T or S; X$_5$ is E or I; X$_6$ is T or D; and X$_7$ is Y or G.

In some embodiments where the ASTR binds to Ror2, and in illustrative embodiments binds to the same epitope of Ror2 as an antibody that includes the antibody heavy chain of SEQ ID NO:151 and the antibody light chain of SEQ ID NO:152, the ASTR can include a heavy chain variable region with three complementarity determining regions, said regions having H1, H2, and H3 sequences, wherein:
the H1 sequence is GYTX$_1$TEX$_2$TX$_3$H (SEQ ID NO:95);
the H2 sequence is GX$_5$NX$_6$NNGGTGYNQKFKG (SEQ ID NO:97); and
the H3 sequence is GSLYSYGNSYFDY (SEQ ID NO:99),
wherein X$_1$ is F or E; X$_2$ is Y or D, X$_3$ is M or D; X$_5$ is E or I; and X$_6$ is T or D.

In some embodiments where the ASTR binds to Ror2, and in illustrative embodiments binds to the same epitope of Ror2 as an antibody that includes the antibody heavy chain of SEQ ID NO:82 or SEQ ID NO:83 and the antibody light chain of SEQ ID NO:84, the ASTR can include a heavy chain variable region with three complementarity determining regions, said regions having H1, H2, and H3 sequences, wherein:
the H1 sequence is X$_4$GYSITTGYYWN (SEQ ID NO:96);
the H2 sequence is YITYDGSKNYNPSLKN (SEQ ID NO:98); and
the H3 sequence is FEGVWX$_7$GLDY (SEQ ID NO:100),
wherein X$_4$ is T or S; and X$_7$ is Y or G.

In some embodiment where the ASTR binds to Ror2, including but not limited to those having a heavy chain with the H1, H2, and H3 sequences above, the ASTR includes a light chain variable region that includes three complementarity determining regions, said regions having L1, L2, and L3 sequences, wherein:
the L1 sequence is SATSSX$_8$SYMH (SEQ ID NO:101) or RASESVDRYGNSFIH (SEQ ID NO:102);
the L2 sequence is X$_9$TSNLAS (SEQ ID NO:103) or RTYNLES (SEQ ID NO:104); and
the L3 sequence is QQRSSYPFT (SEQ ID NO:105) or QQTNEDPWT (SEQ ID NO:106),
wherein X$_8$ is E or V; and X$_9$ is G or H.

In some embodiments where the ASTR binds to Ror2, and in illustrative embodiments binds to the same epitope of Ror2 as an antibody that includes the antibody heavy chain of SEQ ID NO:151 and the antibody light chain of SEQ ID NO:152, the ASTR can include a light chain variable region with three complementarity determining regions, said regions having L1, L2, and L3 sequences, wherein:
the L1 sequence is SATSSX$_8$SYMH (SEQ ID NO:101);
the L2 sequence is X$_9$TSNLAS (SEQ ID NO:103); and
the L3 sequence is QQRSSYPFT (SEQ ID NO:105),
wherein X$_8$ is E or V; and X$_9$ is G or H.

In some embodiments where the ASTR binds to Ror2, and in illustrative embodiments binds to the same epitope of Ror2 as an antibody that includes the antibody heavy chain of SEQ ID NO:82 or SEQ ID NO:83 and the antibody light chain of SEQ ID NO:84, the ASTR can include a light chain variable region with three complementarity determining regions, said regions having L1, L2, and L3 sequences, wherein:
the L1 sequence is RASESVDRYGNSFIH (SEQ ID NO:102);
the L2 sequence is RTYNLES (SEQ ID NO:104); and
the L3 sequence is QQTNEDPWT (SEQ ID NO:106).

In some embodiments where the ASTR binds to Ror2, the ASTR can include a heavy chain variable region including three complementarity determining regions, said regions having H1, H2, and H3 sequences, wherein:
the H1 sequence is GYTX$_1$TEX$_2$X$_3$X$_4$H (SEQ ID NO:140) or GYSITTGX$_{29}$YWN (SEQ ID NO:141);
the H2 sequence is X$_5$X$_6$X$_7$X$_8$NNGGTGYNQKFKG (SEQ ID NO:142) or YITYDGSX$_{30}$NYNPSLKN (SEQ ID NO:143); and
the H3 sequence is X$_9$X$_{10}$X$_{11}$SX$_{12}$YX$_{13}$YX$_{14}$X$_{15}$SYFX$_{16}$X$_{17}$X$_{18}$ (SEQ ID NO:144) or CSX$_{31}$X$_{32}$X$_{33}$X$_{34}$VX$_{35}$X$_{36}$X$_{37}$LDX$_{38}$ (SEQ ID NO:145),
wherein X$_1$ is F or E; X$_2$ is Y or D; X$_3$ is T or C; X$_4$ is M, D, E, or Y; X$_5$ is G or S; X$_6$ is I or E; X$_7$ is N, C, L, or V; X$_8$ is T, D or E; X$_9$ is A, M, or T; X$_{10}$ is R or H; X$_{11}$ is G or E; X$_{12}$ is L or F; X$_{13}$ is S or G; X$_{14}$ is G or D; X$_{15}$ is N or E; X$_{16}$ is D or L; X$_{17}$ is Y, C, or T; X$_{18}$ is W or L; X$_{29}$ is Y, E, R, or T; X$_{30}$ is K or N; X$_{31}$ is R, G, H, W, or Y; X$_{32}$ is F, C, N, or Q; X$_{33}$ is E or S; X$_{34}$ is G, E, F, H, M, Q, or S; X$_{35}$ is W, A, I, P, Q, T, or V; X$_{36}$ is Y, G, N, or Q; X$_{37}$ is G, S, or T; and X$_{38}$ is Y or I.

In some embodiments where the ASTR binds to Ror2, and in illustrative embodiments binds to the same epitope of Ror2 as an antibody that includes the antibody heavy chain of SEQ ID NO:151 and the antibody light chain of SEQ ID NO:152, the ASTR can include a heavy chain variable region including three complementarity determining regions, said regions having H1, H2, and H3 sequences, wherein:
the H1 sequence is GYTX$_1$TEX$_2$X$_3$X$_4$H (SEQ ID NO:140);
the H2 sequence is X$_5$X$_6$X$_7$X$_8$NNGGTGYNQKFKG (SEQ ID NO:142); and
the H3 sequence is X$_9$X$_{10}$X$_{11}$SX$_{12}$YX$_{13}$YX$_{14}$X$_{15}$SYFX$_{16}$X$_{17}$X$_{18}$ (SEQ ID NO:144),
wherein X$_1$ is F or E; X$_2$ is Y or D; X$_3$ is T or C; X$_4$ is M, D, E, or Y; X$_5$ is G or S; X$_6$ is I or E; X$_7$ is N, C, L, or V; X$_8$ is T, D or E; X$_9$ is A, M, or T; X$_{10}$ is R or H; X$_{11}$ is G or E; X$_{12}$ is L or F; X$_{13}$ is S or G; X$_{14}$ is G or D; X$_{15}$ is N or E; X$_{16}$ is D or L; X$_{17}$ is Y, C, or T; and X$_{18}$ is W or L.

In some embodiments where the ASTR binds to Ror2, and in illustrative embodiments binds to the same epitope of Ror2 as an antibody that includes the antibody heavy chain of SEQ ID NO:82 or SEQ ID NO:83 and the antibody light chain of SEQ ID NO:84, the ASTR can include a heavy chain variable region including three complementarity determining regions, said regions having H1, H2, and H3 sequences, wherein:
the H1 sequence is GYSITTGX$_{29}$YWN (SEQ ID NO:141);
the H2 sequence is YITYDGSX$_{30}$NYNPSLKN (SEQ ID NO:143); and
the H3 sequence is CSX$_{31}$X$_{32}$X$_{33}$X$_{34}$VX$_{35}$X$_{36}$X$_{37}$LDX$_{38}$ (SEQ ID NO:145),
wherein X$_{29}$ is Y, E, R, or T; X$_{30}$ is K or N; X$_{31}$ is R, G, H, W, or Y; X$_{32}$ is F, C, N, or Q; X$_{33}$ is E or S; X$_{34}$ is G, E, F, H, M, Q, or S; X$_{35}$ is W, A, I, P, Q, T, or V; X$_{36}$ is Y, G, N, or Q; X$_{37}$ is G, S, or T; and X$_{38}$ is Y or I.

In some embodiments where the ASTR binds to Ror2, the ASTR can include a light chain variable region that includes three complementarity determining regions, said regions having L1, L2, and L3 sequences, wherein:
the L1 sequence is SATSSX$_{19}$X$_{20}$X$_{21}$MX$_{22}$ (SEQ ID NO:146) or RASESVDRYGNSX$_{39}$IH (SEQ ID NO:147);
the L2 sequence is X$_{23}$TSNLAS (SEQ ID NO:148) or X$_{40}$TYX$_{41}$LES (SEQ ID NO:149); and
the L3 sequence is QX$_{24}$X$_{25}$SX$_{26}$YPFX$_{27}$X$_{28}$ (SEQ ID NO:150) or QQX$_{42}$NX$_{43}$DPX$_{44}$TX$_{45}$ (SEQ ID NO:85),
wherein X$_{19}$ is V or E; X$_{20}$ is S or D; X$_{21}$ is Y, C, or D; X$_{22}$ is H, G, or L; X$_{23}$ is G, C, H, or P; X$_{24}$ is Q or E; X$_{25}$ is R or H; X$_{26}$ is S, D, G, I, Q, or V; X$_{27}$ is T or D; X$_{28}$ is F, D, or E; X$_{39}$ is F, S, or T; X$_{40}$ is R, C, D, E, or W; X$_{41}$ is N or D; X$_{42}$ is T, I, or P; X$_{43}$ is E or V; X$_{44}$ is W or T; and X$_{45}$ is F or T.

In some embodiments where the ASTR binds to Ror2, and in illustrative embodiments binds to the same epitope of Ror2 as an antibody that includes the antibody heavy chain of SEQ ID NO:151 and the antibody light chain of SEQ ID NO:152, the ASTR can include a light chain variable region that includes three complementarity determining regions, said regions having L1, L2, and L3 sequences, wherein:
the L1 sequence is SATSSX$_{19}$X$_{20}$X$_{21}$MX$_{22}$ (SEQ ID NO:146);
the L2 sequence is X$_{23}$TSNLAS (SEQ ID NO:148); and
the L3 sequence is QX$_{24}$X$_{25}$SX$_{26}$YPFX$_{27}$X$_{28}$ (SEQ ID NO:150),
wherein X$_{19}$ is V or E; X$_{20}$ is S or D; X$_{21}$ is Y, C, or D; X$_{22}$ is H, G, or L; X$_{23}$ is G, C, H, or P; X$_{24}$ is Q or E; X$_{25}$ is R or H; X$_{26}$ is S, D, G, I, Q, or V; X$_{27}$ is T or D; and X$_{28}$ is F, D, or E.

In some embodiments where the ASTR binds to Ror2, and in illustrative embodiments binds to the same epitope of Ror2 as an antibody that includes the antibody heavy chain of SEQ ID NO:82 or SEQ ID NO:83 and the antibody light chain of SEQ ID NO:84, the ASTR can include a light chain variable region that includes three complementarity determining regions, said regions having L1, L2, and L3 sequences, wherein:

the L1 sequence is RASESVDRYGNSX$_{39}$IH (SEQ ID NO:147);
the L2 sequence is X$_{40}$TYX$_{41}$LES (SEQ ID NO:149); and
the L3 sequence is QQX$_{42}$NX$_{43}$DPX$_{44}$TX$_{45}$ (SEQ ID NO:85),
wherein X$_{39}$ is F, S, or T; X$_{40}$ is R, C, D, E, or W; X$_{41}$ is N or D; X$_{42}$ is T, I, or P; X$_{43}$ is E or V; X$_{44}$ is W or T; and X$_{45}$ is F or T.

In some embodiments, the conditionally active ASTR that binds Ror2, and in illustrative embodiments the conditionally active ASTR that binds to the same epitope of Ror2 as an antibody comprising an antibody heavy chain of SEQ ID NO:151 and an antibody light chain of SEQ ID NO:152, includes a heavy chain variable region having an amino acid sequence selected from the sequences of SEQ ID NOs:115-119 and SEQ ID NO:151. In these illustrative embodiments where the conditionally active ASTR binds to the same epitope of Ror2 as an antibody comprising an antibody heavy chain of SEQ ID NO:151 and an antibody light chain of SEQ ID NO:152, optionally including the heavy chains listed in the previous sentence, the light chain can include the light chain of SEQ ID NO:81, SEQ ID NOs:122-124, or SEQ ID NO:152.

In certain illustrative embodiments, the conditionally active ASTR binds to the same epitope of Ror2 as an antibody comprising an antibody heavy chain of SEQ ID NO:82 or SEQ ID NO:83 and an antibody comprising an antibody light chain of SEQ ID NO:84, and includes an antibody heavy chain variable region of any one of SEQ ID NOs:120-121 and 82-83. In these illustrative embodiment where the conditionally active ASTR binds to the same epitope of Ror2 as an antibody comprising an antibody heavy chain of SEQ ID NO:82 or SEQ ID NO:83 and an antibody comprising an antibody light chain of SEQ ID NO:84, optionally including the heavy chains listed in the previous sentence, the light chance can include the light chain of SEQ ID NOs:84 or 86.

Exemplary conditionally active CARs (CAB-CARs) that have increased binding to Ror2 at pH 6.7 compared to pH 7.4 are found in Example 1 herein. In illustrative embodiments, the CAR or ASTR can bind to the same epitope of Ror2 as a single-chain variable antibody fragment comprising an antibody heavy chain of SEQ ID NO:82 or SEQ ID NO:83 and an antibody light chain of SEQ ID NO:84 or the CAR or ASTR can bind to the same epitope of Ror2 as a single-chain variable antibody fragment comprising an antibody heavy chain of SEQ ID NO:151 and an antibody light chain of SEQ ID NO:152. In further embodiments of such illustrative embodiments, the anti-Ror2 CAR or ASTR comprises or is a single chain variable fragment (scFv) and in further illustrative examples, comprises a light chain that is N terminal to a heavy chain, or comprises a heavy chain that is N-terminal to a light chain. In any of the embodiments herein that includes a CAR or ASTR, and in illustrative embodiments binds to the same epitope of Ror2 as a single-chain variable antibody fragment comprising an antibody heavy chain of SEQ ID NO:82 or SEQ ID NO:83 and an antibody light chain of SEQ ID NO:84 or binds to the same epitope of Ror2 as a single-chain variable antibody fragment comprising an antibody heavy chain of SEQ ID NO:151 and an antibody light chain of SEQ ID NO:152, the ASTR can include any of SEQ ID NOs:130-132, or 153-158. Furthermore, anti-Ror2 CARs of any of the embodiments herein can include any of the CAR components provided herein. In certain exemplary embodiments, the anti-Ror2 CARs can include the CAR components listed in Table 2 and can be any of the CARs in Table 2. More typically for any embodiments herein that include an anti-Ror2 CAR, the CAR is a CAB-CAR, and in non-limiting illustrative embodiments, can include, for example, any of the CAB-CAR components and CAB-CARs provided in Table 2 that demonstrated cytotoxic activity. For example, the anti-Ror2 CAB-CAR can include a CD8 signal peptide, a CD8 or CD28 stalk/transmembrane domain, a CD137 co-stimulatory domain, and/or a CD3Z activation domain. Furthermore, illustrative CARs for any of the embodiments herein that includes an anti-Ror2 CAR and especially an anti-Ror2 CAB-CAR, in non-limiting illustrative embodiments include any of the anti-Ror2 CAB-CARs that demonstrated conditional cytotoxic activity in Table 2. Such illustrative CAB-CARs include F1-1-9, F1-1-10, F1-1-11, F1-1-12, F1-1-15, F1-1-17, F1-1-18, F1-1-19, F1-1-20, F1-1-21, F1-1-23, F1-1-25, or F1-1-26. In any of the embodiments herein that includes an anti-Ror2 ASTR, the ASTR can include the ASTR of F1-1-9, F1-1-10, F1-1-11, F1-1-12, F1-1-15, F1-1-17, F1-1-18, F1-1-19, F1-1-20, F1-1-21, F1-1-23, F1-1-25, or F1-1-26 of Table 2. Furthermore, illustrative CARs for any of the embodiments herein that includes an anti-Ror2 CAR and especially an anti-Ror2 CAB-CAR, in non-limiting illustrative embodiments include any of the anti-Ror2 CAB-CARs that demonstrated high conditional cytotoxic activity in Table 2. Such illustrative CAB-CARs include F1-1-11, F1-1-12, F1-1-15, F1-1-17, F1-1-19, F1-1-20, or F1-1-23. Accordingly, in any of the embodiments herein that includes an anti-Ror2 ASTR, the ASTR can include the ASTR of F1-1-11, F1-1-12, F1-1-15, F1-1-17, F1-1-19, F1-1-20, F1-1-23.

More generally, with respect to any of the embodiments provided herein, whether directed to Axl or Ror2, the ASTR can be a single-chain antibody, an Fab fragment, an Fab' fragment, an (Fab')2 fragment, an Fv fragment, a divalent single-chain antibody, or a diabody. In illustrative embodiments, the conditionally active ASTR that binds Ror2 is a single-chain variable fragment comprising a heavy chain and a light chain.

The heavy chain variable region polypeptides and light chain variable region polypeptides disclosed herein were identified from a parent antibody through the method disclosed in U.S. Pat. No. 8,709,755. A skilled artisan can utilize the method for identifying conditionally active antibodies disclosed in U.S. Pat. No. 8,709,755 to identify additional conditionally active antibodies and antibody fragments that can be used in ASTRs for CAB-CARs of the present disclosure.

Amino acid sequences of the heavy chain variable regions of some exemplary ASTRs are shown in SEQ ID NOs:115-121. The amino acid sequences of the light chain variable regions of these exemplary ASTRs are shown in SEQ ID NOs:81, 86, and 122-124. These heavy chain variable regions and light chain variable regions can specifically bind to human Ror2. Antibodies or antibody fragments including any one of these heavy chain variable regions and light chain variable regions have been found to have higher binding affinity to Ror2 at a pH in the tumor microenvironment than at a pH in a non-tumor microenvironment or in physiological conditions. For example, the antibodies and antibody fragments have a higher binding affinity to Ror2 at pH 6.0 than at pH 7.4. In some embodiments, the antibodies and antibody fragments have a higher binding affinity to Ror2 at pH 6.7 than at pH 7.4.

The anti-Ror2 antibodies or antibody fragments have a higher binding affinity to Ror2 in a tumor in comparison with their binding affinity to Ror2 in a normal tissue. These anti-Ror2 antibodies or antibody fragments are believed to have a longer half-life and reduced side-effects, as well as comparable efficacy, in comparison with monoclonal anti-Ror2 antibodies known in the art. These features permit use of a higher dosage of these anti-Ror2 antibodies or antibody fragments to be delivered to a patient thus being a more effective therapeutic option.

Though the ASTR can include the heavy chain variable regions and light chain variable regions having amino acid sequences with SEQ ID NOs:81, 86, and 115-124, the present invention also provides variants thereof that can specifically bind to human Ror2. In order to derive these variants, the complementarity determining regions (CDRs) of the heavy chain variable regions (H1-H3) and the complementarity determining regions of the light chain variable regions (L1-L3) should remain intact. However, the amino acid sequence of the heavy chain variable regions and light chains variable regions outside of the complementarity determining regions may be mutated in accordance with the principles of substitution, insertion and deletion. The variants of the heavy chain variable regions and light chain variable regions may be prepared by introducing appropriate modifications into the nucleotide sequence encoding the heavy chain variable regions and light chain variable regions, or by peptide synthesis. Such modifications include, for example, deletions from, and/or insertions into and/or substitutions of residues within the amino acid sequences of the heavy chain variable regions and light chain variable regions. Any combination of deletion, insertion, and substitution can be made to arrive at the ASTR for the CARs, provided that they possess the desired characteristics, e.g., conditional antigen-binding to human Ror2.

Multispecific ASTRs

In some embodiments, the ASTR can be multispecific, e.g. bispecific antibodies. Multispecific antibodies have binding specificities for at least two different sites or targets. In certain embodiments, one of the binding specificities is for Axl or Ror2 and the other is for another antigen. In certain embodiments, bispecific antibodies may bind to two different epitopes of Axl or Ror2. Bispecific antibodies may also be used to localize cytotoxic agents to cells which express Axl or Ror2. Bispecific antibodies can be prepared as full length antibodies or antibody fragments. In certain embodiments, one of the binding specificities binds to Axl and the other binds to Ror2, where neither, either or both can be conditionally active.

An ASTR suitable for use in a CAR of the present disclosure can have a variety of antigen-binding specificities. In illustrative embodiments, the ASTR binds to Axl or Ror2, which are known to be expressed on certain cancer cells (i.e. cancer-specific antigens). In some cases, the ASTR is bispecific, and in addition to an antigen-binding domain that binds Axl or Ror2, typically in a conditionally active manner, the ASTR can include a second antigen-binding domain that is specific for a second antigen that is expressed by (synthesized by) a cancer cell, i.e., a cancer cell associated antigen. The cancer cell associated antigen can be an antigen associated with, e.g., a breast cancer cell, a B cell lymphoma, a Hodgkin lymphoma cell, an ovarian cancer cell, a prostate cancer cell, a mesothelioma, a lung cancer cell (e.g., a small cell lung cancer cell), a non-Hodgkin B-cell lymphoma (B-NHL) cell, an ovarian cancer cell, a prostate cancer cell, a mesothelioma cell, a lung cancer cell (e.g., a small cell lung cancer cell), a melanoma cell, a chronic lymphocytic leukemia cell, an acute lymphocytic leukemia cell, a neuroblastoma cell, a glioma, a glioblastoma, a medulloblastoma, a colorectal cancer cell, etc. A cancer cell associated antigen may also be expressed by a non-cancerous cell.

Non-limiting examples of antigens to which a bispecific ASTR of a CAR can bind in addition to Axl or Ror2, include, e.g., CD19, CD20, CD38, CD30, ERBB2, CA125, MUC-1, prostate-specific membrane antigen (PSMA), CD44 surface adhesion molecule, mesothelin, carcinoembryonic antigen (CEA), epidermal growth factor receptor (EGFR), EGFRvIII, vascular endothelial growth factor receptor-2 (VEGFR2), high molecular weight-melanoma associated antigen (HMW-MAA), MAGE-A1, IL-13R-a2, GD2, and the like.

In some cases, a member of a specific binding pair suitable for use in a subject bispecific ASTR of a CAR in addition to a specific binding pair member that binds Axl or Ror2, binds a ligand for a receptor. Ligands include, but are not limited to, cytokines (e.g., IL-13, etc.); growth factors (e.g., heregulin; vascular endothelial growth factor (VEGF); and the like); an integrin-binding peptide (e.g., a peptide comprising the sequence Arg-Gly-Asp); and the like.

Where the member of a specific binding pair in a subject bispecific CAR is a ligand, the CAR can be activated in the presence of a second member of the specific binding pair, where the second member of the specific binding pair is a receptor for the ligand. For example, where the ligand is VEGF, the second member of the specific binding pair can be a VEGF receptor, including a soluble VEGF receptor.

As noted above, in some cases, the member of a specific binding pair that is included in a subject bispecific CAR is an ASTR that is a receptor, e.g., a receptor for a ligand, a co-receptor, etc. The receptor can be a ligand-binding fragment of a receptor. Suitable receptors include, but are not limited to, a growth factor receptor (e.g., a VEGF receptor); a killer cell lectin-like receptor subfamily K, member 1 (NKG2D) polypeptide (receptor for MICA, MICB, and ULB6); a cytokine receptor (e.g., an IL-13 receptor; an IL-2 receptor; etc.); CD27; a natural cytotoxicity receptor (NCR) (e.g., NKP30 (NCR3/CD337) polypeptide (receptor for HLA-B-associated transcript 3 (BAT3) and B7-H6); etc.); etc.

Stalk Region

In some cases, the CAR includes a hinge domain (also referred to herein as a "spacer" or a "stalk") which is located in the CAR portion outside the cell and interposed between the ASTR and the transmembrane domain. In illustrative embodiments, the hinge domain is a CD8 stalk domain or a CD28 stalk domain. In some cases, the stalk domain has at least 85, 90, 95, 96, 97, 98, 99, or 100% identity to a wild-type CD8 stalk region (TTTPAPRPPTPAPTIA-SQPLSLRPEACRPAAGG AVHTRGLDFA (SEQ ID NO:125)), has at least 85, 90, 95, 96, 97, 98, 99, or 100% identity to a wild-type CD28 stalk region (FCKIEVMYPP-PYLDNEKSNGTIIHVKGKHLCPSPLFPGPSKP (SEQ ID NO:126)) or has at least 85, 90, 95, 96, 97, 98, 99, or 100% identity to a wild-type immunoglobulin heavy chain hinge/stalk region. In some cases, the stalk domain is a hinge region polypeptide derived from a receptor (e.g., a CDS-derived hinge region). In a CAR, the stalk employed allows the conditionally active antigen-specific targeting region, and typically the entire CAR, to retains its increased binding to Ror2 or Axl property, in an in vitro tumor surrogate assay condition relative to a corresponding physiological condition.

The stalk region can have a length of from about 4 amino acids to about 50 amino acids, e.g., from about 4 aa to about 10 aa, from about 10 aa to about 15 aa, from about 15 aa to about 20 aa, from about 20 aa to about 25 aa, from about 25 aa to about 30 aa, from about 30 aa to about 40 aa, or from about 40 aa to about 50 aa.

In some cases, the hinge region of a subject CAR includes at least one cysteine. For example, in some cases, the hinge region can include the sequence Cys-Pro-Pro-Cys (SEQ ID NO:62). If present, a cysteine in the hinge region of a first CAR can be available to form a disulfide bond with a hinge region in a second CAR.

Immunoglobulin hinge/stalk region amino acid sequences are known in the art; see, e.g., Tan et al. (1990) *Proc. Natl. Acad. Sci. USA* 87:162; and Huck et al. (1986) *Nucl. Acids Res.* 14:1779. As non-limiting examples, an immunoglobulin hinge region can include a domain with at least 50, 60, 70, 75, 80, 85, 90, 95, 96, 97, 98, 99 or 100% sequence identity to a stretch of at least 10, 15, 20, or all of the amino acids of any of the following amino acid sequences: DKTHT (SEQ ID NO:63); CPPC (SEQ ID NO:62); CPEPKSCDTPPPCPR (SEQ ID NO:64) (see, e.g., Glaser et al. (2005) *J. Biol. Chem.* 280:41494); ELKTPLGDTTHT (SEQ ID NO:65); KSCDKTHTCP (SEQ ID NO:66); KCCVDCP (SEQ ID NO:67); KYGPPCP (SEQ ID NO:68); EPKSCDKTHTCPPCP (SEQ ID NO:69) (human IgG1 hinge); ERKCCVECPPCP (SEQ ID NO:70) (human IgG2 hinge); ELKTPLGDTTHTCPRCP (SEQ ID NO:71) (human IgG3 hinge); SPNMVPHAHHAQ (SEQ ID NO:72) (human IgG4 hinge); and the like. The hinge region can include an amino acid sequence of a human IgG1, IgG2, IgG3, or IgG4, hinge region. The hinge region can include one or more amino acid substitutions and/or insertions and/or deletions compared to a wild-type (naturally-occurring) hinge region. For example, His229 of human IgG 1 hinge can be substituted with Tyr, so that the hinge region includes the sequence EPKSCDKTYTCPPCP; see, e.g., Yan et al. (2012) *J. Biol. Chem.* 287:5891. The hinge region can include an amino acid sequence derived from human CD8; e.g., the hinge region can include the amino acid sequence: TTTPAPRPPTPAPTIASQPLSLRPEACRPAAGGAVHTR-GLDFACD (SEQ ID NO:73), or a variant thereof.

Transmembrane Domain

The CAR of the present disclosure includes transmembrane domains for insertion into a eukaryotic cell membrane. The transmembrane domain can be interposed between the ASTR and the co-stimulatory domain. The transmembrane domain can be interposed between the hinge region and the co-stimulatory domain, such that the chimeric antigen receptor includes, in order from the amino terminus (N-terminus) to the carboxyl terminus (C-terminus): an ASTR; a hinge region; a transmembrane domain; and an activating domain.

Any transmembrane (TM) domain that provides for insertion of a polypeptide into the cell membrane of a eukaryotic (e.g., mammalian) cell is suitable for use in aspects and embodiments disclosed herein. In certain embodiments provided herein, the TM domain for any aspect provided herein that includes a CAR, is a C* alpha TM domain, a CD8 TM domain, a CD4 TM domain, a C3Z TM domain, a C28 TM domain, a C134 TM domain, a CD7 TM domain, a CD8 TM domain, or a CD28 TM domain Illustrative embodiments of CARs provided herein include a CD8 TM domain or a CD28 TM domain. Further non-limiting examples of TM domains suitable for any of the aspects or embodiments provided herein, include a domain with at least 50, 60, 70, 75, 80, 85, 90, 95, 96, 97, 98, 99 or 100% sequence identity to a stretch of at least 10, 15, 20, or all of the amino acids of any of the following TM domains:

a) CD8 alpha
(IYIWAPLAGTCGVLLLSLVITLYC (SEQ ID NO: 46));

b) CD8 beta
(LGLLVAGVLVLLVSLGVAIHLCC (SEQ ID NO: 47));

c) CD4
(ALIVLGGVAGLLLFIGLGIFFCVRC (SEQ ID NO: 48));

d) CD3Z
(LCYLLDGILFIYGVILTALFLRV (SEQ ID NO: 49);

e) CD28
(FWVLVVVGGVLACYSLLVTVAFIIFWV (SEQ ID NO: 50));

f) CD134 (OX40):
(VAAILGLGLVLGLLGPLAILLALYLL (SEQ ID NO: 51));

g) CD7
(ALPAALAVISFLLGLGLGVACVLA (SEQ ID NO: 52)), h) CD8 alpha stalk and TM
(TTTPAPRPPTPAPTIASQPLSLRPEACRPAAGGAVHTRGLDFACDIYIW APLAGTCGVLLLSLVITLYC (SEQ ID NO: 75)),
and i) CD28 stalk and TM
(IEVMYPPPYLDNEKSNGTIIHVKGKHLCPSPLFPGPSKPFWVLVVVGGV LACYSLLVTVAFIIFWV (SEQ ID NO: 76)).

As non-limiting examples, a transmembrane domain of an aspect of the invention can have at least 80, 90, or 95% sequence identity to the SEQ ID NO:46 transmembrane domain, the CD8 beta transmembrane domain, the CD4 transmembrane domain, the CD3 zeta transmembrane domain, the CD28 transmembrane domain, the CD134 transmembrane domain, or the CD7 transmembrane domain.

CAR Linkers

In some cases, the CAR includes a linker between any two adjacent domains. For example, a linker can be between the transmembrane domain and the first co-stimulatory domain. As another example, the ASTR can be an antibody and a linker can be between the heavy chain and the light chain. As another example, a linker can be between the ASTR and the transmembrane domain and a co-stimulatory domain. As another example, a linker can be between the co-stimulatory domain and the intracellular activating domain of the second polypeptide.

The linker peptide may have any of a variety of amino acid sequences. Proteins can be joined by a spacer peptide, generally of a flexible nature, although other chemical linkages are not excluded. A linker can be a peptide of between about 1 and about 100 amino acids in length, or between about 1 and about 25 amino acids in length. These linkers can be produced by using synthetic, linker-encoding oligonucleotides to couple the proteins. Peptide linkers with a degree of flexibility can be used. The linking peptides may have virtually any amino acid sequence, bearing in mind that suitable linkers will have a sequence that results in a generally flexible peptide. The use of small amino acids, such as glycine and alanine, are of use in creating a flexible peptide. The creation of such sequences is routine to those of skill in the art.

Suitable linkers can be readily selected and can be of any of a suitable of different lengths, such as from 1 amino acid (e.g., Gly) to 20 amino acids, from 2 amino acids to 15 amino acids, from 3 amino acids to 12 amino acids, including 4 amino acids to 10 amino acids, 5 amino acids to 9 amino acids, 6 amino acids to 8 amino acids, or 7 amino acids to 8 amino acids, and may be 1, 2, 3, 4, 5, 6, or 7 amino acids.

Exemplary flexible linkers include glycine polymers (G)$_n$, glycine-serine polymers (including, for example, (GS)$_n$, GSGGS$_n$, GGGS$_n$, and GGGGS$_n$ where n is an integer of at least one), glycine-alanine polymers, alanine-serine polymers, and other flexible linkers known in the art. Glycine and glycine-serine polymers are of interest since both of these amino acids are relatively unstructured, and therefore may serve as a neutral tether between components. Glycine polymers are of particular interest since glycine accesses significantly more phi-psi space than even alanine, and is much less restricted than residues with longer side chains (see Scheraga, *Rev. Computational Chem.* 11173-142 (1992)). Exemplary flexible linkers include, but are not limited GGGGSGGGGSGGGGS (SEQ ID NO:53), GGGGSGGGGSGGGGSGGGGSGGGGSGGGGS (SEQ ID NO:54), GGGGSGGGGSGGGGS (SEQ ID NO:55), GGSG (SEQ ID NO:56), GGSGG (SEQ ID NO:57), GSGSG (SEQ ID NO:58), GSGGG (SEQ ID NO:59), GGGGG (SEQ ID NO:60), GSSSG (SEQ ID NO:61), and the like. The ordinarily skilled artisan will recognize that design of a peptide conjugated to any elements described above can include linkers that are all or partially flexible, such that the linker can include a flexible linker as well as one or more portions that confer less flexible structure.

Modulatory Domains

Modulatory domains can change the effect of the activating domain in the CAR, including enhancing or dampening the downstream effects of the activating domain or changing the nature of the response. Modulatory domains suitable for use in a CAR of the present disclosure, and included in certain illustrative embodiments of any aspect herein that includes a CAR, include co-stimulatory domains. In some embodiments, a CAR can have more than one modulatory domain (e.g. co-stimulatory domain) or a modulatory domain (e.g. co-stimulatory domain) of a CAR can be derived from more than one polypeptide. A modulatory domain (e.g. co-stimulatory domain) suitable for inclusion in the CAR can have a length of from about 30 amino acids to about 70 amino acids (aa), e.g., a modulatory domain (e.g. co-stimulatory domain) can have a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa. In other cases, modulatory domain can have a length of from about 70 aa to about 100 aa, from about 100 aa to about 200 aa, or greater than 200 aa.

Co-stimulatory domains typically enhance and/or change the nature of the response to activation of an activation domain. Co-stimulatory domains suitable for use in a CAR of the present disclosure are generally polypeptides derived from receptors. In some embodiments, co-stimulatory domains homodimerize. A subject co-stimulatory domain can be an intracellular portion of a transmembrane protein (i.e., the co-stimulatory domain can be derived from a transmembrane protein). Non-limiting examples of suitable co-stimulatory polypeptides include, but are not limited to, 4-1BB (CD137), B7-H3, CD2, CD7, CD27, CD28, CD28 deleted for Lck binding (ICΔ), ICOS, OX40, BTLA, CD27, CD30, CD40, GITR, HVEM, LFA-1, LIGHT, NKG2C, PD-1, TILR2, TILR4, TILR7, TILR9, Fc receptor gamma chain, Fc receptor ε chain, or a ligand that specifically binds with CD83. For example, a co-stimulatory domain of an aspect of the invention can have at least 80%, 90%, or 95% sequence identity to the co-stimulatory domain of 4-1BB (CD137), CD27, CD28, CD28 deleted for Lck binding (ICΔ), ICOS, OX40, BTLA, CD27, CD30, GITR, or HVEM. In some embodiments, a CAR can include more than one co-stimulatory domain, for example, a CAR can include a co-stimulatory domain from ICA and a co-stimulatory domain from 4-1BB (CD137), In some cases, the co-stimulatory domain is derived from an intracellular portion of the transmembrane protein CD137 (also known as TNFRSF9; CD137; 4-1BB; CDw137; ILA; etc.). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence:

(SEQ ID NO: 1)
KRGRKKLLYIFKQPFMRPVQTTQEEDGCSCRFPEEEEGGCEL.

In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein CD28 (also known as Tp44). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence: RSKRSRLLHSDYMNMTPRRPGPTRKHYQPYAPPRD-FAAYRS (SEQ ID NO:2). In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein CD28 deleted for Lck binding (ICΔ). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence: RSKRSRLLHSDYMNMTPRRPGP-TRKHYQAYAAARDFAAYRS (SEQ ID NO:3). In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein ICOS (also known as AILIM, CD278, and CVID1). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence: TKKKYSSSVHDPNGEYMFM-RAVNTAKKSRLTDVTL (SEQ ID NO:4). In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein OX40 (also known as TNFRSF4, RP5-902P8.3, ACT35, CD134, OX-40, TXGP1L). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence:

(SEQ ID NO: 5)
RRDQRLPPDAHKPPGGGSFRTPIQEEQADAHSTLAKI.

In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain is derived from an intracellular portion of the transmembrane protein CD27 (also known as S 152, T 14, TNFRSF7, and Tp55). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence:

(SEQ ID NO: 6)
HQRRKYRSNKGESPVEPAEPCRYSCPREEEGSTIPIQEDYRKPEPACSP.

In some of these embodiments, the co-stimulatory domain has a length of from about 30 aa to about 35 aa, from about 35 aa to about 40 aa, from about 40 aa to about 45 aa, or from about 45 aa to about 50 aa.

In some cases, the co-stimulatory domain is derived from an intracellular portion of the transmembrane protein BTLA (also known as BTLA1 and CD272). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence:

(SEQ ID NO: 7)
CCLRRHQGKQNELSDTAGREINLVDAHLKSEQTEASTRQNSQVLLSETGI

YDNDPDLCFRMQEGSEVYSNPCLEENKPGIVYASLNHSVIGPNSRLARNV

KEAPTEYASICVRS.

In some cases, the co-stimulatory domain is derived from an intracellular portion of the transmembrane protein CD30 (also known as TNFRSF8, D1S166E, and Ki-1). For example, a suitable co-stimulatory domain can include a domain with at least 50%, 60%, 70%, 75%, 80%, 85%, 90%, 95%, 96%, 97%, 98%, 99% or 100% sequence identity to a stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, from about 150 aa to about 160 aa, or from about 160 aa to about 185 aa of the following amino acid sequence:

(SEQ ID NO: 8)
RRACRKRIRQKLHLCYPVQTSQPKLELVDSRPRRSSTQLRSGASVTEPVA

EERGLMSQPLMETCHSVGAAYLESLPLQDASPAGGPSSPRDLPEPRVSTE

HTNNKIEKIYIMKADTVIVGTVKAELPEGRGLAGPAEPELEEELEADHTP

HYPEQETEPPLGSCSDVMLSVEEEGKEDPLPTAASGK.

In some cases, the co-stimulatory domain is derived from an intracellular portion of the transmembrane protein GITR (also known as TNFRSF18, RP5-902P8.2, AITR, CD357, and GITR-D). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence:

(SEQ ID NO: 9)
HIWQLRSQCMWPRETQLLLEVPPSTEDARSCQFPEEERGERSAEEKGRLG

DLWV.

In some of these embodiments, the co-stimulatory domain has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

In some cases, the co-stimulatory domain derived from an intracellular portion of the transmembrane protein HVEM (also known as TNFRSF14, RP3-395M20.6, ATAR, CD270, HVEA, HVEM, LIGHTR, and TR2). For example, a suitable co-stimulatory domain can include a domain with at least 50%, 60%, 70%, 75%, 80%, 85%, 90%, 95%, 96%, 97%, 98%, 99% or 100% sequence identity to a stretch of at least 10, 15, 20, or all of the amino acids in the following amino acid sequence: CVKRRKPRGDVVKVIVSVQRKRQEAEGEAT-VIEALQAPPDVTTVAVEETIPSFTGRSPNH (SEQ ID NO:10). In some of these embodiments, the co-stimulatory domain of both the first and the second polypeptide has a length of from about 30 aa to about 35 aa, from about 35 aa to about 40 aa, from about 40 aa to about 45 aa, from about 45 aa to about 50 aa, from about 50 aa to about 55 aa, from about 55 aa to about 60 aa, from about 60 aa to about 65 aa, or from about 65 aa to about 70 aa.

Intracellular Activating Domain

Intracellular activating domains suitable for use in a CAR of the present disclosure when activated, typically induce the production of one or more cytokines; increased cell death; and/or increased proliferation of $CD8^+$ T cells, $CD4^+$ T cells, natural killer T cells, γδ T cells, and/or neutrophils. In some embodiments, the intracellular activating domain includes at least one (e.g., one, two, three, four, five, six, etc.) ITAM motifs as described below. Intracellular activating domains can be referred to herein as activating domains or activation domains. The intracellular activating domains for use in an engineered signaling polypeptide can include intracellular signaling domains of several types of immune signaling receptors, including T cell signaling proteins such as CD3, B7 family co-stimulatory, and Tumor Necrosis Factor receptor (TNFR) superfamily receptors; signaling domains used by NK and NKT cells such as NKp30 (B7-H6), DAP12, NKG2D, NKp44, NKp46, DAP10, and CD3z;

and the signaling domains of human immunoglobulin receptors that contain immunoreceptor tyrosine based activation motifs (ITAM) such as FcgammaRI, FcgammaRIIA, FcgammaRIIC, FcgammaRIIIA, and FcRL5. As such, in certain embodiments of CARs for any of aspects of the present disclosure, the intracellular activating domain is a signaling domain from NKp30 (B7-H6), DAP12, NKG2D, NKp44, NKp46, DAP10, CD3z, FcgammaRI, FcgammaRIIA, FcgammaRIIC, FcgammaRIIIA, or FcRL5. These are referred to herein as an NKp30 (B7-H6) activating domain, a DAP12 activating domain, an NKG2D activating domain, an NKp44 activating domain, an NKp46 activating domain, a DAP10 activating domain, a CD3z activating domain, a FcgammaRI activating domain, a FcgammaRIIA activating domain, an FcgammaRIIC activating domain, an FcgammaRIIIA activating domain, or an FcRL5 activating domain, respectively.

In some embodiments, the intracellular activating domain includes DAP10/CD28 type signaling chains. In some embodiments, the intracellular activating domain is not covalently attached to the membrane bound CAR, but is instead diffused in the cytoplasm. As non-limiting examples, an intracellular activating domain of any aspect of the invention that includes a CAR can be a CD3Z activating domain, a CD3D activating domain, a CD3E activating domain, a CD3G activating domain, a CD79A activating domain, a DAP12 activating domain, a FCER1G activating domain, a DAP10/CD28 activating domain, or a ZAP70 activating domain. As non-limiting examples, an intracellular activating domain of any aspect of the invention that includes a CAR can have at least 80%, 90%, or 95% sequence identity to the CD3Z, CD3D, CD3E, CD3G, CD79A, DAP12, FCER1G, DAP10/CD28, or ZAP70 domains as described below.

ITAMs

Intracellular activating domains suitable for use in a CAR of the present disclosure include immunoreceptor tyrosine-based activation motif (ITAM)-containing intracellular signaling polypeptides. An ITAM motif is YX$_1$X$_2$L/I, where X$_1$ and X$_2$ are independently any amino acid. In some cases, the intracellular activating domain of a subject CAR includes 1, 2, 3, 4, or 5 ITAM motifs. In some cases, an ITAM motif is repeated twice [in an intracellular activating domain, where the first and second instances of the ITAM motif are separated from one another by 6 to 8 amino acids, e.g., (YX$_1$X$_2$L/I)(X$_3$)$_n$(YX$_1$X$_2$L/I), where n is an integer from 6 to 8, and each of the 6-8 X$_3$ can be any amino acid. In some cases, the intracellular activating domain of a subject CAR includes 3 ITAM motifs.

A suitable intracellular activating domain can be an ITAM motif-containing portion that is derived from a polypeptide that contains an ITAM motif. For example, a suitable intracellular activating domain can be an ITAM motif-containing domain from any ITAM motif-containing protein. Thus, a suitable intracellular activating domain need not contain the entire sequence of the entire protein from which it is derived. Examples of suitable ITAM motif-containing polypeptides include, but are not limited to: CD3Z (CD3 zeta); CD3D (CD3 delta); CD3E (CD3 epsilon); CD3G (CD3 gamma); CD79A (antigen receptor complex-associated protein alpha chain); DAP12; and FCER1G (Fc epsilon receptor I gamma chain).

In some cases, the intracellular activating domain is derived from T-cell surface glycoprotein CD3 zeta chain (also known as CD3Z, T-cell receptor T3 zeta chain, CD247, CD3-ZETA, CD3H, CD3Q, T3Z, TCRZ, etc.). For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences (2 isoforms):

(SEQ ID NO: 11)
MKWKALFTAAILQAQLPITEAQSFGLLDPKLCYLLDGILFIYGVILTALF

LRVKFSRSADAPAYQQGQNQL[YNELNLGRREEYDVL]DKRRGRDPEMGG

KPRRKNPQEGL[YNELQKDKMAEAYSEI]GMKGERRRGKGHDGL[YQGLS

TATKDTYDAL]HMQALPPR or (SEQ ID NO: 12)
MKWKALFTAAILQAQLPITEAQSFGLLDPKLCYLLDGILFIYGVILTALF

LRVKFSRSADAPAYQQGQNQL[YNELNLGRREEYDVL]DKRRGRDPEMGG

KPQRRKNPQEGL[YNELQKDKMAEAYSEI]GMKGERRRGKGHDGL[YQGL

STATKDTYDAL]HMQALPPR, where the ITAM motifs are set out with brackets.

Likewise, a suitable intracellular activating domain polypeptide can include an ITAM motif-containing a portion of the full length CD3 zeta amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences:

(SEQ ID NO: 13)
RVKFSRSADAPAYQQGQNQL[YNELNLGRREEYDVL]DKRRGRDPEMGGK

PRRKNPQEGL[YNELQKDKMAEAYSEI]GMKGERRRGKGHDGL[YQGLST

ATKDTYDAL]HMQALPPR;

(SEQ ID NO: 127)
RVKFSRSADAPAYQQGQNQL[YNELNLGRREEYDVL]DKRRGRDPEMGGK

PQRRKNPQEGL[YNELQKDKMAEAYSEI]GMKGERRRGKGHDGL[YQGLS

TATKDTYDAL]HMQALPPR;

SEQ ID NO: 14)
NQL[YNELNLGRREEYDVL]DKR;

(SEQ ID NO: 15)
EGL[YNELQKDKMAEAYSEI]GMK;

or (SEQ ID NO: 16)
DGL[YQGLSTATKDTYDAL]HMQ, where the ITAM motifs are set out with brackets.

In some cases, the intracellular activating domain is derived from T-cell surface glycoprotein CD3 delta chain (also known as CD3D; CD3-DELTA; T3D; CD3 antigen, delta subunit; CD3 delta; CD3d antigen, delta polypeptide (TiT3 complex); OKT3, delta chain; T-cell receptor T3 delta chain; T-cell surface glycoprotein CD3 delta chain; etc.). Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences:

(SEQ ID NO: 17)
MEHSTFLSGLVLATLLSQVSPFKIPIEELEDRVFVNCNTSITWVEGTVGT

LLSDITRLDLGKRILDPRGIYRCNGTDIYKDKESTVQVHYRMCQSCVELD

PATVAGIIVTDVIATLLLALGVFCFAGHETGRLSGAADTQALLRNDQV[Y

QPLRDRDDAQYSHL]GGNWARNK or (SEQ ID NO: 18)
MEHSTFLSGLVLATLLSQVSPFKIPIEELEDRVFVNCNTSITWVEGTVGT

LLSDITRLDLGKRILDPRGIYRCNGTDIYKDKESTVQVHYRTADTQALLR

NDQV[YQPLRDRDDAQYSHL]GGNWARNK, where the ITAM motifs are set out with brackets.

Likewise, a suitable intracellular activating domain polypeptide can comprise an ITAM motif-containing portion of the full length CD3 delta amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: DQV[YQPLRDRDDAQYSHL]GGN (SEQ ID NO: 19), where the ITAM motifs are set out with brackets.

In some cases, the intracellular activating domain is derived from T-cell surface glycoprotein CD3 epsilon chain (also known as CD3e, T-cell surface antigen T3/Leu-4 epsilon chain, T-cell surface glycoprotein CD3 epsilon chain, AI504783, CD3, CD3epsilon, T3e, etc.). Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of the following amino acid sequence:

(SEQ ID NO: 20)
MQSGTHWRVLGLCLLSVGVWGQDGNEEMGGITQTPYKVSISGTTVILTCP

QYPGSEILWQHNDKNIGGDEDDKNIGSDEDHLSLKEFSELEQSGYYVCYP

RGSKPEDANFYLYLRARVCENCMEMDMSVATIVIVDICITGGLLLLVYYW

SKNRKAKAKPVTRGAGAGGRQRGQNKERPPPVPNPD[YEPIRKGQRDLYS

GL]NQRRI, where the ITAM motifs are set out with brackets.

Likewise, a suitable intracellular activating domain polypeptide can comprise an ITAM motif-containing portion of the full length CD3 epsilon amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: NPD[YEPIRKGQRDLYSGL]NQR (SEQ ID NO:21), where the ITAM motifs are set out with brackets.

In some cases, the intracellular activating domain is derived from T-cell surface glycoprotein CD3 gamma chain (also known as CD3G, T-cell receptor T3 gamma chain, CD3-GAMMA, T3G, gamma polypeptide (TiT3 complex), etc.). Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of the following amino acid sequence:

(SEQ ID NO: 22)
MEQGKGLAVLILAIILLQGTLAQSIKGNHLVKVYDYQEDGSVLLTCDAEA

KNITWFKDGKMIGFLTEDKKKWNLGSNAKDPRGMYQCKGSQNKSKPLQVY

YRMCQNCIELNAATISGFLFAEIVSIFVLAVGVYFIAGQDGVRQSRASDK

QTLLPNDQL[YQPLKDREDDQYSHL]QGNQLRRN, where the ITAM motifs are set out with brackets.

Likewise, a suitable intracellular activating domain polypeptide can comprise an ITAM motif-containing portion of the full length CD3 gamma amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: DQL[YQPLKDREDDQYSHL]QGN (SEQ ID NO:23), where the ITAM motifs are set out with brackets.

In some cases, the intracellular activating domain is derived from CD79A (also known as B-cell antigen receptor complex-associated protein alpha chain; CD79a antigen (immunoglobulin-associated alpha); MB-1 membrane glycoprotein; Ig-alpha; membrane-bound immunoglobulin-associated protein; surface IgM-associated protein; etc.). Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences:

(SEQ ID NO: 24)
MPGGPGVLQALPATIFLLFLLSAVYLGPGCQALWMHKVPASLMVSLGEDA

HFQCPHNSSNNANVTWWRVLHGNYTWPPEFLGPGEDPNGTLIIQNVNKSH

GGIYVCRVQEGNESYQQSCGTYLRVRQPPPRPFLDMGEGTKNRIITAEGI

ILLFCAVVPGTLLLFRKRWQNEKLGLDAGDEYEDENL[YEGLNLDDCSMY

EDI]SRGLQGTYQDVGSLNIGDVQLEKP or (SEQ ID NO: 25)
MPGGPGVLQALPATIFLLFLLSAVYLGPGCQALWMHKVPASLMVSLGEDA

HFQCPHNSSNNANVTWWRVLHGNYTWPPEFLGPGEDPNEPPPRPFLDMGE

GTKNRIITAEGIILLFCAVVPGTLLLFRKRWQNEKLGLDAGDEYEDENL

[YEGLNLDDCSMYEDI]SRGLQGTYQDVGSLNIGDVQLEKP, where the ITAM motifs are set out with brackets.

Likewise, a suitable intracellular activating domain polypeptide can comprise an ITAM motif-containing portion of the full length CD79A amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: ENL[YEGLNLDDCSMYEDI]SRG (SEQ ID NO:26), where the ITAM motifs are set out with brackets.

In some cases, the intracellular activating domain is derived from DAP12 (also known as TYROBP; TYRO protein tyrosine kinase binding protein; KARAP; PLOSL; DNAX-activation protein 12; KAR-associated protein; TYRO protein tyrosine kinase-binding protein; killer activating receptor associated protein; killer-activating receptor-associated protein; etc.). For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 100 amino acids to about 110 amino acids (aa), from about 110 aa to about 115 aa, from about 115 aa to about 120 aa, from about 120 aa to about 130 aa, from about 130 aa to about 140 aa, from about 140 aa to about 150 aa, or from about 150 aa to about 160 aa, of either of the following amino acid sequences (4 isoforms):

(SEQ ID NO: 27)
MGGLEPCSRLLLLPLLLAVSGLRPVQAQAQSDCSCSTVSPGVLAGIVMGD

LVLTVLIALAVYFLGRLVPRGRGAAEEAATRKQRITETESP[YQELQGQRS

DVYSDL]NTQRPYYK, (SEQ ID NO: 28)
MGGLEPCSRLLLLPLLLAVSGLRPVQAQAQSDCSCSTVSPGVLAGIVMGD

LVLTVLIALAVYFLGRLVPRGRGAAEATRKQRITETESP[YQELQGQRSD

VYSDL]NTQ, (SEQ ID NO: 29)
MGGLEPCSRLLLLPLLLAVSDCSCSTVSPGVLAGIVMGDLVLTVLIALAV

YFLGRLVPRGRGAAEATRKQRITETESP[YQELQGQRSDVYSDL]NTQR

PYYK, or (SEQ ID NO: 30)
MGGLEPCSRLLLLPLLLAVSDCSCSTVSPGVLAGIVMGDLVLTVLIALAV

YFLGRLVPRGRGAAEATRKQRITETESP[YQELQGQRSDVYSDL]NTQRP

YYK, where the ITAM motifs are set out with brackets.

Likewise, a suitable intracellular activating domain polypeptide can comprise an ITAM motif-containing portion of the full length DAP12 amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: ESP[YQELQGQRSDVYSDL]NTQ (SEQ ID NO:31), where the ITAM motifs are set out with brackets.

In some cases, the intracellular activating domain is derived from FCER1G (also known as FCRG; Fc epsilon receptor I gamma chain; Fc receptor gamma-chain; fc-epsilon RI-gamma; fcRgamma; fceRI gamma; high affinity immunoglobulin epsilon receptor subunit gamma; immunoglobulin E receptor, high affinity, gamma chain; etc.). For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 50 amino acids to about 60 amino acids (aa), from about 60 aa to about 70 aa, from about 70 aa to about 80 aa, or from about 80 aa to about 88 aa, of the following amino acid sequence:

(SEQ ID NO: 32)
MIPAVVLLLLLLVEQAAALGEPQLCYILDAILFLYGIVLTLLYCRLKIQV

RKAAITSYEKSDGV[YTGLSTRNQETYETL]KHEKPPQ, where the ITAM motifs are set out with brackets.

Likewise, a suitable intracellular activating domain polypeptide can comprise an ITAM motif-containing portion of the full length FCER1G amino acid sequence. Thus, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: DGV[YTGLSTRNQETYETL]KHE (SEQ ID NO:33), where the ITAM motifs are set out with brackets.

Intracellular activating domains suitable for use in a CAR of the present disclosure include a DAP10/CD28 type signaling chain. An example of a DAP10 signaling chain is the amino acid sequence is: RPRRSPAQDGKV[YINM]PGRG (SEQ ID NO:34). In some embodiments, a suitable intracellular activating domain includes a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence: RPRRSPAQDGKV[YINM]PGRG (SEQ ID NO:34), where a noteworthy motif is set out in brackets.

An example of a CD28 signaling chain is the amino acid sequence is FWVLVVVGGVLACYSLLVTVAFIIFWVR-SKRSRLLHSD[YMNM]TPRRPGPTRKHYQPYAPPRDF-AAYRS (SEQ ID NO:35). In some embodiments, a suitable intracellular domain includes a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequence:

(SEQ ID NO: 35)
FWVLVVVGGVLACYSLLVTVAFIIFWVRSKRSRLLHSD[YMNM]TPRRPG

PTRKHYQPYAPPRDFAAYRS.

Intracellular activating domains suitable for use in a CAR of the present disclosure include a ZAP70 polypeptide, For example, a suitable intracellular activating domain can include a domain with at least 50%, 60%, 70%, 75%, 80%, 85%, 90%, 95%, 96%, 97%, 98%, 99% or 100% sequence identity to a stretch of at least 10, 15, 20, or all amino acids in the following sequences or to a contiguous stretch of from about 300 amino acids to about 400 amino acids, from about 400 amino acids to about 500 amino acids, or from about 500 amino acids to 619 amino acids, of the following amino acid sequence:

(SEQ ID NO: 36)
MPDPAAHLPFFYGSISRAEAEEHLKLAGMADGLFLLRQCLRSLGGYVLSL

VHDVRFHHFPIERQLNGTYAIAGGKAHCGPAELCEFYSRDPDGLPCNLRK

PCNRPSGLEPQPGVFDCLRDAMVRDYVRQTWKLEGEALEQAIISQAPQVE

KLIATTAHERMPWYHSSLTREEAERKLYSGAQTDGKFLLRPRKEQGTYAL

SLIYGKTVYHYLISQDKAGKYCIPEGTKFDTLWQLVEYLKLKADGLIYCL

KEACPNSSASNASGAAAPTLPAHPSTLTHPQRRIDTLNSDGYTPEPARIT

SPDKPRPMPMDTSVYESPYSDPEELKDKKLFLKRDNLLIADIELGCGNFG

SVRQGVYRMRKKQIDVAIKVLKQGTEKADTEEMMREAQIMHQLDNPYIVR

LIGVCQAEALMLVMEMAGGGPLHKFLVGKREEIPVSNVAELLHQVSMGMK

YLEEKNFVHRDLAARNVLLVNRHYAKISDFGLSKALGADDSYYTARSAGK

WPLKWYAPECINFRKFSSRSDVWSYGVTMWEALSYGQKPYKKMKGPEVMA

FIEQGKRMECPPECPPELYALMSDCWIYKWEDRPDFLTVEQRMRACYYSL

ASKVEGPPGSTQKAEAACA.

Additional Domains

The CAR can further include one or more additional polypeptide domains, where such domains include, but are not limited to, a signal sequence; an epitope tag; an affinity domain; and a polypeptide that produces a detectable signal. Non-limiting examples of additional domains for any of the aspects or embodiments provided herein, include a domain with at least 50%, 60%, 70%, 75%, 80%, 85%, 90%, 95%, 96%, 97%, 98%, 99% or 100% sequence identity to any of the following sequences as described below: a signal sequence, an epitope tag, an affinity domain, or a polypeptide that produces a detectable signal.

Signal sequences that are suitable for use in a subject CAR, e.g., in the first polypeptide of a subject CAR, include any eukaryotic signal sequence, including a naturally-occurring signal sequence, a synthetic (e.g., man-made) signal sequence, etc. In some embodiments, for example, the signal sequence can be the CD8 signal sequence MALPVTALLL-PLALLLHAARP (SEQ ID NO:74).

Suitable epitope tags include, but are not limited to, hemagglutinin (HA; e.g., YPYDVPDYA; SEQ ID NO:37); FLAG (e.g., DYKDDDDK; SEQ ID NO:38); c-myc (e.g., EQKLISEEDL; SEQ ID NO:39), and the like.

Affinity domains include peptide sequences that can interact with a binding partner, e.g., such as one immobilized on a solid support, useful for identification or purification. DNA sequences encoding multiple consecutive single amino acids, such as histidine, when fused to the expressed protein, may be used for one-step purification of the recombinant protein by high affinity binding to a resin column, such as nickel sepharose. Exemplary affinity domains include HisS (HHHHH; SEQ ID NO:40), HisX6 (HHHHHH; SEQ ID NO:41), c-myc (EQKLISEEDL; SEQ ID NO:39), Flag (DYKDDDDK; SEQ ID NO:38), Strep Tag (WSHPQFEK; SEQ ID NO:42), hemagluttinin, e.g., HA Tag (YPYDVPDYA; SEQ ID NO:37), GST, thioredoxin, cellulose binding domain, RYIRS (SEQ ID NO:43), Phe-His-His-Thr (SEQ ID NO:44), chitin binding domain, S-peptide, T7 peptide, SH2 domain, C-end RNA tag, WEAAAREAC-CRECCARA (SEQ ID NO:45), metal binding domains, e.g., zinc binding domains or calcium binding domains such as those from calcium-binding proteins, e.g., calmodulin, troponin C, calcineurin B, myosin light chain, recoverin, S-modulin, visinin, VILIP, neurocalcin, hippocalcin, frequenin, caltractin, calpain large-subunit, S100proteins, parvalbumin, calbindin D9K, calbindin D28K, and calretinin, inteins, biotin, streptavidin, MyoD, Id, leucine zipper sequences, and maltose binding protein.

Suitable detectable signal-producing proteins include, e.g., fluorescent proteins; enzymes that catalyze a reaction that generates a detectable signal as a product; and the like.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilized EGFP (dEGFP), destabilized ECFP (dECFP), destabilized EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. Other examples of fluorescent proteins include mHoneydew, mBanana, mOrange, dTomato, tdTomato, mTangerine, mStrawberry, mCherry, mGrape1, mRaspberry, mGrape2, mPlum (Shaner et al. (2005) *Nat. Methods* 2:905-909), and the like. Any of a variety of fluorescent and colored proteins from Anthozoan species, as described in, e.g., Matz et al. (1999) *Nature Biotechnol.* 17:969-973, is suitable for use.

Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, glucose oxidase (GO), and the like.

Recognition and/or Elimination Domains

Any of the CARs disclosed herein can include recognition or elimination domain. In some embodiments, the recognition or elimination domain can be derived from herpes simplex virus-derived enzyme thymidine kinase (HSV-tk) or inducible caspase-9 or can be the FLAG epitope (SEQ ID NO:38). In some embodiments, the recognition or elimination domain is recognized by an antibody that is approved by a government regulatory agency for use in humans, such as but limited to, cetuximab, rituximab, or Herceptin. In some embodiments, the recognition or elimination domain can include a modified endogenous cell-surface molecule as described in U.S. Pat. No. 8,802,374. The modified endogenous cell-surface molecule can be any cell-surface related receptor, ligand, glycoprotein, cell adhesion molecule, antigen, integrin, or cluster of differentiation (CD) that is modified. In some embodiments, the modified endogenous cell-surface molecule is a truncated tyrosine kinase receptor. In one aspect, the truncated tyrosine kinase receptor is a member of the epidermal growth factor receptor family (e.g., ErbB1, ErbB2, ErbB3, ErbB4), for example SEQ ID NO:78. The recognition or elimination domain can be expressed as part of a single polypeptide that also includes the CAR. In some embodiments, the recognition or elimination domain can be at or near the N-terminus of the single polypeptide, such as after an N-terminal signal peptide. In some embodiments, the recognition or elimination domain can be at or near the C-terminus of the polypeptide. In some embodiments, the recognition or elimination domain at or near the C-terminus can be separated from the amino acid sequence encoding the CAR by a cleavage signal or a ribosomal skip sequence. The cleavage signal can be any cleavage signal known in the art. The ribosomal skip sequence can be any ribosomal skip sequence known in the art, for example 2A-1 with amino acid sequence GSGEGRGSLLTCGDVEENPGP (SEQ ID NO:77). In some embodiments, the recognition or elimination domain can be between any of the domains of the CAR, for example, between the stalk and transmembrane domains or the recognition or elimination domain can be in a linker, for example the linker between the heavy and light chains of a single chain antibody.

Epidermal growth factor receptor, also known as EGFR, ErbB1 and HER1, is a cell-surface receptor for members of the epidermal growth factor family of extracellular ligands. Alterations in EGFR activity have been implicated in certain cancers. In some embodiments, a gene encoding an EGFR polypeptide including human epidermal growth factor receptor (EGFR) that is constructed by removal of nucleic acid sequences that encode polypeptides including the membrane distal EGF-binding domain and the cytoplasmic signaling tail, but retains the extracellular membrane proximal epitope recognized by an anti-EGFR antibody. In illustrative embodiments, the antibody is a known, commercially available anti-EGFR monoclonal antibody, such as cetuximab, matuzumab, necitumumab or panitumumab.

Application of biotinylated-cetuximab to immunomagnetic selection in combination with anti-biotin microbeads successfully enriches T cells that have been lentivirally transduced with EGFRt-containing constructs from as low as 2% of the population to greater than 90% purity without observable toxicity to the cell preparation. Constitutive expression of this inert EGFR molecule does not affect T cell phenotype or effector function as directed by the coordinately expressed chimeric antigen receptor (CAR), CD19R. Through flow cytometric analysis, EGFR was successfully utilized as an in vivo tracking marker for T cell engraftment in mice. Furthermore, EGFR was demonstrated to have suicide gene potential through Erbitux® mediated antibody dependent cellular cytotoxicity (ADCC) pathways. Thus, EGFR may be used as a non-immunogenic selection tool, tracking marker, and suicide gene for transduced T cells that have immunotherapeutic potential. The EGFR nucleic acid may also be detected by means well known in the art.

In some embodiments, EGFR is expressed as part of a single polypeptide that also includes the CAR. In some embodiments, the amino acid sequence encoding the EGFR recognition domain can be separated from the amino acid sequence encoding the CAR by a cleavage signal or ribosomal skip sequence. The cleavage signal can be any cleavage signal known in the art. The ribosomal skip sequence can be any ribosomal skip sequence known in the art, for example 2A-1 with amino acid sequence GSGEGRGSLLTCGDVEENPGP (SEQ ID NO:77). In some embodiments, the polynucleotide sequence encoding the recognition domain can be on the same transcript as the CAR but separated from the polynucleotide sequence encoding the CAR by an internal ribosome entry site.

Recombination of Sequences

In certain instances, sequences of the polypeptides of a CAR, e.g., CAR domains, may be rearranged or deleted in a cell through the use of site-specific recombination technology. In certain embodiments, the cellular activation-related response to a particular CAR can be changed by site-specific recombination, e.g., a first intracellular activating domain of a CAR eliciting a first activation-related response may be exchanged for a second intracellular activating domain eliciting a second activation-related response. As will be clear to one skilled in the art, site-specific recombination can be used in a cell to exchange any domain or sequence of a CAR with any other domain or sequence as disclosed herein. As will also be clear to one skilled in the art, site-specific recombination can be used in a cell to delete any domain or sequence of a CAR. Such exchange and excision of sequences and domains is known in the art, see, e.g., domain switching in signalobodies as described in Tone et al. (2013) *Biotechnology and Bioengineering*, 3219-3226, the disclosure of which is disclosed herein by reference. Mechanisms and requirements for performing site-specific recombination in vivo are also well known in the art, see, e.g., Grindley et al. (2006) *Annual Review of Biochemistry*, 567-605 and Tropp (2012) Molecular Biology (Jones & Bartlett Publishers, Sudbury, MA), the disclosures of which are incorporated herein by reference.

CARs are chimeric proteins that are generated by fusing all the different domains discussed above together to form a fusion protein. The CAR is typically generated by an expression vector comprising polynucleotide sequences that encode the different domains of the CAR as discussed herein. The ASTR of the present invention, which functions to recognize and bind with an antigen on target cells, is conditionally active. Specifically, the ASTR is less active or inactive at a normal physiological condition and active at an in vitro tumor surrogate assay condition for binding with the target antigen, in comparison with an ASTR of the corresponding wild-type protein.

The wild-type or native protein that is suitable to be used in whole or in part for at least its binding domain for the target antigen, as an ASTR in the present invention may be discovered by generating a protein library and screening the library for a protein with a desired binding affinity to the target antigen. The wild-type protein may be discovered by screening a cDNA library. A cDNA library is a combination of cloned cDNA (complementary DNA) fragments inserted into a collection of host cells, which together constitute some portion of the transcriptome of the organism. cDNA is produced from fully transcribed mRNA and therefore contains the coding sequence for expressed proteins of an organism. The information in cDNA libraries is a powerful and useful tool for discovery of proteins with desired properties by screening the libraries for proteins with the desired binding affinity to the target antigen.

Tumor Microenvironment

Cancer cells in a solid tumor are able to form a tumor microenvironment in their surroundings to support the growth and metastasis of the cancer cells. A tumor microenvironment is the cellular environment in which the tumor exists, including surrounding blood vessels, immune cells, fibroblasts, other cells, soluble factors, signaling molecules, an extracellular matrix, and mechanical cues that can promote neoplastic transformation, support tumor growth and invasion, protect the tumor from host immunity, foster therapeutic resistance, and provide niches for dormant metastases to thrive. The tumor and its surrounding microenvironment are closely related and interact constantly. Tumors can influence their microenvironment by releasing extracellular signals, promoting tumor angiogenesis and inducing peripheral immune tolerance, while the immune cells in the microenvironment can affect the growth and evolution of cancerous cells. See Swarts et al. "Tumor Microenvironment Complexity: Emerging Roles in Cancer Therapy," Cancer Res, vol., 72, pages 2473-2480, 2012.

The tumor microenvironment is often hypoxic. As the tumor mass increases, the interior of the tumor grows farther away from existing blood supply, which leads to difficulties in fully supplying oxygen to the tumor microenvironment. The partial oxygen pressure in the tumor environment is below 5 mm Hg in more than 50% of locally advanced solid tumors, in comparison with a partial oxygen pressure at about 40 mm Hg in blood plasma. In contrast, other parts of the body are not hypoxic. The hypoxic environment leads to genetic instability, which is associated with cancer progression, via downregulating nucleotide excision repair and mismatch repair pathways. Hypoxia also causes the upregulation of hypoxia-inducible factor I alpha (HIF1-α), which induces angiogenesis, and is associated with poorer prognosis and the activation of genes associated with metastasis. See Weber et al., "The tumor microenvironment," *Surgical Oncology*, vol. 21, pages 172-177, 2012 and Blagosklonny, "Antiangiogenic therapy and tumor progression," *Cancer Cell*, vol. 5, pages 13-17, 2004.

In addition, tumor cells tend to rely on energy generated from lactic acid fermentation, which does not require oxygen. So tumor cells are less likely to use normal aerobic respiration that does require oxygen. A consequence of using lactic acid fermentation is that the tumor microenvironment is acidic (pH 6.5-6.9), in contrast to other parts of the body which are typically either neutral or slightly basic. For example, human blood plasma has a pH of about 7.4. See Estrella et al., "Acidity Generated by the Tumor Microenvironment Drives Local Invasion," *Cancer Research*, vol. 73, pages 1524-1535, 2013. The nutrient availability in the tumor microenvironment is also low due to the relatively high nutrient demand of the proliferating cancer cells, in comparison with cells located in other parts of the body.

Further, the tumor microenvironment also contains many distinct cell types not commonly found in other parts of the body. These cell types include endothelial cells and their precursors, pericytes, smooth muscle cells, fibroblasts, carcinoma-associated fibroblasts, myofibroblasts, neutrophils, eosinophils, basophils, mast cells, T and B lymphocytes, natural killer cells and antigen presenting cells (APC) such as macrophages and dendritic cells (Lorusso et al., "The tumor microenvironment and its contribution to tumor evolution toward metastasis," *Histochem Cell Biol*, vol. 130, pages 1091-1103, 2008).

Accordingly, the tumor microenvironment has at least several physiological conditions that are different from those of other parts of body, such as the physiological conditions in blood plasma. The tumor microenvironment has a pH (acidic) that is lower than other parts of the body, especially the blood plasma (pH 7.4). The tumor microenvironment has a lower concentration of oxygen than other parts of the body, such as blood plasma. Also, the tumor microenvironment has a lower nutrient availability than other parts of the body, especially the blood plasma. The tumor microenvironment also has some distinct cell types that are not commonly found in other parts of the body, especially the blood plasma.

In illustrative embodiments, CARs of the present invention include a conditionally active ASTR generated from a wild-type biological (i.e. native) protein, such as a wild-type or native antibody isolated from a mammalian organism such as a mouse or a human, for example, that may be a candidate for tumor treatment. The conditionally active ASTR in such illustrative embodiments has lower activity under at least one physiological condition in parts of the body other than the tumor microenvironment. such as blood plasma, than the native or wild-type biological protein, while it has higher activity under at least one physiological condition in the tumor microenvironment than the native or wild-type biological protein. Such conditionally active native or biological proteins can preferentially act upon cancer cells in the tumor microenvironment for treating tumors, and thus will be less likely to cause side effects. In embodiments where the native or biological protein is an antibody against an antigen on the surface of the tumor cells where the antigen is exposed to the tumor microenvironment, the conditionally active antibody has lower affinity to the antigen than the native or wild-type antibody in other parts of the body, e.g. a non-tumor microenvironment, while it has higher affinity to the antigen than the native or wild-type antibody in the tumor microenvironment. Such conditionally active antibodies can bind weakly or not at all to the antigen in other parts of the body, but have greater binding, or bind strongly and tightly, to the antigen in the tumor microenvironment.

In Vitro Tumor Surrogate Assay

ASTRs used in CARs or the present disclosure, and typically the CARs herein, which include such ASTRs, in illustrative embodiments are conditionally active in a tumor environment and/or in an in vitro tumor surrogate assay condition. The in vitro tumor surrogate assay condition can be any condition that is tested in vitro by comparing that condition at values or levels found in at least some cancers in vivo, against that condition at values or levels found in physiological tissue under physiological conditions. Provided in the Examples herein, is a non-limiting in vitro tumor surrogate assay for cell lysis at low pH (e.g. 6.0 or 6.7) as compared to physiological pH (e.g. 7.4). In vitro tumor surrogate assay conditions under which a CAR of the present disclosure can be active include but are not limited to high hyaluronan, lactic acid, and/or albumin, wherein the normal condition is low levels of lactic acid, hyaluronan, and albumin. Another in vitro tumor surrogate assay condition is pH, especially specific conditions where the pH in the in vitro tumor surrogate assay condition is less than normal physiological pH. For example, the tumor surrogate assay condition can be a pH of between 6.0, 6.1, 6.2, 6.3, 6.4, and 6.5 on the low end of the range, and 6.6, 6.7, 6.8, and 6.9 on the high end of the range. Whereas physiological pH can be between 7.2, 7.3, and 7.4 on the low end of the range and 7.5, 7.6, 7.7 and 7.8 on the high end of the range. In illustrative embodiments, low pH in the in vitro tumor surrogate assay condition is between 6.5 and 6.9, and can specifically be 6.7. Physiological pH can be pH 7.2 to 7.6, or can specifically be set at pH 7.4. In another embodiment, the pH is unchanged but the in vitro tumor surrogate assay condition differs only in concentrations of lactic acid. In another embodiment, the in vitro tumor surrogate assay condition includes elevated levels of adenosine compared to the physiologic environment. In another embodiment, the in vitro tumor surrogate assay condition includes elevated levels of R-2-hydroxyglutarate as compared to the physiologic environment. In other embodiments, the scFv is grafted from the heavy and light chains of a monoclonal antibody that has been selected for microenvironmental specificity through molecular evolution, such as those described in U.S. Pat. No. 8,709,755 B2 and application WO/2016/033331A1.

Nucleic Acids

The present disclosure provides a nucleic acid that includes a nucleotide sequence encoding the polypeptide of a conditionally active CAR of the present disclosure. A nucleic acid including a nucleotide sequence encoding the conditionally active CAR of the present disclosure will in some embodiments be DNA, including, e.g., a recombinant expression vector. A nucleic acid including a nucleotide sequence encoding the conditionally active CAR of the present disclosure will in some embodiments be RNA, e.g., in vitro synthesized RNA.

In some cases, a nucleic acid provides for production of a CAR of the present disclosure, e.g., in a mammalian cell. In other cases, a subject nucleic acid provides for amplification of the CAR-encoding nucleic acid.

A nucleotide sequence encoding the CAR of the present disclosure can be operably linked to a transcriptional control element, e.g., a promoter, and enhancer, etc.

Suitable promoter and enhancer elements are known in the art. For expression in a bacterial cell, suitable promoters include, but are not limited to, lad, lacZ, T3, T7, gpt, lambda P and trc. For expression in a eukaryotic cell, suitable promoters include, but are not limited to, light and/or heavy chain immunoglobulin gene promoter and enhancer elements; cytomegalovirus immediate early promoter; herpes simplex virus thymidine kinase promoter; early and late SV40 promoters; promoter present in long terminal repeats from a retrovirus; mouse metallothionein-I promoter; and various art-known tissue specific promoters.

Suitable reversible promoters, including reversible inducible promoters are known in the art. Such reversible promoters may be isolated and derived from many organisms, e.g., eukaryotes and prokaryotes. Modification of reversible promoters derived from a first organism for use in a second organism, e.g., a first prokaryote and a second a eukaryote, a first eukaryote and a second a prokaryote, etc., is well known in the art. Such reversible promoters, and systems based on such reversible promoters but also comprising additional control proteins, include, but are not limited to, alcohol regulated promoters (e.g., alcohol dehydrogenase I (alcA) gene promoter, promoters responsive to alcohol transactivator proteins (AlcR), etc.), tetracycline regulated promoters, (e.g., promoter systems including TetActivators, TetON, TetOFF, etc.), steroid regulated promoters (e.g., rat glucocorticoid receptor promoter systems, human estrogen receptor promoter systems, retinoid promoter systems, thyroid promoter systems, ecdysone promoter systems, mifepristone promoter systems, etc.), metal regulated promoters (e.g., metallothionein promoter systems, etc.), pathogenesis-related regulated promoters (e.g., salicylic acid regulated promoters, ethylene regulated promoters, benzothiadiazole regulated promoters, etc.), temperature regulated promoters (e.g., heat shock inducible promoters (e.g., HSP-70, HSP-90, soybean heat shock promoter, etc.), light regulated promoters, synthetic inducible promoters, and the like.

In some instances, the locus or construct or trans gene containing the suitable promoter is irreversibly switched through the induction of an inducible system. Suitable systems for induction of an irreversible switch are well known in the art, e.g., induction of an irreversible switch may make use of a Cre-lox-mediated recombination (see, e.g., Fuhrmann-Benzakein, et al., *PNAS* (2000) 28:e99, the disclosure of which is incorporated herein by reference). Any suitable combination of recombinase, endonuclease, ligase, recombination sites, etc. known to the art may be used in generating an irreversibly switchable promoter. Methods, mechanisms, and requirements for performing site-specific recombination, described elsewhere herein, find use in generating irreversibly switched promoters and are well known in the art, see, e.g., Grindley et al. (2006) *Annual Review of Biochemistry*, 567-605 and Tropp (2012) Molecular Biology (Jones & Bartlett Publishers, Sudbury, MA), the disclosures of which are incorporated herein by reference.

In some cases, the promoter is a CD8 cell-specific promoter, a CD4 cell-specific promoter, a neutrophil-specific promoter, or an NK-specific promoter. For example, a CD4 gene promoter can be used; see, e.g., Salmon et al. (1993) *Proc. Natl. Acad. Sci. USA* 90:7739; and Marodon et al. (2003) *Blood* 101:3416. As another example, a CD8 gene promoter can be used. NK cell-specific expression can be achieved by use of an Neri (p46) promoter; see, e.g., Eckelhart et al. (2011) *Blood* 117:1565.

In some embodiments, e.g., for expression in a yeast cell, a suitable promoter is a constitutive promoter such as an ADH1 promoter, a PGK1 promoter, an ENO promoter, a PYK1 promoter and the like; or a regulatable promoter such as a GAL1 promoter, a GAL10 promoter, an ADH2 promoter, a PH05 promoter, a CUP1 promoter, a GAL7 promoter, a MET25 promoter, a MET3 promoter, a CYC1 promoter, a HIS3 promoter, an ADH1 promoter, a PGK promoter, a GAPDH promoter, an ADC1 promoter, a TRP1 promoter, a URA3 promoter, a LEU2 promoter, an ENO promoter, a TP1 promoter, and AOX1 (e.g., for use in *Pichia*). Selection of the appropriate vector and promoter is well within the level of ordinary skill in the art.

Suitable promoters for use in prokaryotic host cells include, but are not limited to, a bacteriophage T7 RNA polymerase promoter; a trp promoter; a lac operon promoter; a hybrid promoter, e.g., a lac/tac hybrid promoter, a tac/trc hybrid promoter, a trp/lac promoter, a T7/lac promoter; a trc promoter; a tac promoter, and the like; an araBAD promoter; in vivo regulated promoters, such as an ssaG promoter or a related promoter (see, e.g., U.S. Patent Publication No. 20040131637), a pagC promoter (Pulkkinen and Miller, *J. Bacterial.*, 1991: 173(1): 86-93; Alpuche-Aranda et al., *PNAS*, 1992; 89(21): 10079-83), a nirB promoter (Harborne et al. (1992) *Mal. Micro.* 6:2805-2813), and the like (see, e.g., Dunstan et al. (1999) *Infect. Immun.* 67:5133-5141; McKelvie et al. (2004) *Vaccine* 22:3243-3255; and Chatfield et al. (1992) *Biotechnol.* 10:888-892); a sigma70 promoter, e.g., a consensus sigma70 promoter (see, e.g., GenBank Accession Nos. AX798980, AX798961, and AX798183); a stationary phase promoter, e.g., a dps promoter, an spy promoter, and the like; a promoter derived from the pathogenicity island SPI-2 (see, e.g., WO96/17951); an actA promoter (see, e.g., Shetron-Rama et al. (2002) *Infect. Immun.* 70:1087-1096); an rpsM promoter (see, e.g., Valdivia and Falkow (1996). *Mal. Microbial.* 22:367); a tet promoter (see, e.g., Hillen, W. and Wissmann, A. (1989) In Saenger, W. and Heinemann, U. (eds), *Topics in Molecular and Structural Biology, Protein-Nucleic Acid Interaction*. Macmillan, London, UK, Vol. 10, pp. 143-162); an SP6 promoter (see, e.g., Melton et al. (1984) *Nucl. Acids Res.* 12:7035); and the like. Suitable strong promoters for use in prokaryotes such as *Escherichia coli* include, but are not limited to Trc, Tac, T5, T7, and PLambda. Non-limiting examples of operators for use in bacterial host cells include a lactose promoter operator (LacI repressor protein changes conformation when contacted with lactose, thereby preventing the Laci repressor protein from binding to the operator), a tryptophan promoter operator (when complexed with tryptophan, TrpR repressor protein has a conformation that binds the operator; in the absence of tryptophan, the TrpR repressor protein has a conformation that does not bind to the operator), and a tac promoter operator (see, for example, deBoer et al. (1983) Proc. Natl. Acad. Sci. U.S.A. 80:21-25).

A nucleotide sequence encoding a CAR can be present in an expression vector and/or a cloning vector. Where a CAR includes two separate polypeptides, nucleotide sequences encoding the two polypeptides can be cloned in the same or separate vectors. An expression vector can include a selectable marker, an origin of replication, and other features that provide for replication and/or maintenance of the vector. Suitable expression vectors include, e.g., plasmids, viral vectors, and the like.

Large numbers of suitable vectors and promoters are known to those of skill in the art; many are commercially available for generating a subject recombinant constructs. The following vectors are provided by way of example. Bacterial: pBs, phagescript, PsiX174, pBluescript SK, pBs KS, pNH8a, pNH16a, pNH18a, pNH46a (Stratagene, La Jolla, Calif., USA); pTrc99A, pKK223-3, pKK233-3, pDR540, and pRIT5 (Pharmacia, Uppsala, Sweden). Eukaryotic: pWLneo, pSV2cat, pOG44, PXR1, pSG (Stratagene) pSVK3, pBPV, pMSG and pSVL (Pharmacia).

Expression vectors generally have convenient restriction sites located near the promoter sequence to provide for the insertion of nucleic acid sequences encoding heterologous proteins. A selectable marker operative in the expression host may be present. Suitable expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90: 10613-10617); SV40; herpes simplex virus; gamma retrovirus; human immunodeficiency virus (see, e.g., Miyoshi et al., PNAS 94:10319 23, 1997; Takahashi et al., J Virol 73:7812 7816, 1999); a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus); and the like.

As noted above, in some embodiments, a nucleic acid including a nucleotide sequence encoding the conditionally active CAR of the present disclosure will in some embodiments be RNA, e.g., in vitro synthesized RNA. Methods for in vitro synthesis of RNA are known in the art; any known method can be used to synthesize RNA including a nucleotide sequence encoding the conditionally active CAR of the present disclosure. Methods for introducing RNA into a host cell are known in the art. See, e.g., Zhao et al. (2010) Cancer Res. 15:9053. Introducing RNA including a nucleotide sequence encoding the conditionally active CAR of the present disclosure into a host cell can be carried out in vitro or ex vivo or in vivo. For example, a host cell (e.g., an NK cell, a cytotoxic T lymphocyte, etc.) can be electroporated in vitro or ex vivo with RNA comprising a nucleotide sequence encoding the conditionally active CAR of the present disclosure.

Cells

Some aspects of the present disclosure include or are cells, in illustrative examples, mammalian cells, that are used as packaging cells to make viruses, such as lentiviruses, for transduction of T cells and/or NK cells. Any of a wide variety of cells can be selected for in vitro production of a virus, such as a pseudotyped retrovirus, according to the invention. Eukaryotic cells are typically used, particularly mammalian cells including human, simian, canine, feline, equine and rodent cells, in illustrative examples, the cells are human cells. In further illustrative embodiments, the cells reproduce indefinitely, and are therefore immortal. Examples of cells that may be advantageously used in the present invention include NIH 3T3 cells, COS cells, Madin-Darby canine kidney cells, human embryonic 293T cells and any cells derived from such cells, such as gpnislacZ φNX cells, which are derived from 293T cells. Highly transfectable cells, such as human embryonic kidney 293T cells, can be used. By "highly transfectable" it is meant that at least about 50%, more preferably at least about 70% and most preferably at least about 80% of the cells can express the genes of the introduced DNA.

Suitable mammalian cells include primary cells and immortalized cell lines. Suitable mammalian cell lines include human cell lines, non-human primate cell lines, rodent (e.g., mouse, rat) cell lines, and the like. Suitable mammalian cell lines include, but are not limited to, HeLa cells (e.g., American Type Culture Collection (ATCC) No. CCL-2), CHO cells (e.g., ATCC Nos. CRL9618, CCL61, CRL9096), 293 cells (e.g., ATCC No. CRL-1573), Vero cells, NIH 3T3 cells (e.g., ATCC No. CRL-1658), Huh-7 cells, BHK cells (e.g., ATCC No. CCL10), PC12 cells (ATCC No. CRL1721), COS cells, COS-7 cells (ATCC No. CRL1651), RAT1 cells, mouse L cells (ATCC No. CCLI.3), human embryonic kidney (HEK) cells (ATCC No. CRL1573), HLHepG2 cells, Hut-78, Jurkat, HL-60, NK cell lines (e.g., NKL, NK92, and YTS), and the like.

Methods of Activating an Immune Cell

The present disclosure provides methods of activating an immune cell in vitro, in vivo, or ex vivo. The methods generally involve contacting an immune cell (in vitro, in vivo, or ex vivo) with Axl and/or Ror2, where the immune cell has been genetically modified to produce (i.e. express) a conditionally active CAR of the present disclosure. In the presence of Axl and/or Ror2, the conditionally active CAR activates the immune cell, thereby producing an activated immune cell Immune cells include, e.g., a cytotoxic T lymphocyte, an NK cell, a CD4$^+$ T cell, a T regulatory (Treg) cell, a γδ T cell, an NK-T cell, neutrophils, etc. In illustrative embodiments, the immune cell is a T cell or NK cell, in particularly illustrative embodiments, the immune cell is a T cell, which include NK-T cells. In such illustrative embodiments the activating is typically activating the cytotoxic activity of the T cell or NK cell. Such methods can be performed using a plurality of immune cells (e.g. T cells or NK cells). In further illustrative embodiments, the contacting involves contacting a target mammalian cell expressing Axl and/or Ror2 with the immune cell. Such methods for activation of the T cells or NK cells can be detected by detecting the release of cytokines by the T cells or NK cells such as the release of IFN-γ or IL-2, increases in the cytotoxic activity of T cells and/or NK cells against cells expressing Axl or Ror2, increases in the intracellular expression of IFNγ and/or IL-2 in the T cell or NK cells, and increases in the expression of CD107a and/or CD69 by the T cell or NK cells as measured by fluorescence-activated cell sorting (FACS) analysis. Examples 1, 3, and 4 herein provide details for some of these methods of detecting the activation of T cells and/or NK cells.

Further aspects provided herein, include methods for binding an immune cell (e.g. a T cell or NK cell) to a target mammalian cell, that include contacting the target mammalian cell with the immune cell in vitro, in vivo, or ex vivo, wherein the target mammalian cell expresses Axl and/or Ror2, and the immune cell expresses any of the CARs provided herein that bind to Axl or Ror2. Such binding can activate the immune cell. Such methods can be performed using a plurality of immune cells (e.g. T cells or NK cells). Such methods for binding, as detected by detecting activation of the T cells or NK cells by release of cytokines and increase in cytotoxic activity are provided in Example 1, Example 3, and Example 4 herein.

The contacting in methods for binding or activating an immune cell, in illustrative embodiments involves contacting the immune cell (e.g. T cell or NK cell) in a microenvironment at a pH of less than 7.4. For example, the pH can be less than 5.8, 5.9, 6.0, 6.1, 6.2, 6.3, 6.4, 6.5, 6.6, 6.7, 6.8, or 6.9, or in the range of 5.8 to 7.0, in illustrative embodiments in the range of 6.0 to 6.8, in the range of 6.1 to 6.9, in the range of 6.2 to 6.8, or between 6.0, 6.1, 6.2, 6.3, 6.4, and 6.5 on the low end of the range, and 6.6, 6.7, 6.8, and 6.9 on the high end of the range. In such illustrative embodiments, the CAR is any of the CAB-CARs disclosed herein, that recognizes Axl or Ror2 provided herein.

Contacting the genetically modified immune cell (e.g., a T lymphocyte, an NK cell) with Axl and/or Ror2 can increase production of a cytokine by the immune cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared with the amount of cytokine produced by the immune cell in the absence of Axl and/or Ror2. Contacting the genetically modified immune cell (e.g., a T lymphocyte or an NK cell) with Axl and/or Ror2 can increase secretion of a cytokine by the immune cell by at least 10%, at least 15%, at least 20%, at least 25%, at least 30%, at least 40%, at least 50%, at least 75%, at least 2-fold, at least 2.5-fold, at least 5-fold, at least 10-fold, or more than 10-fold, compared with the amount of cytokine secreted by the immune cell in the absence of Axl and/or Ror2. Cytokines whose production can be increased include, but are not limited to, IL-2 and IFN-γ.

Contacting a genetically modified cytotoxic cell (e.g., cytotoxic T lymphocyte) with AAR can increase cytotoxic activity of the cytotoxic cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the cytotoxic cell in the absence of Axl and/or Ror2.

Contacting a genetically modified cytotoxic cell (e.g., cytotoxic T lymphocyte) with Axl and/or Ror2 can increase cytotoxic activity of the cytotoxic cell by at least about 10%, at least about 15%, at least about 20%, at least about 25%, at least about 30%, at least about 40%, at least about 50%, at least about 75%, at least about 2-fold, at least about 2.5-fold, at least about 5-fold, at least about 10-fold, or more than 10-fold, compared to the cytotoxic activity of the cytotoxic cell in the absence of Axl and/or Ror2.

In other embodiments, e.g., depending on the host immune cell, contacting a genetically modified host cell with an antigen can increase or decrease cell proliferation, cell survival, cell death, and the like.

Methods for Making/Isolating a Conditionally Active Antigen-Specific Targeting Region In illustrative embodiments, the anti-Axl and anti-Ror2 antigen receptors disclosed herein are conditionally active such that they exhibit an increase in binding to Axl or Ror2 at a pH 6.7 (an exemplary pH of a tumor environment and/or in an in vitro tumor surrogate assay condition) compared to 7.4 (a normal physiological condition). In some illustrative embodiments of any aspect disclosed herein, the conditionally active anti-Axl or anti-Ror2 ASTR is identified from an initial polypeptide library without mutating/evolving members of the library before screening/evolving and/or without mutating during or between optional repeated rounds of screening. In other embodiments, the conditionally active anti-Axl or anti-Ror2 ASTR is identified by a method that includes mutating/evolving, and in some embodiments starts with a wild-type antibody. Exemplary transmembrane domains and intracellular activating domains can be any of those disclosed herein for CARs.

In one aspect, provided herein is a method for selecting a conditionally active anti-Axl or anti-Ror2 ASTR, comprising panning a polypeptide display library by:
  a. subjecting polypeptides of the polypeptide display library to an Axl or Ror2 binding assay at a pH 7.4 (or other normal physiological condition) and an Axl or Ror2 binding assay at a pH 6.7 (or other in vitro tumor surrogate assay condition); and
  b. selecting a polypeptide which exhibits an increase in Axl or Ror2 binding activity at pH 6.7 compared to pH7.4, or other in vitro tumor surrogate assay condition compared to the normal physiological condition, thereby selecting the conditionally active antigen specific targeting region.

In some embodiments, a single round of selection is performed to obtain the conditionally active anti-Axl or anti-Ror2 targeting region. In certain embodiments, the screening or panning method is repeated after identifying free antibodies that bound antigen under in vitro tumor surrogate assay conditions and did not bind under physiological conditions, or cells expressing a test antibody that had these properties, or phage coated with a test antibody that has such properties in an initial or previous round. In some methods, phage that are collected are used to infect cells, which can be infected with helper phage as well, in order to amplify the collected phage. In other methods where antibodies on the surface of cells are tested, collected cells can be grown to "amplify" the antibodies expressed by the cells by amplifying antibodies in the cells that encode the polypeptides. In some embodiments, the amplifying is done by growing cells that express the identified antibodies without performing a process to mutate the antibodies encoding the identified antibodies between rounds. Thus, antibodies that are collected in a previous round are then enriched by amplifying cells that contain antibodies encoding these collected antibodies.

The panning or screening method can be performed a single time, or repeated for 1 to 1000 times. In illustrative embodiments, the panning is repeated 1 to 20 times or 2 to 10 times or 2 to 5 times.

In other methods, conditionally active anti-Axl or anti-Ror2 ASTRs are generated using one or more rounds of mutation/evolution between rounds of panning. In one method, a wild-type protein (e.g. antibody) is identified for example by generating a polypeptide or protein library and screening the polypeptide or protein library for a polypeptide or protein with a desired binding affinity to a target antigen. In some embodiments where the wild-type proteins are antibodies, the wild-type antibodies can be discovered by generating and screening polyclonal or monoclonal antibody libraries, including phage display antibody libraries, for example phage display humanized antibody libraries.

Evolved anti-Axl or Ror2 ASTRs can be generated by subjecting the wild-type protein, or a nucleic acid sequence encoding the wild-type protein, to a process of mutagenesis to produce a population of mutant polypeptides that can be screened to identify a mutant ASTR with an increased activity (e.g. enhanced binding affinity to the target antigen) in a tumor environment and/or in an in vitro tumor surrogate assay condition, compared to a normal physiological environment. Examples of such methods are provided in WO2016033331 ("CONDITIONALLY ACTIVE CHIMERIC ANTIGEN RECEPTORS FOR MODIFIED T-CELLS") or U.S. Pat. No. 8,709,755.

Conditionally active anti-Axl or anti-Ror2 ASTRs identified using methods provided herein are typically polypeptides and more specifically polypeptide antibodies, and in illustrative embodiments, single chain antibodies, as discussed in more detail herein. These polypeptides can bind to Axl or Ror2 with higher or lower affinity under in vitro tumor surrogate assay conditions vs. normal physiologic conditions, but in illustrative embodiments, bind with higher affinity under in vitro tumor surrogate assay conditions than normal conditions. In some embodiments, these polypeptides can bind to their cognate antigen with a 10%, 20%, 25%, 50%, 75%, 90%, 95% or 99% greater affinity under in vitro tumor surrogate assay conditions than physiological (i.e. normal) conditions. In some embodiments, the ASTRs identifying using methods provided herein do not bind to their cognate antigens under normal physiological conditions to any detectable level above background levels obtained using negative controls, such as negative control antibodies.

The nucleotide sequence encoding a conditionally active anti-Axl or anti-Ror2 ASTR isolated by the method provided herein, can be determined by sequencing nucleotides of the collected cell expressing the conditionally active anti-Axl or anti-Ror2 antigen-specific targeting. This nucleotide sequence information can then be used to make a conditionally active anti-Axl or anti-Ror2 biologic chimeric antigen receptor (CAB-CAR) by generating a polynucleotide that encodes a polypeptide comprising the conditionally active anti-Axl or anti-Ror2 antigen-specific targeting region, a transmembrane domain, and an intracellular activating domain. Conditionally active anti-Axl or anti-Ror2 antigen-specific targeting regions can be cloned into a CAR construct expression system, which can be used to generate recombinant lentiviruses that include the CAR in their genome, and then the recombinant lentiviruses can be used to transduce T cells for testing for CAR-mediated Axl or Ror2-expressing target cell killing in a tumor-selective environment compared to normal physiologic conditions, as illustrated in Example 1 herein.

Methods for Generating a Conditionally Activatable Cell

The present disclosure provides a method of generating a conditionally activatable cell. The method generally involves genetically modifying a mammalian cell with an expression vector (e.g. a plasmid or a virus), or an RNA (e.g., in vitro transcribed RNA), including nucleotide sequences encoding a conditionally active CAR of the present disclosure. The genetically modified cell is conditionally activatable in the presence of Axl and/or Ror2. The genetic modification can be carried out in vivo, in vitro, or ex vivo. The cell is typically an immune cell (e.g., a T lymphocyte, a T-helper cell, or an NK cell), a stem cell, a progenitor cell, etc. In illustrative embodiments, the cell is a T cell.

In some cases, the genetic modification is carried out ex vivo. For example, a T lymphocyte, a stem cell, a T-helper cell, or an NK cell is obtained from an individual; and the cell obtained from the individual is genetically modified to express a CAR of the present disclosure. The genetically modified cell is conditionally activatable in the presence of Axl and/or Ror2. In some cases, the genetically modified cell is activated ex vivo. In other cases, the genetically modified cell is introduced into an individual (e.g., the individual from whom the cell was obtained); and the genetically modified cell is activated in vivo. For example, where Axl and/or Ror2 are present on the surface of a cell in the individual, there is no need to administer the antigen. The genetically modified cell comes into contact with the antigen present on the surface of a cell in the individual and the genetically modified cell is activated. For example, where the genetically modified cell is a T lymphocyte, the genetically modified cell can exhibit cytotoxicity toward a cell that expresses Axl and/or Ror2 on its surface to which the CAR binds.

In one aspect, provided herein is an ex vivo method for making conditionally activatable T cells and/or NK cells comprising a chimeric antigen receptor (CAR) for conditionally binding Axl or Ror2, wherein the method comprises:
  a) enriching peripheral blood mononuclear cells (PBMCs) to isolate PBMCs comprising T cells and/or NK cells from isolated blood;
  b) activating T cells and/or NK cells of the enriched PBMCs under effective conditions;
  c) transducing the activated T cells and/or NK cells with replication incompetent recombinant retroviral particles under effective conditions, thereby producing genetically modified T cells and/or NK cells, wherein the replication incompetent recombinant retroviral particles each comprise a retroviral genome comprising one or more nucleic acid sequences operatively linked to a promoter active in T cells and/or NK cells, wherein a first nucleic acid sequence of the one or more nucleic acid sequences encodes a CAB-CAR according to any embodiment provided herein; and
  d) expanding the genetically modified T cells and/or NK cells, thereby making the conditionally activatable T cells and/or NK cells.

In some embodiments of the above aspect, the method further includes harvesting the expanded genetically modified T cells and/or NK cells. In some embodiments of the above aspect, the method further includes collecting blood from a subject, before enriching PBMCs. In further embodiments, the method further includes introducing the harvested, expanded genetically modified T cells and/or NK cells into the subject. In further embodiments, the genetically modified T cells and/or NK cells are present in the subject 1, 2, 3, 4, 5, 6, 7, or 14 days after they are introduced into the subject.

Blood Collection

Blood containing PBMCs can be collected or obtained from a subject by any suitable method known in the art. For example, the blood can be collected by venipuncture or any other blood collection method by which a sample of blood and/or PBMCs is collected. In some embodiments, PBMCs can be obtained by apheresis as discussed below.

Enrichment of PBMCs

In ex vivo methods for making conditionally activatable T cells and/or NK cells, peripheral blood mononuclear cells (PBMCs) including T cells and/or NK cells, are isolated away from other components of a blood sample in an enrichment step. Enrichment of PBMCs from other blood components and blood cells can be performed using any methods known in the art, for example, using apheresis, and/or density gradient centrifugation. In some embodiments, Ficoll-Paque (GE Healthcare) can be used. In some embodiments, an automated apheresis separator is used which takes blood from the subject, passes the blood through an apparatus that sorts out a particular cell type (such as, for example, PBMCs), and returns the remainder back into the subject. Density gradient centrifugation can be performed after apheresis. In some embodiments, the PBMCs can be enriched and isolated using a leukoreduction filter device. In some embodiments, magnetic bead activated cell sorting is then used for purifying a specific cell population from PBMCs, such as, for example, T cells and/or NK cells, according to a cellular phenotype (i.e. positive selection). In some embodiments, monocytes and/or macrophages can be removed from the PBMCs using methods known in the art. With reference to a subject to be treated, the cells can be allogeneic and/or autologous. During the PBMC enrichment process, one or more washes can be performed as is known in the art, before the enriched PBMCs are isolated and then activated. The wash solution can any solution suitable for washing blood and/or PBMCs. According to methods known in the art, the isolated PBMCs can be resuspended in any suitable base culture medium used for culturing T cells and/or NK cells. In some embodiments, the media can be supplemented with HSA, human AB+ serum, serum derived from the subject and/or serum replacement.

Activation of PBMCs

Ex vivo methods for making conditionally activatable T cells and/or NK cells provided herein typically include a step of activating or stimulating the isolated PBMCs with one or more activating agents to generate activated T cells and/or NK cells. Activating can be performed on either freshly isolated PBMCs or previously cryopreserved PBMCs. In the event that cryopreserved cells are used, the cells may be thawed using developed protocols prior to use.

Media is typically present during the activating, such as those known in the art for ex vivo processes (as non-limiting examples, X-VIVO 15 (Lonza) or CTS media (Thermo Fisher)). In some embodiments, the media can be supplemented with HSA, human AB+ serum, serum derived from the subject, and/or serum replacement. In illustrative embodiments, the media can be supplemented with serum replacement, such as CTS Serum Replacement (Thermo Fisher). In some embodiments, the media can be supplemented with HSA, human AB+ serum, serum derived from the subject and/or serum replacement.

Any combination of one or more activating agents can be added to the media to produce activated T cells and/or NK cells. A reaction mixture is typically formed to perform the activating. In some embodiments, the reaction mixture can be formed by adding one or more activating agents to the media. In any of the embodiments disclosed herein, the one or more activating agents are used in effective amounts such that activated T cells and/or NK cells are produced.

It is noteworthy that such activation in embodiments for making conditionally activatable T cells and/or NK cells can involve activating the cells with Axl or Ror2, such as isolated soluble Axl or Rors, at a pH below 7.0. However, activation in methods for making conditionally activatable T cells and/or NK cells typically utilizes more generic activating agents. Accordingly, in some embodiments, the activating agent can be a polypeptide or an antibody (e.g. anti-CD2, anti-CD3, and/or anti-CD28) or functional fragments thereof that target or bind to a T-cell stimulatory or co-stimulatory molecule, a T cell cytokine, or any other suitable mitogen (e.g., tetradecanoyl phorbol acetate (TPA), phytohaemagglutinin (PHA), concanavalin A (conA), lipopolysaccharide (LPS), pokeweed mitogen (PWM)), a natural ligand to a T-cell stimulatory or co-stimulatory molecule, phospho-antigens, or aminobisphosphonates, such as zoledronate. Various antibodies and functional fragments thereof are known in the art to activate or stimulate T cells and/or NK cells. In some embodiments, the one or more antibodies or functional fragments thereof can be immobilized on a solid surface, such as a bead.

Transduction of T Cells and/or NK Cells

Ex vivo methods for making conditionally activatable T cells and/or NK cells provided herein typically include a step of transforming or transducing activated T cells and/or NK cells. In some embodiments of such methods, T cells and/or NK cells are contacted ex vivo with expression vectors such as replication incompetent recombinant retroviral particles to genetically modify the T cells and/or NK cells. Not to be limited by theory, during the period of contact the replication incompetent recombinant retroviral particles bind to T cells and/or NK cells at which point the retroviral and host cell membranes start to fuse. Then, through the process of transduction, genetic material from the replication incompetent recombinant retroviral particles enters the T cells and/or NK cells and typically is incorporated into the host cell DNA. Accordingly, such methods include genetically modifying T cells and/or NK cells by transduction. Methods are known in the art for transducing T cells and/or NK cells ex vivo with replication incompetent recombinant retroviral particles, such as replication incompetent recombinant lentiviral particles. Exemplary methods are described in, e.g., Wang et al. (2012) J. Immunother. 35(9): 689-701; Cooper et al. (2003) Blood. 101:1637-1644; Verhoeyen et al. (2009) Methods Mol Biol. 506: 97-114; and Cavalieri et al. (2003) Blood. 102(2): 497-505. In some embodiments, the T cells and/or NK cells can be contacted with replication incompetent recombinant retroviral particles. In illustrative embodiments, the T cells and/or NK cells can be contacted with replication incompetent recombinant lentiviral particles.

Expansion of Transduced T Cells and/or NK Cells

In illustrative embodiments of ex vivo methods for making conditionally activatable T cells and/or NK cells provided herein, transduced T cells and/or NK cells are expanded before harvesting. In any of the embodiments disclosed herein, media is present for the activating and transducing and can be further added or exchanged after transducing, to perform the expansion. In some embodiments, media can be added to the reaction mixture formed during the activating. The media used for the expanding typically includes the same base media used in the activating and transducing, such as those known in the art for ex vivo processes, especially for T cells and/or NK cells (as non-limiting examples, X-VIVO 15 (Lonza) or Optimizer CTS media (Thermo Fisher)). In some embodiments, the media can be supplemented with HSA, human AB+ serum, serum derived from the subject, and/or serum replacement, such as CTS Serum Replacement (Thermo Fisher). Cytokines, such as IL-2, IL-7, or IL-15, or those found in HSA can be added to the media before, during, and/or after activation, transduction, and expansion. Cell expanding can be performed for a certain number days. In some embodiments, expanding can be performed for 4, 5, 6, 7, 8, 9, 10, 11, 12, 13, 14, 15, 16, 17, 18, 19, 20, or 21 days. In some embodiments, expanding can be performed for between 4, 5, 6, 7, or 8 days on the low end of the range and 9, 10, 11, 12, 13, 14, 15, 16, 17, 18, 19, 20, or 21 days on the high end of the range. In certain illustrative embodiments, expanding is performed for between 6 and 12 days, or between 8 and 10 days.

Cell Harvesting

In ex vivo methods for making conditionally activatable T cells and/or NK cells provided herein typically include harvesting the genetically modified T cells and/or NK cells after expanding. In some embodiments, the transduced T cells and/or NK cells can be concentrated or collected during harvesting using methods known in the art. In some embodiments, the T cells and/or NK cells can be washed one or more times during the harvesting using any suitable wash solution known in the art. At the end of the harvesting, the T cells and/or NK cells can be resuspended in any suitable media known in the art. In any of the embodiments disclosed herein, harvesting of the expanded T cells and/or NK cells can be performed based on an expansion completion criteria. In some embodiments, the expansion completion criteria can be lactate concentration, cell density, or a number of days in expansion.

In some embodiments, the harvested cells can be introduced, introduced back, reintroduced, infused, or reinfused into a subject. In some embodiments, harvested cells can be cryopreserved as described below before reintroduction into a subject. In illustrative embodiments, harvested cells are introduced, introduced back, reintroduced, infused, or reinfused into a subject without first cryopreserving the cells. The subject is typically the same subject the blood was collected from.

Throughout this disclosure, a transduced T cell and/or NK cell includes progeny of the transduced cells that retain at least one of the nucleic acids that are incorporated into the cell during the ex vivo transduction. In methods herein that recite "reintroducing" a transduced cell, it will be understood that such a cell is typically not in a transduced state when it is collected from the blood of a subject.

Cell Introduction/Reintroduction

In certain embodiments of the ex vivo methods for making conditionally activatable T cells and/or NK cells disclosed herein, the harvested T cells and/or NK cells can be introduced, introduced back, reintroduced, infused, or reinfused in a subject for a therapeutic effect. The number of T cells and/or NK cells to be reintroduced can be a predetermined dose, which can be a therapeutically effective dose. In some embodiments, the predetermined dose can depend on the CAR that is expressed on the cells (e.g., the affinity and density of the antigen-specific targeting region expressed on the transduced T cell and/or NK cell), the type of target cell, the nature of the disease or pathological condition being treated, or a combination. In some embodiments, the predetermined dose of harvested cells can be based on the mass of a subject, for example, cells per kilogram of the subject (cells/kg).

Cell Cryopreservation

In ex vivo methods for making conditionally activatable T cells and/or NK cells provided herein, the harvested cells produced by the methods described herein can be cryopreserved at a predetermined dose for use at a later time. Methods and reagents for cryopreserving cells are well-known in the art. Cryopreservation can include one or more washes and/or a step of concentrating the T cells and/or NK cells. The method can also include a step of forming a cryopreservation mixture, which includes the T cells and/or NK cells in the diluent solution and a suitable cryopreservative solution. In some embodiments, the method can include a step of freezing the cryopreservation mixture as is known in the art. Methods of thawing cryopreserved T cells and/or NK cells are known in the art.

Methods for Modulating Cab-Car-Expressing T Cell and/or NK Cell Activity by Changing pH Provided herein in certain aspects, are methods for modulating activation of an immune cell (e.g. T cell or NK cell) by contacting the immune cell with Axl or Ror2 in a microenvironment at a pH below 7.0 (e.g below 6.9 or 6.8) and then changing the pH of the microenvironment, such that it is at or above 7.0 (e.g. above 7.1, 7.2, or 7.3), wherein the immune cell expresses any of the CAB-CARs provided herein. In illustrative embodiments, the Axl or Ror2 is expressed on the surface of a target mammalian cell. In certain embodiments, such methods for modulating activation are the identical to methods for activating an immune cell provided herein, further comprising the additional step of increasing the pH of the microenvironment to a pH at or above 7.0 (e.g. above 7.1, 7.2, or 7.3), thereby decreasing the activation of the immune cell. In illustrative embodiments, such increase in pH deactivates the immune cell.

Provided herein in certain aspects, are methods for modulating binding and resulting lysis/killing of a target cell by a CAB-CAR-expressing T cell or NK cell by causing a change or shift in pH within a microenvironment that includes a target cell either within a target tissue or within one or more non-target (e.g. healthy/normal) tissues, by modulating binding of the CAB-CAR to its cognate antigen on a target cell(s), wherein the cognate antigen is an Axl polypeptide or an epitope thereof or a Ror2 polypeptide or an epitope thereof. Such methods typically include contacting a target cell, such as a mammalian cell (e.g. a human cell) with a CAB-CAR-expressing T cell or NK cell in a microenvironment and then changing the pH of the microenvironment, either by decreasing or more typically increasing the pH. The microenvironment can be a target microenvironment, for example a tumor, or an off-target microenvironment, where off-target binding can cause side-effects. In some embodiments, such methods can provide a transient reduction of tumor microenvironment sensitive CAR-T target binding.

Accordingly, in one aspect, provided herein is a method for modulating binding of a conditionally active biologic chimeric antigen receptor (CAB-CAR)-expressing T cell or NK cell to a cell expressing a cognate antigen of the CAB-CAR in a subject, that includes the following:
  a. introducing a T cell and/or NK cell comprising a nucleic acid encoding the CAB-CAR into the subject, wherein after (and optionally and/or during) the introducing, the T cell and/or the NK cell comprising the nucleic acid encoding the CAB-CAR expresses the CAB-CAR and binds to the cell expressing the cognate antigen in the subject, wherein the cognate antigen is an Axl polypeptide or an epitope thereof or a Ror2 polypeptide or an epitope thereof; and b. administering a pharmacologic agent to the subject in sufficient amount to increase blood pH and/or pH of a tissue and/or pH of a microenvironment, wherein the administering is performed before, during, or after the introducing, and wherein the increased pH of the blood, the tissue, and/or the microenvironment modulates binding of the CAB-CAR expressing T cell and/or NK cell to the cell expressing the cognate antigen in the blood, the tissue, or the microenvironment with the increased pH.

The change/shift in pH in aspects that include a step of administering a pH-modulating pharmacologic agent of the present disclosure can be accomplished by exposing target or non-target cells/tissue to a pH-modulating pharmacologic agent, such as by administering the pH modulating pharmacologic agent to a subject. Non-limiting examples of pH-modulating pharmacologic agents are provided herein. In certain aspects, provided herein is a pharmacologic agent for use in a method for modulating binding of a CAB-CAR to its cognate antigen or for modulating binding of a CAB-CAR-expressing T cell and/or NK cell to a cell that expresses its cognate antigen or for reducing or alleviating on target off tumor toxicity in a subject. Such aspects in certain embodiments, relate to treating tumor growth, cancer, hyperplasia, or cell proliferative disorders.

In other aspects, provided herein is use of a pH-modulating pharmacologic agent for use in the manufacture of a medicament or a kit for controlling binding of a genetically engineered T cell and/or NK cell to a target mammalian cell in a subject in vivo, wherein the target cell expresses an Axl polypeptide or an epitope thereof or a Ror2 polypeptide or an epitope thereof. In other aspects, provided herein is a kit that includes a container containing a replication incompetent recombinant retroviral particle, and instructions for use thereof for performing a method for treating tumor growth, wherein the instructions instruct a method for controlling binding of a T cell and/or NK cell to a target mammalian cell by modulating pH, wherein the target mammalian cell expresses an Axl polypeptide or an epitope thereof or a Ror2 polypeptide or an epitope thereof. Such method can be any of the methods provided herein this section for modulating CAB-CAR-expressing T cell and/or NK cell binding and/or activity by changing pH. The container that contains the recombinant retroviral particles can be a tube, vial, well of a plate, or other vessel for storage of a recombinant retroviral particle and/or a pH-modulating pharmacologic agent. Any of these can be of industrial strength and grade. The kit can include two or more containers in certain embodiments. One container/vessel can include the recombinant retroviral particles and another container/vessel can include a pH-modulating pharmacologic agent. In such methods the pharmacologic agent is delivered/administered in sufficient amount to increase blood pH and/or a tissue pH and/or a microenvironment pH to modulate binding of the CAB-CAR of a modified/recombinant T cell and/or NK cell expressing the CAB-CAR, to its cognate antigen in the blood and/or the tissue with the increased pH. Non-limiting exemplary details are provided herein for administering a pH modulating pharmacologic agent in sufficient amount and for a sufficient time.

Target cells, whether on target or off target with respect to a tissue, can be contacted with a pH modulating agent, such as a pH modulating pharmacologic agent, after introducing the CAB-CAR into a subject. Accordingly, exemplary aspects provided herein for modulating binding and/or cytotoxic activity of a CAB-CAR-expressing T cell that is capable of binding to (i.e. recognizes) an Axl polypeptide or an epitope thereof, or a Ror2 polypeptide or an epitope thereof, for example for alleviating on target off tumor activity and/or for inhibiting target cell proliferation, such as tumor cell proliferation, can include the following steps:

a. introducing a T cell and/or NK cell comprising a nucleic acid encoding a CAB-CAR into a subject wherein after the introducing, the T cell and/or the NK cell comprising the nucleic acid encoding the CAB-CAR expresses the CAB-CAR, wherein the CAB-CAR is capable of binding to Axl polypeptide or an epitope thereof, or a Ror2 polypeptide or an epitope thereof, and optionally binds to the cell expressing the cognate antigen in the subject; and b. administering a pharmacologic agent to the subject in sufficient amount to increase blood pH and/or a tissue pH and/or a microenvironment pH to modulate binding of the CAB-CAR-expressing T cell and/or NK cell to cells expressing the cognate antigen of the CAB-CAR, in the blood, the tissue, or the microenvironment with the increased pH. It will be understood that depending on the specific method used to introduce the nucleic acid encoding the CAB-CAR into the T cell and/or NK cell, the T cell and/or NK cell may or may not express the CAB-CAR before it is introduced into the subject. However, at some timepoint after introduction into the subject, e.g. 2 hours, 4 hours, 8 hours, 12 hours, 1 day, 2 days, 4 days and/or 7 days, or longer, the T cell and/or NK cell that include the nucleic acid encoding the CAB-CAR, express the CAB-CAR. Then such cells typically bind to a target cell expressing the cognate antigen for the CAB-CAR.

Methods provided herein for genetically modifying and optionally expanding lymphocytes of a subject can be used to introduce a nucleic acid sequence that encodes a CAB-CAR into the genome of a T cell and/or NK cell of the subject to produce an T cell and/or NK cell capable of expressing the CAB-CAR, and then to introduce the T cell and/or NK cell capable of expressing the CAB-CAR into the subject, wherein after introducing the T cell and/or NK cell expresses the CAB-CAR in order to contact the CAB-CAR with a target cells/tissue. The present disclosure provides details of how to perform such methods, along with various alternatives for different CAR components, any of which can be used in aspects of the disclosure that include changing pH to modulate binding of a CAB-CAR-expressing T cell and/or NK cell to a target cell expressing a cognate antigen for the CAB-CAR.

Such methods for genetically modifying and expanding lymphocytes typically involve contacting T cells and/or NK cells, with a replication incompetent recombinant retroviral particle to transduce the T cells and/or NK cells. Such contacting typically occurs ex vivo after removing the lymphocytes from the subject. The T cells and/or NK cells are then introduced/reintroduced into the subject, typically from whom they were removed. The replication incompetent recombinant retroviral particle includes a genome with a polynucleotide that encodes the CAB-CAR. Many alternative embodiments and further details regarding such a replication incompetent recombinant retroviral particle are provided in other sections herein and can be used in methods provided herein for regulating binding and resulting lysis/killing of T cells expressing CAB-CARs that are capable of binding to an Axl polypeptide or an epitope thereof, or a Ror2 polypeptide or an epitope thereof, by modulating pH in a microenvironment of a cell expressing a cognate target polypeptide recognized by the CAB-CAR in a pH-dependent manner.

Such methods for modulating binding of a target cell by a CAB-CAR-expressing T cell and/or NK cell can be used, for example, to reduce on target, off-tumor toxicity by increasing the pH of blood and/or a non-tumor tissue(s) within the subject. For example, in a situation where a "normal" tissue pH within a subject becomes transiently lower, a pH modulating agent can be delivered in a manner where pH of the normal tissue is increased while pH of the tumor remains lower and still at a pH where the CAB-CAR-expressing T cell and/or NK cell binds a target tumor cell. In these embodiments, the pH modulating agent can be delivered at a lower concentration or in a targeted manner to the normal tissue.

In some embodiments, this can be accomplished while allowing the pH within the tumor microenvironment to remain low enough for a CAB-CAR T cell and/or NK cell to bind to its cognate target-expressing cells within the tumor. In illustrative aspects of methods provided herein, the pH of a tissue remains at a pH under which a CAB-CAR-expressing T cell and/or NK cell binds its target for a period of time sufficient for a CAB-CAR-expressing T cell and/or NK cell to contact and bind to a cell expressing its cognate antigen (e.g. 2, 4, 8, 12, or 24 hours, or 2, 4, 7, 14, 28, or 30 days, or 1, 2, 3, 4, 5, 6, 12, 24 months, or longer), and then the pH is shifted/changed, for example by increasing the pH of the tissue to such a magnitude as to affect binding of the CAB-CAR-expressing T cell and/or NK cell to a target cell.

Accordingly, provided herein, in one aspect, is a method for transient reduction of tumor microenvironment sensitive CAR-T cell target binding through pharmacologic modification of vascular and tissue pH, wherein the CAR-T cell expresses a CAB-CAR that is capable of binding to an Axl polypeptide or an epitope thereof, or a Ror2 polypeptide or an epitope thereof. These microenvironmentally controlled ASTRs in CAR-T cells provide an additional level of protection against on-target off tumor toxicity, requiring tumor local environmental conditions to enable T cell engagement. While attractive for some monoclonal antibody therapies, adoptive cellular therapy may create local environments that are transiently permissive for their CAR-T targets. For example, CAR-T cells activated in tissues with a low pH may further reduce the pH of the microenvironment, depending on cytoplasmic domains present in the CAR construct. In other instances, cytokine release syndrome and other morbidity associated with adoptive cellular therapy may result in loss of the bicarbonate buffering capacity of blood, leading to lactic acidosis. It has been established that adoptive cellular therapies administered by intravenous infusion result in temporary pulmonary entrapment. For some cellular therapies, infusion rate requires constant monitoring of dissolved oxygen (Fischer et al. *Stem Cells Dev.* 2009 June; 18(5): 683-691). The extent of pulmonary entrapment is dependent upon cell size, activation state, cell dose, and infusion rate. Cruz et al (*Cytotherapy*. 2010 October; 12(6): 743-749) report the adverse findings from over 300 T cell infusions, that low doses and slow infusion may reduce pulmonary entrapment. However, with certain high potency CAR-T cells, targets present even in low levels on lung endothelium, such as Her2 (Morgan et al. *Mol Ther.* 2010 April; 18(4): 843-851), can result in immediate toxicity that cannot be controlled, and results in rapid patient deterioration due to the initial high CAR-T cellular concentration in the lung following infusion and the presence of the T cell target in these tissues. In other cases, the presence of T cell targets in other off target tissues such as bile duct may create on target off tumor toxicities that cannot be controlled (Lamers *Mol Ther.* 2013 April; 21(4):904-12) and result in severe organ toxicity before other agents such as steroids or cell elimination epitopes can be utilized. While venous and arterial plasma have strong buffering capacity against acidosis, conditions of respiratory acidosis, shock, metabolic acidosis and ischemic acidosis can occur in patients with cancer treated with adoptive cellular therapy.

In some aspects provided herein, the binding of a CAB-CAR in a subject can be modulated by administering a pharmacologic agent to the subject to increase or decrease the pH of the blood, a tissue and/or a microenvironment. In some aspects, on-target off tumor toxicity can be alleviated in a subject by administering a pharmacologic agent to the subject to increase or decrease the blood pH and/or the pH of a tissue and/or the pH of a microenvironment. In some aspects, the binding of a T cell and/or NK cell to a target mammalian cell can be controlled by introducing a pharmacologic agent to increase or decrease the blood pH and/or the pH of a tissue and/or the pH of a microenvironment. In some aspects, the binding of a genetically engineered T cell and/or NK cell to a target mammalian cell in a subject in vivo can be controlled by administering a pH-modulating pharmacologic agent to the subject. In illustrative embodiments, the pharmacologic agent can increase the blood pH and/or the pH of a tissue and/or the pH of a microenvironment. In some embodiments, the microenvironment can be an in vivo microenvironment. In illustrative embodiments, the microenvironment can be a tumor microenvironment. In some embodiments, the microenvironment can include a target mammalian cell, wherein the target mammalian cell expressed the target antigen on its surface. In some embodiments, administering a pharmacologic agent to a subject can increase the pH of blood, a tissue, and/or a microenvironment from a pH of less than 5.8, 5.9, 6.0, 6.1, 6.2, 6.3, 6.4, 6.5, 6.6, 6.7, 6.8, or 6.9 to a pH of at least 6.6, 6.7, 6.8, 6.9, 7.0, 7.1, 7.2, 7.3, 7.4, 7.5, or 7.6, wherein the pH of the blood, tissue, and/or microenvironment is lower before administering the pharmacologic agent than after administering the pharmacologic agent. In some embodiments, administering a pharmacologic agent to a subject can decrease the pH of blood, a tissue, or a microenvironment from a pH of more than 6.6, 6.7, 6.8, 6.9, 7.0, 7.1, 7.2, 7.3, 7.4, 7.5, or 7.6 to a pH of less than 5.8, 5.9, 6.0, 6.1, 6.2, 6.3, 6.4, 6.5, 6.6, 6.7, 6.8, 6.9, or 7.0, wherein the pH of the blood, tissue, and/or microenvironment is higher before administering the pharmacologic agent than after administering the pharmacologic agent. In some embodiments, administering a pharmacologic agent to a subject can cause a pH shift in the subject in the blood, a tissue, and/or a microenvironment. In some embodiments, the pH shift can be at least 0.1, 0.2, 0.3, 0.4, 0.5, 0.6, 0.7, 0.8, 0.9, 1.0, 1.1, 1.2, 1.3, 1.4, 1.5, 1.6, 1.7, or 1.8 pH units in either direction, i.e. an increase or decrease in pH after administering the pharmacologic agent relative to the pH before administering the pharmacologic agent. In illustrative embodiments, the pH shift is an increase in pH.

The CAB-CARs of the present disclosure can have reduced binding to its cognate antigen at one pH than at a different pH. In illustrative embodiments where illustrative pH values for differential binding of a CAB-CAR are not already provided in the broadest aspect and alternatively for other embodiments in place of those values for such aspects, the CAB-CAR can have reduced binding at a higher pH than at a lower pH. For example, the CAB-CAR can have reduced binding to its cognate antigen at a pH above 7.0, 7.1, 7.2, 7.3, 7.4, or 7.5 than at a pH below 6.4, 6.5, 6.6, 6.7, 6.8, 6.9, or 7.0. In other embodiments, the CAB-CAR can have reduced binding at a higher pH than at a lower pH. For example, the CAB-CAR can have reduced binding to its cognate antigen at a pH below 6.4, 6.5, 6.6, 6.7, 6.8, 6.9, or 7.0 than at a pH above 7.0, 7.1, 7.2, 7.3, 7.4, or 7.5. In some illustrative embodiments, the CAB-CAR exhibits increased binding at a pH of 6.5 to 6.7 compared to pH 7.4 to 7.6. In other illustrative embodiments, the CAB-CAR exhibits increased binding at a pH of 6.7 compared to a pH of 7.4. In other embodiments, the CAB-CAR exhibits increased binding in the pH of a tumor compared to the pH of blood. In some embodiments, the CAB-CAR can include an antigen-specific targeting region, a stalk, and an intracellular activating domain. In some embodiments, the CAB-CAR can also include a co-stimulatory domain. In some embodiments, the CAB-CAR can bind to a tumor associated antigen. In some embodiments, the CAB-CAR binds to an Axl polypeptide or an epitope thereof or a Ror2 polypeptide or an epitope thereof.

In methods that include modulating the pH of the blood, a tissue, or a microenvironment, the pH of the microenvironment can be increased from a pH below 7.0 to a pH above 7.0. For example, the pH can be increased from a pH below 6.4, 6.5, 6.6, 6.7, 6.8, 6.9, or 7.0 to a pH above 7.0, 7.1, 7.2, 7.3, or 7.4. In some embodiments, the CAB-CAR can bind to the cognate antigen at the increased pH but not a pH of the microenvironment before introducing the pharmacologic agent. In certain embodiments, the pH can be increased from below 7.0 to a pH of 7.1 to 8.0 or to a pH of 7.1 to 7.8 or to a pH of 7.2 to 7.8 or a pH of 7.2 to 7.6 or a pH of 7.3 to 7.6 or to a pH of 7.4 to 7.8 or to a pH of 7.4 to 7.6. Such an increase in pH can occur for less than 1, 2, 4, 6, 8, 12, or 24 hours or for more than 1, 2, 4, 6, 8, 12 or 24 hours depending on the type and dose of pharmacologic agent administered. In certain embodiments, the pharmacologic agent is administered such that the pH remains above 7.0, 7.1, 7.2, 7.3, 7.4, or 7.5; or between 7.0, 7.1, 7.2, 7.3 on the low end of the range and 7.4, 7.5, 7.6, 7.7, or 7.8 on the high end of the range, in the target tissue, such as a tumor, and for example in at least a surface of a target tissue (e.g. tumor) microenvironment, in at least a portion of a target tissue (e.g. tumor) microenvironment, and in illustrative embodiments throughout a target tissue (e.g. tumor) microenvironment. The microenvironment can be an in vivo microenvironment, such as a tumor, a tissue, a non-tumor tissue, a normal tissue, or a tissue that has undergone a transient shift in pH. For example, tissues that typically undergo transient shifts in pH include a muscle tissue in anaerobic conditions or muscle tissue undergoing exercise or an inflamed tissue or a tissue experiencing inflammation. In some embodiments that include a target mammalian cell, the target mammalian cell can be a tumor cell or a non-tumor or normal cell.

In some aspects, methods for transiently increasing vascular pH to reduce affinity of microenvironmentally controlled CAB-CARs that recognize, are capable of binding, and in some embodiments bind an Axl polypeptide or an epitope thereof, or a Ror2 polypeptide or an epitope thereof are provided. A 0.4 U shift in blood pH can reduce the affinity of certain scFvs that form a portion of a CAB-CAR, for their cognate antigen by greater than 10-fold. In some embodiments, therapeutic pH control can be achieved via IV or oral administration routes of various pharmacologic agents. For example, in some embodiments, inactivation of binding affinity can be achieved with bicarbonate or sodium bicarbonate. In other embodiments, Tris-hydroxymethyl aminomethane (also known as tromethamine, trometamol, and THAM) and/or Carbicarb™ (an equimolar hypertonic solution of sodium bicarbonate and sodium carbonate) can be utilized to increase the pH of the blood in a sufficient amount to alleviate on-target off tumor toxicities. In still other embodiments, small molecule proton pump inhibitors can be utilized to increase blood pH and/or tissue pH in a sufficient amount to alleviate on-target off tumor toxicities. Proton pump inhibitors that can be used in methods that include modulating pH include, but are not limited to, esomeprazole (Nexium), esomeprazole and naproxen (Vimovo), lansoprazole (Prevacid), omeprazole (Prilosec and Zegerid), and rabeprazole (Aciphex). Administration of proton pump inhibitors can be used effectively over longer time periods to modulate the binding affinity of the antigen biding domain to its cognate antigen for days, weeks, months, or years. In other embodiments, the affinity of the antigen binding domain for its cognate antigen can be modulated by altering the blood pH and/or tissue pH by controlling the transcription, translation, membrane expression, and stability of transporters and pumps. Examples of such transporters and pumps whose altered expression can be to modulate pH include, but are not limited to, proton pumps, members of the sodium proton exchange family (NHE), bicarbonate transporter family (BCT), and monocarboxylate transporter family.

In certain embodiments, a pH-modulating pharmacologic agent, such as, for example, bicarbonate, THAM, or Caricarb™ are administered prior to or concurrent with infusion of a patient's CAR-T cells expressing conditionally active biologic ASTRs (e.g. scFvs or scFvFcs). Such treatment will alleviate the immediate cytoxicity that is otherwise associated with the temporary pulmonary entrapment of CAR-T cell infusions. Accordingly, in certain aspects provided herein is a method for reducing cytotoxicity caused to normal, healthy tissue of a subject by administering a pharmacologic agent to the subject in sufficient amount to increase blood pH and/or a tissue pH and/or a microenvironment pH; and either concomitantly or subsequently (e.g. 1, 2, 4, 6, 8, 12, or 24 hours, or 1, 2, 3, 4, or 7 days later) introducing a CAB-CAR-expressing T cell or NK cell into the subject. In certain embodiments, at a target time after such introducing (e.g. 1, 2, 4, 6, 8, 12, or 24 hours, or 1, 2, 3, 4, or 7 days later), administration of the pharmacologic agent is terminated for a period of time or indefinitely, in order to change the pH of the blood, a tissue, or a microenvironment of the subject and modulate binding/activity of the CAB-CAR-expressing T cell.

Various effective dosing regimens for administering the pharmacologic agents capable of modulating pH (e.g. increasing blood pH and/or a tissue pH and/or the pH of a microenvironment in a subject) can be used, as will be understood by a skilled artisan. Herein, administering can refer to giving a pharmacologic agent to a subject including injecting a pharmacologic agent through an IV into a subject or providing an oral dose of a pharmacologic agent to a subject or a subject taking a pharmacologic agent. The pharmacologic agents can be administered to the subject or patient for various lengths of time, for example, at least 1, 2, 3, 4, 5, or 6 days; 1, 2, 3, 4, 5, 6, 7, 8, 9, 10, or 11 weeks; 3, 4, 5, 6, 7, 8, 9, 10, 12, 15, or 18 months; or 2, 2.5, 3, 3.5, 4, 4.5, or 5 years or indefinitely. In some embodiments, the pharmacologic agent can be bicarbonate, sodium bicarbonate ($NaHCO_3$), or a solution of sodium bicarbonate and sodium carbonate and a parenteral or IV dosage can be: 0.2×weight of subject (kg)×base deficit of the subject; $HCO_3$ (mEq) required=0.5×weight (kg)×[24−serum $HCO_3$ (mEq/L)]; or 2 to 5 mEq/kg IV infusion over 4 to 8 hours. In some embodiments, standard dosing regimens of bicarbonate, sodium bicarbonate, or a solution of sodium bicarbonate can be used depending on the severity of the acidosis. For example, 50 to 150 mEq bicarbonate diluted in 1 L of 5% dextrose in water can be administered via IV at a rate of 1 to 1.5 L/hour. In another non-limiting example, 90 to 180 mEq bicarbonate diluted in 1 L of 5% dextrose in water can be administered via IV at a rate of 1 to 1.5 L/hour. In some embodiments where the pharmacologic agent is bicarbonate or sodium bicarbonate ($NaHCO_3$), an enteral or oral dosage can be, for example, 325 to 2000 mg sodium bicarbonate given to a subject 1 to 4 times/day.

In some embodiments, the pharmacologic agent can be tris-hydroxymethyl aminomethane (also known as tromethamine, trometamol, and THAM) and a parenteral or IV dosage can be estimated as: Tromethamine solution (mL of 0.3 M) required=Body Weight (kg)×Base Deficit (mEq/liter)×1.1. In some embodiments, the IV dosage of tris-hydroxymethyl aminomethane can be estimated from the buffer base deficit of the extracellular fluid in mEq/L as determined by means of the Siggaard-Andersen nomogram. In some embodiments, the initial dose can be 500 ml (150 mEq) of tris-hydroxymethyl aminomethane injected by slow IV infusion with up to 1000 mL, wherein the maximum dose is 500 mg/kg (227 mg/lb) over a period of not less than one hour.

In some embodiments, the pharmacologic agent can be a small molecule proton pump inhibitor and can be administered for extended treatment lengths. For example, the small molecule proton pump inhibitor can be administered for at least 1, 2, 3, 4, 5, or 6 days; 1, 2, 3, 4, 5, 6, 7, 8, 9, 10, or 11 weeks; 3, 4, 5, 6, 7, 8, 9, 10, 12, 15, or 18 months; or 2, 2.5, 3, 3.5, 4, 4.5, or 5 years or indefinitely. In some embodiments, the proton pump inhibitor can be esomeprazole (Nexium) and 20 mg or 40 mg esomeprazole can be administered orally once or twice daily. In some embodiments, the proton pump inhibitor can be a combination of esomeprazole and naproxen (Vimovo) and 20 mg esomeprazole with 375 or 500 mg naproxen can be administered orally twice daily. In some embodiments, the proton pump inhibitor can be lansoprazole (Prevacid) and 15, 30, or 60 mg lansoprazole can be administered orally once or twice daily. In some embodiments, lansoprazole can be administered by IV with 30 mg lansoprazole injected over 30 minutes once daily for up to 7 days. The subject can then switch to oral lansoprazole and continue treatment. In some embodiments, the proton pump inhibitor can be omeprazole (Prilosec and Zegerid) and 10, 20, or 40 mg omeprazole can be administered orally once or twice daily. In some embodiments, the proton pump inhibitor can be rabeprazole (Aciphex) and 20 or 60 mg rabeprazole can be administered orally once or twice daily or 100 mg rabeprazole can be administered orally once daily. In any of the embodiments disclosed herein, the pharmacologic agents can be used in combination with each other.

In any of the embodiments disclosed herein, the pH of the blood, a tissue, and/or a microenvironment of a subject can be measured before, during, or after the administration of a pharmacologic agent. In some embodiments, the decision to administer or to continue to administer, to a subject the pharmacologic agent to increase or decrease the pH can be based on the pH measurement of the blood, a tissue, and/or a microenvironment of the subject. Methods to measure the blood pH and/or bicarbonate levels of the blood of a subject are well-known in the art. In some embodiments, positron emission tomography (PET), magnetic resonance spectroscopy (MRS), magnetic resonance imaging (MRI), and optical imaging can be used to measure in vivo pH in microenvironments, for example, in tumors (for details of measuring tumor pH, see: Zhang X, Lin Y, Gillies R J. Tumor pH and its measurement. J Nucl Med. 2010 August; 51(8):1167-70).

In another aspect, provided herein is a method for alleviating on target off tumor toxicity in a subject, that includes the following:
  a. introducing a polynucleotide encoding a conditionally active biologic chimeric antigen receptor (CAB-CAR) into a T cell or NK cell of the subject to produce a T cell and/or NK cell capable of expressing the CAB-CAR, wherein the CAB-CAR is capable of binding to an Axl polypeptide or an epitope thereof, or a Ror2 polypeptide or an epitope thereof;
  b. introducing the T cell and/or NK cell capable of expressing the CAB-CAR into the subject, wherein the T cell and/or NK cell express the CAB-CAR in the subject; and
  c. administering a pharmacologic agent to the subject in sufficient amount to increase blood pH and/or pH of a tissue and/or pH of a microenvironment to modulate binding of the CAB-CAR to its cognate antigen in the blood, the tissue, and/or the microenvironment with the increased pH, thereby alleviating on target off tumor toxicity in the subject.

In the introducing step, the T cell or NK cell is capable of expressing the CAB-CAR that is capable of binding to an Axl polypeptide or an epitope thereof, or a Ror2 polypeptide or an epitope thereof because it is genetically modified to contain the nucleic acid that encodes the CAB-CAR. This genetic modification can be the presence of the CAB-CAR coding sequence on a vector that has been introduced inside the T cell or NK cell by transfection or transduction. In illustrative embodiments the nucleic acid encoding the CAB-CAR is integrated into the genome of the T cell or NK cell.

It is envisioned that various methods known in the art for introducing a polynucleotide into a T cell and/or NK cell could be used with methods provided herein for aspects that include changing pH to affect binding of a CAB-CAR T cell or NK cell to its cognate antigen on a cell using an agent such as a pH-modulating pharmacologic agent (sometimes referred to herein as "pH Switch aspects"). Typically, a vector, in illustrative examples an expression vector, is used to deliver the polynucleotide. Such vectors can include various vectors known in the art for delivery nucleic acids to T cells and/or NK cells. Illustrative aspects of the invention utilize retroviral vectors and retroviral particles, and in some particularly illustrative embodiments lentiviral vectors and in illustrative embodiments, recombinant lentiviral particles.

Other suitable expression vectors can be used in pH switch aspects provided herein. Such expression vectors include, but are not limited to, viral vectors (e.g. viral vectors based on vaccinia virus; poliovirus; adenovirus (see, e.g., Li et al., Invest Opthalmol Vis Sci 35:2543 2549, 1994; Borras et al., Gene Ther 6:515 524, 1999; Li and Davidson, PNAS 92:7700 7704, 1995; Sakamoto et al., H Gene Ther 5:1088 1097, 1999; WO 94/12649, WO 93/03769; WO 93/19191; WO 94/28938; WO 95/11984 and WO 95/00655); adeno-associated virus (see, e.g., Ali et al., Hum Gene Ther 9:81 86, 1998, Flannery et al., PNAS 94:6916 6921, 1997; Bennett et al., Invest Opthalmol Vis Sci 38:2857 2863, 1997; Jomary et al., Gene Ther 4:683 690, 1997, Rolling et al., Hum Gene Ther 10:641 648, 1999; Ali et al., Hum Mol Genet 5:591 594, 1996; Srivastava in WO 93/09239, Samulski et al., J. Vir. (1989) 63:3822-3828; Mendelson et al., Virol. (1988) 166:154-165; and Flotte et al., PNAS (1993) 90: 10613-10617); SV40; herpes simplex virus; or a retroviral vector (e.g., Murine Leukemia Virus, spleen necrosis virus, and vectors derived from retroviruses such as Rous Sarcoma Virus, Harvey Sarcoma Virus, avian leukosis virus, human immunodeficiency virus, myeloproliferative sarcoma virus, and mammary tumor virus), for example a gamma retrovirus; or human immunodeficiency virus (see, e.g., Miyoshi et al., PNAS 94:10319 23, 1997; Takahashi et al., J Virol 73:7812 7816, 1999); and the like.

In some embodiments, DNA-containing viral particles are utilized instead of recombinant retroviral particles. Such viral particles can be adenoviruses, adeno-associated viruses, herpesviruses, cytomegaloviruses, poxviruses, avipox viruses, influenza viruses, vesicular stomatitis virus (VSV), or Sindbis virus. A skilled artisan will appreciate how to modify the methods disclosed herein for use with different viruses and retroviruses. Where viral particles are used that include a DNA genome, a skilled artisan will appreciate that functional units can be included in such genomes to induce integration of all or a portion of the DNA genome of the viral particle into the genome of a T cell and/or NK cell transduced with such virus. Alternatively, functional DNA can be delivered to a T cell and/or NK cell that is expressed in the cell but is not integrated into the genome of the T cell and/or NK cell.

In illustrative embodiments, the vector used in a pH switch aspect of the present disclosure is a recombinant retroviral particle and in certain embodiments, a recombinant lentiviral particle. Such retroviral particle typically includes a retroviral genome within a capsid which is located within a viral envelope. The present disclosure in various sections herein, provide various embodiments of recombinant retroviral particles that disclose elements that can be included on the surface or within, and/or in the genome of a recombinant retroviral particle. Any of these recombinant retroviral particle embodiments can be used in the pH switch aspects provided herein.

In any of the embodiments disclosed above, the cognate antigen to which the CAB-CAR binds can be an Axl polypeptide or an epitope thereof, or a Ror2 polypeptide or an epitope thereof. In some embodiments, the cognate antigen can be a polypeptide with at least 50%, 55%, 60%, 65%, 70%, 75%, 80%, 85%, 90%, 95%, 96%, 97%, 98%, 99%, or 100% sequence identity to a stretch of at least 10, 15, 20, or all of the amino acids of an Axl polypeptide or an epitope thereof or to a Ror2 polypeptide or an epitope thereof. As disclosed herein, the CAB-CAR capable of binding to an Axl polypeptide or an epitope thereof, or a Ror2 polypeptide or an epitope thereof typically binds its cognate antigen with a higher binding affinity at a pH of 6.7 than a pH of 7.4. Thus, such anti-ROR2 and anti-AXL CAB-CARs of the present disclosure typically bind to their cognate antigen with a higher binding affinity in a tumor microenvironment than a normal tissue with a physiological pH.

Treatment Methods

The present disclosure provides various methods for treating a disorder that include an anti-Axl or anti-Ror2 CAB-CAR provided herein. In some embodiments, the methods take advantage of the fact that a CAB-CAR of the present disclosure, when present in and expressed by a T lymphocyte or an NK cell, can mediate cytotoxicity toward a target cell. A CAB-CAR of the present disclosure binds to an antigen present on a target cell under certain target conditions, thereby mediating killing of a target cell by a T lymphocyte or an NK cell genetically modified to produce the CAB-CAR. The ASTR of the CAB-CAR typically binds to an antigen present on the surface of a target cell.

Target cells include, but are not limited to, cancer cells. Thus, the present disclosure provides methods of killing, or inhibiting the growth of, a target cancer cell, the method involving contacting a cytotoxic immune effector cell (e.g., a cytotoxic T cell, or an NK cell) that is genetically modified to produce a subject CAR, such that the T lymphocyte or NK cell recognizes an antigen present on the surface of a target cancer cell, and mediates killing of the target cell. Illustrative aspects of such methods provide methods for treating cancer. CAB-CARs are not limited to uses for treating cancer or targeting tumor or cancer cells, but rather could be appropriate for use in one or more indication including the treatment of circulatory disorders, arthritis, multiple sclerosis, autoimmune disorders, dermatologic disorders, viral diseases and disorders and use in various diagnostic formats.

In certain aspects, the present disclosure provides a method of treating cancer in a subject having a cancer. As such the present disclosure provides methods for adoptive cellular therapy against cancer, especially a cancer that expresses Axl or Ror2, that use the anti-Axl and Anti-Ror2 CAB-CARs provided herein. Accordingly, in one aspect the method includes the following: A. introducing an expression vector configured to express a polynucleotide sequence encoding a CAB-CAR directed to Axl or Ror2 as provided herein, into peripheral blood cells obtained from the subject to produce a genetically engineered cytotoxic cell (such as a T cell or NK cell); and B. administering the genetically engineered cytotoxic cell to the subject. Detailed methods for processing T cells to activate, transduce and typically expand such cells that provide illustrative embodiments of step A above are provided herein.

The cancer typically expresses Ror2 or Axl, respectively, and in illustrative embodiments the cancer is any cancer in which cells of such cancer express Ror2 and/or Axl, such as renal cell carcinoma. The CAR can be any of the CAB-CARs that recognize Axl or Ror2 disclosed herein, especially those that are cytotoxic to cancer cells expressing these antigens. The expression vector encoding an anti-Axl CAB-CAR or anti-Ror2 CAB-CAR can be introduced into peripheral blood cells by transducing peripheral blood leucocytes that include T cell and/or NK cells with the vector. In certain illustrative embodiments, the vector is a recombinant virus, such as a recombinant retrovirus that in some embodiments is a recombinant lentivirus. In some embodiments, the cancer is a soft tissue sarcoma or mesothelioma that expresses Ror2 and T cells and/or NK cells of the subject (e.g. soft tissue sarcoma patient or mesothelioma patient) are transduced with an anti-Ror2 CAR, for example an anti-Ror2 CAB-CAR disclosed herein.

Methods for treating a disorder provided herein typically include administering a genetically modified T cells or NK cells that express anti-Axl or anti-Ror2 CAB-CARs provided herein, to a subject. The administration can be, for example, intravenous administration, subcutaneous administration, or intratumor administration. In methods in which genetically modified T cells and/or NK cells are intravenously administered, typically between $1 \times 10^4$ cells/kg and $1 \times 10^8$ cells/kg cells are delivered in a suitable buffer for parenteral administration. In methods in which genetically modified T cells and/or NK cells are administered intratumorally, typically between $1 \times 10^6$ cells and $5 \times 10^8$ cells are delivered in an isotonic solution.

In some embodiments, the administration is preceded, accompanied by, and/or followed by administration of an interleukin or a modified version thereof. For example, some embodiments provided herein include co-administration of IL-2, or a modified version of IL-2 that has sustained release and/or binds to certain IL-2 receptors that are biased toward activating proliferation and/or killing activity of T cells. For example, the modified IL-2 in certain embodiments is a pegylated IL-2, and can be NKTR-214 (Nektar Therapeutics, San Francisco, CA). In other embodiments, the modified IL-2 is ALKS 4230 (Alkermes, Inc.).

Carcinomas that can be amenable to therapy by a method disclosed herein include, but are not limited to, esophageal carcinoma, hepatocellular carcinoma, basal cell carcinoma (a form of skin cancer), squamous cell carcinoma (various tissues), bladder carcinoma, including transitional cell carcinoma (a malignant neoplasm of the bladder), bronchogenic carcinoma, colon carcinoma, colorectal carcinoma, gastric carcinoma, lung carcinoma, including small cell carcinoma and non-small cell carcinoma of the lung, adrenocortical carcinoma, thyroid carcinoma, pancreatic carcinoma, breast carcinoma, ovarian carcinoma, prostate carcinoma, adenocarcinoma, sweat gland carcinoma, sebaceous gland carcinoma, papillary carcinoma, papillary adenocarcinoma, cystadenocarcinoma, medullary carcinoma, renal cell carcinoma, ductal carcinoma in situ or bile duct carcinoma, choriocarcinoma, seminoma, embryonal carcinoma, Wilm's tumor, cervical carcinoma, uterine carcinoma, testicular carcinoma, osteogenic carcinoma, epithelial carcinoma, and nasopharyngeal carcinoma.

Sarcomas that can be amenable to therapy by a method disclosed herein include, but are not limited to, fibrosarcoma, myxosarcoma, liposarcoma, chondrosarcoma, chordoma, osteogenic sarcoma, osteosarcoma, angiosarcoma, endotheliosarcoma, lymphangiosarcoma, lymphangioendotheliosarcoma, synovioma, mesothelioma, Ewing's sarcoma, leiomyosarcoma, rhabdomyosarcoma, and other soft tissue sarcomas.

Other solid tumors that can be amenable to therapy by a method disclosed herein include, but are not limited to, glioma, astrocytoma, medulloblastoma, craniopharyngioma, ependymoma, pinealoma, hemangioblastoma, acoustic neuroma, oligodendroglioma, menangioma, melanoma, neuroblastoma, and retinoblastoma.

Leukemias that can be amenable to therapy by a method disclosed herein include, but are not limited to, a) chronic myeloproliferative syndromes (neoplastic disorders of multipotential hematopoietic stem cells); b) acute myelogenous leukemias (neoplastic transformation of a multipotential hematopoietic stem cell or a hematopoietic cell of restricted lineage potential; c) chronic lymphocytic leukemias (CLL; clonal proliferation of immunologically immature and functionally incompetent small lymphocytes), including B-cell CLL, T-cell CLL prolymphocytic leukemia, and hairy cell leukemia; and d) acute lymphoblastic leukemias (characterized by accumulation of lymphoblasts). Lymphomas that can be treated using a subject method include, but are not limited to, B-cell lymphomas (e.g., Burkitt's lymphoma); Hodgkin's lymphoma; non-Hodgkin's lymphoma, and the like.

Other cancers that can be amenable to treatment according to the methods disclosed herein include atypical meningioma (brain), islet cell carcinoma (pancreas), medullary carcinoma (thyroid), mesenchymoma (intestine), hepatocellular carcinoma (liver), hepatoblastoma (liver), clear cell carcinoma (kidney), and neurofibroma mediastinum.

Combination Therapy

In some embodiments, a CAR cell is administered as an adjuvant therapy to a standard cancer therapy. Standard cancer therapies include surgery (e.g., surgical removal of cancerous tissue), radiation therapy, bone marrow transplantation, chemotherapeutic treatment, antibody treatment, biological response modifier treatment, and certain combinations of the foregoing.

Radiation therapy includes, but is not limited to, x-rays or gamma rays that are delivered from either an externally applied source such as a beam, or by implantation of small radioactive sources.

Suitable antibodies for use in cancer treatment include, but are not limited to, naked antibodies, e.g., trastuzumab (Herceptin), bevacizumab (Avastin™), cetuximab (Erbitux™) panitumumab (Vectibix™), Ipilimumab (Yervoy™), rituximab (Rituxan), alemtuzumab (Lemtrada™), Ofatumumab (Arzerra™), Oregovomab (OvaRex™), Lambrolizumab (MK-3475), pertuzumab (Perjeta™), ranibizumab (Lucentis™) etc., and conjugated antibodies, e.g., gemtuzumab ozogamicin (Mylortarg™), Brentuximab vedotin $^{90}$Y-labelled ibritumomab tiuxetan (Zevalin™) $^{131}$I-labelled tositumoma (Adcetris™), (Bexxar™), etc. Suitable antibodies for use in cancer treatment include, but are not limited to, antibodies raised against tumor-associated antigens. Such antigens include, but are not limited to, CD20, CD30, CD33, CD52, EpCAM, CEA, gpA33, Mucins, TAG-72, CAIX, PSMA, Folate-binding protein, Gangliosides (e.g., GD2, GD3, GM2, etc.), Le$^y$, VEGF, VEGFR, Integrin alpha-V-beta-3, Integrin alpha-5-beta-1, EGFR, ERBB2, ERBB3, MET, IGF1R, EPHA3, TRAILR1, TRAILR2, RANKL, PAP, Tenascin, etc.

Biological response modifiers suitable for use in connection with the methods of the present disclosure include, but are not limited to, (1) inhibitors of tyrosine kinase (RTK) activity; (2) inhibitors of serine/threonine kinase activity; (3) tumor-associated antigen antagonists, such as antibodies that bind specifically to a tumor antigen; (4) apoptosis receptor agonists; (5) interleukin-2; (6) interferon-α; (7) interferon-γ; (8) colony-stimulating factors; (9) inhibitors of angiogenesis; and (10) antagonists of tumor necrosis factor.

Chemotherapeutic agents are non-peptidic (i.e., non-proteinaceous) compounds that reduce proliferation of cancer cells, and encompass cytotoxic agents and cytostatic agents. Non-limiting examples of chemotherapeutic agents include alkylating agents, nitrosoureas, antimetabolites, antitumor antibiotics, plant (vinca) alkaloids, and steroid hormones.

Agents that act to reduce cellular proliferation are known in the art and widely used. Such agents include alkylating agents, such as nitrogen mustards, nitrosoureas, ethylenimine derivatives, alkyl sulfonates, and triazenes, including, but not limited to, mechlorethamine, cyclophosphamide (Cytoxan™), melphalan (L-sarcolysin), carmustine (BCNU), lomustine (CCNU), semustine (methyl-CCNU), streptozocin, chlorozotocin, uracil mustard, chlormethine, ifosfamide, chlorambucil, pipobroman, triethylenemelamine, triethylenethiophosphoramine, busulfan, dacarbazine, and temozolomide.

Antimetabolite agents include folic acid analogs, pyrimidine analogs, purine analogs, and adenosine deaminase inhibitors, including, but not limited to, cytarabine (CYTOSAR-U), cytosine arabinoside, fluorouracil (5-FU), floxuridine (FudR), 6-thioguanine, 6-mercaptopurine (6-MP), pentostatin, 5-fluorouracil (5-FU), methotrexate, 10-propargyl-5,8-dideazafolate (PDDF, CB37 1 7), 5,8-dideazatetrahydrofolic acid (DDATHF), leucovorin, fludarabine phosphate, pentostatine, and gemcitabine.

Suitable natural products and their derivatives, (e.g., vinca alkaloids, antitumor antibiotics, enzymes, lymphokines, and epipodophyllotoxins), include, but are not limited to, Ara-C, paclitaxel (Taxol®), docetaxel (Taxotere®), deoxycoformycin, mitomycin-C, L-asparaginase, azathioprine; brequinar;

alkaloids, e.g. vincristine, vinblastine, vinorelbine, vindesine, etc.; podophyllotoxins, e.g. etoposide, teniposide, etc.; antibiotics, e.g. anthracycline, daunorubicin hydrochloride (daunomycin, rubidomycin, cerubidine), idarubicin, doxorubicin, epirubicin and morpholino derivatives, etc.; phenoxizone biscyclopeptides, e.g. dactinomycin; basic glycopeptides, e.g. bleomycin; anthraquinone glycosides, e.g. plicamycin (mithramycin); anthracenediones, e.g. mitoxantrone; azirinopyrrolo indolediones, e.g. mitomycin; macrocyclic immunosuppressants, e.g. cyclosporine, FK-506 (tacrolimus, prograf), rapamycin, etc.; and the like.

Other anti-proliferative cytotoxic agents are navelbene, CPT-11, anastrazole, letrazole, capecitabine, reloxafine, cyclophosphamide, ifosamide, and droloxafine.

Microtubule affecting agents that have antiproliferative activity are also suitable for use and include, but are not limited to, allocolchicine (NSC 406042), Halichondrin B (NSC 609395), colchicine (NSC 757), colchicine derivatives (e.g., NSC 33410), dolastatin 10 (NSC 376128), maytansine (NSC 153858), rhizoxin (NSC 332598), paclitaxel (Taxol®), Taxol® derivatives, docetaxel (Taxotere®), thiocolchicine (NSC 361792), trityl cysteine, vinblastine sulfate, vincristine sulfate, natural and synthetic epothilones including but not limited to, eopthilone A, epothilone B, discodermolide; estramustine, nocodazole, and the like.

Hormone modulators and steroids (including synthetic analogs) that are suitable for use include, but are not limited to, adrenocorticosteroids, e.g. prednisone, dexamethasone, etc.; estrogens and progestins, e.g. hydroxyprogesterone caproate, medroxyprogesterone acetate, megestrol acetate, estradiol, clomiphene, tamoxifen; etc.; and adrenocortical suppressants, e g aminoglutethimide; 17a-ethinylestradiol; diethylstilbestrol, testosterone, fluoxymesterone, dromostanolone propionate, testolactone, methylprednisolone, methyl-testosterone, prednisolone, triamcinolone, chlorotrianisene, hydroxyprogesterone, aminoglutethimide, estramustine, medroxyprogesterone acetate, leuprolide, Flutamide (Drogenil), Toremifene (Fareston), and Zoladex®. Estrogens stimulate proliferation and differentiation, therefore compounds that bind to the estrogen receptor are used to block this activity. Corticosteroids may inhibit T cell proliferation.

Other chemotherapeutic agents include metal complexes, e.g. cisplatin (cis-DDP), carboplatin, etc.; ureas, e.g. hydroxyurea; and hydrazines, e.g. N-methylhydrazine; epidophyllotoxin; a topoisomerase inhibitor; procarbazine; mitoxantrone; leucovorin; tegafur; etc. Other anti-proliferative agents of interest include immunosuppressants, e.g. mycophenolic acid, thalidomide, desoxyspergualin, azasporine, leflunomide, mizoribine, azaspirane (SKF 105685); Iressa® (ZD 1839, 4-(3-chloro-4-fluorophenylamino)-7-methoxy-6-(3-(4-morpholinyl)propoxy)quinazoline); etc.

"Taxanes" include paclitaxel, as well as any active taxane derivative or pro-drug. "Paclitaxel" (which should be understood herein to include analogues, formulations, and derivatives such as, for example, docetaxel, TAXOL™, TAXOTERE™ (a formulation of docetaxel), 10-desacetyl analogs of paclitaxel and 3'N-desbenzoyl-3'N-t-butoxycarbonyl analogs of paclitaxel) may be readily prepared utilizing techniques known to those skilled in the art (see also WO 94/07882, WO 94/07881, WO 94/07880, WO 94/07876, WO 93/23555, WO 93/10076; U.S. Pat. Nos. 5,294,637; 5,283,253; 5,279,949; 5,274,137; 5,202,448; 5,200,534; 5,229,529; and EP 590,267), or obtained from a variety of commercial sources, including for example, Sigma Chemical Co., St. Louis, Mo. (T7402 from *Taxus brevifolia*; or T-1912 from *Taxus yannanensis*).

Paclitaxel should be understood to refer to not only the common chemically available form of paclitaxel, but analogs and derivatives (e.g., Taxotere™ docetaxel, as noted above) and paclitaxel conjugates (e.g., paclitaxel-PEG, paclitaxel-dextran, or paclitaxel-xylose).

Also included within the term "taxane" are a variety of known derivatives, including both hydrophilic derivatives, and hydrophobic derivatives. Taxane derivatives include, but are not limited to, galactose and mannose derivatives described in International Patent Application No. WO 99/18113; piperazino and other derivatives described in WO 99/14209; taxane derivatives described in WO 99/09021, WO 98/22451, and U.S. Pat. No. 5,869,680; 6-thio derivatives described in WO 98/28288; sulfenamide derivatives described in U.S. Pat. No. 5,821,263; and taxol derivative described in U.S. Pat. No. 5,415,869. It further includes prodrugs of paclitaxel including, but not limited to, those described in WO 98/58927; WO 98/13059; and U.S. Pat. No. 5,824,701.

Subjects Suitable for Treatment

A variety of subjects are suitable for treatment with a method of treating cancer. Suitable subjects include any individual, e.g., a human or non-human animal who has cancer, who has been diagnosed with cancer, who is at risk for developing cancer, who has had cancer and is at risk for recurrence of the cancer, who has been treated with an agent for the cancer and failed to respond to such treatment, or who has been treated with an agent for the cancer but relapsed after initial response to such treatment.

Subjects suitable for treatment with an immunomodulatory method include individuals who have an autoimmune disorder; individuals who are organ or tissue transplant recipients; and the like; individuals who are immunocompromised; and individuals who are infected with a pathogen.

EXEMPLARY EMBODIMENTS

The present disclosure provides chimeric antigen receptors (CARs), and nucleic acids comprising the nucleotide sequences encoding the CARs, that bind to Axl and/or Ror2, and conditionally active CARs that bind to Axl and Ror2. The present disclosure provides cells genetically modified to produce the CARs, and methods for making such cells. The CARs of the present disclosure can be used in various methods, which are also provided, including methods for performing adoptive cell therapy such as CAR therapy, for example CAR therapy against cancer, for example renal cell carcinoma.

Some non-limiting exemplary embodiments that are aspects of the present disclosure are provided in the following Embodiments:

Embodiment 1

A chimeric antigen receptor (CAR) for binding Axl or Ror2, comprising:

a) a conditionally active antigen-specific targeting region (ASTR) that exhibits an increased binding to Axl or Ror2 at a pH of 6.7 compared to a pH of 7.4;

b) a transmembrane domain; and c) an intracellular activating domain

Embodiment A1

A chimeric antigen receptor (CAR) for binding Axl or Ror2, comprising:
a) a conditionally active antigen-specific targeting region (ASTR) that exhibits an increase in (i.e. a greater) activity in a tumor microenvironment and/or in an in vitro tumor surrogate assay condition, compared to a normal physiological environment, wherein the ASTR binds to Axl or Ror2;
b) a transmembrane domain; and
c) an intracellular activating domain

Embodiment A2

The CAR of any one of Embodiments 1 or A1, or according to any other Embodiment provided herein unless explicitly recited otherwise, wherein the ASTR is selected from an antibody, an antigen, a ligand, a receptor binding domain of a ligand, a receptor, a ligand binding domain of a receptor, and an affibody.

Embodiment A3

The CAR of Embodiment A2, or according to any other Embodiment provided herein unless explicitly recited otherwise, wherein the ASTR is an antibody fragment.

Embodiment A4

The CAR of any one of Embodiments 1 or A1 to A3, or according to any other Embodiment provided herein unless explicitly recited otherwise, wherein the conditionally active ASTR exhibits an increase in antigen binding in a tumor microenvironment and/or in an in vitro tumor surrogate assay condition relative to a corresponding physiological condition, wherein the tumor microenvironment and/or the in vitro tumor surrogate assay conditions are selected from the group consisting of hypoxia, an acidic pH, a higher concentration of lactic acid, a higher concentration of hyaluronan, a higher concentration of albumin, a higher concentration of adenosine, a higher concentration of R-2-hydroxyglutarate, and a lower nutrient availability.

Embodiment A5

The CAR of any one of Embodiments A1 to A4, or according to any other Embodiment provided herein unless explicitly recited otherwise, wherein the conditionally active ASTR exhibits an increase in (or a higher) antigen binding at a pH of 6.7 as compared to a pH of 7.4.

Embodiment A6

The CAR of any one of Embodiments 1 or A1 to A5, or according to any other Embodiment provided herein unless explicitly recited otherwise, wherein the intracellular activating domain is a human CD3Z activating domain, a human CD3D activating domain, a human CD3E activating domain, a human CD3G activating domain, a human CD28 activating domain, a human CD79A activating domain, a human DAPIO activating domain, a human DAP12 activating domain, a human FCER1G activating domain, a human CD137 activating domain, or a human ZAP70 activating domain.

Embodiment A7

The CAR of any one of Embodiments 1 or A1 to A6, or according to any other Embodiment provided herein unless explicitly recited otherwise, further comprising a first, second, third, or fourth co-stimulatory domain that has a different amino acid sequence than the intracellular activating domain.

Embodiment A8

The CAR of Embodiment A7, or according to any other Embodiment provided herein unless explicitly recited otherwise, wherein the first, second, third, and/or fourth co-stimulatory domain comprise a co-stimulatory domain of 4-1BB (CD137), B7-H3, CD2, CD7, CD27, CD28, CD28 deleted for Lck binding (ICΔ), ICOS, OX40, BTLA, CD27, CD30, CD40, GITR, HVEM, LFA-1, LIGHT, NKG2C, PD-1, TILR2, TILR4, TILR7, TILR9, Fc receptor gamma chain, Fc receptor c chain, or a ligand that specifically binds with CD83.

Embodiment A9

The CAR of Embodiment A7, or according to any other Embodiment provided herein unless explicitly recited otherwise, wherein the first co-stimulatory domain retains a co-stimulating activity and is a human CD137 co-stimulatory domain, a human CD28 co-stimulatory domain, a human ICA co-stimulatory domain, a human ICOS co-stimulatory domain, a human OX40 co-stimulatory domain, a human BTLA co-stimulatory domain, a human CD27 costimulatory domain, a human CD30 co-stimulatory domain, a human GITR co-stimulatory domain, or a human HVEM co-stimulatory domain.

Embodiment B1

A replication incompetent recombinant retroviral particle, comprising a retroviral genome comprising one or more nucleic acid sequences operably linked to a promoter active in T cells and/or NK cells, wherein the one or more nucleic acid sequences encode the CAR of any one of Embodiments 1 or A1 to A9, or of any other Embodiment provided herein unless explicitly recited otherwise.

Embodiment B2

An isolated recombinant T cell or NK cell genetically modified with the replication incompetent recombinant retroviral particle of Embodiment B1.

Embodiment B3

An isolated recombinant T cell genetically modified with the replication incompetent recombinant retroviral particle of Embodiment B1.

Embodiment B4

A reaction mixture comprising the replication incompetent recombinant retroviral particle of Embodiment B1, and a T cell and/or an NK cell.

Embodiment B5

A reaction mixture comprising the replication incompetent recombinant retroviral particle of Embodiment B1, and a T cell.

Embodiment C1

An isolated (e.g. recombinant or genetically modified) T cell or NK cell, comprising a genome comprising one or more nucleic acid sequences (for example, two or more, three or more, four or more, five or more, or six or more nucleic acid sequences) operably linked to a promoter active in T cells and/or NK cells, wherein the one or more (or two or more, three or more, four or more, five or more, or six or more) nucleic acid sequences encode the CAR of any one of Embodiments 1 or A1 to A8, or of any other Embodiment provided herein unless explicitly recited otherwise.

Embodiment C2

An isolated (e.g. recombinant or genetically modified) T cell or NK cell of Embodiment C1, wherein the isolated cell is a T cell.

Embodiment C3

An isolated (e.g. recombinant or genetically modified) T cell or NK cell (in certain illustrative embodiments, a T cell) comprising one or more nucleic acid sequences operably linked to a promoter active in T cells and/or NK cells, wherein the one or more nucleic acid sequences encode a chimeric antigen receptor (CAR) for binding Axl or Ror2, comprising:
  a) a conditionally active antigen-specific targeting region (ASTR) that exhibits an increased binding to Axl or Ror2 at a pH of 6.7 compared to a pH of 7.4;
  b) a transmembrane domain; and
  c) an intracellular activating domain.

Embodiment D1

A method for binding a T cell and/or NK cell to a target mammalian cell, comprising contacting the target mammalian cell with the T cell and/or the NK cell in a microenvironment at a pH of less than 7.4 (for example, less than 5.8, 5.9, 6.0, 6.1, 6.2, 6.3, 6.4, 6.5, 6.6, 6.7, 6.8, or 6.9, or in the range of 5.8 to 7.0, in illustrative embodiments in the range of 6.0 to 6.8, in the range of 6.1 to 6.9, in the range of 6.2 to 6.8, or between 6.0, 6.1, 6.2, 6.3, 6.4, and 6.5 on the low end of the range, and 6.6, 6.7, 6.8, and 6.9 on the high end of the range), wherein the T cell and/or NK cell expresses the CAR of any one of Embodiments 1 or A1 to A8, or of any other Embodiment provided herein unless explicitly recited otherwise, and the target mammalian cell expresses Axl and/or Ror2.

Embodiment D2

A method for binding a T cell or NK cell to a target mammalian cell, comprising contacting the target mammalian cell with the T cell and/or the NK cell in a microenvironment at a pH of less than 7.4 (for example, less than 5.8, 5.9, 6.0, 6.1, 6.2, 6.3, 6.4, 6.5, 6.6, 6.7, 6.8, or 6.9, or in the range of 5.8 to 7.0, in illustrative embodiments in the range of 6.0 to 6.8, in the range of 6.2 to 6.8, or between 6.0, 6.1, 6.2, 6.3, 6.4, and 6.5 on the low end of the range, and 6.6, 6.7, 6.8, and 6.9 on the high end of the range), wherein the target mammalian cell expresses Axl or Ror2, and wherein the T cell or NK cell expresses a chimeric antigen receptor (CAR) for binding Axl or Ror2, respectively, wherein the CAR comprises:
  a) a conditionally active antigen-specific targeting region (ASTR) that exhibits an increased binding to Axl or Ror2 at a pH of 6.7 compared to a pH of 7.4;
  b) a transmembrane domain; and
  c) an intracellular activating domain.

Embodiment D3

The method of any one of Embodiments D1 to D3, wherein the binding activates the T cell and/or NK cell.

Embodiment D4

A method for activating a T cell or NK cell, comprising contacting a target mammalian cell with the T cell and/or the NK cell in a microenvironment at a pH of less than 7.4 (for example, less than 5.8, 5.9, 6.0, 6.1, 6.2, 6.3, 6.4, 6.5, 6.6, 6.7, 6.8, or 6.9, or in the range of 5.8 to 7.0, in illustrative embodiments in the range of 6.0 to 6.8, in the range of 6.2 to 6.8, or between 6.0, 6.1, 6.2, 6.3, 6.4, and 6.5 on the low end of the range, and 6.6, 6.7, 6.8, and 6.9 on the high end of the range), wherein the target mammalian cell expresses Axl or Ror2, and wherein the T cell or NK cell expresses a chimeric antigen receptor (CAR) for binding Axl or Ror2, respectively, wherein the CAR comprises:
  a) a conditionally active antigen-specific targeting region (ASTR) that exhibits an increased binding to Axl or Ror2 at a pH of 6.7 compared to a pH of 7.4;
  b) a transmembrane domain; and
  c) an intracellular activating domain.

Embodiment D5

The method of Embodiment D5, wherein the CAR is any of the CARs provided in another Embodiment. in non-limiting illustrative examples, Embodiments 1 or A1 to A8.

Embodiment D6

The method of Embodiment D5, wherein the CAR is a CAR provided in any one of Embodiments 1 or A1 to A8.

Embodiment D7

The method of any one of Embodiments D3 to D6, wherein activation comprises increased expression and/or production and/or secretion of a cytokine.

Embodiment D8

The method of any one of Embodiments D3 to D7, wherein upon activation, the T cell and/or NK cell increases expression of IL-2 or IFN-γ.

Embodiment D9

The method of Embodiment D8, wherein expression of IL-2 or IFN-γ is increased by at least 10%, at least 15%, at least 20%, at least 25%, at least 30%, at least 40%, at least 50%, at least 75%, at least 2-fold, at least 2.5-fold, at least 5-fold, at least 10-fold, or more than 10-fold, compared with the amount of IL-2 or IFN-γ produced by the T cell or NK cell before the contacting.

Embodiment D10

The method of Embodiment D8, wherein secretion of IL-2 or IFN-γ is increased by at least 10%, at least 15%, at least 20%, at least 25%, at least 30%, at least 40%, at least 50%, at least 75%, at least 2-fold, at least 2.5-fold, at least 5-fold, at least 10-fold, or more than 10-fold, compared with the amount of IL-2 or IFN-γ secreted by the T cell or NK cell before the contacting.

Embodiment D11

The method of any one of Embodiments D3 to D7, wherein upon activation, cytotoxic activity of the T cell or NK cell is increased by at least 10%, at least 15%, at least 20%, at least 25%, at least 30%, at least 40%, at least 50%, at least 75%, at least 2-fold, at least 2.5-fold, at least 5-fold, at least 10-fold, or more than 10-fold, compared to the cytotoxic activity of the T cell or NK cell before the contacting.

Embodiment D12

The method of any one of embodiments D1 to D11, wherein the target mammalian cell is lysed after activation of the T cell or NK cell.

Embodiment D13

The method of any one of Embodiments D1 to D12, further comprising before the contacting, transducing the T cell or the NK cell with the replication incompetent recombinant retroviral particle of any one of Embodiments B1 or B2 to genetically modify the T cell or NK cell to express the CAR.

Embodiment D14

The method of Embodiment D13, wherein the transducing is performed ex vivo.

Embodiment D15

The method of any one of Embodiments D1 to D14, further comprising, increasing the pH of the microenvironment to a pH at or above 7.0 (e.g. above 7.1, 7.2, or 7.3), thereby decreasing the activation of the T cell or NK cell.

Embodiment D16

The method of any one of Embodiments D1 to D14, further comprising, increasing the pH of the microenvironment to a pH at or above 7.0 (e.g. above 7.1, 7.2, or 7.3), thereby deactivating the T cell or NK cell.

Embodiment D17

The method of any one of Embodiments D1 to D16, wherein the microenvironment is a tumor.

Embodiment D18

The method of claim D17, wherein the tumor is in a human subject.

Embodiment D19

The method of any one of Embodiments D1 to D16, wherein the microenvironment is in vitro or ex vivo.

Embodiment E1

A method for genetically modifying a lymphocyte, comprising contacting a T cell and/or NK cell with a replication incompetent recombinant retroviral particle comprising in its genome a polynucleotide comprising one or more nucleic acid sequences (for example, two or more, three or more, four or more, five or more, or six or more nucleic acid sequences) operatively linked to a promoter active in T cells and/or NK cells, wherein the one or more (or two or more, three or more, four or more, five or more, or six or more) nucleic acid sequences encode the chimeric antigen receptor of any one of Embodiments 1 or A1 to A8, or of any other Embodiment provided herein unless explicitly recited otherwise, wherein said contacting facilitates transduction of the T cell and/or NK cell by the replication incompetent recombinant retroviral particle, thereby producing a genetically modified T cell and/or NK cell.

Embodiment F1

A replication incompetent recombinant retroviral particle for use in a method for genetically modifying a lymphocyte, wherein the replication incompetent recombinant retroviral particle comprises in its genome a polynucleotide comprising one or more nucleic acid sequences (for example, two or more, three or more, four or more, five or more, or six or more nucleic acid sequences) operatively linked to a promoter active in T cells and/or NK cells, wherein the one or more (or two or more, three or more, four or more, five or more, or six or more) nucleic acid sequences encode the chimeric antigen receptor of any one of Embodiments 1 or A1 to A8, or of any other Embodiment provided herein unless explicitly recited otherwise, wherein the method comprises contacting a T cell and/or NK cell, and said contacting facilitates transduction of the T cell and/or NK cell by the replication incompetent recombinant retroviral particles, thereby producing a genetically modified T cell and/or NK cell.

Embodiment G1

A replication incompetent recombinant retroviral particle for use in a method for genetically modifying a T cell and/or NK cell, for treating tumor growth, wherein the method comprises contacting the T cell and/or NK cell with a replication incompetent recombinant retroviral particle comprising in its genome a polynucleotide comprising one or more nucleic acid sequences (for example, two or more, three or more, four or more, five or more, or six or more nucleic acid sequences) operatively linked to a promoter active in T cells and/or NK cells, wherein the one or more (or two or more, three or more, four or more, five or more, or six or more) nucleic acid sequences encode the chimeric antigen receptor of any one of Embodiments 1 or A1 to A8, or of any other Embodiment provided herein unless explicitly recited otherwise, wherein said contacting facilitates transduction of the T cell and/or NK cell by the replication incompetent recombinant retroviral particles, thereby producing a genetically modified T cell and/or NK cell.

Embodiment H1

Use of a replication incompetent recombinant retroviral particle in the manufacture of a kit for genetically modifying a T cell and/or NK cell, wherein the use of the kit comprises contacting the T cell and/or NK cell with a replication incompetent recombinant retroviral particle comprising in its genome a polynucleotide comprising one or more nucleic acid sequences (for example, two or more, three or more, four or more, five or more, or six or more nucleic acid sequences) operatively linked to a promoter active in T cells and/or NK cells, wherein the one or more (or two or more, three or more, four or more, five or more, or six or more) nucleic acid sequences encode the chimeric antigen receptor of any one of Embodiments 1 or A1 to A8, or of any other Embodiment provided herein unless explicitly recited otherwise, wherein said contacting facilitates transduction of the T cell and/or NK cell by the replication incompetent recombinant retroviral particles, thereby producing a genetically modified T cell and/or NK cell.

Embodiment I1

A commercial container containing a replication incompetent recombinant retroviral particle and instructions for the use thereof, wherein the replication incompetent recombinant retroviral particle comprises in its genome a polynucleotide comprising one or more nucleic acid sequences (for example, two or more, three or more, four or more, five or more, or six or more nucleic acid sequences) operatively linked to a promoter active in T cells and/or NK cells, wherein the one or more (or two or more, three or more, four or more, five or more, or six or more) nucleic acid sequences encode the chimeric antigen receptor of any one of Embodiments 1 or A1 to A8, or of any other Embodiment provided herein unless explicitly recited otherwise.

Embodiment J1

A kit containing a container containing a replication incompetent recombinant retroviral particle, and instructions for use thereof, wherein the instructions instruct a method for binding a T cell and/or NK cell to a target mammalian cell, in a method comprising:
a) transducing the T cell and/or NK cell with the replication incompetent recombinant retroviral particle, comprising in its genome a polynucleotide comprising one or more nucleic acid sequences (for example, two or more, three or more, four or more, five or more, or six or more nucleic acid sequences) operatively linked to a promoter active in T cells and/or NK cells, wherein the one or more (or two or more, three or more, four or more, five or more, or six or more) nucleic acid sequences encode the CAR of any one of Embodiments 1 or A1 to A8, or of any other Embodiment provided herein unless explicitly recited otherwise; and
b) contacting the target mammalian cell with the transduced T cell and/or the NK cell in a microenvironment at a pH of less than 7.4 (for example, less than 5.8, 5.9, 6.0, 6.1, 6.2, 6.3, 6.4, 6.5, 6.6, 6.7, 6.8, or 6.9, or in the range of 5.8 to 7.0, more commonly in the range of 6.0 to 6.8, in the range of 6.2-6.8, or between 6.0, 6.1, 6.2, 6.3, 6.4, and 6.5 on the low end of the range, and 6.6, 6.7, 6.8, and 6.9 on the high end of the range), wherein the T cell and/or NK cell expresses the CAR of any one of Embodiments 1 or A1 to A8, and the target mammalian cell expresses Axl and/or Ror2.

Embodiment K1

A method for activating a T cell and/or NK cell, comprising contacting a target mammalian cell with the T cell and/or the NK cell in a microenvironment at a pH of less than 7.4 (for example, less than 5.8, 5.9, 6.0, 6.1, 6.2, 6.3, 6.4, 6.5, 6.6, 6.7, 6.8, or 6.9, or in the range of 5.8 to 7.0, more commonly in the range of 6.0 to 6.8, in the range of 6.2-6.8, or between 6.0, 6.1, 6.2, 6.3, 6.4, and 6.5 on the low end of the range, and 6.6, 6.7, 6.8, and 6.9 on the high end of the range), wherein the T cell and/or NK cell expresses the chimeric antigen receptor of any one of Embodiments 1 or A1 to A8, or of any other Embodiment provided herein unless explicitly recited otherwise, and the target mammalian cell expresses Axl and/or Ror2.

Embodiment K2

The method of Embodiment K1, further comprising before the contacting, transducing the T cell and/or the NK cell with the replication incompetent recombinant retroviral particle of any one of Embodiments B1 or B2.

Embodiment K3

The method of Embodiment K1, wherein after the activating, the T cell and/or NK cell induces expression and/or production and/or secretion of a cytokine.

Embodiment K4

The method of Embodiment K3, wherein the cytokine is chosen from the group consisting of IL-2 or IFN-γ.

Embodiment L1

A method for inducing expression and/or production of a cytokine in a T cell and/or NK cell and/or inducing secretion of a cytokine from a T cell and/or NK cell, comprising contacting a target mammalian cell with the T cell and/or the NK cell in a microenvironment at a pH of less than 7.4 (for example, less than 5.8, 5.9, 6.0, 6.1, 6.2, 6.3, 6.4, 6.5, 6.6, 6.7, 6.8, or 6.9, or in the range of 5.8 to 7.0, more commonly in the range of 6.0 to 6.8, in the range of 6.2-6.8, or between 6.0, 6.1, 6.2, 6.3, 6.4, and 6.5 on the low end of the range, and 6.6, 6.7, 6.8, and 6.9 on the high end of the range), wherein the T cell and/or NK cell expresses the chimeric antigen receptor of any one of Embodiments 1 or A1 to A8, or of any other Embodiment provided herein unless explicitly recited otherwise, and the target mammalian cell expresses Axl and/or Ror2.

Embodiment L2

The method of Embodiment L1, further comprising before the contacting, transducing the T cell and/or the NK cell with the replication incompetent recombinant retroviral particle of any one of Embodiments B1 or B2.

Embodiment M1

An isolated nucleic acid encoding a chimeric antigen receptor for binding Axl or Ror2 according to any of Embodiments 1 or A1 to A8, or of any other Embodiment provided herein unless explicitly recited otherwise.

Embodiment M2

An isolated nucleic acid of Embodiment M1, wherein the nucleic acid further comprises a promoter active in T cells and/or NK cells, and wherein nucleic acid sequences encoding the CAR are operably linked to the promoter.

Embodiment M3

The isolated nucleic acid of Embodiment M2, wherein the isolated nucleic acid sequence further encodes a recognition domain.

Embodiment M4

The isolated nucleic acid of Embodiment M3, wherein nucleic acids encoding the recognition domain are separated from nucleic acids encoding the CAR by a ribosomal skip sequence.

Embodiment M5

The isolated nucleic acid of Embodiment M4, wherein the ribosomal skip sequence is 2A-1.

Embodiment M6

A replication incompetent recombinant retroviral particle comprising any of the nucleic acids of Embodiments M1 to M5.

Embodiment M7

The replication incompetent recombinant retroviral particle of Embodiment M6, wherein the replication incompetent recombinant retroviral particle is a lentiviral particle.

Embodiment N1

An expression vector comprising a nucleic acid encoding a chimeric antigen receptor according to any one of Embodiments 1 or A1 to A8, or of any other Embodiment provided herein unless explicitly recited otherwise, operably linked to a promoter.

Embodiment O1

A mammalian cell infected with any one of the expression vectors of Embodiment N1.

Embodiment P1

A mammalian cell expressing any of the chimeric antigen receptors of Embodiments 1 or A1 to A8, or of any other Embodiment provided herein unless explicitly recited otherwise.

Embodiment Q1

A method for making a conditionally activatable cell comprising a chimeric antigen receptor (CAR) for conditionally binding Axl or Ror2, wherein the method comprises genetically modifying a mammalian cell with an expression vector comprising a promoter operably linked to nucleotide sequences encoding the CAR, wherein the CAR comprises:
a) a conditionally active antigen-specific targeting region (ASTR) that exhibits an increase in activity in a tumor environment and/or in an in vitro tumor surrogate assay condition, compared to a normal physiological environment, wherein the ASTR binds to Axl or Ror2;
b) a transmembrane domain; and
c) an intracellular activating domain.

Embodiment R1

A method for treating a cancer in a subject, comprising the steps of:
a) introducing an expression vector comprising a nucleic acid encoding any of the CARs of Embodiments 1 or A1 to A8, or of any other Embodiment provided herein unless explicitly recited otherwise, into cytotoxic cells obtained from the subject to produce genetically modified cytotoxic cells; and
b) administering the genetically modified cytotoxic cells to the subject.

Embodiment S1

An ex vivo method for making conditionally activatable T cells and/or NK cells comprising a chimeric antigen receptor (CAR) for conditionally binding Axl or Ror2, wherein the method comprises:
a) enriching peripheral blood mononuclear cells (PBMCs) to isolate PBMCs comprising T cells and/or NK cells from isolated blood;
b) activating T cells and/or NK cells of the enriched PBMCs under effective conditions;
c) transducing the activated T cells and/or NK cells with replication incompetent recombinant retroviral particles under effective conditions, thereby producing genetically modified T cells and/or NK cells, wherein the replication incompetent recombinant retroviral particles each comprise a retroviral genome comprising one or more nucleic acid sequences operatively linked to a promoter active in T cells and/or NK cells, wherein a first nucleic acid sequence of the one or more nucleic acid sequences encodes a CAR of any of Embodiments 1 or A1 to A8, or of any other Embodiment provided herein unless explicitly recited otherwise; and
d) expanding the genetically modified T cells and/or NK cells, thereby making the conditionally activatable T cells and/or NK cells.

Embodiment T1

A modified T cell produced by a method of any of Embodiments D3, E1, K2, Q1, R1, or S1.

Embodiment U1

A modified NK cell produced by a method of any of claims Embodiments D3, E1, K2, Q1, R1, or S1.

In any of the embodiments herein that includes a chimeric antigen receptor (CAR), the antigen-specific targeting region (ASTR) can be selected from an antibody, an antigen, a ligand, a receptor binding domain of a ligand, a receptor, a ligand binding domain of a receptor, and an affibody. In any of the embodiments herein that includes a CAR, the ASTR can be an antibody selected from a full-length antibody, a single-chain antibody, an Fab fragment, an Fab' fragment, an (Fab')2 fragment, an Fv fragment, and a divalent single-chain antibody or a diabody. In any of the embodiments herein that includes a CAR, the ASTR can include a heavy chain and a light chain from an antibody. In any of the embodiments herein that includes a CAR with an ASTR that includes an antibody, the antibody can be a single-chain variable fragment with a heavy chain and a light chain. In any of the embodiments herein that includes a CAR with an ASTR that includes a heavy chain and a light chain from an antibody, the heavy and light chains can be separated by a linker, and the linker can be between 3, 4, 5, 6, 7, 8, 9, or 10 amino acids in length on the low end of the range and 20, 25, 30, 40, 50, 60 70, 80, 90, 100, 125, 150, 175, or 200 amino acids in length on the high end of the range. In some embodiments, the ASTR can be a single-chain variable fragment comprising a heavy chain and a light chain, wherein the heavy and light chains are separated by a linker, wherein the linker is between 6 and 100 amino acids in length. In any of the embodiments herein that includes a CAR with an ASTR that includes a single-chain variable fragment including a heavy chain and a light chain, the heavy and light chains can be separated by a linker and the linker can be between 6 and 100 amino acids in length, and the ASTR can include a conditionally active antibody heavy chain or a conditionally active antibody light chain and the other of the antibody heavy chain or antibody light chain can be wild type.

In any of the embodiments herein that includes a CAR with an ASTR that includes a heavy chain and a light chain from an antibody, the heavy chain can be positioned N-terminal to the light chain on the chimeric antigen receptor or the light chain can be positioned N-terminal to the heavy chain on the chimeric antigen receptor. In any of the embodiments herein that includes a CAR with an ASTR that includes a heavy chain and a light chain from an antibody, the heavy chain and the light chain can be from a conditionally active antibody. In any of the embodiments herein that includes a CAR, the CAR can include a bispecific ASTR. In any of the embodiments herein that includes a CAR, the ASTR can be a conditionally active ASTR. In any of the embodiments herein that includes a CAR with a conditionally active ASTR, the conditionally active ASTR can exhibit an increase in antigen binding in a tumor microenvironment and/or in an in vitro tumor surrogate assay condition relative to a corresponding physiological condition, wherein the tumor microenvironment and/or in vitro tumor surrogate assay conditions can be selected from the group consisting of hypoxia, an acidic pH, a higher concentration of lactic acid, a higher concentration of hyaluronan, a higher concentration of albumin, a higher concentration of adenosine, a higher concentration of R-2-hydroxyglutarate, and a lower nutrient availability. In any of the embodiments herein that includes a CAR with a conditionally active ASTR, the conditionally active ASTR can exhibit an increase in antigen binding at a pH of 6.7 as compared to a pH of 7.4. In any of the embodiments herein that includes a CAR with a conditionally active ASTR, the conditionally active ASTR can exhibit an increase in antigen binding at a pH of 6.0 (instead of or in addition to at a pH of 6.7) as compared to a pH of 7.4.

In any of the embodiments herein that includes a CAR, the ASTR can bind to Axl. In any of the embodiments herein that includes a CAR with an ASTR that binds to Axl, the ASTR can bind to the same epitope of Axl as an antibody comprising the antibody heavy chain of SEQ ID NO:79 and an antibody light chain of SEQ ID NO:80.

In any of the embodiments herein that includes a CAR with an ASTR that binds to Axl, and in illustrative embodiments binds to the same epitope of Axl as an antibody that includes the antibody heavy chain of SEQ ID NO:79 and the antibody light chain of SEQ ID NO:80, the ASTR can include an antibody heavy chain variable region with three complementarity determining regions having H1, H2, and H3 sequences, wherein: a) the H1 sequence is $X_1GX_2TMN$ (SEQ ID NO:87); b) the H2 sequence is LIKPSNGGTSYN-QKFKG (SEQ ID NO:88); and c) the H3 sequence is $GX_3YX_4SYX_5AMDY$ (SEQ ID NO:89), wherein $X_1$ is T or W; $X_2$ is H or A; $X_3$ is H or D; $X_4$ is E or H; and $X_5$ is E or F. In any of the embodiments herein that includes a CAR with an ASTR that binds to Axl, and in illustrative embodiments binds to the same epitope of Axl as an antibody that includes the antibody heavy chain of SEQ ID NO:79 and the antibody light chain of SEQ ID NO:80, the ASTR can include an antibody light chain variable region with three complementarity determining regions having L1, L2, and L3 sequences, wherein: d) the L1 sequence is $KASQDVX_6SAVA$ (SEQ ID NO:90); e) the L2 sequence is $WX_7X_8TRX_9T$ (SEQ ID NO:91); and f) the L3 sequence is $QEHFSX_{10}PLX_{11}$ (SEQ ID NO:92), wherein $X_6$ is S or V; $X_7$ is A or Q; $X_8$ is S or D; $X_9$ is H or D; $X_{10}$ is T or P; and $X_{11}$ is T or R. In any of the embodiments herein that includes a CAR with an ASTR that binds to Axl, and in illustrative embodiments binds to the same epitope of Axl as an antibody that includes the antibody heavy chain of SEQ ID NO:79 and the antibody light chain of SEQ ID NO:80, the ASTR can include an antibody heavy chain variable region with three complementarity determining regions having H1, H2, and H3 sequences, wherein: a) the H1 sequence is $X_1GX_2X_3MX_4$ (SEQ ID NO:134); b) the H2 sequence is $LIKX_5SNGGTX_6YNQKFKG$ (SEQ ID NO:135); and c) the H3 sequence is $GX_7X_8X_9X_{10}X_{11}X_{12}X_{13}X_{14}DYX_{15}X_{16}$ (SEQ ID NO:136), wherein $X_1$ is T, A, or W; $X_2$ is H or A; $X_3$ is T or I; $X_4$ is N or I; $X_5$ is P or N; $X_6$ is 5, I, or T; $X_7$ is H, D, E, P, R, or W; $X_8$ is Y or N; $X_9$ is E, A, D, F, G, H, I, L, M, N, R, V, or Y; $X_{10}$ is S, D, M, N, or Q; $X_{11}$ is Y, C, E, or P; $X_{12}$ is F, E, N, S, T, or V; $X_{13}$ is A, D, G, L, or Y; $X_{14}$ is M, E, or F; $X_{15}$ is W, A, D, H, L, N, P, R, or T; and $X_{16}$ is G or H. In any of the embodiments herein that includes a CAR with an ASTR that binds to Axl, and in illustrative embodiments binds to the same epitope of Axl as an antibody that includes the antibody heavy chain of SEQ ID NO:79 and the antibody light chain of SEQ ID NO:80, the ASTR can include an antibody light chain variable region with three complementarity determining regions having L1, L2, and L3 sequences, wherein: d) the L1 sequence is $KASQDX_{17}X_{18}SX_{19}VX_{20}$ (SEQ ID NO:137); e) the L2 sequence is $X_{21}X_{22}X_{23}TRX_{24}T$ (SEQ ID NO:138); and f) the L3 sequence is $QEX_{25}X_{26}SX_{27}X_{28}X_{29}X_{30}$ (SEQ ID NO:139), wherein $X_{17}$ is V, D, G, N, or W; $X_{18}$ is S or V; $X_{19}$ is A, L, or M; $X_{20}$ is A, D, N, or Q; $X_{21}$ is W or F; $X_{22}$ is A, I, N, P, or Q; $X_{23}$ is S or D; $X_{24}$ is H or D; $X_{25}$ is H, C, F, I, L, Q, S, T, V, or Y; $X_{26}$ is F, C, D, E, G, N, or S; $X_{27}$ is T, C, or P; $X_{28}$ is P, A, C, D, E, H, K, S, T, V, or W; $X_{29}$ is L, G, or R; and $X_{30}$ is T, I, or R. In any of the embodiments herein that includes a CAR with an ASTR that binds to Axl and includes a light chain variable region, the light chain variable region can be selected from SEQ ID NOs:108-111. In any of the embodiments herein that includes a CAR with an ASTR that binds to Axl and includes a heavy chain variable region, the heavy chain variable region can be selected from SEQ ID NOs:112-114.

In any of the embodiments herein that include a CAB-CAR that binds to Axl, the heavy chain can be N-terminal to the light chain. In these embodiments, the ASTR can include an amino acid sequence of SEQ ID NO:128, SEQ ID NO:129, or SEQ ID NO:159.

In any of the embodiments herein that include a CAB-CAR that binds to Axl, the light chain can be N-terminal to the heavy chain. In these embodiments, the ASTR can comprise an amino acid sequence of SEQ ID NO:160 or SEQ ID NO:161.

In any of the embodiments herein that includes a CAR, the ASTR can bind to Ror2. In any of the embodiments herein that includes a CAR with an ASTR that binds to Ror2, the ASTR can bind to the same epitope of Ror2 as an antibody that includes the antibody heavy chain of SEQ ID NO:82 or SEQ ID NO:83 and the antibody light chain of SEQ ID NO:84 and/or the ASTR can bind to the same epitope of Ror2 as a single-chain variable antibody fragment comprising the antibody heavy chain of SEQ ID NO:151 and the antibody light chain of SEQ ID NO:152. In any of the embodiments herein that includes a CAR with an ASTR that binds to Ror2, the ASTR can include a heavy chain variable region with three complementarity determining regions, said regions having H1, H2, and H3 sequences, wherein: a) the H1 sequence is GYTX$_1$TEX$_2$TX$_3$H (SEQ ID NO:95) or X$_4$GYSITTGYYWN (SEQ ID NO:96); b) the H2 sequence is GX$_5$NX$_6$NNGGTGYNQKFKG (SEQ ID NO:97) or YITYDGSKNYNPSLKN (SEQ ID NO:98); and c) the H3 sequence is GSLYSYGNSYFDY (SEQ ID NO:99) or FEGVWX$_7$GLDY (SEQ ID NO:100), wherein X$_1$ is F or E; X$_2$ is Y or D, X$_3$ is M or D; X$_4$ is T or S; X$_5$ is E or I; X$_6$ is T or D; and X$_7$ is Y or G. In any of the embodiments herein that includes a CAR with an ASTR that binds to Ror2, and in illustrative embodiments binds to the same epitope of Ror2 as an antibody that includes the antibody heavy chain of SEQ ID NO:151 and the antibody light chain of SEQ ID NO:152, the ASTR can include a heavy chain variable region with three complementarity determining regions, said regions having H1, H2, and H3 sequences, wherein: a) the H1 sequence is GYTX$_1$TEX$_2$TX$_3$H (SEQ ID NO:95); b) the H2 sequence is GX$_5$NX$_6$NNGGTGYNQKFKG (SEQ ID NO:97); and c) the H3 sequence is GSLYSYGNSYFDY (SEQ ID NO:99), wherein X$_1$ is F or E; X$_2$ is Y or D, X$_3$ is M or D; X$_5$ is E or I; and X$_6$ is T or D. In any of the embodiments herein that includes a CAR with an ASTR that binds to Ror2, and in illustrative embodiments binds to the same epitope of Ror2 as an antibody that includes the antibody heavy chain of SEQ ID NO:82 or SEQ ID NO:83 and the antibody light chain of SEQ ID NO:84, the ASTR can include a heavy chain variable region with three complementarity determining regions, said regions having H1, H2, and H3 sequences, wherein: a) the H1 sequence is X$_4$GYSITTGYYWN (SEQ ID NO:96); b) the H2 sequence is YITYDGSKNYNPSLKN (SEQ ID NO:98); and c) the H3 sequence is FEGVWX$_7$GLDY (SEQ ID NO:100), wherein X$_4$ is T or S; and X$_7$ is Y or G. In any of the embodiments herein that includes a CAR with an ASTR that binds to Ror2, the ASTR can include a light chain variable region with three complementarity determining regions, said regions having L1, L2, and L3 sequences, wherein: a) the L1 sequence is SATSSX$_8$SYMH (SEQ ID NO:101) or RAS-ESVDRYGNSFIH (SEQ ID NO:102); b) the L2 sequence is X$_9$TSNLAS (SEQ ID NO:103) or RTYNLES (SEQ ID NO:104); and c) the L3 sequence is QQRSSYPFT (SEQ ID NO:105) or QQTNEDPWT (SEQ ID NO:106), wherein X$_8$ is E or V; and X$_9$ is G or H. In any of the embodiments herein that includes a CAR with an ASTR that binds to Ror2, and in illustrative embodiments binds to the same epitope of Ror2 as an antibody that includes the antibody heavy chain of SEQ ID NO:151 and the antibody light chain of SEQ ID NO:152, the ASTR can include a light chain variable region with three complementarity determining regions, said regions having L1, L2, and L3 sequences, wherein: a) the L1 sequence is SATSSX$_8$SYMH (SEQ ID NO:101); b) the L2 sequence is X$_9$TSNLAS (SEQ ID NO:103); and c) the L3 sequence is QQRSSYPFT (SEQ ID NO:105), wherein X$_8$ is E or V; and X$_9$ is G or H. In any of the embodiments herein that includes a CAR with an ASTR that binds to Ror2, and in illustrative embodiments binds to the same epitope of Ror2 as an antibody that includes the antibody heavy chain of SEQ ID NO:82 or SEQ ID NO:83 and the antibody light chain of SEQ ID NO:84, the ASTR can include a light chain variable region with three complementarity determining regions, said regions having L1, L2, and L3 sequences, wherein: a) the L1 sequence is RASESVDRYGNSFIH (SEQ ID NO:102); b) the L2 sequence is RTYNLES (SEQ ID NO:104); and c) the L3 sequence is QQTNEDPWT (SEQ ID NO:106).

In any of the embodiments herein that includes a CAR with an ASTR that binds to Ror2, the ASTR can include a heavy chain variable region including three complementarity determining regions, said regions having H1, H2, and H3 sequences, wherein: a) the H1 sequence is GYTX$_1$TEX$_2$X$_3$X$_4$H (SEQ ID NO:140) or GYSITTGX$_{29}$YWN (SEQ ID NO:141); b) the H2 sequence is X$_5$X$_6$X$_7$X$_8$NNGGTGYNQKFKG (SEQ ID NO:142) or YITYDGSX$_{30}$NYNPSLKN (SEQ ID NO:143); and c) the H3 sequence is X$_9$X$_{10}$X$_{11}$SX$_{12}$YX$_{13}$YX$_{14}$X$_{15}$SYFX$_{16}$X$_{17}$X$_{18}$ (SEQ ID NO:144) or CSX$_{31}$X$_{32}$X$_{33}$X$_{34}$VX$_{35}$X$_{36}$X$_{37}$LDX$_{38}$ (SEQ ID NO:145), wherein X$_1$ is F or E; X$_2$ is Y or D; X$_3$ is T or C; X$_4$ is M, D, E, or Y; X$_5$ is G or S; X$_6$ is I or E; X$_7$ is N, C, L, or V; X$_8$ is T, D or E; X$_9$ is A, M, or T; X$_{10}$ is R or H; X$_{11}$ is G or E; X$_{12}$ is L or F; X$_{13}$ is S or G; X$_{14}$ is G or D; X$_{15}$ is N or E; X$_{16}$ is D or L; X$_{17}$ is Y, C, or T; X$_{18}$ is W or L; X$_{29}$ is Y, E, R, or T; X$_{30}$ is K or N; X$_{31}$ is R, G, H, W, or Y; X$_{32}$ is F, C, N, or Q; X$_{33}$ is E or S; X$_{34}$ is G, E, F, H, M, Q, or S; X$_{35}$ is W, A, I, P, Q, T, or V; X$_{36}$ is Y, G, N, or Q; X$_{37}$ is G, S, or T; and X$_{38}$ is Y or I. In any of the embodiments herein that includes a CAR with an ASTR that binds to Ror2, and in illustrative embodiments binds to the same epitope of Ror2 as an antibody that includes the antibody heavy chain of SEQ ID NO:151 and the antibody light chain of SEQ ID NO:152, the ASTR can include a heavy chain variable region including three complementarity determining regions, said regions having H1, H2, and H3 sequences, wherein: a) the H1 sequence is GYTX$_1$TEX$_2$X$_3$X$_4$H (SEQ ID NO:140); b) the H2 sequence is X$_5$X$_6$X$_7$X$_8$NNGGTGYNQKFKG (SEQ ID NO:142); and c) the H3 sequence is X$_9$X$_{10}$X$_{11}$SX$_{12}$YX$_{13}$YX$_{14}$X$_{15}$SYFX$_{16}$X$_{17}$X$_{18}$ (SEQ ID NO:144), wherein X$_1$ is F or E; X$_2$ is Y or D; X$_3$ is T or C; X$_4$ is M, D, E, or Y; X$_5$ is G or S; X$_6$ is I or E; X$_7$ is N, C, L, or V; X$_8$ is T, D or E; X$_9$ is A, M, or T; X$_{10}$ is R or H; X$_{11}$ is G or E; X$_{12}$ is L or F; X$_{13}$ is S or G; X$_{14}$ is G or D; X$_{15}$ is N or E; X$_{16}$ is D or L; X$_{17}$ is Y, C, or T; and X$_{18}$ is W or L. In any of the embodiments herein that includes a CAR with an ASTR that binds to Ror2, and in illustrative embodiments binds to the same epitope of Ror2 as an antibody that includes the antibody heavy chain of SEQ ID NO:82 or SEQ ID NO:83 and the antibody light chain of SEQ ID NO:84, the ASTR can include a heavy chain variable region including three complementarity determining regions, said regions having H1, H2, and H3 sequences, wherein: a) the H1 sequence is GYSITTGX$_{29}$YWN (SEQ ID NO:141); b) the H2 sequence is YITYDGSX$_{30}$NYNPSLKN (SEQ ID NO:143); and c) the H3 sequence is CSX$_{31}$X$_{32}$X$_{33}$X$_{34}$VX$_{35}$X$_{36}$X$_{37}$LDX$_{38}$ (SEQ ID NO:145), wherein X$_{29}$ is Y, E, R, or T; X$_{30}$ is K or N; X$_{31}$ is R, G, H, W, or Y; X$_{32}$ is F, C, N, or Q; X$_{33}$ is E or S; X$_{34}$ is G, E, F, H, M, Q, or S; X$_{35}$ is W, A, I, P, Q, T, or V; X$_{36}$ is Y, G, N, or Q; X$_{37}$ is G, S, or T; and X$_{38}$ is Y or I.

In any of the embodiments herein that includes a CAR with an ASTR that binds to Ror2, the ASTR can include a light chain variable region that includes three complementarity determining regions, said regions having L1, L2, and L3 sequences, wherein: a) the L1 sequence is SATSSX$_{19}$X$_{20}$X$_{21}$MX$_{22}$ (SEQ ID NO:146) or RASESVDRYGNSX$_{39}$IH (SEQ ID NO:147); b) the L2 sequence is X$_{23}$TSNLAS (SEQ ID NO:148) or X$_{40}$TYX$_{41}$LES (SEQ ID NO:149); and c) the L3 sequence is QX$_{24}$X$_{25}$SX$_{26}$YPFX$_{27}$X$_{28}$ (SEQ ID NO:150) or QQX$_{42}$NX$_{43}$DPX$_{44}$TX$_{45}$ (SEQ ID NO:85), wherein X$_{19}$ is V or E; X$_{20}$ is S or D; X$_{21}$ is Y, C, or D; X$_{22}$ is H, G, or L; X$_{23}$ is G, C, H, or P; X$_{24}$ is Q or E; X$_{25}$ is R or H; X$_{26}$ is 5, D, G, I, Q, or V; X$_{27}$ is T or D; X$_{28}$ is F, D, or E; X$_{39}$ is F, S, or T; X$_{40}$ is R, C, D, E, or W; X$_{41}$ is N or D; X$_{42}$ is T, I, or P; X$_{43}$ is E or V; X$_{44}$ is W or T; and X$_{45}$ is F or T. In any of the embodiments herein that includes a CAR with an ASTR that binds to Ror2, and in illustrative embodiments binds to the same epitope of Ror2 as an antibody that includes the antibody heavy chain of SEQ ID NO:151 and the antibody light chain of SEQ ID NO:152, the ASTR can include a light chain variable region that includes three complementarity determining regions, said regions having L1, L2, and L3 sequences, wherein: a) the L1 sequence is SATSSX$_{19}$X$_{20}$X$_{21}$MX$_{22}$ (SEQ ID NO:146); b) the L2 sequence is X$_{23}$TSNLAS (SEQ ID NO:148); and c) the L3 sequence is QX$_{24}$X$_{25}$SX$_{26}$YPFX$_{27}$X$_{28}$ (SEQ ID NO:150), wherein X$_{19}$ is V or E; X$_{20}$ is S or D; X$_{21}$ is Y, C, or D; X$_{22}$ is H, G, or L; X$_{23}$ is G, C, H, or P; X$_{24}$ is Q or E; X$_{25}$ is R or H; X$_{26}$ is S, D, G, I, Q, or V; X$_{27}$ is T or D; and X$_{28}$ is F, D, or E. In any of the embodiments herein that includes a CAR with an ASTR that binds to Ror2, and in illustrative embodiments binds to the same epitope of Ror2 as an antibody that includes the antibody heavy chain of SEQ ID NO:82 or SEQ ID NO:83 and the antibody light chain of SEQ ID NO:84, the ASTR can include a light chain variable region that includes three complementarity determining regions, said regions having L1, L2, and L3 sequences, wherein: a) the L1 sequence is RASESVDRYGNSX$_{39}$IH (SEQ ID NO:147); b) the L2 sequence is X$_{40}$TYX$_{41}$LES (SEQ ID NO:149); and c) the L3 sequence is QQX$_{42}$NX$_{43}$DPX$_{44}$TX$_{45}$ (SEQ ID NO:85), wherein X$_{39}$ is F, S, or T; X$_{40}$ is R, C, D, E, or W; X$_{41}$ is N or D; X$_{42}$ is T, I, or P; X$_{43}$ is E or V; X$_{44}$ is W or T; and X$_{45}$ is F or T.

In any of the embodiments herein that includes a CAR with an ASTR that binds to Ror2, in illustrative embodiments wherein the ASTR binds to the same epitope of Ror2 as an antibody comprising an antibody heavy chain of SEQ ID NO:82 or SEQ ID NO:83 and an antibody light chain of SEQ ID NO:84, the heavy chain variable region can comprise an amino acid sequence of SEQ ID NO:82, SEQ ID NO:83, SEQ ID NO:120 or SEQ ID NO:121.

In any of the embodiments herein that includes a CAR with an ASTR that binds to Ror2, in illustrative embodiments wherein the ASTR binds to the same epitope of Ror2 as an antibody comprising an antibody heavy chain of SEQ ID NO:82 or SEQ ID NO:83 and an antibody light chain of SEQ ID NO:84, the heavy chain variable region can comprise an amino acid sequence of SEQ ID NO:82 or SEQ ID NO:83.In some embodiments, the light chain variable region comprises an amino acid sequence of SEQ ID NO:86.

In any of the embodiments herein that includes a CAR with an ASTR that binds to Ror2, in illustrative embodiments wherein the ASTR binds to the same epitope of Ror2 as an antibody comprising an antibody heavy chain of SEQ ID NO:82 or SEQ ID NO:83 and an antibody light chain of SEQ ID NO:84, the light chain variable region can comprise an amino acid sequence of SEQ ID NO:84.

In any of the embodiments herein that includes a CAR with an ASTR that binds to Ror2, in illustrative embodiments wherein the ASTR binds to the same epitope of Ror2 as an antibody comprising an antibody heavy chain of SEQ ID NO:82 or SEQ ID NO:83 and an antibody light chain of SEQ ID NO:84, the heavy chain variable region can comprise an amino acid sequence of SEQ ID NO:82, SEQ ID NO:83, SEQ ID NO:120, or SEQ ID NO:121.

In any of the embodiments herein that includes a CAR with an ASTR that binds to Ror2, in illustrative embodiments wherein the ASTR binds to the same epitope of Ror2 as an antibody comprising an antibody heavy chain of SEQ ID NO:82 or SEQ ID NO:83 and an antibody light chain of SEQ ID NO:84, the heavy chain variable region can comprise an amino acid sequence of SEQ ID NO:82 or SEQ ID NO:83.

In any of the embodiments herein that includes a CAR with an ASTR that binds to Ror2, in illustrative embodiments wherein the ASTR binds to the same epitope of Ror2 as an antibody comprising an antibody heavy chain of SEQ ID NO:82 or SEQ ID NO:83 and an antibody light chain of SEQ ID NO:84, the ASTR can comprise an amino acid sequence of SEQ ID NO:130, SEQ ID NO:131, or SEQ ID NO:132, SEQ ID NO:153, SEQ ID NO:154, SEQ ID NO:157, or SEQ ID NO:158.

In any of the embodiments herein that includes a CAR with an ASTR that binds to Ror2, in illustrative embodiments wherein the ASTR binds to the same epitope of Ror2 as an antibody comprising an antibody heavy chain of SEQ ID NO:151 and an antibody light chain of SEQ ID NO:152, the light chain variable region can comprise an amino acid sequence of SEQ ID NO:81, SEQ ID NO:122, SEQ ID NO:123, SEQ ID NO: 124, or SEQ ID NO:152.

In any of the embodiments herein that includes a CAR with an ASTR that binds to Ror2, in illustrative embodiments wherein the ASTR binds to the same epitope of Ror2 as an antibody comprising an antibody heavy chain of SEQ ID NO:151 and an antibody light chain of SEQ ID NO:152, the light chain variable region can comprise an amino acid sequence of SEQ ID NO:152.

In any of the embodiments herein that includes a CAR with an ASTR that binds to Ror2, in illustrative embodiments wherein the ASTR binds to the same epitope of Ror2 as an antibody comprising an antibody heavy chain of SEQ ID NO:151 and an antibody light chain of SEQ ID NO:152, the heavy chain variable region can comprise an amino acid sequence of SEQ ID NO:115, SEQ ID NO:116, SEQ ID NO:117, SEQ ID NO:118, SEQ ID NO:119, or SEQ ID:151.

In any of the embodiments herein that includes a CAR with an ASTR that binds to Ror2, in illustrative embodiments wherein the ASTR binds to the same epitope of Ror2 as an antibody comprising an antibody heavy chain of SEQ ID NO:151 and an antibody light chain of SEQ ID NO:152, the heavy chain variable region can comprise an amino acid sequence of SEQ ID:151.

In any of the embodiments herein that includes a CAR with an ASTR that binds to Ror2, in illustrative embodiments wherein the ASTR binds to the same epitope of Ror2 as an antibody comprising an antibody heavy chain of SEQ ID NO:151 and an antibody light chain of SEQ ID NO:152, the ASTR can comprise an amino acid sequence of SEQ ID NO:155 or SEQ ID NO:156.

In any of the embodiments herein that includes a CAR, the transmembrane domain can have at least 50%, 60%, 70%, 75%, 80%, 85%, 90%, 95%, 96%, 97%, 98%, 99%, or 100% sequence identity to the sequence of SEQ ID NO:46, at least 50%, 60%, 70%, 75%, 80%, 85%, 90%, 95%, 96%, 97%, 98%, 99%, or 100% sequence identity to the CD8 transmembrane domain, for example, SEQ ID NOs:47 or 75, at least 50%, 60%, 70%, 75%, 80%, 85%, 90%, 95%, 96%, 97%, 98%, 99%, or 100% sequence identity to the CD4 transmembrane domain, for example, SEQ ID NO:48, at least 50%, 60%, 70%, 75%, 80%, 85%, 90%, 95%, 96%, 97%, 98%, 99%, or 100% sequence identity to the CD3 zeta transmembrane domain, for example, SEQ ID NO:49, at least 50%, 60%, 70%, 75%, 80%, 85%, 90%, 95%, 96%, 97%, 98%, 99%, or 100% sequence identity to the CD28 transmembrane domain, for example, SEQ ID NOs:50 or 76, at least 50%, 60%, 70%, 75%, 80%, 85%, 90%, 95%, 96%, 97%, 98%, 99%, or 100% sequence identity to the OX40 transmembrane domain, for example, SEQ ID NO:51, at least 50%, 60%, 70%, 75%, 80%, 85%, 90%, 95%, 96%, 97%, 98%, 99%, or 100% sequence identity to the CD134 transmembrane domain, or at least 50%, 60%, 70%, 75%, 80%, 85%, 90%, 95%, 96%, 97%, 98%, 99%, or 100% sequence identity to the CD7 transmembrane domain, for example, SEQ ID NO:52, and the conditionally active ASTR can retain an increased binding to Ror2 or Axl in a tumor microenvironment and/or in an in vitro tumor surrogate assay condition relative to a corresponding physiological condition when the ASTR is part of the CAR. In any of the embodiments herein that includes a CAR, the transmembrane can be the CD8 transmembrane domain or the CD28 transmembrane domain. In any of the embodiments herein that includes a CAR, the transmembrane domain can be located between the ASTR and the intracellular activating domain. In any of the embodiments herein that includes a CAR, the intracellular activating domain can retain an activating activity and have at least 50%, 60%, 70%, 75%, 80%, 85%, 90%, 95%, 96%, 97%, 98%, 99%, or 100% sequence identity to the CD3Z activating domain, for example, SEQ ID NOs:11-16, at least 50%, 60%, 70%, 75%, 80%, 85%, 90%, 95%, 96%, 97%, 98%, 99%, or 100% sequence identity to the CD3D activating domain, for example, SEQ ID NOs:17-19, at least 50%, 60%, 70%, 75%, 80%, 85%, 90%, 95%, 96%, 97%, 98%, 99%, or 100% sequence identity to the CD3E activating domain, for example, SEQ ID NOs:20-21, at least 50%, 60%, 70%, 75%, 80%, 85%, 90%, 95%, 96%, 97%, 98%, 99%, or 100% sequence identity to the CD3G activating domain, for example, SEQ ID NOs:22-23, at least 50%, 60%, 70%, 75%, 80%, 85%, 90%, 95%, 96%, 97%, 98%, 99%, or 100% sequence identity to the CD28 activating domain, for example, SEQ ID NO:35, at least 50%, 60%, 70%, 75%, 80%, 85%, 90%, 95%, 96%, 97%, 98%, 99%, or 100% sequence identity to the CD79A activating domain, for example, SEQ ID NOs:24-26, at least 50%, 60%, 70%, 75%, 80%, 85%, 90%, 95%, 96%, 97%, 98%, 99%, or 100% sequence identity to the DAP10 activating domain, for example, SEQ ID NO:34, at least 50%, 60%, 70%, 75%, 80%, 85%, 90%, 95%, 96%, 97%, 98%, 99%, or 100% sequence identity to the DAP12 activating domain, for example, SEQ ID NOs:27-31, at least 50%, 60%, 70%, 75%, 80%, 85%, 90%, 95%, 96%, 97%, 98%, 99%, or 100% sequence identity to the FCER1G activating domain, for example, SEQ ID NOs:32-33, at least 50%, 60%, 70%, 75%, 80%, 85%, 90%, 95%, 96%, 97%, 98%, 99%, or 100% sequence identity to the CD137 activating domain, or at least 50%, 60%, 70%, 75%, 80%, 85%, 90%, 95%, 96%, 97%, 98%, 99%, or 100% sequence identity to the ZAP70 activating domain, for example, SEQ ID NO:36.

In any of the embodiments herein that includes a CAR, the CAR can further include a stalk domain. In any of the embodiments herein that includes a CAR, the CAR can further include a co-stimulatory domain. In some embodiments, the CAR can include a stalk domain and a co-stimulatory domain. In some embodiments, the CAR can include from amino terminus to carboxy terminus, an ASTR, a stalk domain, a transmembrane domain, a co-stimulatory domain, and an intracellular activating domain.

In any of the embodiments herein that includes a CAR with a stalk domain, the stalk domain can have at least 50%, 60%, 70%, 75%, 80%, 85%, 90%, 95%, 96%, 97%, 98%, 99%, or 100% sequence identity to any CD8 stalk domain known in the art, for example, SEQ ID NO:125, or at least 50%, 60%, 70%, 75%, 80%, 85%, 90%, 95%, 96%, 97%, 98%, 99%, or 100% sequence identity to any CD28 stalk domain known in the art, for example, SEQ ID NO:126, and the conditionally active antigen-specific targeting region can retain an increased binding to Ror2 or Axl in a tumor microenvironment and/or an in vitro tumor surrogate assay condition relative to a corresponding physiological condition when the ASTR is part of the CAR.

In any of the embodiments herein that includes a CAR, the CAR can further include a co-stimulatory domain. In any of the embodiments herein that includes a CAR with a co-stimulatory domain, the intracellular co-stimulatory domain can include a DAP10/CD28 type signaling chain or an immunoreceptor tyrosine-based activation motif (ITAM)-containing intracellular signaling polypeptide. In any of the embodiments herein that includes a CAR with a co-stimulatory domain, the CAR can include a co-stimulatory domain that has a different amino acid sequence than the intracellular activating domain. In any of the embodiments herein that includes a CAR with a co-stimulatory domain, the co-stimulatory domain can have at least 50%, 60%, 70%, 75%, 80%, 85%, 90%, 95%, 96%, 97%, 98%, 99%, or 100% sequence identity to the CD137 co-stimulatory domain, for example, SEQ ID NO:1, at least 50%, 60%, 70%, 75%, 80%, 85%, 90%, 95%, 96%, 97%, 98%, 99%, or 100% sequence identity to the CD28 co-stimulatory domain, for example, SEQ ID NO:2, at least 50%, 60%, 70%, 75%, 80%, 85%, 90%, 95%, 96%, 97%, 98%, 99%, or 100% sequence identity to the ICA co-stimulatory domain, for example, SEQ ID NO:3, at least 50%, 60%, 70%, 75%, 80%, 85%, 90%, 95%, 96%, 97%, 98%, 99%, or 100% sequence identity to the ICOS co-stimulatory domain, for example, SEQ ID NO:4, at least 50%, 60%, 70%, 75%, 80%, 85%, 90%, 95%, 96%, 97%, 98%, 99%, or 100% sequence identity to the OX40 co-stimulatory domain, for example, SEQ ID NO:5, at least 50%, 60%, 70%, 75%, 80%, 85%, 90%, 95%, 96%, 97%, 98%, 99%, or 100% sequence identity to the BTLA co-stimulatory domain, for example, SEQ ID NO:7, at least 50%, 60%, 70%, 75%, 80%, 85%, 90%, 95%, 96%, 97%, 98%, 99%, or 100% sequence identity to the CD27 co-stimulatory domain, for example, SEQ ID NO:6, at least 50%, 60%, 70%, 75%, 80%, 85%, 90%, 95%, 96%, 97%, 98%, 99%, or 100% sequence identity to the CD30 co-stimulatory domain, for example, SEQ ID NO:8, at least 50%, 60%, 70%, 75%, 80%, 85%, 90%, 95%, 96%, 97%, 98%, 99%, or 100% sequence identity to the GITR co-stimulatory domain, for example, SEQ ID NO:9, or at least 50%, 60%, 70%, 75%, 80%, 85%, 90%, 95%, 96%, 97%, 98%, 99%, or 100% sequence identity to the HVEM co-stimulatory domain, for example, SEQ ID NO:10. In any of the embodiments herein that includes a CAR with a co-stimulatory domain, the co-stimulatory domain can be the CD28 co-stimulatory domain or the CD137 co-stimulatory domain. In any of the embodiments herein that includes a CAR with a co-stimulatory domain, the co-stimulatory domain can be the ICA co-stimulatory domain. In any of the embodiments herein that includes a CAR with a co-stimulatory domain, the co-stimulatory domain can be an ICA co-stimulatory domain and the intracellular activating domain can be a CD3Z activating domain. In any of the embodiments herein that includes a CAR with a stalk domain and a co-stimulatory domain, the stalk domain can be a CD8 stalk domain or a CD28 stalk domain, the transmembrane domain can be a CD8 transmembrane domain or a CD28 transmembrane domain, the intracellular activating domain can be a CD3Z activating domain, and the co-stimulatory domain can be a CD137 co-stimulatory domain, an ICA co-stimulatory domain, or a CD28 co-stimulatory domain, or the co-stimulatory domain can include both a CD137 co-stimulatory domain and an ICA co-stimulatory domain.

In any of the embodiments herein that includes a CAR, the CAR can further include a recognition domain. In any of the embodiments that includes a CAR with a recognition domain, the recognition domain can be expressed on the same polypeptide as the CAR. In any of the embodiments that includes a CAR with a recognition domain on the same polypeptide as the CAR, the recognition domain can be at or near the N-terminus, such as within 10, 20, 30, 40, or 50 amino acids of the N-terminus. In any of the embodiments that includes a CAR with a recognition domain on the same polypeptide as the CAR, the recognition domain can be at or near the C-terminus, such as within 10, 20, 30, 40, or 50 amino acids of the C-terminus. In any of the embodiments that includes a CAR with a recognition domain on the same polypeptide as the CAR, the recognition domain can be between any of the domains of the CAR, such as between the stalk and transmembrane domains. In any of the embodiments herein that includes a CAR with a recognition domain, the recognition domain can be expressed such that it is covalently attached to the CAR and the recognition domain can be separated from the CAR by a cleavage signal or a ribosomal skip sequence. In any of the embodiments herein that includes a CAR with a recognition domain with a ribosomal skip sequence, the ribosomal skip sequence can be 2A-1, for example SEQ ID NO:77. In any of the embodiments herein that includes a CAR with a recognition domain, the recognition domain can be at least 10, 15, 20, 25, 30, 35, 40, 45, or 50 contiguous amino acids of EGFR. In any of the embodiments that includes a CAR with a recognition domain, the recognition domain can be the FLAG epitope (SEQ ID NO:38).

In any of the embodiments herein that includes a CAR, the CAR can further include a signal sequence. In any of the embodiments herein that includes a CAR with a signal sequence, the signal sequence can be an epitope tag, an affinity domain, and/or a polypeptide that produces a detectable signal. In any of the embodiments herein that includes a CAR with a signal sequence, the signal sequence can be at the amino terminus.

In any of the embodiments herein that includes an expression vector that includes a nucleic acid encoding a CAR, the expression vector can further include nucleotides encoding a recognition domain. In any of the embodiments herein that includes an expression vector that includes a nucleic acid encoding a CAR and nucleotides encoding a recognition domain, the nucleotides encoding the recognition domain can encode at least 10, 15, 20, 25, 30, 35, 40, 45, or 50 contiguous amino acids of EGFR. In any of the embodiments herein that includes an expression vector that includes a nucleic acid encoding a CAR and nucleotides encoding a recognition domain, the nucleotides encoding the recognition domain can be separated from the nucleotides encoding the CAR by an internal ribosome entry site. In any of the embodiments herein that includes an expression vector that includes a nucleic acid encoding a CAR and nucleotides encoding a recognition domain, the recognition domain can be expressed as part of a single polypeptide that further includes the CAR and the recognition domain on the single polypeptide can be separated from the CAR by a cleavage signal or a ribosomal skip sequence, which can be a 2A-1 sequence, for example SEQ ID NO:77. In any of the embodiments herein that includes an expression vector, the expression vector can be a viral vector. In any of the embodiments herein that includes an expression vector that is a viral vector, the viral vector can be replication incompetent recombinant retroviral particle, replication incompetent recombinant lentiviral particle, a vaccinia virus, a poliovirus, an adeno-associated virus, SV40, a herpes simplex virus, a gamma retrovirus, a human immunodeficiency virus, a lentivirus, or an adenovirus.

In any of the embodiments herein that includes a mammalian cell expressing a CAR, the cell can be a lymphocyte. In any of the embodiments herein that includes a lymphocyte expressing a CAR, the lymphocyte can be a T cell. In any of the embodiments herein that includes a T cell expressing a CAR, the T cell can be a CD4+ T cell or the T cell can be a CD8+ T cell. In any of the embodiments herein that includes a lymphocyte expressing a CAR, the lymphocyte can be a cytotoxic cell that preferentially kills antigen-expressing cells in a tumor microenvironment, and the lymphocyte can include a nucleic acid encoding any of the CARs of Embodiments 1 or A1 to A8.

In any of the embodiments herein that includes a kit containing a container containing a replication incompetent recombinant retroviral particle, and instructions for use thereof, the instructions can further include increasing the pH of the microenvironment after contacting the target mammalian cell by introducing a pH-modulating pharmacologic agent to the microenvironment in sufficient amount, thereby affecting the binding of the target mammalian cell with the T cell and/or NK cell. In any of the embodiments herein that includes a kit containing a container containing a replication incompetent recombinant retroviral particle, and instructions for use thereof, the kit can further include a pH-modulating pharmacologic agent. In any of the embodiments herein that includes a kit containing a container containing a replication incompetent recombinant retroviral particle, and instructions for use thereof, the instructions can include a step of introducing the T cell and/or NK cell capable of expressing the CAR into a subject before the contacting, wherein after the introducing, the T cell and/or the NK cell including the one or more nucleic acid sequences encoding the CAR expresses the CAR and binds to the target mammalian cell expressing the cognate antigen in the subject.

In any of the embodiments herein that includes treating a cancer, the cancer can be renal cell carcinoma. In any of the embodiments herein that includes treating a cancer, the cancer can be soft tissue sarcoma or mesothelioma. In any of the embodiments herein that includes treating a cancer and include a CAR with a recognition domain, the method can further include administering a dose of antibodies directed against the recognition domain after administering the genetically engineered cytotoxic cell to the subject. In any of the embodiments herein that includes treating a cancer, the cancer can express Axl and the CAR can include an ASTR that bind Axl. In any of the embodiments herein that includes treating a cancer, the cancer can express Ror2 and the CAR can include an ASTR that bind Ror2. In any of the embodiments herein that includes treating a cancer, the cytotoxic cells can be T cells and/or NK cells. In any of the embodiments herein that includes treating a cancer, the cytotoxic cells can be T cells. In any of the embodiments herein that includes expanding T cells and/or NK cells, the method can further include harvesting the genetically modified T cells and/or NK cells after the expanding. In any of the embodiments herein that includes harvesting T cells and/or NK cells, the method can further include cryopreserving the harvested genetically modified T cells and/or NK cells. In any of the embodiments herein that includes cryopreserving T cells and/or NK cells, the cryopreserved genetically modified T cells and NK cells can be thawed. In any of the embodiments herein that includes harvesting T cells and/or NK cells, the method can further include introducing the harvested genetically modified T cells and/or NK cells into a subject.

Exemplary conditionally active CARs (CAB-CARs) that have increased binding to Axl at pH 6.7 compared to ph7.4 are found in Example 1 herein. In illustrative embodiments, the CAR or ASTR can bind to the same epitope of Axl as a single-chain variable antibody fragment comprising an antibody heavy chain of SEQ ID NO:79 and an antibody light chain of SEQ ID NO:80. In further embodiments of such illustrative embodiments, the anti-Axl CAR or ASTR comprises or is a single chain variable fragment (scFv) and in further illustrative examples, the anti-Axl scFv comprises either a heavy chain that is N-terminal to a light chain or a light chain that is N-terminal to a heavy chain. In any of the embodiments herein that includes a CAR, and in illustrative embodiments binds to the same epitope of Axl as an antibody that includes the antibody heavy chain of SEQ ID NO:79 and the antibody light chain of SEQ ID NO:80, the ASTR can include any of SEQ ID NOs:128, 129, 159, 160, or 161. Furthermore, anti-Axl CARs of any of the embodiments herein can include any of the CAR components provided herein. In certain exemplary embodiments, the anti-Axl CARs can include the CAR components listed in Table 1 and can be any of the CARs in Table 1. More typically for any embodiments herein that include an anti-Axl CAR, the CAR is a CAB-CAR, and in non-limiting illustrative embodiments, can include, for example, any of the CAB-CAR components and CAB-CARs provided in Table 1 that demonstrated cytotoxic activity. For example, the anti-Axl CAB-CAR can include a CD8 signal peptide, a CD8 or CD28 stalk/transmembrane domain, a CD137, ICΔ, or both a ICΔ co-stimulatory domain and a CD137 co-stimulatory domain, and/or a CD3Z activation domain. Furthermore, illustrative CARs for any of the embodiments herein that includes an anti-Axl CAR, and especially an anti-Axl CAB-CAR, in non-limiting illustrative embodiments include any of the anti-Axl CAB-CARs that demonstrated conditional cytotoxic activity in Table 1. Such illustrative CAB-CARs include F1-2-1, F1-2-2, F1-2-3, F1-2-6, F1-2-8, F1-2-10, F1-2-13, F1-2-14, F1-2-15, F1-2-22, or F1-2-23 of Table 1. In any of the embodiments herein that includes an ASTR, the ASTR can include the ASTR of F1-2-1, F1-2-2, F1-2-3, F1-2-6, F1-2-8, F1- 2-10, F1-2-13, F1-2-14, F1-2-15 F1-2-22, or F1-2-23. Furthermore, illustrative CARs for any of the embodiments herein that includes an anti-Axl CAR, and especially an anti-Axl CAB-CAR, in non-limiting illustrative embodiments include any of the anti-Axl CAB-CARs that demonstrated high conditional cytotoxic activity in Table 1. Such illustrative CAB-CARs include F1-2-13, F1-2-15, F1-2-22, or F1-2-23. Accordingly, in any of the embodiments herein that includes an ASTR, the ASTR can include the ASTR of F1-2-1, F1-2-2, F1-2-3, F1-2-6, F1-2-8, F1-2-10, F1-2-13, F1-2-14, F1-2-15, F1-2-22, or F1-2-23.

Exemplary conditionally active CARs (CAB-CARs) that have increased binding to Ror2 at pH 6.7 compared to pH 7.4 are found in Example 1 herein. In illustrative embodiments, the CAR or ASTR can bind to the same epitope of Ror2 as a single-chain variable antibody fragment comprising an antibody heavy chain of SEQ ID NO:82 or SEQ ID NO:83 and an antibody light chain of SEQ ID NO:84 or the CAR or ASTR can bind to the same epitope of Ror2 as a single-chain variable antibody fragment comprising an antibody heavy chain of SEQ ID NO:151 and an antibody light chain of SEQ ID NO:152. In further embodiments of such illustrative embodiments, the anti-Ror2 CAR or ASTR comprises or is a single chain variable fragment (scFv) and in further illustrative examples, comprises a light chain that is N terminal to a heavy chain, or comprises a heavy chain that is N-terminal to a light chain. In any of the embodiments herein that includes a CAR or ASTR, and in illustrative embodiments binds to the same epitope of Ror2 as a single-chain variable antibody fragment comprising an antibody heavy chain of SEQ ID NO:82 or SEQ ID NO:83 and an antibody light chain of SEQ ID NO:84 or binds to the same epitope of Ror2 as a single-chain variable antibody fragment comprising an antibody heavy chain of SEQ ID NO:151 and an antibody light chain of SEQ ID NO:152, the ASTR can include any of SEQ ID NOs:130-132, or 153-158. Furthermore, anti-Ror2 CARs of any of the embodiments herein can include any of the CAR components provided herein. In certain exemplary embodiments, the anti-Ror2 CARs can include the CAR components listed in Table 2 and can be any of the CARs in Table 2. More typically for any embodiments herein that include an anti-Ror2 CAR, the CAR is a CAB-CAR, and in non-limiting illustrative embodiments, can include, for example, any of the CAB-CAR components and CAB-CARs provided in Table 2 that demonstrated cytotoxic activity. For example, the anti-Ror2 CAB-CAR can include a CD8 signal peptide, a CD8 or CD28 stalk/transmembrane domain, a CD137 co-stimulatory domain, and/or a CD3Z activation domain. Furthermore, illustrative CARs for any of the embodiments herein that includes an anti-Ror2 CAR and especially an anti-Ror2 CAB-CAR, in non-limiting illustrative embodiments include any of the anti-Ror2 CAB-CARs that demonstrated conditional cytotoxic activity in Table 2. Such illustrative CAB-CARs include F1-1-9, F1-1-10, F1-1-11, F1-1-12, F1-1-15, F1-1-17, F1-1-18, F1-1-19, F1-1-20, F1-1-21, F1-1-23, F1-1-25, or F1-1-26. In any of the embodiments herein that includes an anti-Ror2 ASTR, the ASTR can include the ASTR of F1-1-9, F1-1-10, F1-1-11, F1-1-12, F1-1-15, F1-1-17, F1-1-18, F1-1-19, F1-1-20, F1-1-21, F1-1-23, F1-1-25, or F1-1-26 of Table 2. Furthermore, illustrative CARs for any of the embodiments herein that includes an anti-Ror2 CAR and especially an anti-Ror2 CAB-CAR, in non-limiting illustrative embodiments include any of the anti-Ror2 CAB-CARs that demonstrated high conditional cytotoxic activity in Table 2. Such illustrative CAB-CARs include F1-1-11, F1-1-12, F1-1-15, F1-1-17, F1-1-19, F1-1-20, or F1-1-23. Accordingly, in any of the embodiments herein that includes an anti-Ror2 ASTR, the ASTR can include the ASTR of F1-1-11, F1-1-12, F1-1-15, F1-1-17, F1-1-19, F1-1-20, F1-1-23.

In another aspect, provided herein is a method for modulating binding of a conditionally active biologic chimeric antigen receptor (CAB-CAR)-expressing T cell or NK cell to a cell expressing a cognate antigen of the CAB-CAR in a subject, including:

a. introducing a T cell and/or NK cell including a nucleic acid encoding the CAB-CAR into the subject, wherein after the introducing, the T cell and/or the NK cell including the nucleic acid encoding the CAB-CAR expresses the CAB-CAR and binds to the cell expressing the cognate antigen in the subject, and wherein the cognate antigen is an Axl polypeptide or an epitope thereof, or a Ror2 polypeptide or an epitope thereof; and b. administering a pharmacologic agent to the subject in sufficient amount to increase blood pH and/or pH of a tissue and/or pH of a microenvironment, wherein the administering is performed before, during, or after the introducing, and wherein the increased pH of the blood, the tissue, and/or the microenvironment modulates binding of the CAB-CAR expressing T cell and/or NK cell to the cell expressing the cognate antigen in the blood, the tissue, or the microenvironment with the increased pH.

In another aspect, provided herein is a method for alleviating on target off tumor toxicity in a subject, including:

a. introducing a nucleic acid encoding a conditionally active biologic chimeric antigen receptor (CAB-CAR) into a T cell or NK cell of the subject to produce a T cell and/or NK cell including a nucleic acid encoding the CAB-CAR;

b. introducing the T cell and/or NK cell including the nucleic acid encoding the CAB-CAR into the subject, wherein after the introducing, the T cell and/or the NK cell including the nucleic acid encoding the CAB-CAR expresses the CAB-CAR and binds to the cell expressing a cognate antigen in the subject, wherein the cognate antigen is an Axl polypeptide or an epitope thereof, or a Ror2 polypeptide or an epitope thereof; and c. administering a pharmacologic agent to the subject in sufficient amount to increase blood pH and/or pH of a tissue and/or pH of a microenvironment to modulate binding of the CAB-CAR to its cognate antigen in the blood, the tissue, and/or the microenvironment with the increased pH, thereby alleviating on target off tumor toxicity in the subject.

In some embodiments, the nucleic acid can be a vector. In illustrative embodiments, the vector is a retroviral vector.

In another aspect, provided herein is a method for controlling binding of a T cell and/or NK cell to a target mammalian cell, including:

a. contacting the target mammalian cell with the T cell and/or NK cell in a microenvironment, wherein the target mammalian cell expresses a cognate antigen, and the T cell and/or NK cell expresses a conditionally active biologic chimeric antigen receptor (CAB-CAR) that binds to the cognate antigen differentially at pH 6.7 as compared to pH 7.4, wherein the cognate antigen is an Axl polypeptide or an epitope thereof, or a Ror2 polypeptide or an epitope thereof; and b. increasing the pH of the microenvironment by introducing a pharmacologic agent to the microenvironment in sufficient amount, thereby controlling the binding of the T cell and/or NK cell to the target mammalian cell.

In another aspect, provided herein is a method for controlling the binding of a T cell and/or NK cell expressing a conditionally active biologic chimeric antigen receptor (CAB-CAR) to a target mammalian cell in a subject in vivo, including administering a pH-modulating pharmacologic agent to the subject through an effective dosing regimen that increases the pH of a microenvironment within the subject, wherein the subject includes the T cell and/or the NK cell expressing the CAB-CAR, wherein the CAB-CAR binds to its cognate antigen differentially at pH 6.7 as compared to pH 7.4, wherein the cognate antigen is an Axl polypeptide or an epitope thereof, or a Ror2 polypeptide or an epitope thereof, wherein the microenvironment include the target mammalian cell, wherein the target mammalian cell expresses the cognate antigen on its surface, and wherein the T cell and/or NK cell binds to the target mammalian cell differentially before versus after the pH of the microenvironment is increased, thereby controlling the binding of the T cell and/or NK cell to the target mammalian cell in a subject in vivo.

In any of the aspects provided immediately above that include a pharmacologic agent and a CAB-CAR, the CAB-CAR can have reduced binding to its cognate antigen at one pH than at a different pH. In illustrative embodiments where illustrative pH values for differential binding of a CAB-CAR are not already provided in the broadest aspect and alternatively for other embodiments in place of those values for such aspects, the CAB-CAR can have reduced binding at a higher pH than at a lower pH. For example, the CAB-CAR can have reduced binding to its cognate antigen at a pH above 7.0, 7.1, 7.2, 7.3, 7.4, or 7.5 than at a pH below 6.4, 6.5, 6.6, 6.7, 6.8, 6.9, or 7.0. In other embodiments, the CAB-CAR can have reduced binding at a higher pH than at a lower pH. For example, the CAB-CAR can have reduced binding to its cognate antigen at a pH below 6.4, 6.5, 6.6, 6.7, 6.8, 6.9, or 7.0 than at a pH above 7.0, 7.1, 7.2, 7.3, 7.4, or 7.5. In some illustrative embodiments, the CAB-CAR exhibits increased binding at a pH of 6.5 to 6.7 compared to pH 7.4 to 7.6. In other illustrative embodiments, the CAB-CAR exhibits increased binding at a pH of 6.7 compared to a pH of 7.4. In other embodiments, the CAB-CAR exhibits increased binding in the pH of a tumor compared to the pH of blood. In some embodiments, the CAB-CAR can include an antigen-specific targeting region, a stalk, and an intracellular activating domain. In some embodiments, the CAB-CAR can also include a co-stimulatory domain. In some embodiments, the CAB-CAR can bind to a tumor associated antigen.

In any of the aspects provided immediately above that include a pharmacologic agent and a CAB-CAR, the pH of the microenvironment can be increased from a pH below 7.0 to a pH above 7.0. For example, the pH can be increased from a pH below 6.4, 6.5, 6.6, 6.7, 6.8, 6.9, or 7.0 to a pH above 7.0, 7.1, 7.2, 7.3, or 7.4. In some embodiments, the CAB-CAR can bind to the cognate antigen at the increased pH but not a pH of the microenvironment before introducing the pharmacologic agent. In certain embodiments, the pH can be increased from below 7.0 to a pH of 7.1 to 8.0 or to a pH of 7.1 to 7.8 or to a pH of 7.2 to 7.8 or a pH of 7.2 to 7.6 or a pH of 7.3 to 7.6 or to a pH of 7.4 to 7.8 or to a pH of 7.4 to 7.6. Such an increase in pH can occur for less than 1, 2, 4, 6, 8, 12, or 24 hours or for more than 1, 2, 4, 6, 8, 12 or 24 hours depending on the type and dose of pharmacologic agent administered. In certain embodiments, the pharmacologic agent is administered such that the pH remains above 7.0, 7.1, 7.2, 7.3, 7.4, or 7.5; or between 7.0, 7.1, 7.2, 7.3 on the low end of the range and 7.4, 7.5, 7.6, 7.7, or 7.8 on the high end of the range, in the target tissue, such as a tumor, and for example in at least a surface of a target tissue (e.g. tumor) microenvironment, in at least a portion of a target tissue (e.g. tumor) microenvironment, and in illustrative embodiments throughout a target tissue (e.g. tumor) microenvironment.

In any of the aspects provided immediately above that include a pharmacologic agent and a CAB-CAR, the microenvironment can be an in vivo microenvironment, such as a tumor, a tissue, a non-tumor tissue, a normal tissue, or a tissue that has undergone a transient shift in pH. For example, tissues that typically undergo transient shifts in pH include a muscle tissue in anaerobic conditions or muscle tissue undergoing exercise or an inflamed tissue or a tissue experiencing inflammation. In some embodiments that include a target mammalian cell, the target mammalian cell can be a tumor cell or a non-tumor or normal cell.

In any of the aspects provided immediately above that include a pharmacologic agent and a CAB-CAR, the pharmacologic agent can be sodium bicarbonate, tris-hydroxylmethyl aminomethane, an equimolar hypertonic solution of sodium bicarbonate and sodium carbonate, or proton pump inhibitors such esomeprazole, esomeprazole and naproxen, lansoprazole, omeprazole, and rabeprazole.

In any embodiment provided immediately above that includes a replication incompetent recombinant retroviral particle in a method that includes a CAB-CAR and a pharmacologic agent, the polynucleotide that includes a transcriptional unit operatively linked to a promoter active in T cells and/or NK cells that encodes the CAB-CAR is taken up by the T cell(s) and/or NK cell(s) such that such the cell(s) is capable of expressing the CAB-CAR. In illustrative embodiments, the T cell(s) and/or NK cell(s) integrate the polynucleotide into their genome.

In any embodiment provided immediately above that includes a replication incompetent recombinant retroviral particle in a method that includes a CAB-CAR and a pharmacologic agent, the replication incompetent recombinant retroviral particle can include on its surface a recognition domain of a monoclonal antibody approved biologic. For example, the recognition domain can include a polypeptide that is recognized by an antibody that recognizes EGFR, or an epitope thereof.

In another aspect, provided herein is a pH-modulating pharmacologic agent for use in a method for controlling the binding of a T cell and/or NK cell to a target mammalian cell in a subject in vivo, including administering the pH-modulating pharmacologic agent to the subject through an effective dosing regimen that increases the pH of a microenvironment within the subject, wherein the subject includes the T cell and/or the NK cell, wherein the T cell and/or NK cell expresses a conditionally active biologic chimeric antigen receptor (CAB-CAR) that binds to its cognate antigen differentially at pH 6.7 as compared to pH 7.4, wherein the cognate antigen is an Axl polypeptide or an epitope thereof, or a Ror2 polypeptide or an epitope thereof, wherein the T cell and/or NK cell expresses the CAB-CAR, wherein the microenvironment includes the target mammalian cell, wherein the target mammalian cell expresses the cognate antigen on their surface, and wherein the T cell and/or NK cell binds to the target mammalian cell differentially before versus after the pH of the microenvironment is increased by administering the pH-modulating pharmacologic agent thereby controlling the binding of the T cell and/or NK cell to the target mammalian cell in a subject in vivo.

In another aspect, provided herein is a pharmacologic agent for use in a method for modulating the binding of a conditionally active biologic chimeric antigen receptor (CAB-CAR) expressing T cell or NK cell to a cell expressing a cognate antigen of the CAB-CAR in a subject, for treating tumor growth, wherein the method includes:
   a. introducing a T cell and/or NK cell capable of expressing the CAB-CAR into the subject, wherein the cognate antigen is an Axl polypeptide or an epitope thereof, or a Ror2 polypeptide or an epitope thereof, wherein the CAB-CAR binds to the cell expressing the cognate antigen in the subject, wherein after the introducing, the T cell and/or the NK cell including the nucleic acid encoding the CAB-CAR expresses the CAB-CAR and binds to the cell expressing the cognate antigen in the subject; and
   b. administering the pharmacologic agent to the subject in sufficient amount to increase blood pH and/or a tissue pH and/or a microenvironment pH to modulate binding of the CAB-CAR expressing T cell and/or NK cell to the cell expressing the cognate antigen in the blood, the tissue, or the microenvironment with the increased pH.

In another aspect, provided herein is a pharmacologic agent for use in a method for alleviating on target off tumor toxicity in a subject, wherein the method includes:
   a. introducing a nucleic acid encoding a conditionally active biologic chimeric antigen receptor (CAB-CAR) into a T cell or NK cell of the subject, to produce a T cell and/or NK cell capable of expressing the CAB-CAR;
   b. introducing the T cell and/or NK cell capable of expressing the CAB-CAR into the subject, wherein after the introducing, the T cell and/or the NK cell including the nucleic acid encoding the CAB-CAR expresses the CAB-CAR and binds to the cell expressing the cognate antigen in the subject; and
   c. administering the pharmacologic agent to the subject in sufficient amount to increase blood pH and/or a tissue pH and/or a microenvironment pH to modulate binding of the CAB-CAR to its cognate antigen in the blood, the tissue, and/or the microenvironment with the increased pH, wherein the cognate antigen is an Axl polypeptide or an epitope thereof, or a Ror2 polypeptide or an epitope thereof, thereby alleviating on target off tumor toxicity in the subject.

In another aspect, provided herein is a pharmacologic agent for use in a method for controlling the binding of a T cell and/or NK cell expressing a conditionally active biologic chimeric antigen receptor (CAB-CAR) to a target mammalian cell, for treating tumor growth, wherein the method includes:
   a. contacting the target mammalian cell with the T cell and/or NK cell expressing the CAB-CAR in a microenvironment, wherein the target mammalian cell expresses a cognate antigen, wherein the cognate antigen is an Axl polypeptide or an epitope thereof, or a Ror2 polypeptide or an epitope thereof, and wherein the T cell and/or NK cell expresses the CAB-CAR that binds to the cognate antigen differentially at pH 6.7 as compared to pH 7.4; and
   b. increasing the pH of the microenvironment by introducing the pharmacologic agent to the microenvironment in sufficient amount, thereby controlling the binding of the T cell and/or NK cell expressing the CAB-CAR to the target mammalian cell.

In another aspect, provided herein is a pharmacologic agent for use in a method for controlling the binding of a T cell and/or NK cell expressing a conditionally active biologic chimeric antigen receptor (CAB-CAR) to a target mammalian cell in a subject in vivo, for treating tumor growth, wherein the pharmacologic agent is a pH-modulating pharmacologic agent, and wherein the method includes administering the pH-modulating pharmacologic agent to the subject through an effective dosing regimen that increases the pH of a microenvironment within the subject, wherein the subject includes the T cell and/or NK cell expressing the CAB-CAR, wherein the CAB-CAR binds to its cognate antigen differentially at pH 6.7 as compared to pH 7.4, wherein the cognate antigen is an Axl polypeptide or an epitope thereof, or a Ror2 polypeptide or an epitope thereof, wherein the microenvironment includes the target mammalian cell, wherein the target mammalian cell expresses the cognate antigen on its surface, and wherein the T cell and/or NK cell binds to the target mammalian cell differentially before versus after the pH of the microenvironment is increased.

In another aspect, provided herein is a pH-modulating pharmacologic agent for use in a method for controlling the binding of a T cell and/or NK cell expressing a conditionally active biologic chimeric antigen receptor (CAB-CAR) to a target mammalian cell in a subject in vivo, for treating tumor growth, wherein the method includes administering the pH-modulating pharmacologic agent to the subject through an effective dosing regimen that increases the pH of a microenvironment within the subject, wherein the subject includes the T cell and/or NK cell expressing the CAB-CAR, wherein the CAB-CAR binds to its cognate antigen differentially at pH 6.7 as compared to pH 7.4, wherein the cognate antigen is an Axl polypeptide or an epitope thereof, or a Ror2 polypeptide or an epitope thereof, wherein the microenvironment includes the target mammalian cell, wherein the target mammalian cell expresses the cognate antigen on its surface, and wherein the T cell and/or NK cell binds to the target mammalian cell differentially before versus after the pH of the microenvironment is increased by administering the pH-modulating pharmacologic agent.

In another aspect, provided herein is a use of a pH-modulating pharmacologic agent for use in the manufacture of a medicament for controlling the binding of a T cell and/or NK cell expressing a conditionally active biologic chimeric antigen receptor (CAB-CAR) to a target mammalian cell in a subject in vivo, wherein the pH-modulating pharmacologic agent is to be administered to the subject through an effective dosing regimen that increases the pH of a microenvironment within the subject, wherein the subject includes the T cell and/or NK cell expressing the CAB-CAR, wherein the CAB-CAR binds to its cognate antigen differentially at pH 6.7 as compared to pH 7.4, wherein the cognate antigen is an Axl polypeptide or an epitope thereof, or a Ror2 polypeptide or an epitope thereof, wherein the microenvironment includes the target mammalian cell, wherein the target mammalian cell expresses the cognate antigen on their surface, and wherein the T cell binds to the target mammalian cell differentially before versus after the pH of the microenvironment is increased by administering the pH-modulating pharmacologic agent.

In any of the aspects provided immediately above that include a pH-modulating pharmacologic agent or a pharmacologic agent for use in a method and a CAB-CAR or include the use of a pH-modulating pharmacologic agent and a CAB-CAR, the CAB-CAR can have reduced binding to its cognate antigen at one pH than at a different pH. In illustrative embodiments where illustrative pH values for differential binding of a CAB-CAR are not already provided in the broadest aspect and alternatively for other embodiments in place of those values for such aspects, the CAB-CAR can have reduced binding at a higher pH than at a lower pH. For example, the CAB-CAR can have reduced binding to its cognate antigen at a pH above 7.0, 7.1, 7.2, 7.3, 7.4, or 7.5 than at a pH below 6.4, 6.5, 6.6, 6.7, 6.8, 6.9, or 7.0. In other embodiments, the CAB-CAR can have reduced binding at a higher pH than at a lower pH. For example, the CAB-CAR can have reduced binding to its cognate antigen at a pH below 6.4, 6.5, 6.6, 6.7, 6.8, 6.9, or 7.0 than at a pH above 7.0, 7.1, 7.2, 7.3, 7.4, or 7.5. In some illustrative embodiments, the CAB-CAR exhibits increased binding at a pH of 6.5 to 6.7 compared to pH 7.4 to 7.6. In other illustrative embodiments, the CAB-CAR exhibits increased binding at a pH of 6.7 compared to a pH of 7.4. In other embodiments, the CAB-CAR exhibits increased binding in the pH of a tumor compared to the pH of blood. In some embodiments, the CAB-CAR can include an antigen-specific targeting region, a stalk, and an intracellular activating domain. In some embodiments, the CAB-CAR can also include a co-stimulatory domain. In some embodiments, the CAB-CAR can bind to a tumor associated antigen.

In any of the aspects provided immediately above that include a pH-modulating pharmacologic agent or a pharmacologic agent for use in a method and a CAB-CAR or include the use of a pH-modulating pharmacologic agent and a CAB-CAR, the pH of the microenvironment can be increased from a pH below 7.0 to a pH above 7.0. For example, the pH can be increased from a pH below 6.4, 6.5, 6.6, 6.7, 6.8, 6.9, or 7.0 to a pH above 7.0, 7.1, 7.2, 7.3, or 7.4. In some embodiments, the CAB-CAR can bind to the cognate antigen at the increased pH but not a pH of the microenvironment before introducing the pharmacologic agent. In certain embodiments, the pH can be increased from below 7.0 to a pH of 7.1 to 8.0 or to a pH of 7.1 to 7.8 or to a pH of 7.2 to 7.8 or a pH of 7.2 to 7.6 or a pH of 7.3 to 7.6 or to a pH of 7.4 to 7.8 or to a pH of 7.4 to 7.6. Such an increase in pH can occur for less than 1, 2, 4, 6, 8, 12, or 24 hours or for more than 1, 2, 4, 6, 8, 12 or 24 hours depending on the type and dose of pharmacologic agent administered. In certain embodiments, the pharmacologic agent is administered such that the pH remains above 7.0, 7.1, 7.2, 7.3, 7.4, or 7.5; or between 7.0, 7.1, 7.2, 7.3 on the low end of the range and 7.4, 7.5, 7.6, 7.7, or 7.8 on the high end of the range, in the target tissue, such as a tumor, and for example in at least a surface of a target tissue (e.g. tumor) microenvironment, in at least a portion of a target tissue (e.g. tumor) microenvironment, and in illustrative embodiments throughout a target tissue (e.g. tumor) microenvironment.

In any of the aspects provided immediately above that include a pH-modulating pharmacologic agent or a pharmacologic agent for use in a method and a CAB-CAR or include the use of a pH-modulating pharmacologic agent and a CAB-CAR, wherein the cognate antigen is an Axl polypeptide or an epitope thereof, or a Ror2 polypeptide or an epitope thereof; the microenvironment can be an in vivo microenvironment, such as a tumor, a tissue, a non-tumor tissue, a normal tissue, or a tissue that has undergone a transient shift in pH. For example, tissues that typically undergo transient shifts in pH include a muscle tissue in anaerobic conditions or muscle tissue undergoing exercise or an inflamed tissue or a tissue experiencing inflammation. In some embodiments that include a target mammalian cell, the target mammalian cell can be a tumor cell or a non-tumor or normal cell.

In any of the aspects provided immediately above that include a pH-modulating pharmacologic agent or a pharmacologic agent for use in a method and a CAB-CAR or include the use of a pH-modulating pharmacologic agent and a CAB-CAR, wherein the cognate antigen is an Axl polypeptide or an epitope thereof, or a Ror2 polypeptide or an epitope thereof, the pharmacologic agent can be sodium bicarbonate, tris-hydroxylmethyl aminomethane, an equimolar hypertonic solution of sodium bicarbonate and sodium carbonate, or proton pump inhibitors such esomeprazole, esomeprazole and naproxen, lansoprazole, omeprazole, and rabeprazole.

In any of the aspects provided immediately above that include a pH-modulating pharmacologic agent or a pharmacologic agent for use in a method and a CAB-CAR or include the use of a pH-modulating pharmacologic agent and a CAB-CAR, wherein the cognate antigen is an Axl polypeptide or an epitope thereof, or a Ror2 polypeptide or an epitope thereof, the pharmacologic agent can be used in a method for the treatment of cancer, tumors, tumor growth, or a cell proliferative disorder.

In another aspect, provided herein is a kit containing a container containing a replication incompetent recombinant retroviral particle, and instructions for use thereof for treating tumor growth, wherein the instructions instruct a method for controlling the binding of a T cell and/or NK cell to a target mammalian cell, in a method including:

a. transducing the T cell and/or NK cell with the replication incompetent recombinant retroviral particle including in its genome a conditionally active biologic chimeric antigen receptor (CAB-CAR) that binds to the cognate antigen differentially at pH 6.7 as compared to pH 7.4 to produce a T cell and/or NK cell capable of expressing the CAB-CAR, wherein the cognate antigen is an Axl polypeptide or an epitope thereof, or a Ror2 polypeptide or an epitope thereof;

b. introducing the T cell and/or NK cell capable of expressing the CAB-CAR into the subject, wherein after the introducing, the T cell and/or the NK cell including the nucleic acid encoding the CAB-CAR expresses the CAB-CAR and binds to the cell expressing the cognate antigen in the subject;

c. contacting the target mammalian cell with the CAB-CAR expressing T cell and/or NK cell in a microenvironment, wherein the target mammalian cell expresses a cognate antigen of the CAB-CAR, and the T cell and/or NK cell expresses the CAB-CAR; and d. increasing the pH of the microenvironment by introducing a pH-modulating pharmacologic agent to the microenvironment in sufficient amount, thereby affecting the binding of the target mammalian cell with the T cell and/or NK cell.

In some embodiments, the kit can further include a pH-modulating pharmacologic agent.

In some embodiments of the kit, the CAB-CAR can have reduced binding to an Axl polypeptide or an epitope thereof, or a Ror2 polypeptide or an epitope thereof at one pH than at a different pH. In illustrative embodiments where illustrative pH values for differential binding of a CAB-CAR are not already provided in the broadest aspect and alternatively for other embodiments in place of those values for such aspects, the CAB-CAR can have reduced binding at a higher pH than at a lower pH. For example, the CAB-CAR can have reduced binding to its cognate antigen at a pH above 7.0, 7.1, 7.2, 7.3, 7.4, or 7.5 than at a pH below 6.4, 6.5, 6.6, 6.7, 6.8, 6.9, or 7.0. In other embodiments, the CAB-CAR can have reduced binding at a higher pH than at a lower pH. For example, the CAB-CAR can have reduced binding to its cognate antigen at a pH below 6.4, 6.5, 6.6, 6.7, 6.8, 6.9, or 7.0 than at a pH above 7.0, 7.1, 7.2, 7.3, 7.4, or 7.5. In some illustrative embodiments, the CAB-CAR exhibits increased binding at a pH of 6.5 to 6.7 compared to pH 7.4 to 7.6. In other illustrative embodiments, the CAB-CAR exhibits increased binding at a pH of 6.7 compared to a pH of 7.4. In other embodiments, the CAB-CAR exhibits increased binding in the pH of a tumor compared to the pH of blood. In some embodiments, the CAB-CAR can include an antigen-specific targeting region, a stalk, and an intracellular activating domain. In some embodiments, the CAB-CAR can also include a co-stimulatory domain. In some embodiments, the CAB-CAR can bind to a tumor associated antigen.

In some embodiments of the kit, the pH of the microenvironment can be increased from a pH below 7.0 to a pH above 7.0. For example, the pH can be increased from a pH below 6.4, 6.5, 6.6, 6.7, 6.8, 6.9, or 7.0 to a pH above 7.0, 7.1, 7.2, 7.3, or 7.4. In some embodiments, the CAB-CAR can bind to the cognate antigen at the increased pH but not a pH of the microenvironment before introducing the pharmacologic agent. In certain embodiments, the pH can be increased from below 7.0 to a pH of 7.1 to 8.0 or to a pH of 7.1 to 7.8 or to a pH of 7.2 to 7.8 or a pH of 7.2 to 7.6 or a pH of 7.3 to 7.6 or to a pH of 7.4 to 7.8 or to a pH of 7.4 to 7.6. Such an increase in pH can occur for less than 1, 2, 4, 6, 8, 12, or 24 hours or for more than 1, 2, 4, 6, 8, 12 or 24 hours depending on the type and dose of pharmacologic agent administered. In certain embodiments, the pharmacologic agent is administered such that the pH remains above 7.0, 7.1, 7.2, 7.3, 7.4, or 7.5; or between 7.0, 7.1, 7.2, 7.3 on the low end of the range and 7.4, 7.5, 7.6, 7.7, or 7.8 on the high end of the range, in the target tissue, such as a tumor, and for example in at least a surface of a target tissue (e.g. tumor) microenvironment, in at least a portion of a target tissue (e.g. tumor) microenvironment, and in illustrative embodiments throughout a target tissue (e.g. tumor) microenvironment. In some embodiments, the microenvironment can be an in vivo microenvironment, such as a tumor, a tissue, a non-tumor tissue, a normal tissue, or a tissue that has undergone a transient shift in pH. For example, tissues that typically undergo transient shifts in pH include a muscle tissue in anaerobic conditions or muscle tissue undergoing exercise or an inflamed tissue or a tissue experiencing inflammation. In some embodiments that include a target mammalian cell, the target mammalian cell can be a tumor cell or a non-tumor or normal cell.

In some embodiments of the kit, the pharmacologic agent can be sodium bicarbonate, tris-hydroxylmethyl aminomethane, an equimolar hypertonic solution of sodium bicarbonate and sodium carbonate, or proton pump inhibitors such esomeprazole, esomeprazole and naproxen, lansoprazole, omeprazole, and rabeprazole.

As disclosed above, the cognate antigen to which the CAB-CAR binds can be an Axl polypeptide or an epitope thereof or a Ror2 polypeptide or an epitope thereof. In some embodiments, the cognate antigen can be a polypeptide with at least 50%, 55%, 60%, 65%, 70%, 75%, 80%, 85%, 90%, 95%, 96%, 97%, 98%, 99%, or 100% sequence identity to a stretch of at least 10, 15, 20, or all of the amino acids of an Axl polypeptide or an epitope thereof or to a Ror2 polypeptide or an epitope thereof. As disclosed herein, the CAB-CAR capable of binding to an Axl polypeptide or an epitope thereof, or a Ror2 polypeptide or an epitope thereof typically binds its cognate antigen with a higher binding affinity at a pH of 6.7 than a pH of 7.4.

A skilled will recognize that when the specification refers to "Axl CAB" or "Axl CAB-CAR" the "Axl" refers to an ASTR that recognizes Axl or an epitope thereof. Similarly, a skilled will recognize that when the specification refers to "Ror2 CAB" or "Ror2 CAB-CAR" the "Ror2" refers to an ASTR that recognizes Ror2 or an epitope thereof.

Any section headings used herein are for organizational purposes only and are not to be construed as limiting the described subject matter in any way.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g. amounts, temperature, etc.) but some experimental errors and deviations should be accounted for. Unless indicated otherwise, parts are parts by weight, molecular weight is weight average molecular weight, temperature is in degrees Celsius, and pressure is at or near atmospheric. Standard abbreviations may be used, e.g., bp, base pair(s); kb, kilobase(s); pl, picoliter(s); s or sec, second(s); min, minute(s); h or hr, hour(s); aa, amino acid(s); kb, kilobase(s); bp, base pair(s); nt, nucleotide(s); i.m., intramuscular(ly); i.p., intraperitoneal (ly); s.c., subcutaneous(ly); i.v., intravenous(ly); and the like.

Example 1: Production and Analysis of Chimeric Antigen Receptors for Targeting Axl and Ror2

This example demonstrates methods for making and using conditionally active CARs of certain embodiments of the present invention. Nucleic acids encoding conditionally active ASTRs targeting Axl and Ror2 were obtained and used to generate lentiviral expression vectors encoding conditionally active CARs. T cells were transduced with lentivirus containing these expression vectors and the transduced cells were tested in various in vitro tumor surrogate assays against target cells.

Generation of Lentiviral Expression Vectors Expressing Conditionally Active CAR

A nucleic acid encoding a conditionally active ASTR targeting Axl (an scFv construct containing SEQ ID NOs:79 and 80) and 3 nucleic acids encoding conditionally active ASTRs targeting Ror2 (an scFv construct containing SEQ ID NOs:83 and 84, an scFv construct containing SEQ ID NOs:82 and 84, and an scFv construct containing SEQ ID NOs:151 and 152) were obtained. The detailed description herein provides methods for making conditionally active ASTRs (sometimes referred to as conditionally active biologics (CABs)), including methods for making CABs by evolving and selecting antibody fragments that was used to make the CABs that were obtained. Minor modifications to the sequences were made, including codon optimization for expression in human cells and the removal of splice donor and acceptor sites. The heavy chains of the single-chain antibodies (SEQ ID NOs:79, 83, and 82) and the light chains of the single-chain antibodies (SEQ ID NOs:80 and 84) were joined by linkers of various lengths (SEQ ID NOs: 53, 54, and 55) and incorporated into lentiviral expression vectors with the other domains to make the candidate CARs listed in Tables 1 and 2.

Production of Lentiviruses

Lentiviruses were produced by transient transfection of 293T cells (Lenti-X 293T, Clontech) with the lentiviral expression vectors. The cells were adapted to suspension culture by serial growth in Freestyle 293 Expression Medium (Thermo Fisher Scientific). The cells in suspension were transfected using PEI (Polysciences) dissolved in weak acid. Cells (30 mL) were grown to $1 \times 10^6$ cells/mL in a 125 mL Erlenmeyer flask.

Plasmid DNA was diluted in 1.5 ml Opti-MEM media for 30 mL of cells. Total DNA (1 μg/mL of culture volume) was a mixture of 4 plasmids with the following molar ratios: 2× genomic plasmid, 1× Rev-containing plasmid, 1×VSVg-containing plasmid, and 1× Gagpol-containing plasmid. Separately, the PEI was diluted in 1.5 ml Opti-MEM to 2 μg/mL (culture volume, 2:1 ratio to DNA). After a 5 minute room temperature incubation, the two solutions were mixed together well and incubated at room temperature for 20 more minutes. The final volume (3 ml) was added to the cells. The cells were then incubated at 37° C. for 72 hours with rotation at 120 rpm and with 5-8% $CO_2$.

After 72 hours, the supernatant was harvested by centrifugation at 1,000 g for 10 minutes. The supernatant was decanted to a fresh tube and ¼ of the supernatant volume in PEG solution (PEG-IT, System Biosciences) was added. The virus was precipitated by incubation overnight at 4° C. followed by centrifugation at 1,500 g for 20 minutes at 4° C. The supernatant was removed, and the virus was resuspended in 1:100 volume of Ex-Vivo15 media. Viruses were titered by GFP on HT1080 cells or by eTAG expression on Jurkat cells.

T Cell Transduction/Expansion for Axl and Ror2

In an initial method for T cell transduction and expansion Pan-T cells were obtained from All Cells (Allcells, PB009-1F). Anti-Axl CAB-CAR and Anti-ROR2 CAB-CAR replication incompetent recombinant lentiviral particles were made as discussed above. Two days prior to lentiviral transduction, cells were thawed and cultured in human T cell medium, consisting of X-VIVO15 (Lonza #04-418Q), 5% human AB serum (Valley Biomedical Inc., #HP1022), and 10 mM N-acetyl L-Cysteine (Sigma-Aldrich #A9165). Recombinant human IL-2 (R&D 202-IL-010) was added to a final concentration of 100 IU/mL. Twenty-four hours prior to viral transduction, primary human T cells were seeded into 12-well plate at $0.5 \times 10^6$ cells/well and activated using Dynabeads Human T-Activator CD3/CD28 (Thermo #11131D) at a 1:3 cell:bead ratio. On the day of transduction, lentiviral particle solution was added to the wells at MOI 5 for Axl and MOI 20 for Ror2. Transduced T cells were maintained at $\sim 10^6$/mL in human T cell medium for 3 days, then transferred into 6-well-G-Rex with 30 mL/well of human T cell medium contain IL-2. Cells were cultured for at least 10 days before experiments were conducted and IL-2 was added every other day.

Certain follow-on experiments were performed with slightly modified transduction and expansion conditions. Where indicated, in place of Pan T cells from AllCells, T cells were enriched from buffy coats (San Diego Blood Bank) by density gradient centrifugation with Ficoll-Paque PREMIUM® (GE Healthcare Life Sciences) according to the manufacturer's instructions followed by lysis of red blood cells. To study conditional CAR dependent killing of the human kidney cell lines Caki-1 and HEK293, CD56+ cells were depleted from transduced Pan T cells (AllCells) using the EasySep Human CD56 Positive Selection Kit II (Stem Cell Technologies #17855) prior to expansion.

FACS Analysis of eTAG Expression

Transduced primary T cells ($0.5 \times 10^6$) were collected 8 days after transduction, washed and resuspended in FACS buffer (PBS+2% FBS+0.1% sodium azide). Cells were stained with 100 tit FACS buffer containing 0.9 μg/ml biotinylated-cetuximab (Promab) for 30 mins on ice. Stained cells were washed with FACS buffer and stained with Streptavidin PE (eBioscience, 12-4317-87, 0.2 mg/ml), CD3-BV421 (Biolegend, 317344), CD4-PE-Dazzle 594 (Biolegend, 300548), and CD8-BV570 (Biolegend, 301038) for 30 mins on ice. Cells were washed twice in FACS buffer, fixed in a 1:1 mixture of the FACS buffer and BD Cytofix (BD #554655), processed with Novocyte (ACEA), and the resulting data was analyzed with NovoExpress software (ACEA).

Real-Time Cell Killing Assays

Cytotoxic activity of transduced T cells was measured by xCELLigence System (ACEA). Briefly, transduced primary T cells (effector cells) were produced as above, stored frozen, thawed and rested for 2 days in human T cell medium containing 100 IU/ML of IL-2. Target cells included CHO cells (ATCC) and CHO cells stably transfected to express human Axl (CHO-Axl) or ROR2 (CHO-ROR2) or in other experiments, human renal cell carcinoma lines Caki-1 (source) and HEK293 (Lenti-X 293T, Clontech) which tested positive by FACS for Axl and ROR2, respectively. Target cells were seeded to E-plates at 20K cells/well one day before the experiment with human T cell medium containing 40 mM HEPES and PIPES at pH 6.7 and 7.4 or at a range of pHs from pH 6.3 to pH 7.4 in 0.1 pH increments. On the day of the assay, rested effector cells were added into experimental wells at effector cell/target cell ratios (E/T) of 3:1, 1:1, and in some instances, 0.3:1. Impedance readings were taken every 5 minutes for approximately 40 hours after effector cell addition and impedance was reported as the Cell Index (CI). Percentage of specific cytolysis was calculated as follows ((CI Target+ Control virus transduced effector T cells)–(CI Target+ effector T cells transduced with CARs directed to Axl or Ror2))/(CI Target+ Control virus transduced effector T cells)×100.

Results

Chimeric antigen receptor (CARs) for binding Axl or Ror2 with increased activity at the reduced pH of a tumor environment compared to normal tissue (sometimes referred to herein as (CAB-CARs) were made by incorporating the heavy chains and light chains of conditionally active single-chain antibodies into lentiviral expression vectors along with other CAR domains and an eTag domain. The wild-type control CARS and conditionally active (CAB) CARs that were made and tested included various combinations of different CAR modules/components as indicated in Table 1 (Axl) and Table 2 (Ror2) with further detailed sequence information provided in Table 3. The various combinations of modules from amino to carboxy terminus are indicated in Table 1 and Table 2. These modules included a CD8 signal sequence peptide ("sp") (P1) (SEQ ID NO:74); Axl CAB VH (SEQ ID NO:79), Axl CAB VL (SEQ ID NO:80), Axl VH (SEQ ID NO:93), Axl VL (SEQ ID NO:94), Ror2 VH (SEQ ID NO:107), Ror2 VL (SEQ ID NO:84), Ror2 CAB VL (SEQ ID NO:152) Ror2 CAB1 VH (SEQ ID NO:82), Ror2 CAB2 VH (SEQ ID NO:83), Ror2 CAB3 VH (SEQ ID NO:151) (P2) and (P4); linker 1 (SEQ ID NO:53), linker 2 (SEQ ID NO:54), or linker 3 (SEQ ID NO:55) (P3); stalk/hinge and transmembrane domain from CD8 (SEQ ID NO:75) or CD28 (SEQ ID NO:76) (P5); co-stimulatory domain from CD137 (SEQ ID NO:1), CD28 (SEQ ID NO:2), ICΔ (SEQ ID NO:3), or both ICΔ and CD137 (SEQ ID NO:133) (P6); activation domain from CD3Z (SEQ ID NO:13) (P7); a 2A-1 ribosomal skip sequence (SEQ ID NO:77) (P8); an eTAG (SEQ ID NO:78) (P9).

Primary T cells were transduced with the recombinant lentiviral particles expressing the candidate CARs of Table 1 and Table 2 and the percent transfected cells was determined by determining the percent of cells expressing the eTag using FACS. Primary T cells were successfully transduced with the recombinant lentiviral particles encoding the candidate CARs as shown for representative Axl CARs in FIG. 1.

The cytotoxic activity of the candidate CARs against target cells expressing either Axl or Ror2 was analyzed at a pH of 7.4 (physiological pH) or a pH of 6.7 (surrogate tumor assay condition). As explained in more detail below, many of the candidate CARs were more effective at lysing target cells at a pH of 6.7 than a pH of 7.4. CAB activity was not detected in control CARs that included fully wild-type heavy and light chains (i.e. both VH and VL chains that were identified under physiologic conditions and were not further evolved).

In certain initial experiments related to Axl, eighteen anti-Axl CAB-CARs (F1-2-1 to F1-2-18) were tested using a first conditionally active heavy chain and a first conditionally active light chain that were both evolved from wild type heavy and light chain, respectively. As shown in Table 1, nine of the eighteen anti-AXL CAB-CARs initially tested had detectable cytotoxic activity (indicated in the table as "CAB activity"). None of the CAB-CARs tested that had only wild type ASTR antibody heavy and light chains had conditional activity (identified in Table 1 as "Axl VH" and "Axl VL" (F1-2-19, F1-2-20)). In follow-on experiments using the same transduction and expansion conditions provided above, anti-Axl CAB-CARs that included different co-stimulatory domains exhibited conditional cytotoxic activity (F1-2-22 and F1-2-23).

In certain initial experiments related to Ror2, conditionally active ASTRs against two different epitopes were analyzed. With respect to Ror2 CAB-CARs against epitope 1 (F1-1-9 to F1-1-24), eleven of the sixteen anti-Ror2 CAB-CARs initially tested had conditional cytotoxic activity (Table 2). With respect to Ror2 CAB-CARs against epitope 2, two (F1-1-25 and F1-1-26) of six anti-Ror2 CAB-CARs that exhibited killing activity in initial experiments, had conditional cytotoxic activity (Table 2). None of the CAB-CARs tested that had only wild type ASTR antibody heavy and light chains had conditional activity in these killing assays (identified in Table 2 as "Ror2 VH" and "Ror2 VL" (F1-1-1 to F1-1-8)).

In summary, many of the candidate CAB-CARs made and tested had higher cytotoxic activity on the target cells at a pH of 6.7 than at a pH of 7.4. Exemplary CAB-CARs that were more effective at lysing target cells at a pH of 6.7 than at a pH of 7.4 included CAB-CAR F1-2-3, which included an anti-Axl ASTR (SEQ ID NO:159), CAB-CAR F1-2-8, which included an anti-Axl ASTR (SEQ ID NO:160), CAB-CAR F1-2-10, which included an anti-Axl ASTR (SEQ ID NO:161), CAB-CAR F1-2-13, which included an anti-Axl ASTR (SEQ ID NO:129), CAB-CAR F1-2-15, which included an anti-Axl ASTR (SEQ ID NO:128), CAB-CAR F1-1-9, which included an anti-Ror2 ASTR (SEQ ID NO:157), CAB-CAR F-1-11, which included an anti-Ror2 ASTR (SEQ ID NO:153), CAB-CAR F-1-15, which included an anti-Ror2 ASTR (SEQ ID NO:132), CAB-CAR F-1-17, which included an anti-Ror2 ASTR (SEQ ID NO:154), CAB-CAR F-1-19, which included an anti-Ror2 ASTR (SEQ ID NO:130), CAB-CAR F1-1-21, which included an anti-Ror2 ASTR (SEQ ID NO:158), CAB-CAR F1-1-23, which included an anti-Ror2 ASTR (SEQ ID NO:131), CAB-CAR F-1-25, which included an anti-Ror2 ASTR (SEQ ID NO:155), and CAB-CAR F-1-26, which included an anti-Ror2 ASTR (SEQ ID NO:156). The ASTRs all included at least one module of either the VH or VL that was identified under physiologic conditions and was further evolved.

Figure 2A:
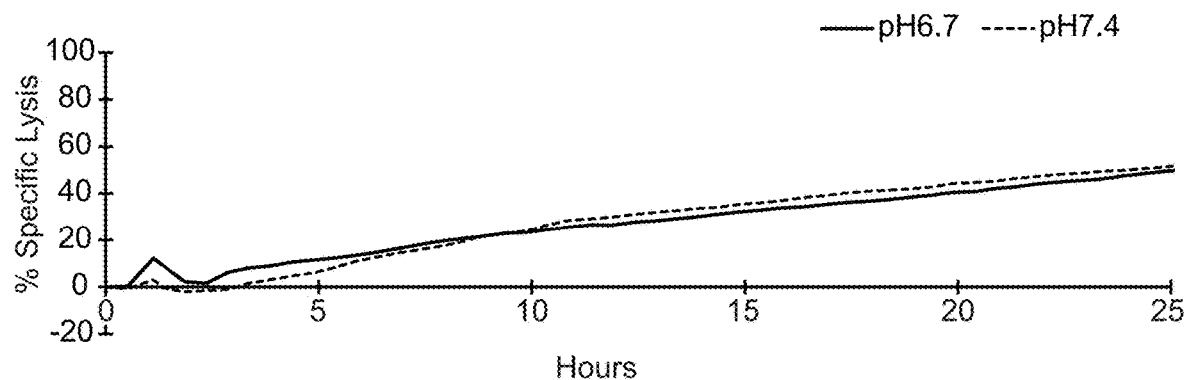
FIGS. 2A-2F show the results from real-time killing assays of CHO-Axl cells at pH 6.7 and pH 7.4 by T cells expressing a control CAR with a wild-type ASTR that recognizes Axl (FIG. 2A) and T cells expressing candidate CAB-CARs that recognize Axl, which have conditionally active ASTRs that recognize Axl (FIGS. 2B-2F). The effector to target ratio was 3:1 in FIGS. 2A and 2B, and 1:1 in FIGS. 2C-2F.
Figure 2B:
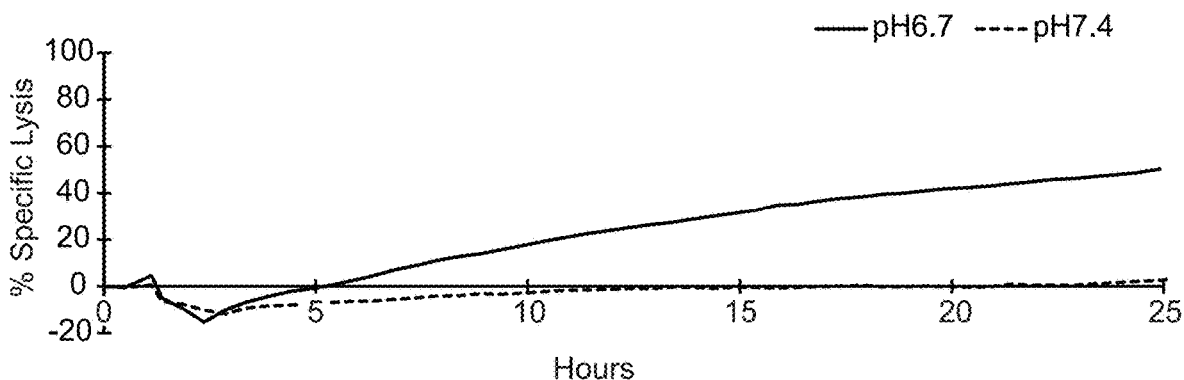
Figure 2C:
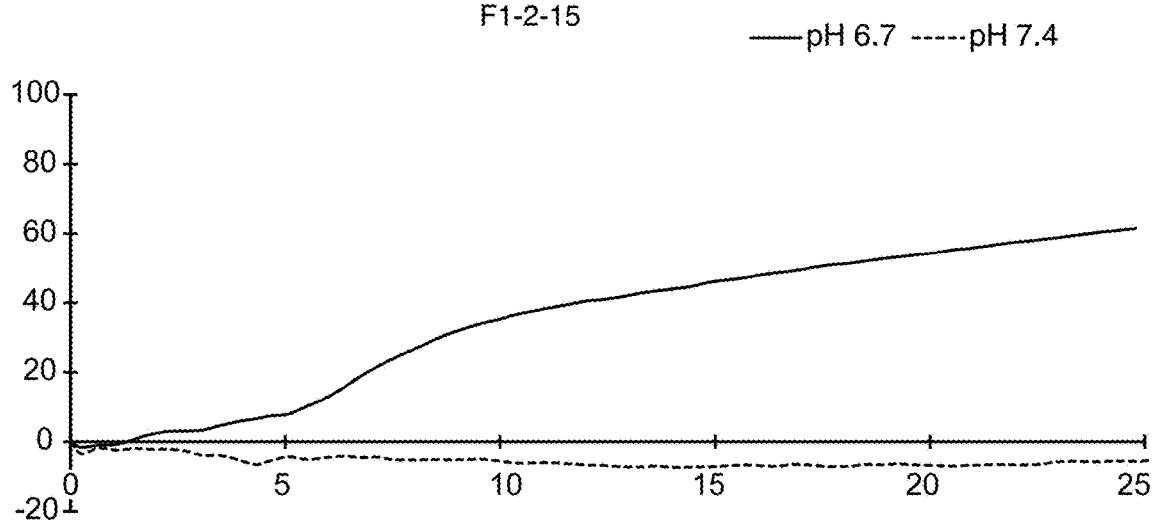
Figure 2D:
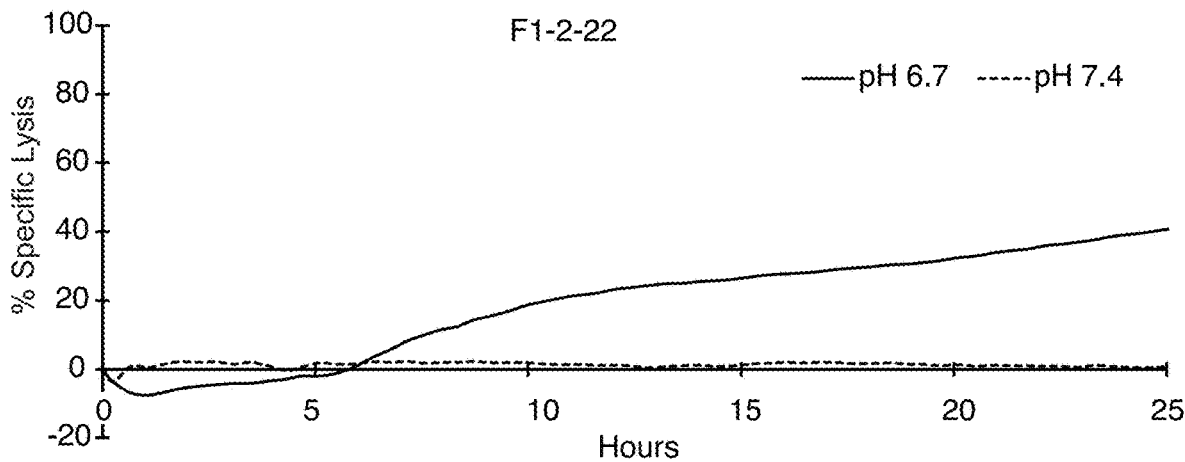
Figure 2E:
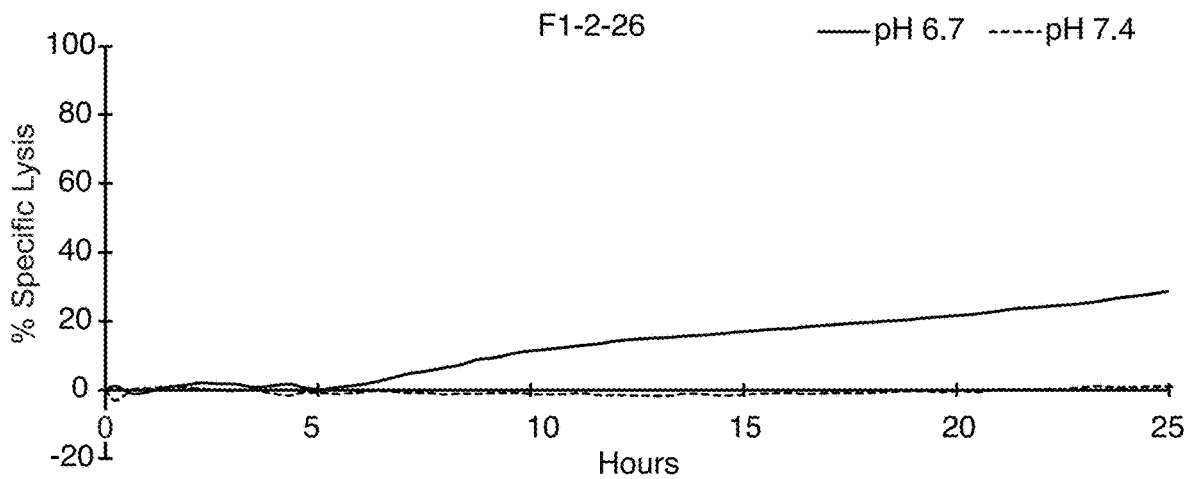
Figure 2F:
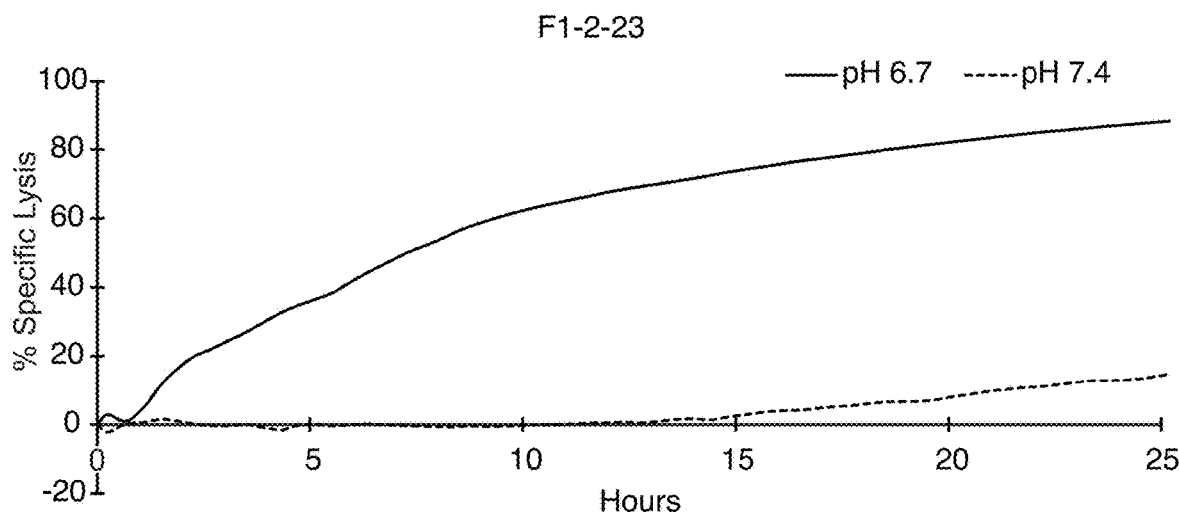
Figure 3A:
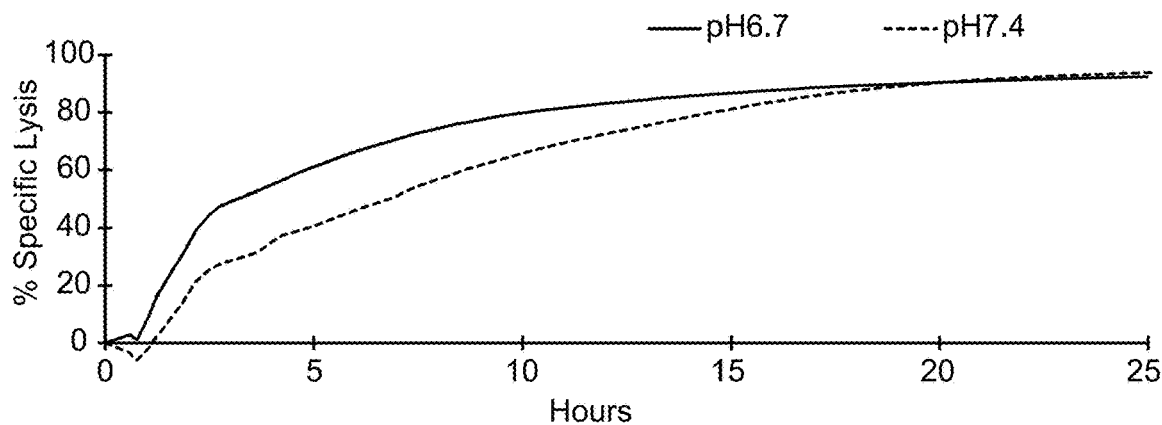
FIGS. 3A-3J show the results from real-time killing assays of CHO-Ror2 cells at pH 6.7 and pH 7.4 by T cells expressing a control CAR with a wild-type ASTR that recognizes Ror2 (FIG. 3A) and T cells expressing candidate CAB-CARs that recognize Ror2, which have conditionally active ASTRs that recognize Ror2 (FIGS. 3B-J). The effector to target ratio was 1:1.
Figure 3B:
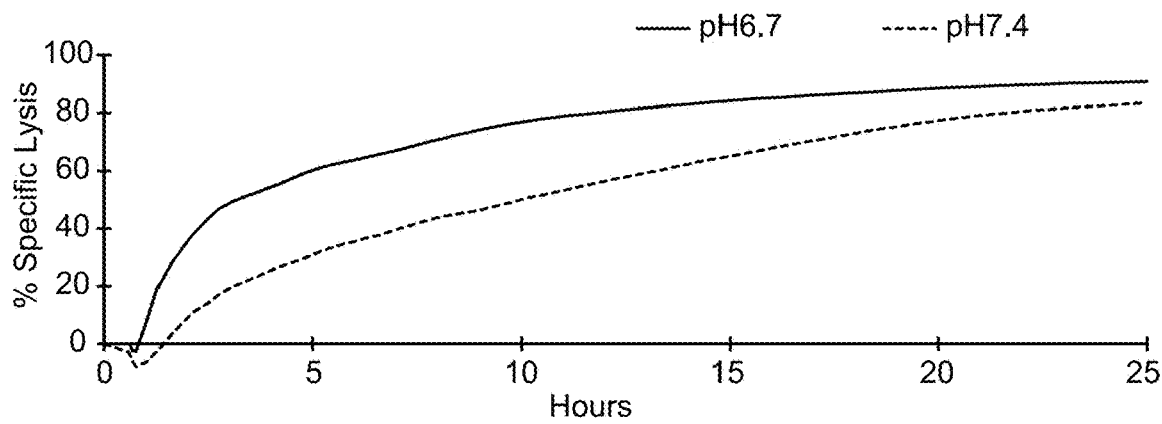
Figure 3C:
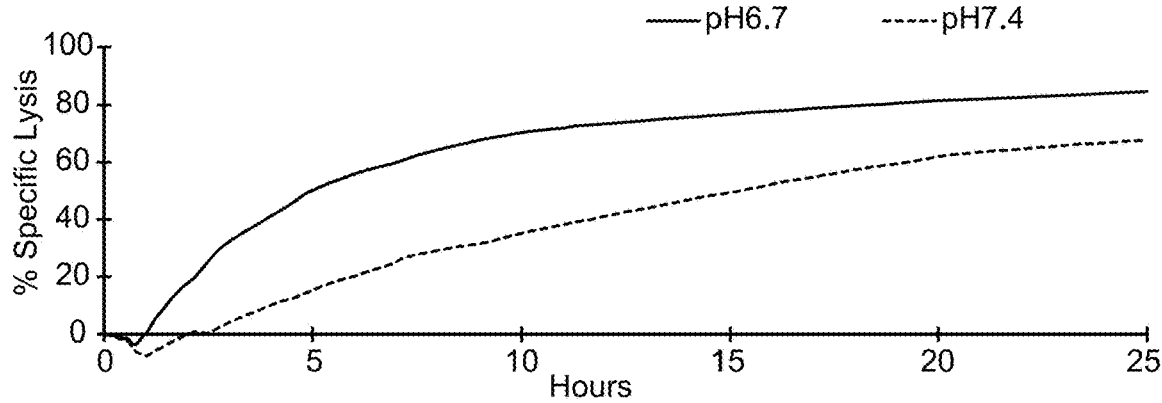
Figure 3D:
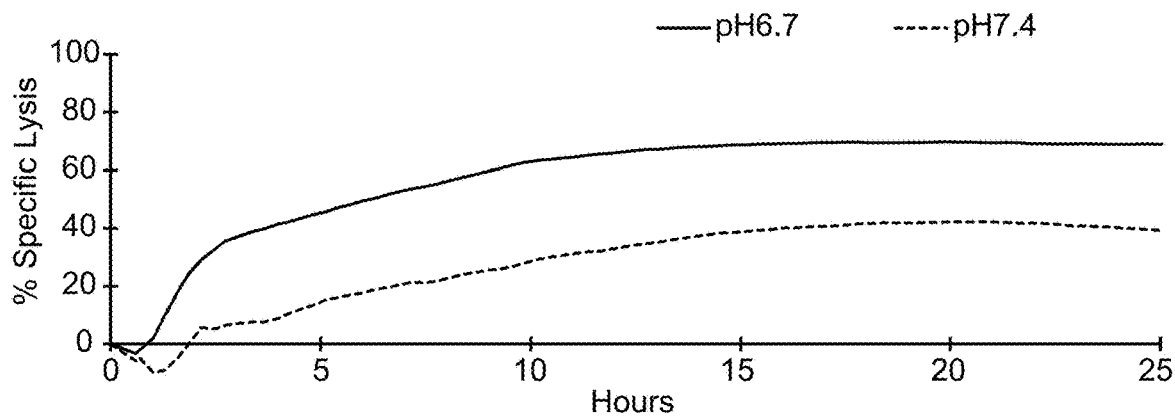
Figure 3E:
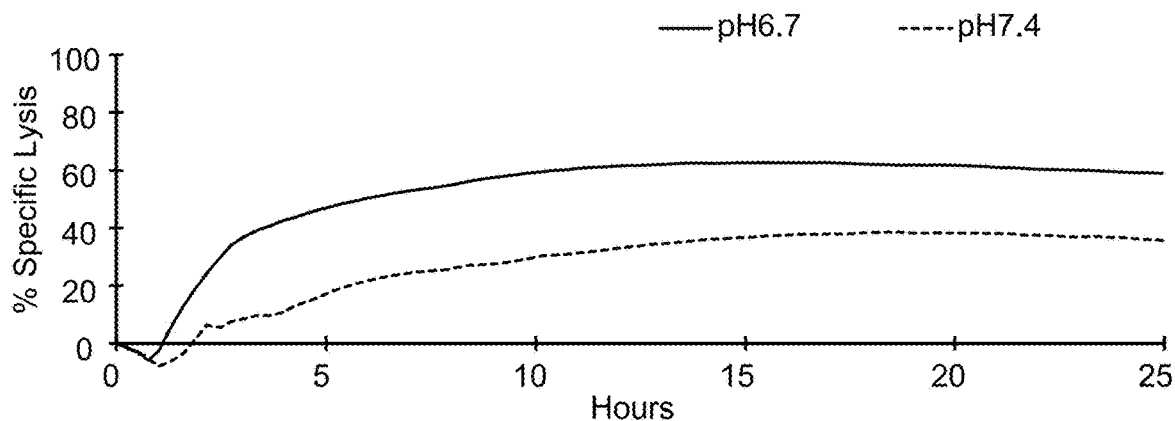
Figure 3F:
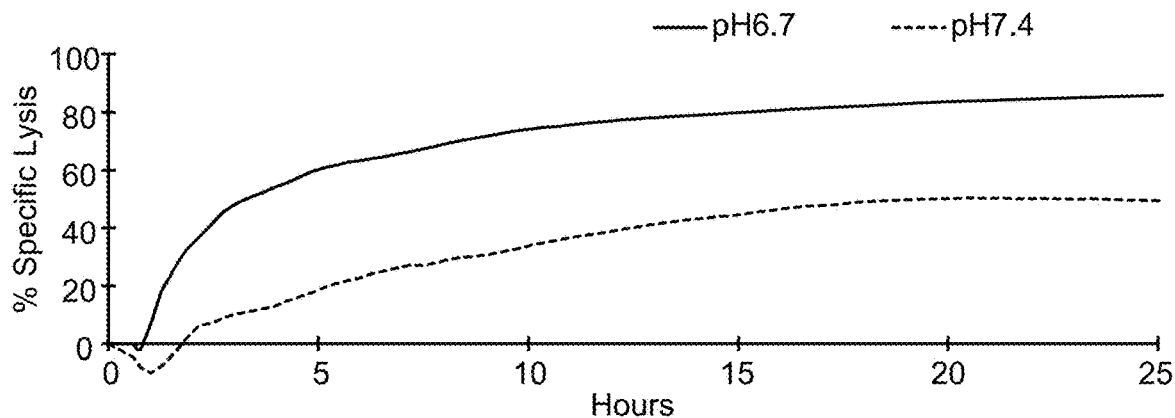
Figure 3G:
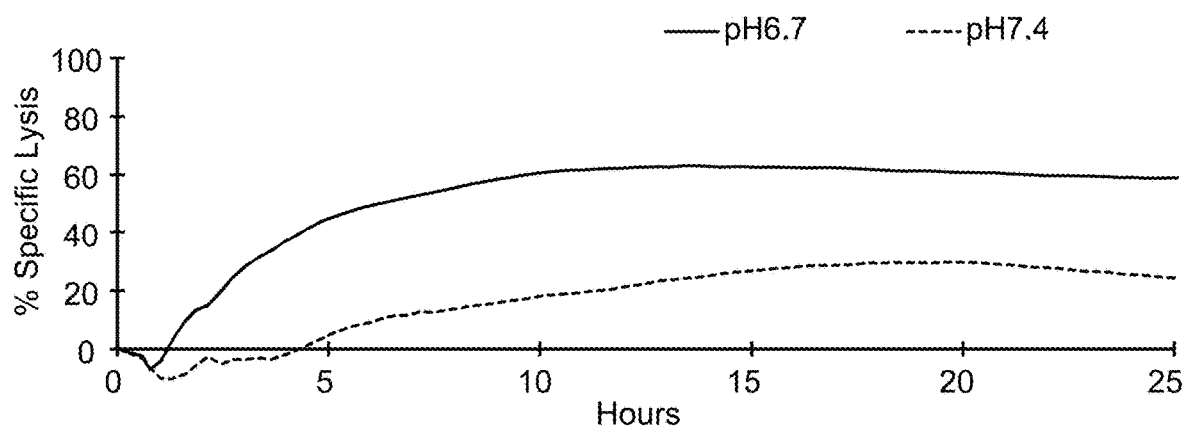
Figure 3H:
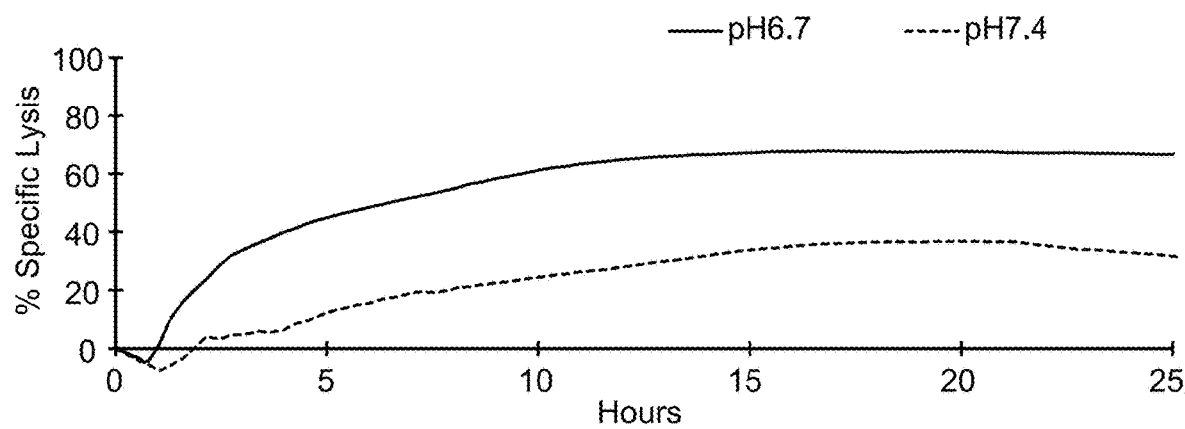
Figure 3I:
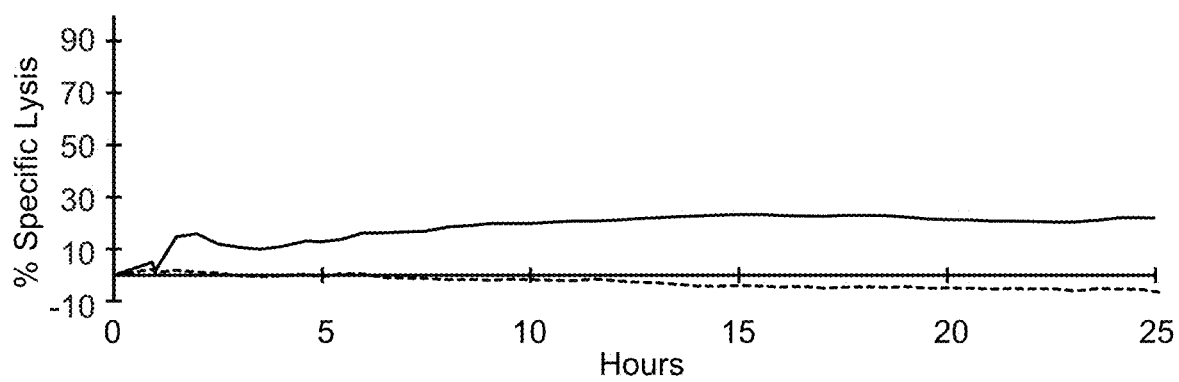
Figure 3J:
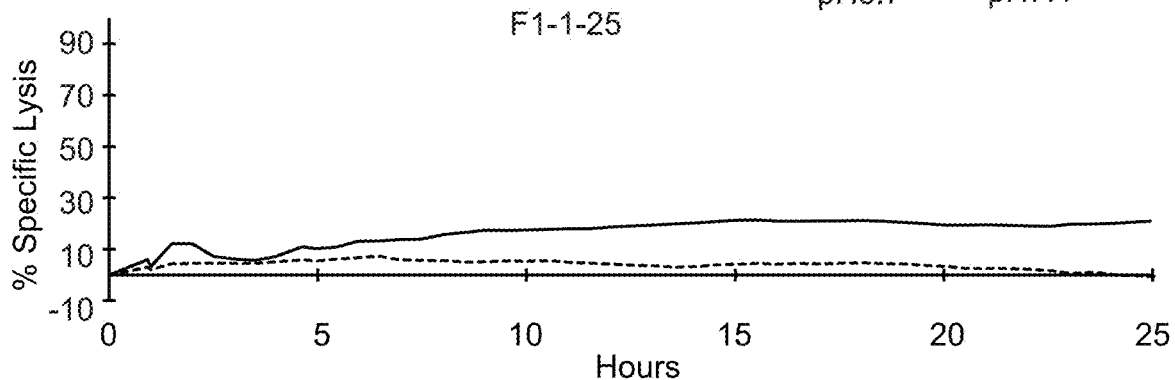

FIGS. 2B-2F show representative in vitro killing of CHO-Axl tumors over time for some of the more conditionally active CAB-CARs against Axl versus a control CAR having a wild-type ASTR that is not conditionally active (FIG. 2A). A 3:1 ratio of effector to target cells was used in FIGS. 2A and 2B. A 1:1 ratio of effector to target was used in FIGS. 2C-2F. Similarly, FIGS. 3B-3J show representative in vitro killing of CHO-Ror2 tumors over time at a 3:1 ratio of effector to target cells for some of the more conditionally active CAB-CARs against Ror2 versus a control CAR having a wild-type ASTR that is not conditionally active (FIG. 3A).

Figure 4B:
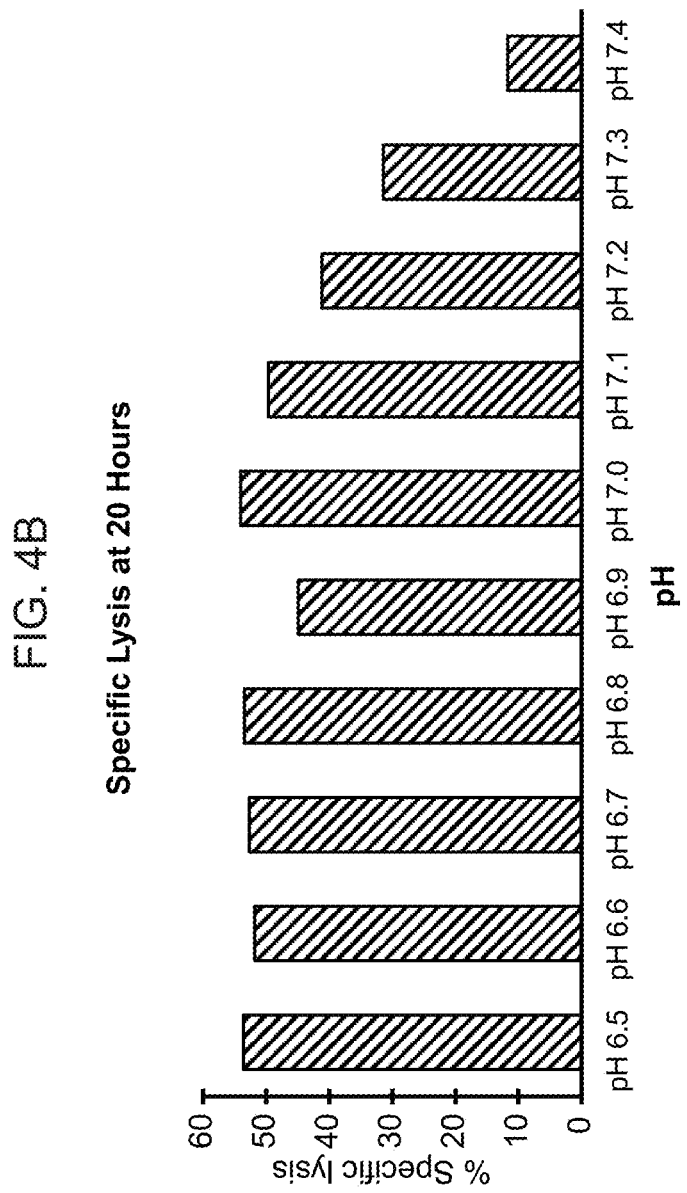
FIG. 4B provides lysis results at the 20 hour time point at various pHs as noted, for the same CAB-CAR as FIG. 4A.

The conditional activity of some of the candidate CARs was analyzed at a range of pHs from 7.4 to 6.7 in pH increments of 0.1 pH (pH titration) over time. As shown in the representative curves for CAB-CAR F1-2-13 (AXL) in FIG. 4A and CAB-CAR F1-1-15 (Ror2) in FIG. 5A, all of the candidate CARs tested (5 CAB-CARs directed to each of Axl and Ror2) that included the conditionally active ASTRs (CAB-CARs) demonstrated pH-dependent killing of CHO cells expressing their cognate antigen, that was low at physiologic pH and increased as the culture became more acidic. FIG. 4B shows that the pH dependent killing by CAB-CAR F1-2-13 increased from pH 7.4 to pH 7.0 and was consistently high from pH 7.0 to pH 6.5. FIG. 5B shows that the pH dependent killing by CAB-CAR F1-1-15 increased gradually from pH 7.4 to pH 6.6.

Figure 6A:
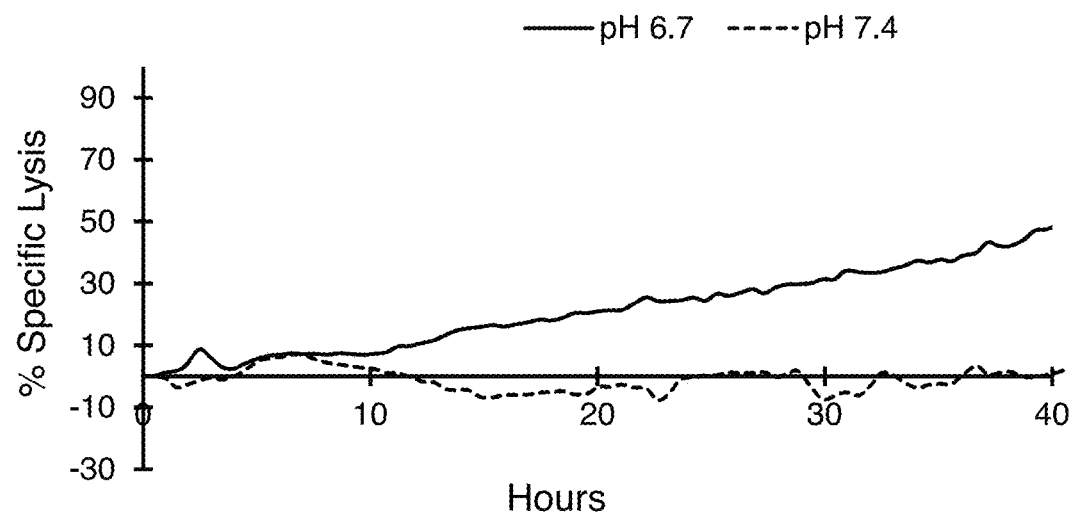
FIG. 6A shows the results from real-time killing assays of human Caki-1 cells at pH 6.7 and pH 7.4 by T cells expressing one of the conditionally active CAB-CARs against Axl.
Figure 6B:
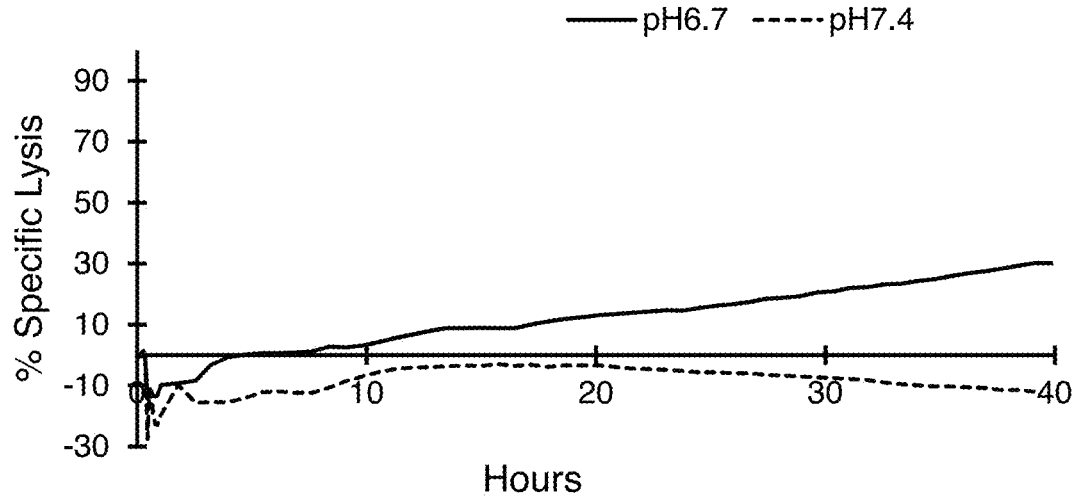
FIG. 6B shows the results from real-time killing assays of human HEK293 cells at pH 6.7 and pH 7.4 by T cells expressing one of the conditionally active CAB-CARs against Ror2.

The conditional killing of candidate CAB-CARs was also tested on human kidney cells that express endogenous levels of Axl and Ror2 in the absence of transgene expression of these proteins. FIG. 6A shows conditional killing of Axl-expressing Caki-1 cells by T cells expressing F1-2-15. FIG. 6B shows conditional killing of Ror2-expressing HEK293 cells by T cells expressing F1-1-15.

Thus, the methods provided herein were effective at making and identifying conditionally active CARs against Axl and Ror2 that demonstrated conditional killing activity when expressed on T cells in vitro.

TABLE 1

Real-time cell analysis results for T cells expressing various anti-Axl CARs.

| ID | P1 | P2 | P3 | P4 | P5 | P6 | P7 | P8 | P9 | CAB activity |
|---|---|---|---|---|---|---|---|---|---|---|
| F1-2-1 | CD8 sp | Axl CAB VH | Linker 1 | Axl CAB VL | CD8 | CD137 | CD3Z | 2A-1 | eTAG | Medium |
| F1-2-2 | CD8 sp | Axl CAB VH | Linker 1 | Axl CAB VL | CD28 | CD137 | CD3Z | 2A-1 | eTAG | Medium |
| F1-2-3 | CD8 sp | Axl CAB VH | Linker 2 | Axl CAB VL | CD8 | CD137 | CD3Z | 2A-1 | eTAG | Medium |
| F1-2-4 | CD8 sp | Axl CAB VH | Linker 2 | Axl CAB VL | CD28 | CD137 | CD3Z | 2A-1 | eTAG | None |
| F1-2-5 | CD8 sp | Axl CAB VH | Linker 3 | Axl CAB VL | CD8 | CD137 | CD3Z | 2A-1 | eTAG | None |
| F1-2-6 | CD8 sp | Axl CAB VH | Linker 3 | Axl CAB VL | CD28 | CD137 | CD3Z | 2A-1 | eTAG | Medium |
| F1-2-7 | CD8 sp | Axl CAB VL | Linker 1 | Axl CAB VH | CD8 | CD137 | CD3Z | 2A-1 | eTAG | None |
| F1-2-8 | CD8 sp | Axl CAB VL | Linker 1 | Axl CAB VH | CD28 | CD137 | CD3Z | 2A-1 | eTAG | Medium |
| F1-2-9 | CD8 sp | Axl CAB VL | Linker 2 | Axl CAB VH | CD8 | CD137 | CD3Z | 2A-1 | eTAG | None |
| F1-2-10 | CD8 sp | Axl CAB VL | Linker 2 | Axl CAB VH | CD28 | CD137 | CD3Z | 2A-1 | eTAG | Medium |
| F1-2-11 | CD8 sp | Axl CAB VL | Linker 3 | Axl CAB VH | CD8 | CD137 | CD3Z | 2A-1 | eTAG | None |
| F1-2-12 | CD8 sp | Axl CAB VL | Linker 3 | Axl CAB VH | CD28 | CD137 | CD3Z | 2A-1 | eTAG | None |
| F1-2-13 | CD8 sp | Axl CAB VH | Linker 1 | Axl CAB VL | CD28 | ICΔ | CD3Z | 2A-1 | eTAG | High |
| F1-2-14 | CD8 sp | Axl CAB VH | Linker 2 | Axl CAB VL | CD28 | ICΔ | CD3Z | 2A-1 | eTAG | Medium |
| F1-2-15 | CD8 sp | Axl CAB VH | Linker 3 | Axl CAB VL | CD28 | ICΔ | CD3Z | 2A-1 | eTAG | High |
| F1-2-16 | CD8 sp | Axl CAB VL | Linker 1 | Axl CAB VH | CD28 | ICΔ | CD3Z | 2A-1 | eTAG | None |
| F1-2-17 | CD8 sp | Axl CAB VL | Linker 2 | Axl CAB VH | CD28 | ICΔ | CD3Z | 2A-1 | eTAG | None |
| F1-2-18 | CD8 sp | Axl CAB VL | Linker 3 | Axl CAB VH | CD28 | ICΔ | CD3Z | 2A-1 | eTAG | None |
| F1-2-19 | CD8 sp | Axl VH | Linker 3 | Axl VL | CD8 | CD137 | CD3Z | 2A-1 | eTAG | None |
| F1-2-20 | CD8 sp | Axl VH | Linker 3 | Axl VL | CD28 | CD137 | CD3Z | 2A-1 | eTAG | None |
| F1-2-21 | CD8 sp | Axl VH | Linker 3 | Axl VL | CD28 | ICΔ | CD3Z | 2A-1 | eTAG | None |
| F1-2-22 | CD8 sp | Axl CAB VH | Linker 3 | Axl CAB VL | CD28 | ICΔCD137 | CD3Z | 2A-1 | eTAG | High |
| F1-2-23 | CD8 sp | Axl CAB VH | Linker 3 | Axl CAB VL | CD28 | CD28 | CD3Z | 2A-1 | eTAG | High |

TABLE 2

Real-time cell analysis results for T cells expressing various anti Ror2 CARs.

| ID | P1 | P2 | P3 | P4 | P5 | P6 | P7 | P8 | P9 | CAB activity |
|---|---|---|---|---|---|---|---|---|---|---|
| F1-1-1 | CD8 sp | Ror2 VH | Linker 1 | Ror2 VL | CD8 | CD137 | CD3Z | 2A-1 | eTAG | none |
| F1-1-2 | CD8 sp | Ror2 VH | Linker 1 | Ror2 VL | CD28 | CD137 | CD3Z | 2A-1 | eTAG | none |
| F1-1-3 | CD8 sp | Ror2 VH | Linker 2 | Ror2 VL | CD8 | CD137 | CD3Z | 2A-1 | eTAG | none |
| F1-1-4 | CD8 sp | Ror2 VH | Linker 2 | Ror2 VL | CD28 | CD137 | CD3Z | 2A-1 | eTAG | none |
| F1-1-5 | CD8 sp | Ror2 VL | Linker 1 | Ror2 VH | CD8 | CD137 | CD3Z | 2A-1 | eTAG | none |
| F1-1-6 | CD8 sp | Ror2 VL | Linker 1 | Ror2 VH | CD28 | CD137 | CD3Z | 2A-1 | eTAG | none |
| F1-1-7 | CD8 sp | Ror2 VL | Linker 2 | Ror2 VH | CD8 | CD137 | CD3Z | 2A-1 | eTAG | none |
| F1-1-8 | CD8 sp | Ror2 VL | Linker 2 | Ror2 VH | CD28 | CD137 | CD3Z | 2A-1 | eTAG | none |
| F1-1-9 | CD8 sp | Ror2 CAB1 VH | Linker 1 | Ror2 VL | CD8 | CD137 | CD3Z | 2A-1 | eTAG | Medium |
| F1-1-10 | CD8 sp | Ror2 CAB1 VH | Linker 1 | Ror2 VL | CD28 | CD137 | CD3Z | 2A-1 | eTAG | Medium |
| F1-1-11 | CD8 sp | Ror2 CAB1 VH | Linker 2 | Ror2 VL | CD8 | CD137 | CD3Z | 2A-1 | eTAG | High |
| F1-1-12 | CD8 sp | Ror2 CAB1 VH | Linker 2 | Ror2 VL | CD28 | CD137 | CD3Z | 2A-1 | eTAG | High |
| F1-1-13 | CD8 sp | Ror2 VL | Linker 1 | Ror2 CAB1 VH | CD8 | CD137 | CD3Z | 2A-1 | eTAG | none |
| F1-1-14 | CD8 sp | Ror2 VL | Linker 1 | Ror2 CAB1 VH | CD28 | CD137 | CD3Z | 2A-1 | eTAG | none |
| F1-1-15 | CD8 sp | Ror2 VL | Linker 2 | Ror2 CAB1 VH | CD8 | CD137 | CD3Z | 2A-1 | eTAG | high |
| F1-1-16 | CD8 sp | Ror2 VL | Linker 2 | Ror2 CAB1 VH | CD28 | CD137 | CD3Z | 2A-1 | eTAG | none |
| F1-1-17 | CD8 sp | Ror2 CAB2 VH | Linker 1 | Ror2 VL | CD8 | CD137 | CD3Z | 2A-1 | eTAG | High |

TABLE 2-continued

Real-time cell analysis results for T cells expressing various anti Ror2 CARs.

| | | | Modules | | | | | | | CAB |
|---|---|---|---|---|---|---|---|---|---|---|
| ID | P1 | P2 | P3 | P4 | P5 | P6 | P7 | P8 | P9 | activity |
| F1-1-18 | CD8 sp | Ror2 CAB2 VH | Linker 1 | Ror2 VL | CD28 | CD137 | CD3Z | 2A-1 | eTAG | Medium |
| F1-1-19 | CD8 sp | Ror2 CAB2 VH | Linker 2 | Ror2 VL | CD8 | CD137 | CD3Z | 2A-1 | eTAG | High |
| F1-1-20 | CD8 sp | Ror2 CAB2 VH | Linker 2 | Ror2 VL | CD28 | CD137 | CD3Z | 2A-1 | eTAG | High |
| F1-1-21 | CD8 sp | Ror2 VL | Linker 1 | Ror2 CAB2 VH | CD8 | CD137 | CD3Z | 2A-1 | eTAG | Medium |
| F1-1-22 | CD8 sp | Ror2 VL | Linker 1 | Ror2 CAB2 VH | CD28 | CD137 | CD3Z | 2A-1 | eTAG | none |
| F1-1-23 | CD8 sp | Ror2 VL | Linker 2 | Ror2 CAB2 VH | CD8 | CD137 | CD3Z | 2A-1 | eTAG | High |
| F1-1-24 | CD8 sp | Ror2 VL | Linker 2 | Ror2 CAB2 VH | CD28 | CD137 | CD3Z | 2A-1 | eTAG | none |
| F1-1-25 | CD8 sp | Ror2 CAB VL | Linker 1 | Ror2 CAB3 VH | CD28 | CD137 | CD3Z | 2A-1 | eTAG | Medium |
| F1-1-26 | CD8 sp | Ror2 CAB VL | Linker 2 | Ror2 CAB3 VH | CD28 | CD137 | CD3Z | 2A-1 | eTAG | Medium |

Example 2: Elimination of eTAG Expressing Target Cells

Effect of Cetuximab Concentration on Elimination

PBMCs were isolated from ACD-peripheral blood from a healthy donor by Ficoll-Paque Premium (GE Healthcare, 45-001-751). To prepare target cells, PBMCs were transduced with lentivirus, which contain coding regions for GFP and eTag operably linked to a promoter, to express GFP fluorescent protein and an eTag target. PBMCs activated and expanded at the same time without transduction were used as nontarget control cells. Expanded target cells and nontarget control cells were stored in freezing medium in liquid nitrogen until use. Freshly isolated PBMCs from the same donor were pre-stimulated overnight with 10 ng/mL huGM-CSF (R&D Systems, 215-GM-010) and used as effector cells. Target cells and nontarget cells were allowed to recover for one day from cryopreservation and then nontarget control cells were labeled with CT-Violet before use. Target cell and nontarget control cells were mixed at a 1:1 ratio and then were co-incubated with effector PBMCs at 50:1 effector cell:target cell ratio in a U-bottom 96 well plate, with different concentrations of cetuximab or isotype control antibody. After incubation for 22 hours, samples were centrifuged at 400 g for 5 minutes. Pelleted cells were resuspended in FACS wash buffer (PBS+2% FBS+0.1% sodium azide) and fixed with an equal volume of BD Cytofix (BD #554655) prior to flow cytometry. Control samples containing only the target cells were used to set FACS gating. The numbers of target cells and nontarget control cells were quantified. A ratio of the surviving target cells (GFP+) to non-target control cells (CT-Violet) was calculated and normalized to samples without Ab. Percentage of depletion was calculated as follows: 1-((Target/NonTarget)/(Target without Ab/Non-target without Ab)).

Effect of Ratios of Effector Cells:Target Cells on Cetuximab Elimination

The experiment was performed as described above except the PBMCs used were previously frozen and the target cells and nontarget control cells were mixed at a 1:1 ratio and then co-incubated with effector PBMCs at 50:1, 25:1, 5:1, and 1:1 effector cell:target cell ratios in a U-bottom 96 well plate, with 1 µg/mL of cetuximab or isotype control.

Results

Figure 7A:
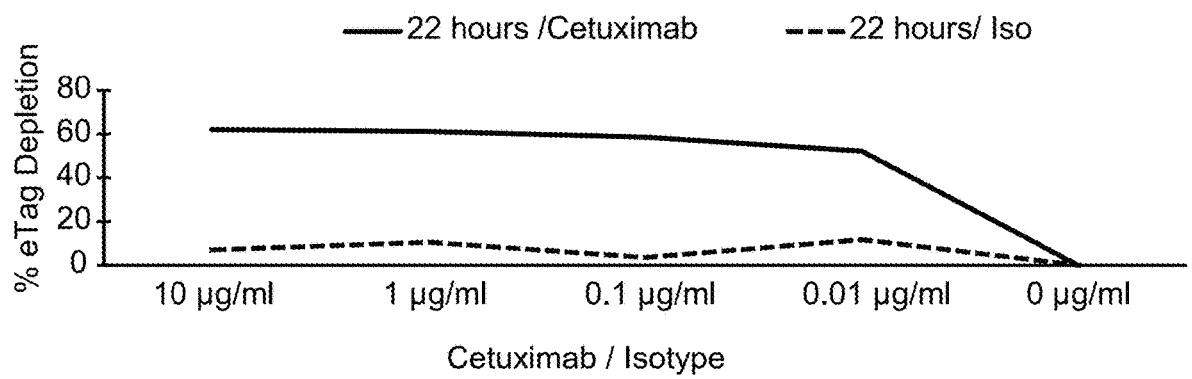
FIG. 7A shows cell depletion results for PBMCs transduced with a lentivirus expression vector expressing eTag after treatment with Cetuximab at various concentrations, or a control (isotype).
Figure 7B:
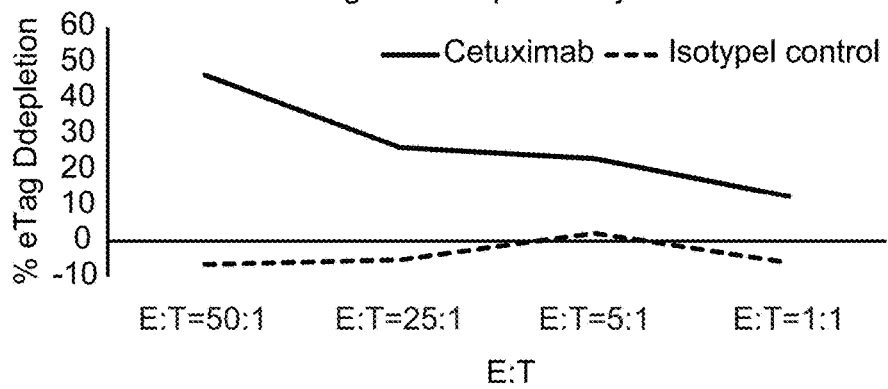
FIG. 7B provides cell depletion results for PBMCs transduced with a lentivirus expression vector expressing eTag after treatment with Cetuximab or a control (isotype) at various ratios of transduced (E) to non-transduced (T) cells.

The effectiveness of expression of an eTag as an elimination domain was tested in peripheral blood mononuclear cells (PBMCs). PBMCs were isolated and transduced with a lentiviral vector that included an eTag operably linked to a promoter. Control cells were not transduced. Cells were treated with Cetuximab at concentrations from 0-10 ug/ml and cell depletion was detected at 22 hours after Cetuximab administration at all concentrations tested (FIG. 7A). Using a 1 ug/ml Cetuximab concentration, depletion was observed at all ratios of transduced effector (E) vs control (T) cells with generally increasing depletion with increasing ratio of transduced effector (E) cells (FIG. 7B). Thus, T cells expressing an eTag can be effectively eliminated by antibody to the eTag in the presence of PBMCs. It is noteworthy that follow-up experiments were performed with a FLAG epitope in which the FLAG epitope was expressed as part of the CAB-CAR polypeptide positioned between a CD8 signal peptide and a conditionally active ASTR of CAB-CARs F1-1-15 and F1-2-15. Although slightly diminished in some cases with these initial non-optimized constructs, these CAB-CARs retained their ability to kill target cells expressing their cognate antigen and to elicit cytokine responses. Thus, an elimination domain can be expressed as part of a CAB-CAR without destroying its activity.

Example 3. Conditionally Active Chimeric Antigen Receptor Induction of Cytokines This example demonstrates pH-dependent cytokine induction by conditionally active chimeric antigen receptors targeting Axl or Ror2. The cytokine levels of IL-2 and IFN-γ in the media were measured after a pH 6.7 or pH 7.4 co-incubation of control CHO cells or CHO cells expressing Axl (CHO-AXL) or Ror2 cells (CHO-ROR2) with T cells expressing a CAB-CAR with an anti-Axl ASTR (F1-2-15) or T cells expressing a CAB-CAR with an anti-Ror2 ASTR (F1-1-15), respectively. The cytokine levels from these co-incubations were compared with cytokine levels in negative and positive controls.

Cryopreserved effector cells were produced in advance by transducing Pan T cells (AllCells) with lentiviral particles encoding the CAB-CARs F1-1-15 (Ror2), F1-2-15 (Axl), or eTag alone (F1-0-01), and expanded as described in Example 1. On Day 1, effector cells were thawed and allowed to recover from cryopreservation for 2 days by culture at 37° C. and 5% CO2 in human T cell medium consisting of X-VIVO15 (Lonza #04-418Q), 5% human AB serum (Valley Biomedical Inc., #HP1022), 10 mM N-acetyl L-Cysteine (Sigma-Aldrich #A9165), and supplemented with 100 IU/ml IL2. On Day 2, $3.0 \times 10^4$ CHO, CHO-Ror2, or CHO-Axl target cells were seeded in the wells of a 96 well flat bottom tissue culture plate in 100 µl human T cell medium containing 40 mM HEPES/PIPES and adjusted to pH 6.7 or pH 7.4 and cultured overnight at 37° C. and 5% $CO_2$. On Day 3, rested effector cells were added to experimental wells at an effector cell/target cell ratio of 3:1 in 140

μl of human T cell medium at the appropriate pH. Effector and target cells were co-incubated overnight at 37° C. and 5% CO2 and the supernatant was collected the next day and assayed for cytokine levels by ELISA. Each experimental condition was run in triplicate.

Results

Figure 8A:
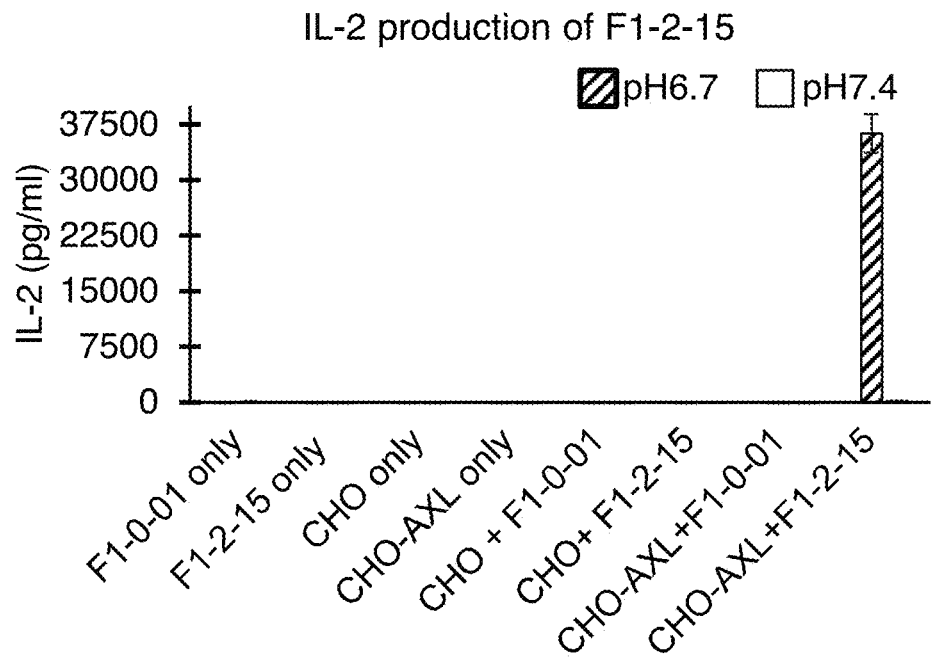
FIGS. 8A-8D show bar graphs of the cytokine levels in media with or without co-incubation of different cells at pH 6.7 or pH 7.4. The various cells used were T cells expressing the GMCSF signal sequence and eTag (F1-0-01), T cells expressing an Axl CAB-CAR (F1-2-15), T cells expressing a Ror2 CAB-CAR (F1-1-15), CHO cells, CHO cells expressing Axl (CHO-AXL), and CHO cells expressing Ror2 (CHO-ROR2).
Figure 8B:
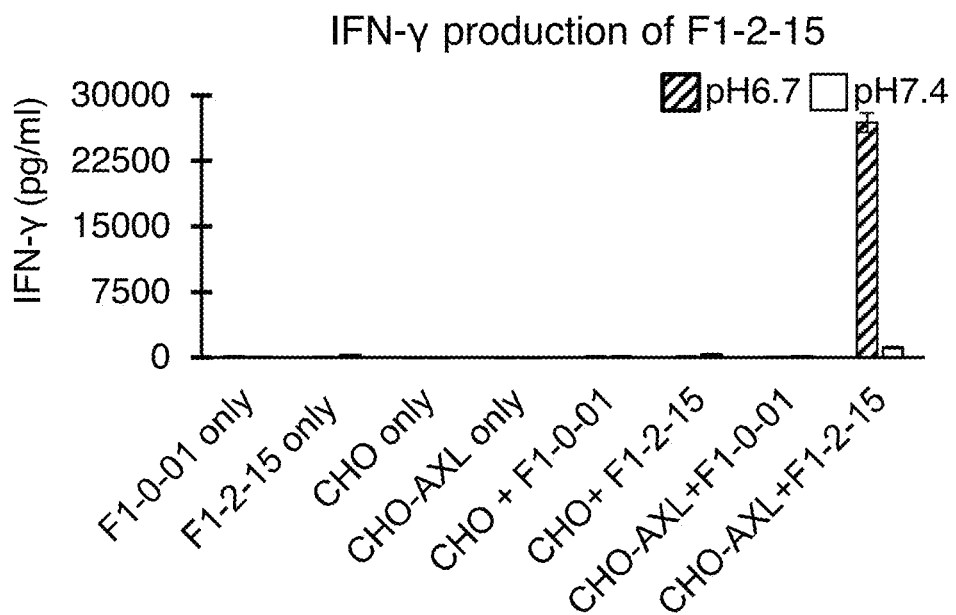
Figure 8C:
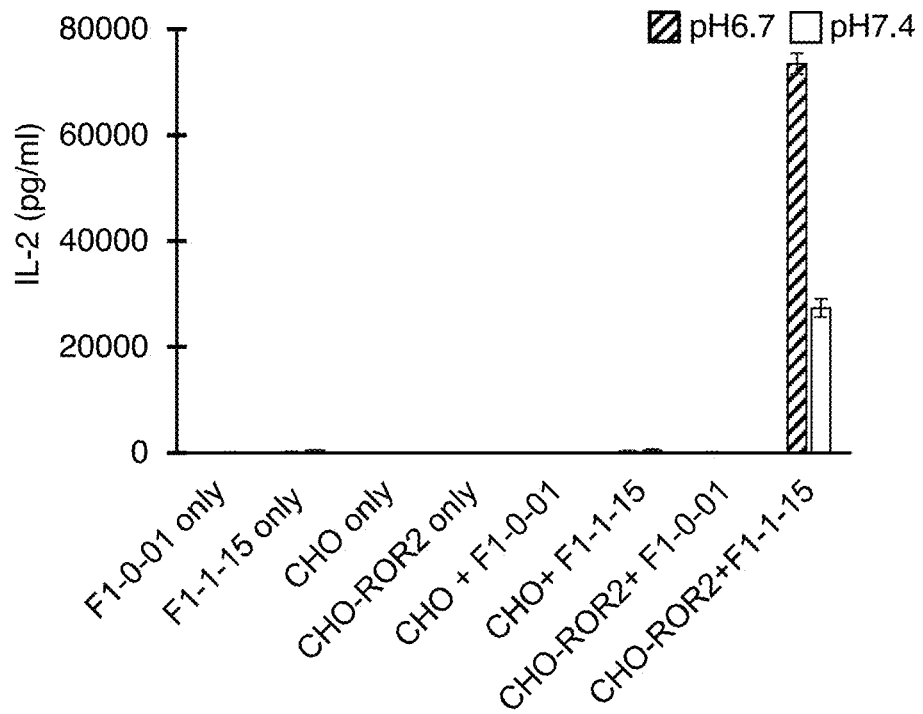
Figure 8D:
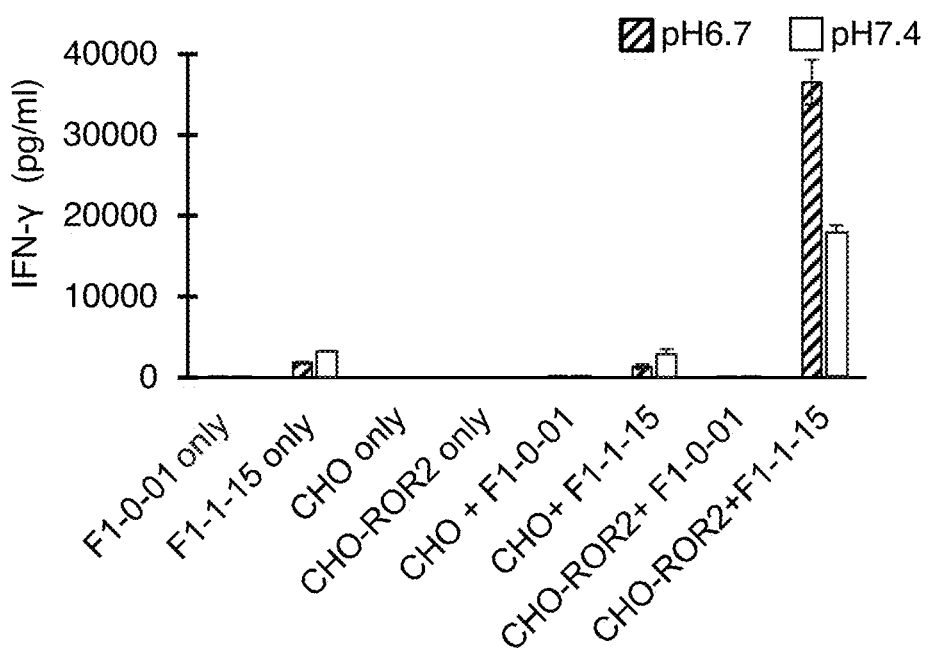

As shown in FIGS. 8A-8D, T cells transduced with a lentiviral particle containing a nucleic acid encoding the anti-Axl CAB-CAR F-2-15 or the anti-Ror2 CAB-CAR F-1-15 were activated to secrete cytokines in response to recognizing CHO cells expressing Axl or Ror2 respectively, in a pH dependent manner. As shown in FIG. 8A, T cells transduced with a lentiviral particle containing a nucleic acid encoding the anti-Axl CAB-CAR F1-2-15 secreted IL-2 when cultured at a pH of 6.7 but not at a pH of 7.4, and only in the presence of CHO cells expressing Axl. Similarly, as shown in FIG. 8B, T cells transduced with a lentiviral particle containing a nucleic acid encoding the anti-Axl CAB-CAR F1-2-15 secreted IFN-γ when cultured at a pH of 6.7 but not at a pH of 7.4, and only in the presence of CHO cells expressing Axl. As shown in FIG. 8C, T cells expressing the anti-Ror2 CAB-CAR F-1-15 secreted approximately 2.5-fold as much IL-2 when cultured at pH 6.7 as compared to pH 7.4, and only secreted appreciable amounts of IL-2 in the presence of CHO cells expressing Ror2. Similarly, as shown in FIG. 8D, T cells expressing the anti-Ror2 CAB-CAR F-1-15 secreted approximately 2-fold as much IFN-γ when cultured at pH 6.7 as compared to pH 7.4, and only in the presence of CHO cells expressing Ror2. Samples that included effector T cells that expressed a control EGFR polypeptide instead of the anti-Axl or anti-Ror2 CAB-CARs did not increase secretion of IL2 or IFN-γ in response to co-culture with any of the CHO cells at either pH. Thus, exemplary conditionally active CARs against Axl and Ror2 identified herein when expressed on T cells in vitro, elicited conditional cytokine secretion from these T cells when exposed to the CARs cognate antigen. Furthermore, these experiments provide non-limiting exemplary in vitro methods for activating T cells that express CAB-CARs provided herein.

Example 4. Cytotoxic Activity of Conditionally Active Biologic CAR-Expressing T Cells can be Controlled by Changing pH The following example illustrates how the cytotoxic activity of transduced T cells (also referred to as effector cells) expressing CAB-CARs can be modulated by changes in the pH of the microenvironment. In this example, nucleic acids encoding a CAB-CAR capable of binding the cognate antigen Axl (anti-Axl) were used to generate replication incompetent recombinant lentiviral particles. Pan T cells were transduced with the lentiviral particles and the cytotoxic activity of the effector cells were compared using Real-Time Cell Analysis (RTCA) before and after changing the pH of the media.

Production of CAB-CAR Effector T Cells

Lentiviral particles encoding a CAB-CAR directed to Axl (F1-2-15) and a negative control (C1) containing an eTag (SEQ ID NO:78) but lacking a CAR (F1-0-01) were produced as described in Example 1. These lentiviral particles were used to transduce Pan T cells (AllCells) and the transduced T cells were allowed to expand for 10 to 12 days as described in Example 1. These transduced T cells were cryopreserved for later use as effector cells.

pH Shift Cytotoxicity Assay

The cytotoxic activity of transduced T cells before and after pH change by addition of $NaHCO_3$ or NaOH was measured using the xCELLigence System. Briefly, one day before the experiment, target cells (CHO cells stably transfected with a construct to express Axl on the cell surface (CHO-Axl cells)), were seeded into a 96-well E-plate (ACEA; San Diego, CA) at 10,000 cells/well with X-VIVO 15 media containing 40 mM HEPES and 40 mM PIPES, pH 6.7. Cryopreserved effector cells previously transduced with either lentiviral particles containing the nucleic acid encoding F1-2-15 or C1 (F1-2-15-VP and C1VP, respectively) produced as discussed above, were thawed and cultured for two days in X-VIVO 15 media containing 100 IU/mL of IL-2 (R&D Systems, Minneapolis, MN). On the day of the experiment, cells transduced with F1-2-15-VP or C1VP were washed and resuspended in X-VIVO 15 media containing 40 mM HEPES and 40 mM PIPES, pH 6.7 and then added into the experimental wells at effector cell/target cell ratios (E/T) of 1:1.

Impedance readings measured on the xCELLigence System (ACEA) were taken every 5 minutes and reported as the Cell Index (CI) to quantitate cell confluency as a measure of cell proliferation/cell lysis. Approximately 3 hours after effector cell addition, 8 μl of 7.5% $NaHCO_3$ or 14 μl of 0.5 M NaOH was added into the wells with X-VIVO 15 media containing 40 mM HEPES and 40 mM PIPES, pH 6.7 to increase the pH from 6.7 to 7.4. Impedance readings were continued for approximately 20 hours after effector cell addition. Percentage of specific cytolysis was calculated as follows ((CI Target+C1VP transduced effector T cells)−(CI Target+F1-2-15-VP transduced effector T cells))/(CI Target+C1VP transduced effector T cells)×100.

HCl Switch on RTCA Killing Assay

The cytotoxic activity of transduced T cells before and after pH change by addition of HCl was measured using the xCELLigence System. Briefly, one day before the experiment, CHO-Axl cells were seeded into a 96 well E-plate at 10,000 cells/well with X-VIVO 15 media containing 40 mM HEPES and 40 mM PIPES, pH 7.4. Cryopreserved effector cells previously transduced with either C1VP or F1-2-15-VP, were thawed and cultured for two days in X-VIVO 15 media containing 100 IU/mL of IL-2. On the day of the experiment, cells transduced with F1-2-15-VP or C1VP were washed and resuspended in X-VIVO 15 media containing 40 mM HEPES and 40 mM PIPES, pH 7.4 and then added into experimental wells at effector cell/target cell ratios (E/T) of 1:1.

Impedance readings were taken every 5 minutes and reported as the Cell Index (CI). Approximately 3 hours after effector cell addition, 8 μl of 1 M HCl was added into the wells with X-VIVO 15 media containing 40 mM HEPES and 40 mM PIPES, pH 7.4 to switch the pH from 7.4 to 6.7. Impedance readings were continued for approximately 20 hours after effector cell addition. Percentage of specific cytolysis was calculated as follows ((CI Target+C1VP transduced effector T cells)−(CI Target+F1-2-15-VP transduced effector T cells))/(CI Target C1VP)×100.

Results

Figure 9A:
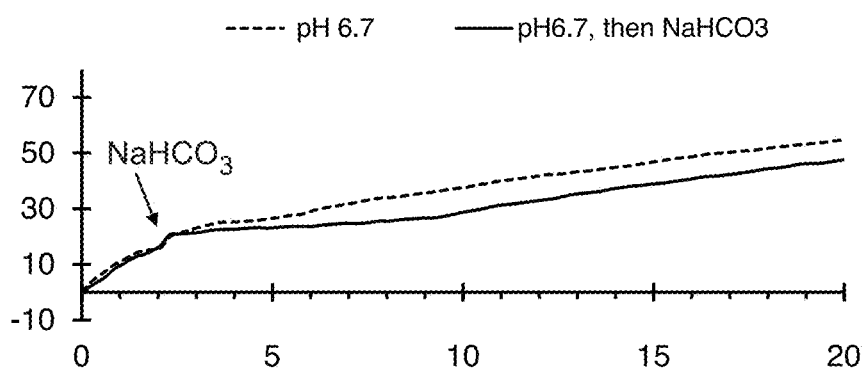
FIGS. 9A-9C show representative results from a real-time killing assay of CHO-Axl cells by T cells expressing one of the conditionally active CAB-CARs against Axl provided herein, with and without treatment with a pH-modulating pharmacologic agent.
Figure 9B:
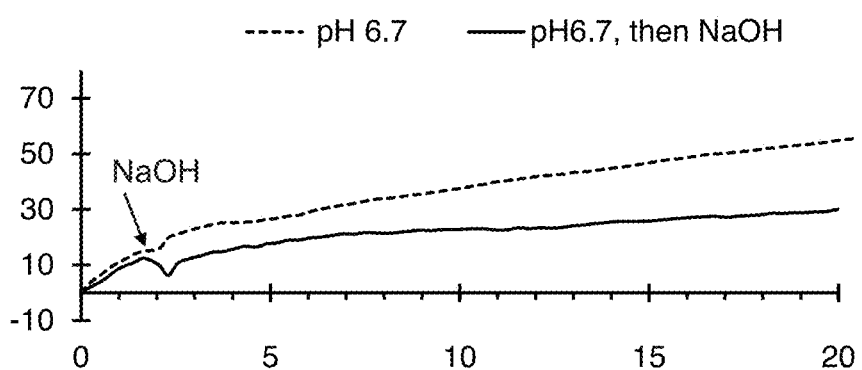

The cytotoxic activity of a CAB-CAR capable of binding cognate antigen Axl with increased activity at a reduced pH was compared in pH 6.7 and pH 7.4. T cells that were transduced with lentiviral particles containing a nucleic acid encoding F1-2-15, an anti-Axl CAB-CAR, were used to kill CHO cells expressing Axl, and then the pH was increased to determine whether the cytotoxic activity could be inhibited by a pH shift. As shown in FIGS. 9A and 9B, the addition of either NaHCO$_3$ or NaOH to the microenvironment of active CAR-T cells to increase the pH of the media inhibited the cytotoxic activity of the T cells expressing the CAB-CAR. These results show that active CAB-CAR expressing T cells can kill target-expressing cells and then this killing activity can be inhibited by increasing the pH of the microenvironment.

Figure 9C:
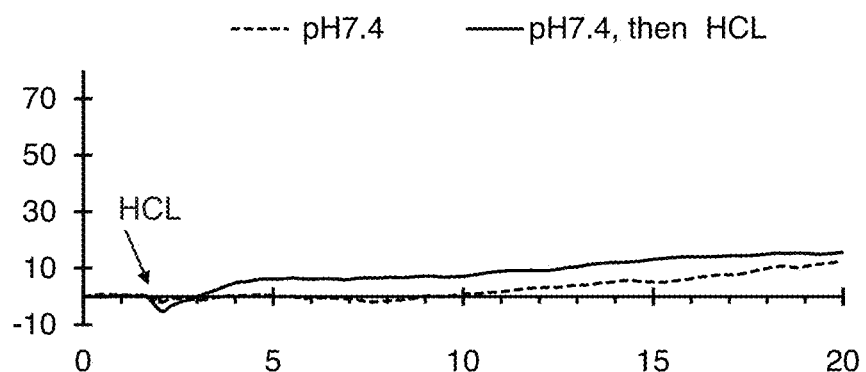

The ability of the cytotoxic activity of T cells expressing the CAB-CAR to be activated by a pH change was also determined. As shown in FIG. 9C, the cytotoxic activity of anti-Axl CAB-CAR expressing T cells on CHO-Axl cells was low at a pH of 7.4 and was increased by the addition of HCl to reduce the pH of the microenvironment.

Similar results were obtained when these experiments were repeated using F1-2-22 (CAB-CAR directed to Axl) and F1-1-15 (CAB-CAR directed to Ror2). Cumulatively, these results demonstrate the cytotoxic activity of T cells expressing CAB-CARs can be modulated by a shift in pH within the microenvironment, both by reducing cytotoxic activity after an increase in pH and increasing cytotoxic activity after a decrease in pH. In this non-limiting example, pH was increased from pH 6.7 and decreased from 7.4.

Example 5. Bicarbonate Administration can Increase pH of the Tumor Microenvironment in Mice The following example demonstrates the pH of an in vivo tumor microenvironment can be modulated by administering a pharmacologic agent. In this example, the pharmacologic agent is sodium bicarbonate and the tumor microenvironment is a CHO xenograft tumor in mice. The example includes two methods of measuring the pH of a tumor microenvironment, both in vivo and ex vivo.

The extracellular microenvironment of most solid tumors is acidic, with a pH typically between 6.5 and 6.9. On the contrary, normal tissue pH is basic, with a pH typically between 7.2 and 7.5. However, directly measuring the in vivo pH of a tumor microenvironment can be difficult. Fortunately, the relative protease activity of cathepsin is higher at lower pH and lower at higher pH. Therefore, the measurement of intratumoral cathepsin activity can serve as a surrogate measure of the pH of the tumor microenvironment. To measure in vivo activities of cathepsin B, L, S, K, V, and D, the near-infrared ProSense 750 FAST probe (PerkinElmer) was used. To further confirm modulation of the pH in the tumor microenvironment by administration of sodium bicarbonate, excised tumors were treated with phenol red and the color was noted. Phenol red is a pH indicator which undergoes a pH-dependent color transition. The sodium salt of phenol red is widely used in cell culture media to identify pH values. A solution of phenol red has a yellow color at a pH of 6.4 or below, an orange color around pH 7.0, a red color around pH 7.4, and a purple color above pH 7.8.

Mice were handled in accordance with Institutional Animal Care and Use Committee approved protocols. Subcutaneous (sc) Chinese Hamster Ovary (CHO) tumor xenografts were established in the hind flank of 12-14 week old female NOD-Prkdc$^{scid}$Il2rg$^{tm1}$/Begen (B-NSG) mice (Beijing Biocytogen Co. Ltd.). Briefly, cultured CHO cells (ATCC, Manassas, VA) were washed in DPBS (Thermo Fisher), counted, resuspended in cold DPBS and mixed with an appropriate volume of Matrigel ECM (Corning; final concentration 5 mg/mL) at a concentration of 1.5×10$^6$ cells/200 µl on ice.

Animals were prepared for injection using standard approved anesthesia with hair removal (Nair) prior to injection. 200 µl of the cell suspension in ECM was injected sc into the rear flanks of the mice. Once tumors were palpable, the tumors were measured using calipers 2 times/week. Tumor volume was calculated using the following equation: (longest diameter*shortest diameter$^2$)/2. When average tumor volume reached 200 mm$^3$, mice were randomly assigned to the respective treatment groups.

Two days before the administration of bicarbonate, the drinking water for the B-NSG mice was changed from acidic to regular pH autoclaved purified water. The following day, the 750 ProSense FAST probe was administered to 6 CHO-xenograft tumor bearing mice via 100 µl tail vein injections (4 nmol ProSense 750 FAST probe/100 µl PBS). A separate group of CHO-xenograft tumor bearing mice was left untreated. The following day, sodium bicarbonate was administered and imaging of the mice treated with the ProSense 750 FAST probe was performed using a Caliper IVIS Lumina XR. Briefly, mice were anesthetized using 3% O$_2$ 2 L/min isoflurane in O$_2$ carrier gas at 2 L/min and then placed with nose cones supplying 1.5% isoflurane to anesthetized mice during imaging. Image acquisitions consisted of a 5 sec exposure for near-infrared probes (745/810 nm excitation/emission wavelength). Fluorescence images were overlaid on normal light images of the mice. Time 0 (pretreatment) images were acquired before administration of either PBS (control) or sodium bicarbonate. The mice were then administered either 1 ml/mouse PBS (control, ThermoFisher) or 1 ml/mouse 1 M sodium bicarbonate (Shanghai Experiment Reagent Co., LTD) via intraperitoneal injection (ip). Mice were then imaged at 30 min post administration of PBS or bicarbonate. The collected fluorescence images were adjusted to have identical minimums, maximums, and threshold values. The photon counts were defined in this study as relative fluorescence units (RFU). RFU was calculated by normalizing the photon counts from the 30 min time point to the pretreatment time point (time 0; 100%) in each mouse. Due to variability between fluorescence values in each mouse at the time 0 pretreatment value, the observed fluorescence intensity values at different time points were normalized only to the individual mouse and not to a mean pretreatment value.

In a separate arm of the experiment, the 6 mice that did not receive the NIR cathepsin probe were euthanized by cervical dislocation at 1.5 hours post ip administration of PBS or sodium bicarbonate. The CHO xenograft tumor was excised from each mouse. The xenograft tumors were split into two halves with a scalpel and placed on a petri dish. The tumor tissue halves were then cut/sliced repeatedly using the scalpel. Water or 0.05% phenol red solution (50 mg phenol red/100 ml water) was added dropwise to each tumor half, respectively. The color was noted and images were taken of the treated tumor xenografts and of the phenol red solution remaining on the petri plate once the tumor xenograft samples were removed.

Results

Figure 10:
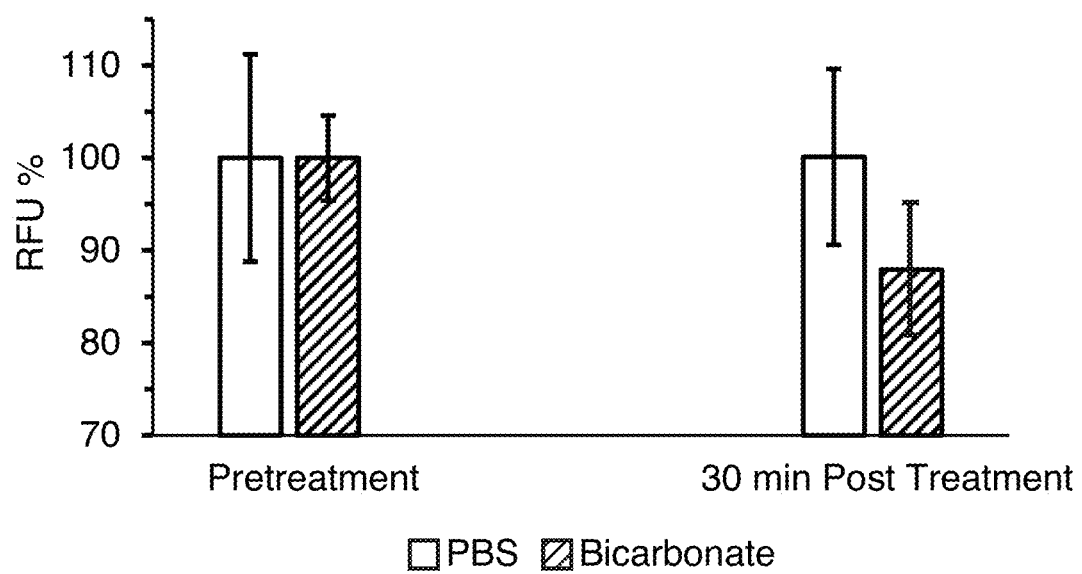
FIG. 10 is a graph showing the RFU percentage from ProSense FAST probe in CHO-xenograft tumor bearing mice before and after administration of PBS or bicarbonate.

FIG. 10 shows the RFU results (mean with SEM) from imaging intratumoral cathepsin activity in CHO-xenograft tumor bearing mice before and after administration of PBS (control; n=3) or bicarbonate (n=3). These results suggest that sodium bicarbonate administration can increase the pH of the tumor microenvironment in vivo as evidenced by the decreased cathepsin activity observed following ip sodium bicarbonate administration.

A color change of the phenol red indicator from yellow/orange to red was observed using the tumor tissue excised from sodium bicarbonate-treated mice (n=3) relative to the PBS-treated mice (n=3). These results support that sodium bicarbonate administration increased the pH of the tumor microenvironment in vivo following ip administration as evidenced by the color change of the phenol red indicator from yellow/orange to red.

Example 6. Target Dependent Killing of Tumors In Vivo by Cab-Cars Directed to Ror2 and Axl Experiments were performed that demonstrated that CAB-CARs with conditional cytotoxic activity against Axl or Ror2 expressing cells in in vitro assays, had cytotoxic activity against Axl or Ror2 expressing tumor cells in vivo. A xenograft model using NSG, or NOD Scid Gamma mice was chosen that is non-reactive with anti-human scFv targets as a mechanism to probe the specificity and efficacy of CAB-CARs. NSG is a strain of mice that lack mature T cells, NK cells, and B cells and is among the most immunodeficient described to date. Removal of these cellular components is necessary to enable human peripheral blood derived mononuclear cells to engraft without innate, humoral or adaptive immune reactions from the host. Concentrations of homeostatic cytokines normally present only after radiation or lymphodepleting chemotherapy in humans is achieved due to the absence of the murine extracellular common gamma chain, which enables adoptively transferred human cells to receive such cytokines. At the same time, these animals can also be utilized to engraft tumor xenograft targets to examine the efficacy of CARs to kill target-expressing tumors. While the presence of xenoreactive T cell receptor antigens in the effector cellular product will eventually give rise to graft versus host disease, these models enable short term evaluation of animal pharmacology and acute tolerability.

Parental Chinese hamster ovary (CHO) cells and transgenic CHO cells stably transfected to express human ROR2 (CHO-ROR2) or human Axl (CHO-Axl) were utilized to generate a uniform target tumor to determine the specificity and efficacy of CAB-CAR effector cells to kill cognate antigen-expressing tumors. As all 3 cell lines have the same xenoreactive human leukocyte antigens (HLAs) and other non-specific antigens, the specificity of the CAB-CAR cells to tumor targets in the tumor microenvironment can be examined without consideration for variations in HLA reactivity of donor lymphocytes and target tumor cells. The parental and transgenic CHO variants grew rapidly with disseminated malignancy after subcutaneous administration into NSG mice in combination with Matrigel artificial basement membrane.

PBMCs were isolated from ACD-peripheral blood from healthy volunteers with informed consent by density gradient centrifugation with Ficoll-Pacque™ (General Electric) using a CS-900.2 kit (BioSafe; 1008) on a Sepax 2 S-100 device (Biosafe; 14000) according to the manufacturer's instructions. $5.0 \times 10^7$ viable PBMCs were seeded in a 1 L G-Rex (Wilson-Wolf) and the volume was brought to 100 ml with Complete OpTmizer™ CTS™ T-Cell Expansion SFM supplemented with 100 IU/ml (IL-2) (Novoprotein), 10 ng/ml (IL-7) (Novoprotein), and 50 ng/ml anti-CD3 antibody (OKT3, Novoprotein) to activate the PBMCs for viral transduction. After incubation overnight at 37° C. and 5% $CO_2$, lentiviral particles encoding CAR constructs made as described in Example 1 were added directly to the activated PBMCs and incubated overnight at 37° C. and 5% $CO_2$. The following day, the media volume of each G-Rex brought to 1 L with Complete OpTmizer™ CTS™ T-Cell Expansion SFM supplemented with 10 mM NAC. Additionally, 100 IU/ml of IL-2 (Novoprotein) and 10 ng/ml IL-7 (Novoprotein) were added to each well on Day 2 and every 48 hours thereafter. The cells were allowed to expand up to Day 12 from the original blood collection (Day 0) before being harvested.

To examine CAB-CARs directed to ROR2, female NOD-Prkdc$^{scid}$Il2rg$^{tm1}$/Begen (B-NSG) mice (Beijing Biocytogen Co. Ltd.) 12-14 weeks old were inoculated subcutaneously with either parental CHO cells or CHO-ROR2 cells in Matrigel ECM at a concentration of $1.5 \times 10^6$ cells/200 µl on ice as described in Example 5. Mice were dosed intravenously (IV) by tail vein injection with either $4 \times 10^6$ T cells transduced with lentiviral particle containing a nucleic acid encoding F1-1-15 (n=6) or F1-0-01 (n=6) (See Examples 1 and 3 for construct details) prepared using the cell processing protocol provided in the above paragraph, or with PBS (n=6), when tumors had reached >200 mm$^3$ to model heavy tumor burden therapy. Tumors were measured using calipers 3 times a week and tumor volume was calculated using the following equation: (longest diameter*shortest diameter$^2$)/2. All animals reached necropsy guidelines from tumor burden by Day 13.

To examine CAB-CARs directed to AXL, female B-NSG mice 7-9 weeks old were inoculated subcutaneously with either parental CHO cells or CHO-AXL cells in Matrigel ECM (final concentration 5 mg/ml) at a concentration of $1.5 \times 10^6$ cells/200 µl on ice as described in Example 5. IV or intratumoral (IT) administration of effector cells commenced when tumors reached >100 mm$^3$ to model heavy tumor burden therapy. A first group of mice were dosed IV by tail vein injection with either $8 \times 10^6$ T cells transduced with lentiviral particle containing a nucleic acid encoding F1-2-15 (n=6), F1-2-22 (n=6), or F1-0-01 (n=6) (See Examples 1 and 3 for construct details) prepared using the cell processing protocol provided in the above paragraph, or with PBS (n=6). A second group of mice were dosed IT with either $8 \times 10^6$ T cells transduced with lentiviral particle containing a nucleic acid encoding F1-2-15 (n=6), F1-2-22 (n=6), or F1-0-01 (n=6), or with PBS (n=6). A third group of mice were dosed IV by tail vein injection with either $8 \times 10^6$ T cells transduced with lentiviral particle containing a nucleic acid encoding F1-2-15 (n=6), F1-2-22 (n=6), or F1-0-01 (n=6), or with PBS ((n=6) and the mice received subcutaneous injections of IL-2 (50KIU) in the contralateral subcutaneous site away from the tumor every day for the first 3 days. Tumors were measured using calipers 3 times a week and tumor volume was calculated using the following equation: (longest diameter*shortest diameter$^2$)/2. All animals were euthanized consistent with necropsy guidelines from tumor burden.

Results

Figure 11A:
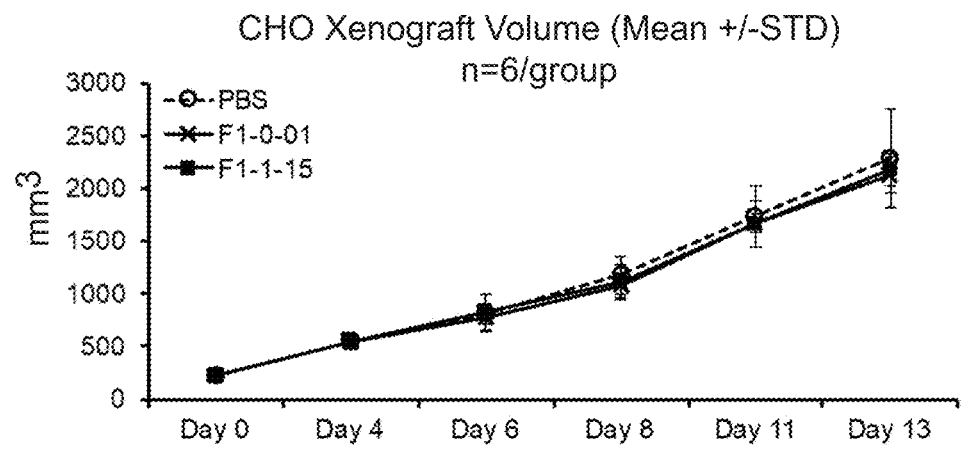
FIG. 11A shows the mean tumor volume of CHO tumors in B-NSG mice dosed intravenously with PBS or human T cells transduced with either a lentiviral particle containing a nucleic acid encoding F1-0-01 (eTag) or F1-1-15, one of the conditionally active CAB-CARs against Ror2.
Figure 11B:
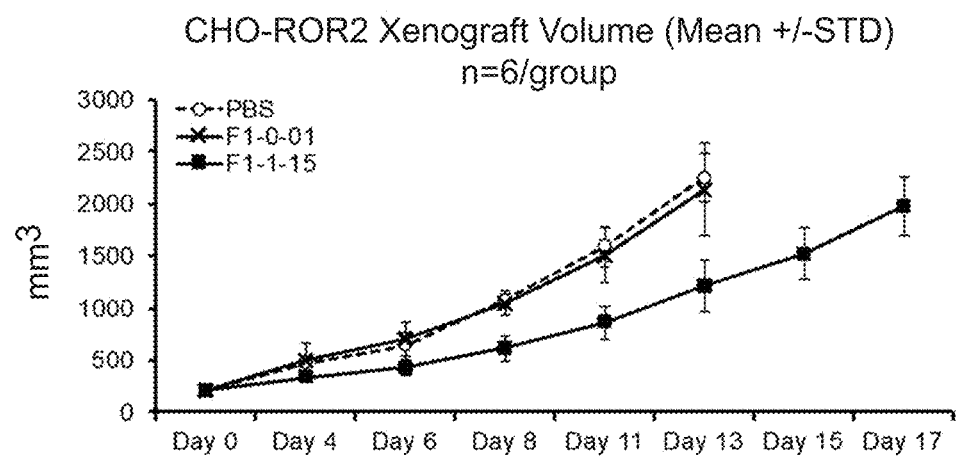
FIG. 11B shows the mean tumor volume of CHO-Ror2 tumors in B-NSG mice dosed intravenously with PBS or human T cells transduced with either a lentiviral particle containing a nucleic acid encoding F1-0-01 or F1-1-15.

The in vivo tumor cell killing activity of some representative CAB-CARs disclosed in Example 1 was tested in a mouse model using engrafted tumor cells expressing Ror2, Axl, or neither. With respect to anti-Ror2 CAB-CARs, as shown in FIG. 11A, mice dosed IV with $4 \times 10^6$ T cells transduced with a lentiviral particle containing a nucleic acid encoding F1-1-15 had no effect on ROR2 negative tumor growth compared to PBS controls or E-Tag only lentivirus transduced T cells (F1-0-01). In contrast, as shown in FIG. 11B, IV dosing of the same cell preparations into human Ror2-expressing tumors demonstrated significant tumor suppression of Ror2 positive tumors only by F1-1-15. These data demonstrate that the tumor microenvironment is reproduced in vivo in this engrafted tumor mouse model and that the genetically modified T cells expressing an exemplary anti-Ror2 CAB-CAR provided herein were capable of accessing the solid tumor and driving target cell killing in vivo despite the rapid doubling time of the target engrafted tumor cells.

Figure 12A:
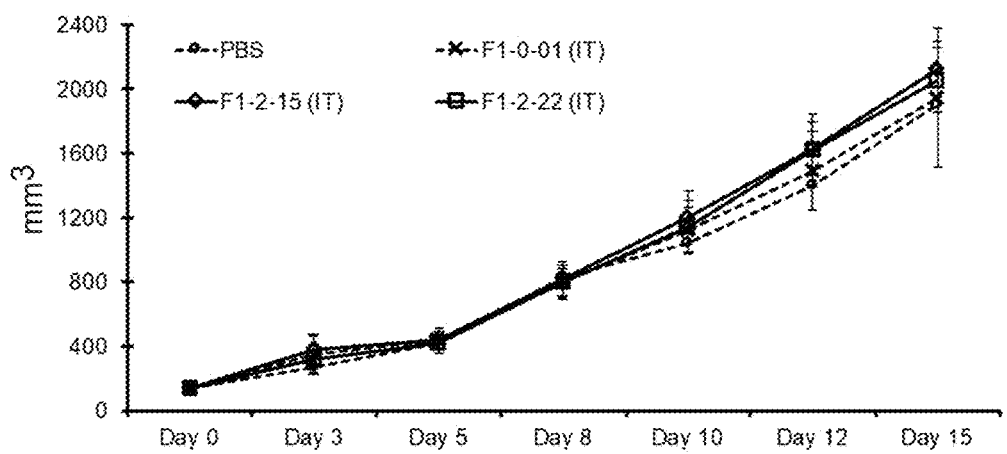
FIG. 12A shows the mean tumor volume of CHO tumors in B-NSG mice dosed intratumorally with PBS or human T cells transduced with either a lentiviral particle containing a nucleic acid encoding F1-0-01 (eTag) or F1-2-15 or F1-2-22. F1-2-15 and F1-2-22 encode two of the conditionally active CAB-CARs against Axl.
Figure 12B:
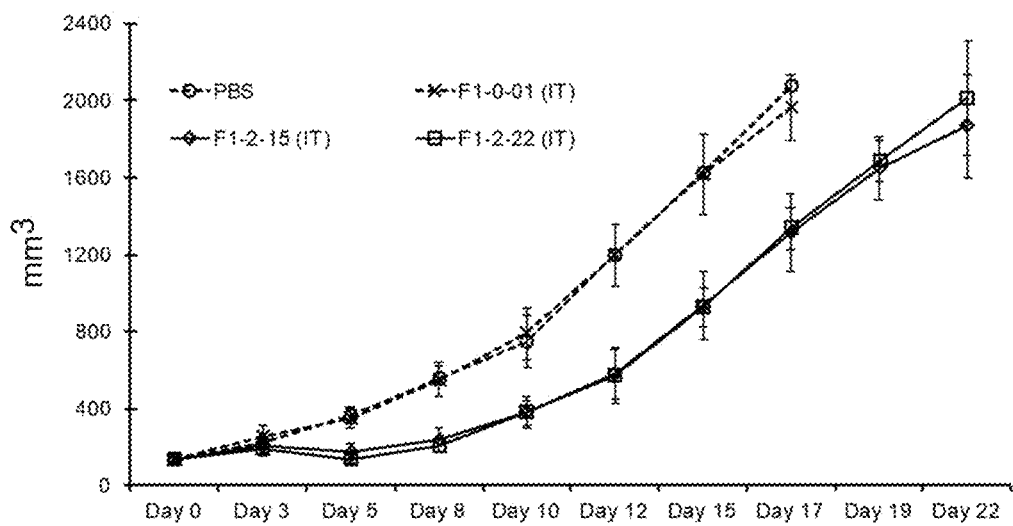
FIG. 12B shows the mean tumor volume of CHO-Axl tumors in B-NSG mice dosed intratumorally with PBS or human T cells transduced with a lentiviral particle containing a nucleic acid encoding either F1-0-01, F1-2-15, or F1-2-22.
Figure 13A:
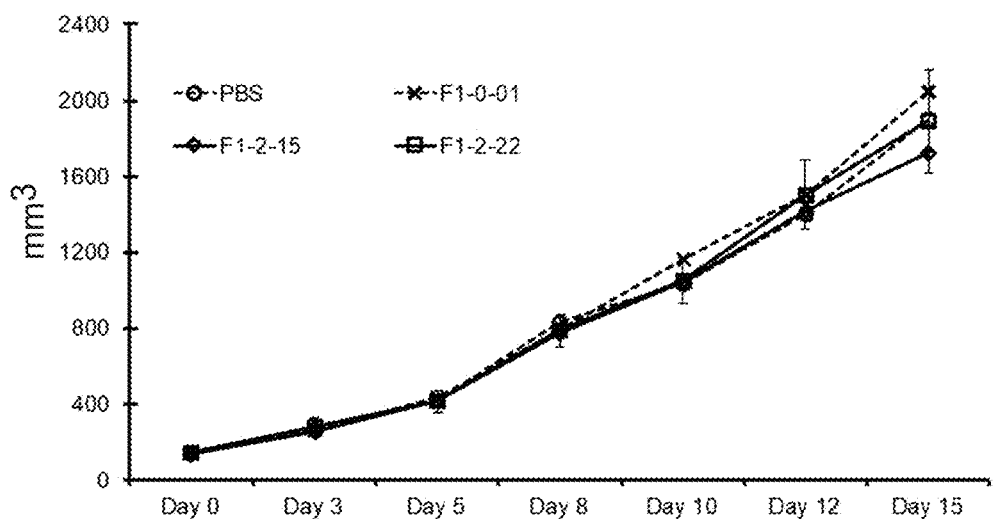
FIG. 13A shows the mean tumor volume of CHO tumors in B-NSG mice dosed intravenously with PBS or human T cells transduced with a lentiviral particle containing a nucleic acid encoding either F1-0-01 (eTag) or F1-2-15 or F1-2-22. F1-2-15 and F1-2-22 encode two of the conditionally active CAB-CARs against Axl.
Figure 13B:
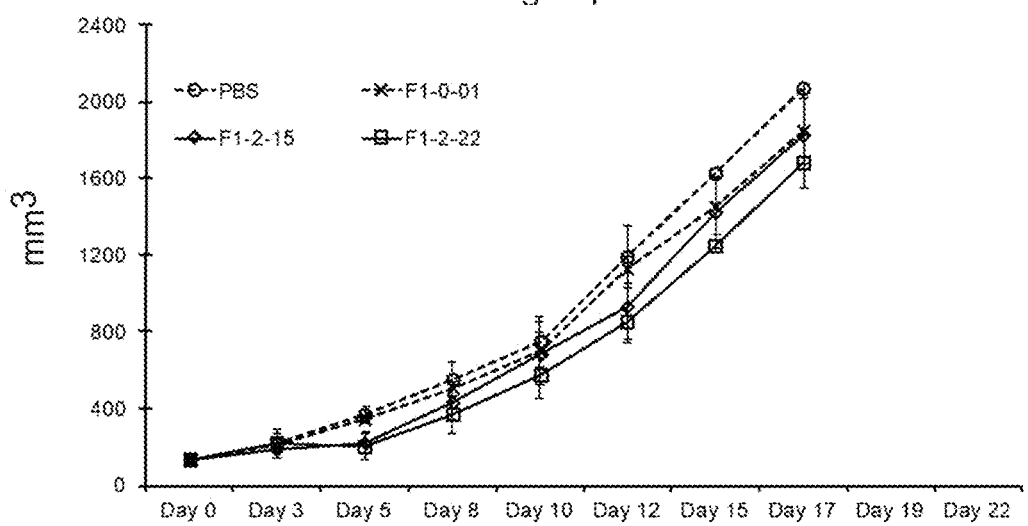
FIG. 13B shows the mean tumor volume of CHO-Axl tumors in B-NSG mice dosed intravenously with PBS or human T cells transduced with a lentiviral particle containing a nucleic acid encoding either F1-0-01, F1-2-15, or F1-2-22.
Figure 14A:
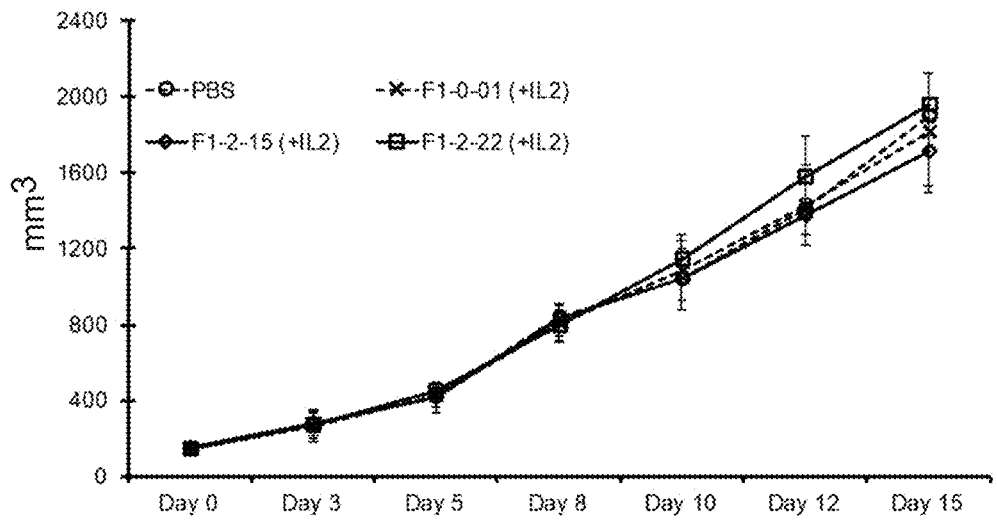
FIG. 14A shows the mean tumor volume of CHO tumors in B-NSG mice dosed intravenously with PBS or human T cells transduced with a lentiviral particle containing a nucleic acid encoding either F1-0-01 (eTag) or F1-2-15 or F1-2-22. F1-2-15 and F1-2-22 encode two of the conditionally active CAB-CARs against Axl.
Figure 14B:
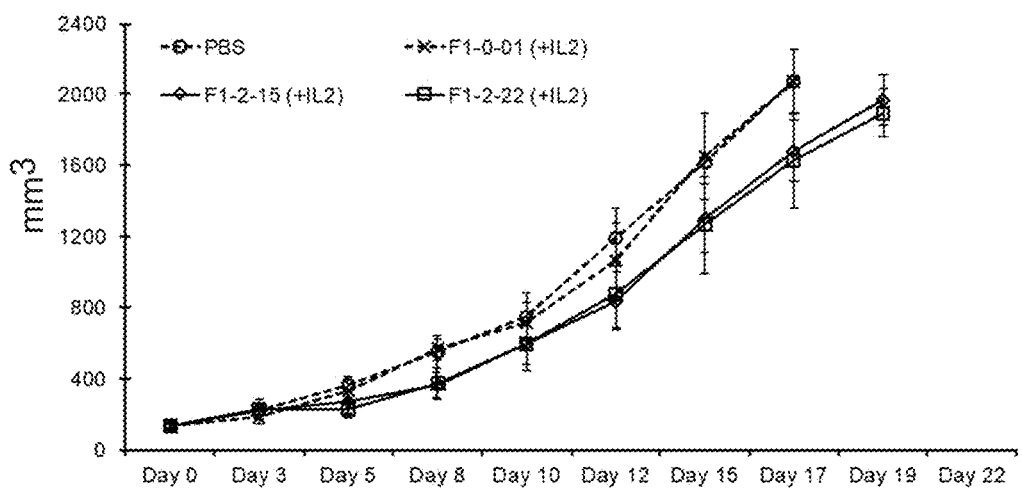
FIG. 14B shows the mean tumor volume of CHO-Axl tumors in B-NSG mice dosed intravenously with PBS or human T cells transduced with a lentiviral particle containing a nucleic acid encoding either F1-0-01, F1-2-15, or F1-2-22. Mice dosed with T cells in FIGS. 14A and 14B also received subcutaneous injections of IL-2 (50,000 IU) in the contralateral site away from the tumor every day for the first 3 days.

With respect to anti-Axl CAB-CARs, as shown in FIG. 12A, mice dosed intratumorally (IT) with 8×10⁶ T cells transduced with a lentiviral particle containing a nucleic acid encoding either F1-2-15 or F1-2-22 had no effect on Axl negative tumor growth compared to PBS controls or E-Tag only lentiviral particle transduced T cells (F1-0-01). In contrast, as shown in FIG. 12B, IT dosing of the same cell preparations into human Axl-expressing tumors demonstrated significant tumor suppression of Axl positive tumors by F1-2-15 and F1-2-22. While cells expressing F1-2-15 or F1-2-22 were equipotent in in vitro killing assays against tumors expressing Axl as compared to the ability of cells expressing F1-1-15 to kill tumors expressing Ror2, tumor growth inhibition in vivo was not as sustained over time following IV administration compared to local injection (FIG. 13A control vs FIG. 13B). Administration of systemic IL-2 into animals for 3 days (FIG. 14A control vs FIG. 14B) led to improved anti-tumor activity as compared to IV dosing without IL-2. These data demonstrate that the tumor microenvironment is again reproduced in vivo in this engrafted tumor mouse model and that the genetically modified T cells expressing exemplary anti-Ror2 CAB-CARs F1-2-15 and F1-2-22 were capable of accessing the solid tumor and cell killing in vivo despite the rapid doubling time of the target engrafted tumor cells. Furthermore, these experiments using exemplary anti-Ror2 and anti-Axl CAB-CARs provided herein, demonstrate that such CAB-CARs are effective in in vivo methods for activating T cells that express these CAB-CARs.

Those skilled in the art can devise many modifications and other embodiments within the scope and spirit of the present disclosure. Indeed, variations in the materials, methods, drawings, experiments, examples, and embodiments described may be made by skilled artisans without changing the fundamental aspects of the present disclosure. Any of the disclosed embodiments can be used in combination with any other disclosed embodiment.

In some instances, some concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

TABLE 3

Sequences of SEQ ID NOs.

| SEQ ID NO | Name | Sequence |
|---|---|---|
| 1 | CD137 Co-stimulatory domain | KRGRKKLLYIFKQPFMRPVQTTQEEDGCSCRFPEEEEGGCEL |
| 2 | CD28 Co-stimulatory domain | RSKRSRLLHSDYMNMTPRRPGPTRKHYQPYAPPRDFAAYRS |
| 3 | ICA Co-stimulatory domain | RSKRSRLLHSDYMNMTPRRPGTRKHYQAYAAARDFAAYRS |
| 4 | ICOS Co-stimulatory domain | TKKKYSSSVHDPNGEYMFMRAVNTAKKSRLTDVTL |
| 5 | OX40 Co-stimulatory domain | RRDQRLPPDAHKPPGGGSFRTPIQEEQADAHSTLAKI |
| 6 | CD27 Co-stimulatory domain | HQRRKYRSNKGESPVEPAEPCRYSCPREEEGSTIPIQEDYRKPEPACSP |
| 7 | BLTA Co-stimulatory domain | CCLRRHQGKQNELSDTAGREINLVDAHLKSEQTEASTRQNSQVLLSETGIYDNDPDLCFR MQEGSEVYSNPCLEENKPGIVYASLNHSVIGPNSRLARNVKEAPTEYASICVRS |
| 8 | CD30 Co-stimulatory domain | RRACRKRIRQKLHLCYPVQTSQPKLELVDSRPRRSSTQLRSGASVTEPVAEERGLMSQPL METCHSVGAAYLESLPLQDASPAGGPSSPRDLPEPRVSTEHTNNKIEKIYIMKADTVIVG TVKAELPEGRGLAGPAEPELEEELEADHTPHYPEQETEPPLGSCSDVMLSVEEEGKEDPL PTAASGK |
| 9 | GITR Co-stimulatory domain | HIWQLRSQCMWPRETQLLLEVPPSTEDARSCQFPEEERGERSAEEKGRLGDLWV |
| 10 | HVEM Co-stimulatory domain | CVKRRKPRGDVVKVIVSVQRKRQEAEGEATVIEALQAPPDVTTVAVEETIPSFTGRSPNH |
| 11 | CD3Z isoform 1 Activating domain | MKWKALFTAAILQAQLPITEAQSFGLLDPKLCYLLDGILFIYGVILTALFLRVKFSRSAD APAYQQGQNQLYNELNLGRREEYDVLDKRRGRDPEMGGKPRRKNPQEGLYNELQKDKMAE AYSEIGMKGERRRGKGHDGLYQGLSTATKDTYDALHMQALPPR |
| 12 | CD3Z isoform 2 Activating domain | MKWKALFTAAILQAQLPITEAQSFGLLDPKLCYLLDGILFIYGVILTALFLRVKFSRSAD APAYQQGQNQLYNELNLGRREEYDVLDKRRGRDPEMGGKPQRRKNPQEGLYNELQKDKMA EAYSEIGMKGERRRGKGHDGLYQGLSTATKDTYDALHMQALPPR |
| 13 | CD3Z 3 Activating domain | RVKFSRSADAPAYQQGQNQLYNELNLGRREEYDVLDKRRGRDPEMGGKPRRKNPQEGLYN ELQKDKMAEAYSEIGMKGERRRGKGHDGLYQGLSTATKDTYDALHMQALPPR |

TABLE 3-continued

Sequences of SEQ ID NOs.

| SEQ ID NO: | Name | Sequence |
|---|---|---|
| 14 | CD3Z 4 Activating domain | NQLYNELNLGRREEYDVLDKR |
| 15 | CD3Z 5 Activating domain | EGLYNELQKDKMAEAYSEIGMK |
| 16 | CD3Z 6 Activating domain | DGLYQGLSTATKDTYDALHMQ |
| 17 | CD3D 1 Activating domain | MEHSTFLSGLVLATLLSQVSPFKIPIEELEDRVFVNCNTSITWVEGTVGTLLSDITRLDL GKRILDPRGIYRCNGTDIYKDKESTVQVHYRMCQSCVELDPATVAGIIVTDVIATLLLAL GVFCFAGHETGRLSGAADTQALLRNDQVYQPLRDRDDAQYSHLGGNWARNK |
| 18 | CD3D 2 Activating domain | MEHSTFLSGLVLATLLSQVSPFKIPIEELEDRVFVNCNTSITWVEGTVGILLSDITRLD LGKRILDPRGIYRCNGTDIYKDKESTVQVHYRTADTQALLRNDQVYQPLRDRDDAQYSH LGGNWARNK |
| 19 | CD3D 3 Activating domain | DQVYQPLRDRDDAQYSHLGGN |
| 20 | CD3E 1 Activating domain | MQSGTHWRVLGLCLLSVGVWGQDGNEEMGGITQYPYKVSISGTTVILTCPQYPGSEILWQ HNDKNIGGEDDKNIGSDEDHLSLKEFSELEQSGYYVCYPRGSKPEDANFYLYLRARVCEN CMEMDMSVATIVIVDICITGGLLLLVYYWSKNRKAKAKPVTRGAGAGGRQRGQNKERPPP VPNPDYEPIRKGQRDLYSGLNQRRI |
| 21 | CD3E 2 Activating domain | NPDYEPIRKGQRDLYSGLNQR |
| 22 | CD3G 1 Activating domain | MEQGKGLAVLIKAIILLQGTLAQSIKGNHLVKYDYQEDGSVLLTCDAEAKNITWFKDGKM IGFLTEDKKKWNLGSNAKKPRGMYQCKGSQNKSKPLQVYYRMCQNCIELNAATISGFLFA EIVSIFVLAVGVYFIAGQDGVRQSRASDKQTLLPNDQLYQPLKDREDDQYSHLQGNQLRR N |
| 23 | CD3G 2 Activating domain | DQLYQPLKDREDDQYSHLQGN |
| 24 | CD79A 1 Activating domain | MPGGPGVLQALPATIFLLFLLSAVYLGPGCQALWMHKVPASLMVSLGEDAHFQCPHNSSN NANVTWWRVLHGNYTWPPEFLGPGEDPNGTLIIQNVNKSHGGIYVCRVQEGNESYQQSCG TYLRVRQPPPRPFLDMGEGTKNRIITAEGIILLFCAVVPGTLLLFRKRWQNEKLGLDAGD EYEDENLYEGLNLDDCSMYEDISRGLQGTYQDVGSLNIGDVQLEKP |
| 25 | CD79A 2 Activating domain | MPGGPGVLQALPATIFLLFLLSAVYLGPGCQALWMHKVPSSLMVSLGEDAHFQCPHNSSN NANVTWWRVLHGNYTWPPEFLGPGEDPNEPPPRPFLDMGEGTKNRIITAEGIILLFCAVV PGTLLLFRKRWQNEKLGLDAGDEYEDENLYEGLNLDDCSMYEDISRGLQGTYQDVGSLNI GDVQLEKP |
| 26 | CD79A 3 Activating domain | ENLYEGLNLDDCSMYEDISRG |
| 27 | DAP12 1 Activating domain | MGGLEPCSRLLLLPLLLAVSGLRPVQAQAQSDCSCSTVSPGVLAGIVMGDLVLTVLIALA VYFLGRLVPRGRGAAEEAATRKQRITETESPYQELQGQRSDVYSDLNTQRPYYK |
| 28 | DAP12 2 Activating domain | MGGLEPCSRLLLLPLLLAVSGLRPVQAQAQSDCSCSTVSPGVLAGIVMGDLVLTVLIALA VYFLGRLVPRGRGAAEEATRKQRITETESPYQELQGQRSDVYSDLNTQ |
| 29 | DAP12 3 Activating domain | MGGLEPCSRLLLLPLLLAVSDCSCSTVSPGVLAGIVMGDLVLTVLIALAVYFLGRLVPRG RGAAEEAATRKQRITETESPYQELQGQRSDVYSDLNTQRPYYK |
| 30 | DAP12 4 Activating domain | MGGLEPCSRLLLLPLLLAVSDCSCSTVSPGVLAGIVMGDLVLTVLIALAVYFLGRLVPRG RGAAEEATRKQRITETESPYQELQGQRSDVYSDLNTQRPYYK |
| 31 | DAP12 5 Activating domain | ESPYQELQGQRSDVYSDLNTQ |
| 32 | FCER1G 1 Activating domain | MIPAVVLLLLLLVEQAAALGEPQLCYILDAILFLYGIVLTLLYCRLKIQVRKAAITSYEK SDGVYTGLSTRNQETYETLKHEKPPQ |
| 33 | FCER1G 2 Activating domain | DGVYTGLSTRNQETYETLKHE |
| 34 | DAP10 Activating domain | RPRRSPAQDGKVYINMPGRG |
| 35 | CD28 Activating domain | FWVLVVVGGVLACYSLLVTVAFIIFWVRSKRSRLLHSDYMNMTPRRPGPTRKHYQPYAPP RDFAAYRS |

TABLE 3-continued

Sequences of SEQ ID NOs.

| SEQ ID NO: | Name | Sequence |
|---|---|---|
| 36 | ZAP70 Activating domain | MPDPAAHLPFFYGSISRAEAEEHLKLAGMADGLFLLRQCLRSLGGYVLSLVHDVRFHHFP IERQLNGTYAIAGGKAHCGPAELCEFYSRDPDGLPCNLRKPCNRPSGLEPQPGVFDCLRD AMVRDYVRQTWKLEGEALEQAIISQAPQVEKLIATTAHERMPWYHSSLTREEAERKLYSG AQTDGKFLLRPRKEQGTYALSLIYGKTVYHYLISQDKAGKYCIPEGTKFDTLWQLVEYLK ;LADGLIYCLKEACPNSSASNASGAAAPTLPAHPSTLTHPQRRIDTLNSDGYTPEPARIT SPDKPRPMPMDTSVYESPYSDPEELKDKKLFLKRDNLLIADIELGCGNFGSVRQGVYRMR KKQIDVAIKVLKQGTEKADTEEMMREAQEIMQLDNPYIVRLIGVCQAEALMLVMEMAGGG PLHKFLVGKREEIPVSNVAELLHQVSMGMKYLEEKNFVHRDLAARNVLLVNRHYAKISDF GLSKALGADDSYYTARSAGKWPLKWYAPECINFRKFSSRSDVWSYGVTMWEALSYGQKPY KKMKGPEVMAFIEQGKRMECPPECPPELYALMSDCWIYKWEDRPDFLTVEQRMRACYYSL ASKVEGPPGSTQKAEAACA |
| 37 | HA Epitope | YPYDVPDYA |
| 38 | FLAG Epitope | DYKDDDDK |
| 39 | c-myc Epitope | EQKLISEEDL |
| 40 | His5 Affinity | HHHHH |
| 41 | HisX6 Affinity | HHHHHH |
| 42 | Strep Tag Affinity | WSHPQFEK |
| 43 | RYIRS Affinity | RYIRS |
| 44 | FHHT Affinity | FHHT |
| 45 | Affinity | WEAAAREACCRECCARA |
| 46 | CD8 alpha Transmembrane domain | IYIWAPLAGTCGVLLLSLVITLYC |
| 47 | CD8 beta Transmembrane domain | LGLLVAGVLVLLVSLGVAIHLCC |
| 48 | CD4 Transmembrane domain | ALIVLGGVAGLLLFIGLGIFFCVRC |
| 49 | CD3 zeta Transmembrane domain | LCYLLDGILFIYGVILTALFLRV |
| 50 | CD28 Transmembrane domain | FWVLVVVGGVLACYSLLVTVAFIIFWV |
| 51 | OX40 Transmembrane domain | VAAILGLGLVLGLLGPLAILLALYLL |
| 52 | CD7 Transmembrane domain | ALPAALAVISFLLGLGLGVACVLA |
| 53 | Linker 1 | GGGGSGGGGSGGGGS |
| 54 | Linker 2 | GGGGSGGGGSGGGGSGGGGSGGGGSGGGGS |
| 55 | Linker 3 | GGGGSGGGGSGGGGS |
| 56 | Linker 4 | GGSG |
| 57 | Linker 5 | GGSGG |
| 58 | Linker 6 | GSGSG |
| 59 | Linker 7 | GSGGG |
| 60 | Linker 8 | GGGSG |
| 61 | Linker 9 | GSSSG |
| 62 | Hinge 1 | CPPC |
| 63 | Hinge 2 | DKTHT |
| 64 | Hinge 3 | CPEPKSCDTPPPCPR |

TABLE 3-continued

Sequences of SEQ ID NOs.

| SEQ ID NO: | Name | Sequence |
|---|---|---|
| 65 | Hinge 4 | ELKTPLGDTTHT |
| 66 | Hinge 5 | KSCDKTHTCP |
| 67 | Hinge 6 | KCCVDCP |
| 68 | Hinge 7 | KYGPPCP |
| 69 | Hinge 8 | ELPSCDKTHTCPPCP |
| 70 | Hinge 9 | ERKCCVECPPCP |
| 71 | Hinge 10 | ELKTPLGDTTHTCPRCP |
| 72 | Hinge 11 | SPNMVPHAHHAQ |
| 73 | Hinge 12 | TTTPAPRPPTPAPTIASQPLSLRPEACRPAAGGAVHTRGLDFACD |
| 74 | CD8 Signal peptide | MALPVTALLLPLALLLHAARP |
| 75 | CD8 Stalk-TM | TTTPAPRPPTPAPTIASQPLSLRPEACRPAAGGAVHTRGLDFACDIYWAPLAGTCGVLLL SLVITLYC |
| 76 | CD28 Stalk-TM | IEVMYPPPYLDNEKSNGTIIHVKGKHLCPSPLFPGPSKPFWVLVVVGGVLACYSLLVTVA FIIFWV |
| 77 | 2A-1 Cleavage signal | GSGEGRGSLLTCGDVEENPGP |
| 78 | eTAG Elimination domain | MLLLVTSLLLCELPHPAFLLIPRKVCNGIGIGEFKDSLSINATNIKHFKNCTSISGDLHI LPVAFRGDSFTHTPPLDPQELDILKTVKEITGFLLIQAWPENRTDLHAFENLEIIRGRTK QHGQFSLAVVSLNITSLGLRSLKEISDGDVIISGNKNLCYANTINWKKLFGTSGQKTKII SNRGENSCKATGQVCHALCSPEGCWGPEPRDCVSCRNCSRGRECVDKCNLLEGEPREFVE NSECIQCHPECLPQAMNITCTGRGPDNCIQCAHYIDGPHCVKTCPAGVMGENNTLVWKYA DAGHVCHLCHPNCTYGCTGPGLEGCPTNGPKIPSIATGMVGALLLLLVVALGIGLFM |
| 79 | Axl 4007V VH of conditionally active scFv | EVQLVQSGAEVKKPGATVKISCKVSGYSFWGATMNWIRQPPGKGLEWIGLIKPSNGGTSY NQKFKGRVTISADKSISTAYLQWSSLKASDTAMYYCAHGHYESYEAMDYWGQGTLVTVSS |
| 80 | Axl 4007V VL of conditionally active scFv | DIQMTQSPSSLSASVGDRVTITCKASQDVVSAVAWYQQKPGQAPRLLIYWQDTRHTGVPS RFSGSGSGTEFTLTISSLQPDDFATYYCQEHFSPPLTFGQGTKVEIK |
| 81 | Ror2 VL 4 of conditionally active scFv | AIQLTQSPSSLSASVGDRVTITCSATSSVSYMHWYLQKPGQSPQLLIYGTSNLASGVPDR FSGSGSGTDFTLKISRVEAEDVGVYYCQQRSSYPFTFGQGTKVEIK |
| 82 | Ror2 R98H VH of conditionally active scFv | QVQLQESGPGLVKPSQTLSLTCTVSGYSITTGYYWNWVRQARGQRLEWIGYITYDGSKNY NPSLKNRVTISVDTSKNQFSLKLSSVTAADTAVYYCSHFEGVWYGLDYGWQGTLVTVSS |
| 83 | Ror2 YEE3 VH of conditionally active scFv | QVQLQESGPGLVKPSQTLSLTCTVSGYSITTGEYWNWVRQARGQRLEWIGYITYDGSKNY NPSLKNRVTISVDTSKNQFSLKLSSVTAADTAVYYCSRFEGVWYGLDYGWQGTLVTVSS |
| 84 | Ror2 VL of conditionally active scFv | AIQLTQSPSSLSASVGDRVTITCRASESVDRYGNSFIHWYQQKPGKAPKLLIYRTYNLES GIPARFSGSGSGTEFTLTISSLQSEDFAVYYCQQTNEDPWTFGWGTKVEIK |
| 85 | Ror2 L3 4 of conditionally active scFv | QQX$_{42}$NX$_{43}$DPX$_{44}$TX$_{45}$ (where X$_{42}$ is T, I, or P; X$_{43}$ is E or V; X$_{44}$ is W or T; and X$_{45}$ is F or T) |
| 86 | Ror2 VL 5 of conditionally active scFv | DIVLTQSPDSLAVSLGQRATISCRASESVDRYGNSFIHWYLQKPGQPPKLLIYRTYNLES GIPARFSGTGSRTDFTLTINPVEADDVATYYCQQTNEDPWTFGQGTKVEIK |
| 87 | Axl H1 1 of conditionally active scFv | X$_1$GX$_2$TMN (where X$_1$ is T or W; and X$_2$ is H or A) |
| 88 | Axl H2 1 of conditionally active scFv | LIKPSNGGTSYNQKFKG |

TABLE 3-continued

Sequences of SEQ ID NOs.

| SEQ ID NO: | Name | Sequence |
|---|---|---|
| 89 | Axl H3 1 of conditionally active scFv | GX$_3$YX$_4$SYX$_5$AMDY (where X$_3$ is H or D; X$_4$ is E or H; and X$_5$ is E or F) |
| 90 | Axl L1 1 of conditionally active scFv | KASQDVX$_6$SAVA (where X$_6$ is S or V) |
| 91 | Axl L2 1 of conditionally active scFv | WX$_7$X$_8$TRX$_9$T (where X$_7$ is A or Q; X$_8$ is S or D; and X$_9$ is H or D) |
| 92 | Axl L3 1 of conditionally active scFv | QEHFSX$_{10}$PLX$_{11}$ (where X$_{10}$ is T or P; and X$_{11}$ is T or R) |
| 93 | Axl WT VH of conditionally active scFv | EVQLVQSGAEVKKPGATVKISCKVSGYSFTGHTMNWIRQPPGKGLEWIGLIKPSNGGTSY NQKFKGRVTISADKSISTAYLQWSSLKASDTAMYYCAHGHYESYFAMDYWGQGTLVTVSS |
| 94 | Axl WT VL of conditionally active scFv | DIQMTQSPSSLSASVGDRVTITCKASQDVSSAVAWYQQKPGQAPRLLIYWASTRHTGVPS RFSGSGSGTEFTLTISSLQPDDFATYYCQEHFSTPLTFGQGTKVEIK |
| 95 | Ror2 H1 1 of conditionally active scFv | GYTX$_1$TEX$_2$TX$_3$H (where X$_1$ is F or E; X$_2$ is Y or D; and X$_3$ is M or D) |
| 96 | Ror2 H1 2 of conditionally active scFv | X$_4$GYSITTGYYWN (where X$_4$ is T or S) |
| 97 | Ror2 H2 1 of conditionally active scFv | GX$_5$NX$_6$NNGGTGYNQKFKG (where X$_5$ is E or I; and X$_6$ is T or D) |
| 98 | Ror2 H2 2 of conditionally active scFv | YITYDGSKNYNPSLKN |
| 99 | Ror2 H3 1 of conditionally active scFv | GSLYSYGNSYFDY |
| 100 | Ror2 H3 2 of conditionally active scFv | FEGVWX$_7$GLDY (where X$_7$ is Y or G) |
| 101 | Ror2 L1 1 of conditionally active scFv | SATSSX$_8$SYMH (where X$_8$ is E or V) |
| 102 | Ror2 L1 2 of conditionally active scFv | RASESVDRYGNSFIH |
| 103 | Ror2 L2 1 of conditionally active scFv | X$_9$TSNLAS (where X$_9$ is G or H) |
| 104 | Ror2 L2 2 of conditionally active scFv | RTYNLES |
| 105 | Ror2 L3 1 of conditionally active scFv | QQRSSYPFT |
| 106 | Ror2 L3 2 of conditionally active scFv | QQTNEDPWT |
| 107 | Ror2 WT VH of conditionally active scFv | QVQLQESGPGLVKPSQTLSLTCTVSGYSITTGYYWNSVRQARGQRLEWIGYITYDGSKNY NPSLKNRVTISVDTSKNQFSLKLSSVTAADTAVYYCSRFEGVWYGLDYWGQGTLVTVSS |

TABLE 3-continued

Sequences of SEQ ID NOs.

| SEQ ID NO: | Name | Sequence |
|---|---|---|
| 108 | Axl VL 1 of conditionally active scFv | DIQMTQSPSSLSASVGDRVTITCKASQDVVSAVAWYQQKPGQAPRLLIYWQDTRHTGVPS RFSGSGSGTEFTLTISSLQPDDFATYYCQEHFSTPLTFGQGTKVEIK |
| 109 | Axl VL 2 of conditionally active scFv | DIQMTQSPSSLSASVGDRVTITCKASQDVSSAVAWYQQKPGQAPRLLIYWQDTRHTGVPS RFSGSGSGTEFTLTISSLQPDDFATYYCQEHFSPPLTFGQGTKVEIK |
| 110 | Axl VL 3 of conditionally active scFv | DIQMTQSPSSLSASVGDRVTITCKASQDVVSAVAWYQQKPGQAPRLLIYWQDTRHTGVPS RFSGSGSGTEFTLTISSLQPDDFATYYCQEHFSPPLTFGQGTKVEIK |
| 111 | Axl VL 4 of conditionally active scFv | DIQMTQSPSSLSASVGDRVTITCKASQDVVSAVAWYQQKPGQAPRLLIYWQDTRHTGVPS RFSGSGSGTEFTLTISSLQPDDFATYYCQEHFSPPLRFGQGTKVEIK |
| 112 | Axl VH 1 of conditionally active scFv | EVQLVQSGAEVKKPGATVKISCKVSGYSFTGATMNWIRQPPGKGLEWIGLIKPSNGGTSY NQKFKGRVTISADKSISTAYLQWSSLKASDTAMYYCAHGHYESYEAMDYWGQGTLVTVSS |
| 113 | Axl VH 2 of conditionally active scFv | EVQLVQSGAGEVKKPGATVKISCKVSGYSFWGATMNWIRQPPGKGLEWIGLIKPSNGGTSY NQKFKGRVITSADKISSTAYLQWSSLKASDTAMYYCAHGHYESYEAMDYWGQGTLVTVSS |
| 114 | Axl VH 3 of conditionally active scFv | EVQLVQSGAEVKKPGATVKISCKVSGYSFTGHTMNWIRQPPGKGLEWIGLIKPSNGGTSY NQKFKGRVTISADKSISTAYLQWSSLKASDTAMYYCAHGHYESYEAMDYWGQGTLVTVSS |
| 115 | Ror2 VH 1 of conditionally active scFv | EVQLQQSGPELVKPGASVKISCKTSGYTFTEYTMHWMKQSHRKSLEWIGGINTNNGGTGY NQKFKGKATLTVDKSSSTAYMELRSLTSEDSAVYFCARGSLYSYGNSYFDYWGQGTLVTV SS |
| 116 | Ror2 VH 2 of conditionally active scFv | EVQLQQSGPELVKPGASVKISCKTSGYTETEDTDHWMKQSHRKSLEWIGGENDNNGGTGY NQKFKGKATLTVDKSSSTAYMELRSLTSEDSAVYFCAHGSLYSYGNSYFDYWGQGTLVTV SS |
| 117 | Ror2 VH 3 of conditionally active scFv | QVQLVQSGAEVKKPGASVKVSCKASGYTFTEYTMHWVRQARGQRLEWIGGINTNNGGTGY NQKFKGRVTISADKSISTAYLQWSSLKASDTAMYYCAHGSLYSYGNSYFDYWGQGTLVTV SS |
| 118 | Ror2 VH 4 of conditionally active scFv | EVQLVQSGAEVKKPGESLRISCKGSGYTFTEYTMHWVRQAPGQGLEWMGGINTNNGGTGY NQKFKGRVTISADKSISTAYLQWSSLKASDTAMYYCAHGSLYSYGNSYFDYWGQGTLVTV SS |
| 119 | Ror2 VH 5 of conditionally active scFv | EVQLVQSGAEVKKPGESLRISCKGSGYTFTEYTMHWIRQSPSRGLEWLGGINTNNGGTGY NQKFKGRVTISADKSISTAYLQWSSLKASDTAMYYCAHGSLYSYGNSYFDYWGQGTLVTV SS |
| 120 | Ror2 VH 6 of conditionally active scFv | DVQLQESGPGLVKPSQSLSLTCSVTGYSITTGYYWNWIRQFPGNKLEWMAYITYDGSKNY NPSLKNRISITRDTSKNKFFLKLNSVTSEDTATYYCSRFEGVWYGLDYWGQGTLVTVSS |
| 121 | Ror2 VH 7 of conditionally active scFv | DVQLQESGPGLVKPSQSLSLTCSVTGYSITTGYYWNWIRQFPGNKLEWMAYITYDGSKNY NPSLKNRISITRDTSKNKFFLKLNSVTSEDTATYYCSHFEGVWGGLDYWGQGTLVTVSS |
| 122 | Ror2 VL 1 of conditionally active scFv | QIVLTQSPAIMSASPGEKVTITCSATSSVSYMHWFQQKPGTSPKLWIYGTSNLASGVPAR FSGSGSGTSYSLTISRMEAEDAATYYCQQRSSYPFTFGQGTKVEIK |
| 123 | Ror2 VL 2 of conditionally active scFv | QIVLTQSPAIMSASPGEKVTITCSATSSESYMHWFQQKPGTSPKLWIYHTSNLASGVPAR FSGSGSGTSYSLTISRMEAEDAATYYCQQRSSYPFTFGQGTKVEIK |
| 124 | Ror2 VL 3 of conditionally active scFv | AIQLTQSPSSLSASVGDRVTITCSATSSVSYMHWYQQKPGQAPRLLIYGTSNLASGVPDR FSGSGSGTDFTLISRVEAEDVGVYYCQQRSSYPFTFGQGTKVEIK |
| 125 | wild-type CD8 Stalk | TTTPAPRPPTPAPTIASQPLSLRPEACRPAAGGAVHTRGLDFA |
| 126 | wild-type CD28 Stalk | FCKIEVMYPPPYLDNEKSNGTIIHVKGKHLCPSPLFPGPSKP |
| 127 | CD3Z 7 Activating domain | RVKFSRSADAPAYQQGQNQLYNELNLGRREEYDVLDKRRGRDPEMGGKPQRRKNPQEGLY NELQKDKMAEAYSEIGMKGERRRGKGHDGLYQGLSTATKDTYDALHMQALPPR |

TABLE 3-continued

Sequences of SEQ ID NOs.

| SEQ ID NO: | Name | Sequence |
|---|---|---|
| 128 | scFv from F1-2-15 | EVQLVQSGAEVKKPGATVKISCKVSGYSFWGATMNWIRQPPGKGLEWIGLIKPSNGGTSY NQKFKGRVTISADKSISTAYLQWSSLKASDTAMYYCAHGHYESYEAMDYWGQGTLVTVSS GGGGSGGGGSGGGGSDIQMTQSPSSLSASVGDRVTITCKASQDVVSAVAWYQQKPGQAPR LLIYWQDTRHTGVPSRFSGSGSGTEFTLTISSLQPDDFATYYCQEHFSPPLTFGQGTKVE IK |
| 129 | scFv from F1-2-13 | EVQLVQSGAEVKKPGATVKISCKVSGYSFWGATMNWIRQPPGKGLEWIGLIKPSNGGTSY NQKFKGRVTISADKSISTAYLQWSSLKASDTAMYYCAHGHYESYEAMDYWGQGTLVTVSS GGGGSGGGGSGGGGSDIQMTQSPSSLSASVGDRVTITCKASQDVVSAVAWYQQKPGQAPR LLIYWQDTRHTGVPSRFSGSGSGTEFTLTISSLQPDDFATYYCQEHFSPPLTFGQGTKVE IK |
| 130 | scFv from F1-1-19 | QVQLQESGPGLVKPSQTLSLTCTVSGYSITTGEYWMWVRQARGQRLEWIGYITYDGSKNY NPSLKNRVTISVDTSKNQFSLKLSSVTAADTAVYYCSRFEGVWYGLDYWGQGTLVTVSSG GGGSGGGGSGGGGSGGGGSGGGGSAIQLTQSPSSLSASVGDRVTITCRASESVDR YGNSFIHWYQQKPGKAPKLLIYRTYNLESGIPARFSGSGSGTEFTLTISSLQSEDFAVYY CQQTNEDPWTFGQGTKVEIK |
| 131 | scFv from F1-1-23 | AIQLTQSPSSLSASVGDRVTITCRASESVDRYGNSFIHWYQQKPGKAPKLLIYRTYNLES GIPARFSGSGSGTEFTLTISSLQSEDFAVYYCQQTNEDPWTFGQGTKVEIKGGGGSGGGG SGGGGSGGGGSGGGGSGGGGSQVQLQESGPGLVKPSQTLSLTCTVSGYSITTGEYWNWVR QARGQRLEWIGYITYDGSKNYNPSLKNRVTISVDTSKNQFSLKLSSVTAADTAVYYCSRF EGVWYGLDYWGQGTLVTVSS |
| 132 | scFv from F1-1-15 | AIQLTQSPSSLSASVGDRVTITCRASESVDRYGNSFIHWYQQKPGKAPKLLIYRTYNLES GIPARFSGSGSGTEFTLTISSLQSEDFAVYYCQQTNEDPWTFGQGTKVEIKGGGGSSSSS SGGGGSGGGGSGGGGSGGGGSQVQLQESGPGLVKPSQTLSLTCTVSGYSITTGYYWNWVR QARGQRLEWIGYITYDGSKNYNPSLKNRVTISVDTSKNQFSLKLSSVTAADTAVYYCSHF EGVWYGLDYWGQGTLVTVSS |
| 133 | ICΔ CD137 Dual Co-stimulatory domain | RSKRSRLLHSDYMNMTPRRPGPTRKHYQAYAAARDFAAYRSKRGRKKLLYIFKQPFMRPV QTTQEEDGCSCRFPEEEEGGCEL |
| 134 | Axl H1 2 of conditionally active scFv | $X_1GX_2X_3MX_4$ (where $X_1$ is T, A, or W; $X_2$ is H or A; $X_3$ is T or I; and $X_4$ is N or I) |
| 135 | Axl H2 2 of conditionally active scFv | $LIKX_5SNGGTX_6YNQKFKG$ (where $X_5$ is P or N; and $X_6$ is S, I, or T) |
| 136 | Axl H3 2 of conditionally active scFv | $GX_7X_8X_9X_{10}X_{11}X_{12}X_{13}X_{14}DYX_{15}X_{16}$ (where $X_7$ is H, D, E, P, R, or W; $X_8$ is Y or N; $X_9$ is E, A, D, F, G, H, I, L, M, N, R, V, or, Y; $X_{10}$ is S, D, M, N, or Q; $X_{11}$ is Y, C, E, or P; $X_{12}$ is F, E, N, S, T, or V; $X_{13}$ is A, D, G, L, or Y; $X_{14}$ is M, E, or F; $X_{15}$ is W, A, D, H, L, N, P, R, or T; and $X_{16}$ is G or H) |
| 137 | Axl L1 2 of conditionally active scFv | $KASQDX_{17}X_{18}SX_{19}VX_{20}$ (where $X_{17}$ is V, D, G, N, or W; $X_{18}$ is S or V; $X_{19}$ is A, L, or M; and $X_{20}$ is A, D, N, or Q) |
| 138 | Axl L2 2 of conditionally active scFv | $X_{21}X_{22}X_{23}TRX_{24}T$ (where $X_{21}$ is W or F; $X_{22}$ is A, I, N, P, or Q; $X_{23}$ is S or D; and $X_{24}$ is H or D) |
| 139 | Axl L3 2 of conditionally active scFv | $QEX_{25}X_{26}SX_{27}X_{28}X_{29}X_{30}$ (where $X_{25}$ is H, C, F, I, L, Q, S, T, V, or Y; $X_{26}$ is F, C, D, E, G, N, or S; $X_{27}$ is T, C, or P; $X_{28}$ is P, A, C, D, E, H, K, S, T, V, or W; $X_{29}$ is L, G, or R; and $X_{30}$ is T, I, or R) |
| 140 | Ror2 H1 3 of conditionally active scFv | $GYTXI_1TEX_2X_3X_4H$ (where $X_1$ is F or E; $X_2$ is Y or D; $X_3$ is T or C; and $X_4$ is M, D, E, or Y) |
| 141 | Ror2 H1 4 of conditionally active scFv | $GYSITTGX_{29}YWN$ (where $X_{29}$ is Y, E, R, or T) |
| 142 | Ror2 H3 3 of conditionally active scFv | $X_5X_6X_7X_8NNGGTGYNQKFKG$ (where $X_5$ is G or S; $X_6$ is I or E; $X_7$ is N, C, L, or V; and $X_8$ is T, D or E) |
| 143 | Ror2 H2 4 of conditionally active scFv | $YITYDGSX_{30}NYNPSLKN$ (where $X_{30}$ is K or N) |

TABLE 3-continued

Sequences of SEQ ID NOs.

| SEQ ID NO: | Name | Sequence |
|---|---|---|
| 144 | Ror2 H3 3 of conditionally active scFv | $X_9X_{10}X_{11}SX_{12}YX_{13}YX_{14}X_{15}SYFX_{16}X_{17}X_{18}$ (where $X_9$ is A, M, or T; $X_{10}$ is R or H; $X_{11}$ is G or E; $X_{12}$ is L or F; $X_{13}$ is S or G; $X_{14}$ is G or D; $X_{15}$ is N or E; $X_{16}$ is D or L; $X_{17}$ is Y, C, or T; and $X_{18}$ is W or L) |
| 145 | Ror2 H3 4 of conditionally active scFv | $CSX_{31}X_{32}X_{33}X_{34}VX_{35}X_{36}X_{37}LDX_{38}$ (where $X_{31}$ is R, G, H, W, or Y; $X_{32}$ is F, C, N, or Q; $X_{33}$ is E or S; $X_{34}$ is G, E, F, H, M, Q, or S; $X_{35}$ is W, A, I, P, Q, T, or V; $X_{36}$ is Y, G, N, or Q; $X_{37}$ is G, S, or T; and $X_{38}$ is Y or I) |
| 146 | Ror2 L1 3 of conditionally active scFv | $SATSSX_{19}X_{20}X_{21}MX_{22}$ (where $X_{19}$ is V or E; $X_{20}$ is S or D; $X_{21}$ is Y, C, or D; and $X_{22}$ is H, G, or L) |
| 147 | Ror2 L1 4 of conditionally active scFv | $RASESVDRYGNSX_{39}IH$ (where $X_{39}$ is F, S, or T) |
| 148 | Ror2 L2 3 of conditionally active scFv | $X_{23}TSNLAS$ (where $X_{23}$ is G, C, H, or P) |
| 149 | Ror2 L2 4 of conditionally active scFv | $X_{40}TYX_{41}LES$ (where $X_{40}$ is R, C, D, E, or W; and $X_{41}$ is N or D) |
| 150 | Ror2 L3 3 of conditionally active scFv | $QX_{24}X_{25}SX_{26}YPFX_{27}X_{28}$ (where $X_{24}$ is Q or E; $X_{25}$ is R or H; $X_{26}$ is S, D, G, I, Q, or V; $X_{27}$ is T or D; and $X_{28}$ is F, D, or E) |
| 151 | Ror2 CAB3 VH | QVQLVQSGAEVKKPGASVKVSCKASGYTFTEYTMHWIRQSPSRGLEWLGGINDNNGGTGY NQKFKGRFTISRDNSKNTLYLQMNSLRAEDTAVYYCARGSLYSYGNSYFDYWGQGLTVTV SS |
| 152 | Ror2 CAB VL | EIVLTQSPATLSLSPGERATLSCSATSSVSYMHWFQQRPGQSPRRLIYHTSNLASGVPSR FSGSGSGTDFTLKISRVEAEDVGVYYCQQRSSYPFTFGQGTKVEIK |
| 153 | scFv from F1-1-11 | QVQLQESGPGLVKPSQTLSLTCTVSGYSITTGYYWNWVRQARGQRLEWIGYITYDGSKNY NPSLKNRVTISVDTSKNQFSLKLSSVTAADTAVYYCSHFEGVWYGLDYQGQGTLVTVSSG GGGSGGGGSGGGGSGGGGSGGGGSAIQLTQSPSSLSASVGDRVTITCRASESVDR YGNSFIHWYQQKPGKAPKLLIYRTYNLESGIPARFSGSGSGTEFTLTISSLQSEDFAVYY CQQTNEDPWTFGQGTKVEIK |
| 154 | scFv from F1-1-17 | QVQLQESGPGLVKPSQTLSLTCTVSGYSITTGEYWNWVRQARGQRLEWIGYITYDGSKNY NPSLKNRVTISVDTSKNQFSLKLSSVTAADTAVYYCSRFEGVWYGLDYWGQGTLVTVSSG GGGSGGGGSGGGGSAIQLTQSPSSLSASVGDRVTITCRASESVDRYGNSFIHWYQQKPGK APKLLIYRTYNLESGIPARFSGSGSGTEFTLTISSLQSEDFAVYYCQQTNEDPWTFGQGT KVEIK |
| 155 | scFv from F1-1-25 | EIVLTQSPATLSLSPGERATLSCSATSSVSYMHWFQQRPGQSPRRLIYHTSNLASGVPDR FSGSGSGTDFTLKISRVEAEDVGVYYCQQRSSYPFTFGQGTKVEIKGGGGSGGGGSGGGG SQVQLVQSGAEVKKPGASVKVSCKASGYTFTEYTMHWIRQSPSRGLEWLGGINDNNGGTG YNQKFKGRFTISRDNSKNTLYLQMNSLRAEDTAVYYCARGSLYSYGNSYFDYWGQGTLVT VSS |
| 156 | scFv from F1-1-26 | LVQSGAEVKKPGASVKVSCKASGYTFTEYTMHWIRQSPSRGLEWLGGINDNNGGTGYNQK FKGRFTISRDNSKNTLYLQMNSLRAEDTAVYYCARGSLYSYGNSYFDYWGQGTLVTVSS |
| 157 | scFv from F1-1-19 | QVQLQESGPGLVKPSQTLSLTCTVSGYSITTGYYWNWVRQARGQRLEWIGYITYDGSKNY NPSLKNRVTISVDTSKNQFSLKLSSVTAADTAVYYCSHFEGVWYGLDYWGQGTLVTVSSG GGGSGGGGSGGGGSAIQLTQSPSSLSASVGDRVTITCRASESVDRYGNSFIHWYQQKPGK APKLLIYRTYNLESGIPARFSGSGSGTEFTLTISSLQSEDFAVYYCQQTNEDPWTFGQGT KVEIK |
| 158 | scFv from F1-1-21 | AIQLTQSPSSLSASVGDRVTITCRASESVDRYGNSFIHWYQQKPGKAPKLLIYRTYNLES GIPARFSGSGSGTEFTLTISSLQSEDFAVYYCQQTNEDPWTFGQGTKVEIKGGGGSGGGG SGGGGSQVQLQESGPGLVKPSQTLSLTCTVSGYSITTGEYWNWVRQARGQRLEWIGYITY DGSKNYNPSLKNRVTISVDTSKNQFSLKLSSVTAADTAVYYCSRFEGVWYGLDYWGQGTL VTVSS |
| 159 | scFv from F1-2-3 | EVQLVQSGAEVKKPGATVKISCKVSGYSFWGATMNWIRQPPGKGLEWIGLIKPSNGGTSY NQKFKGRVTISADKSISTAYLQWSSLKASDTAMYYCAHGHYESYEAMDYWGQGTLVTVSS GGGGSGGGGSGGGGSGGGGSGGGGSGGGGSGGGGSDIQMTQSPSSLSASVGDRVTITCKASQDVV SAVAWYQQKPGQAPRLLIYWQDTRHTGVPSRFSGSGSGTEFTLTISSLQPDDFATYYCQE HFSPPLTFGQGTKVEIK |

TABLE 3-continued

Sequences of SEQ ID NOs.

| SEQ ID NO:Name | Sequence |
|---|---|
| 160  scFv from F1-2-8 | DIQMTQSPSSLSASVGDRVTITCKASQDVVSAVAWYQQKPGQAPRLLIYWQDTRHTGVPS RFSGSGSGTEFTLTISSLQPDDFATYYCQEHFSPPLTFGQGTKVEIKGGGGSGGGGSGGG GSEVQLVQSGAEVKKPGATVKISCKVSGYSFWGATMNWIRQPPGKGLEWIGLIKPSNGGT SYNQKFKGRVTISADKSISTAYLQWSSLKASDTAMYYCAHGHYESYEAMDYWGQGTLVTV SS |
| 161  scFv from F1-2-10 | DIQMTQSPSSLSASVGDRVTITCKASQDVVSAVAWYQQKPGQAPRLLIYWQDTRHTGVPS RFSGSGSGTEFTLTISSLQPDDFATYYCQEHFSPPLTFGQGTKVEIKGGGGSGGGGSGGG GSGGGGSGGGGSEVQLVQSGAEVKKPGATVKISCKVSGYSFWGATMNWIRQPPGKGLEWI GLIKPSNGGTSYNQKFKGRVTISADKSISTAYLQWSSLKASDTAMYYCAHGHYESYEAMD YWGQGTLVTVSS |

What is claimed is:

1. A nucleic acid encoding a chimeric antigen receptor for binding Axl, comprising:
   a) an antigen-specific targeting region (ASTR), wherein the ASTR binding to Axl comprises a heavy chain variable region comprising three complementarity determining regions having H1, H2, and H3 sequences and a light chain variable region comprising three complementarity determining regions having L1, L2, and L3 sequences, wherein:
      i) the H1 sequence is X1GX2TMN (SEQ ID NO:87);
      ii) the H2 sequence is LIKPSNGGTSYNQKFKG (SEQ ID NO:88);
      iii) the H3 sequence is GX3YX4SYX5AMDY (SEQ ID NO:89);
      iv) the L1 sequence is KASQDVX6SAVA (SEQ ID NO:90);
      v) the L2 sequence is WX7X8TRX9T (SEQ ID NO:91); and
      vi) the L3 sequence is QEHFSX10PLX11 (SEQ ID NO:92),
      wherein X1 is T or W; X2 is H or A; X3 is H or D; X4 is E or H; X5 is E or F; X6 is S or V; X7 is A or Q; X8 is S or D; X9 is H or D; X10 is T or P; and X11 is T or R;
   b) a transmembrane domain; and
   c) an intracellular activating domain, wherein the transmembrane domain is located between the ASTR and the intracellular activating domain.

2. A nucleic acid encoding a chimeric antigen receptor for binding Axl, comprising:
   a) an antigen-specific targeting region (ASTR), wherein the ASTR binding to Axl comprises a heavy chain variable region comprising three complementarity determining regions having H1, H2, and H3 sequences and a light chain variable region comprising three complementarity determining regions having L1, L2, and L3 sequences, wherein:
      i) the H1 sequence is X1GX2TMN (SEQ ID NO:87);
      ii) the H2 sequence is LIKPSNGGTSYNQKFKG (SEQ ID NO:88);
      iii) the H3 sequence is GX3YX4SYX5AMDY (SEQ ID NO:89);
      iv) the L1 sequence is KASQDVX6SAVA (SEQ ID NO:90);
      v) the L2 sequence is WX7X8TRX9T (SEQ ID NO:91); and
      vi) the L3 sequence is QEHFSX10PLX11 (SEQ ID NO:92),
      wherein X1 is T or W; X2 is H or A; X3 is H; X4 is E; X5 is E; X6 is S or V; X7 is Q; X8 is D; X9 is H; X10 is T or P; and X11 is T or R;
   b) a transmembrane domain; and
   c) an intracellular activating domain, wherein the transmembrane domain is located between the ASTR and the intracellular activating domain.

3. The nucleic acid of claim 1, wherein the ASTR binds to the same epitope of Axl as a single-chain variable antibody fragment comprising an antibody heavy chain variable region of SEQ ID NO:79 and an antibody light chain variable region of SEQ ID NO:80.

4. The nucleic acid of claim 1, wherein the heavy chain variable region comprises an amino acid sequence having at least 80% sequence identity to SEQ ID NO:79.

5. The nucleic acid of claim 1, wherein the light chain variable region comprises an amino acid sequence having at least 80% sequence identity to SEQ ID NO:80.

6. The nucleic acid of claim 5, wherein the heavy chain variable region comprises an amino acid sequence having at least 80% sequence identity to SEQ ID NO:79.

7. The nucleic acid of claim 1, wherein the ASTR comprises an amino acid sequence having at least 80% sequence identity to any one of SEQ ID NOs: 128-129 or 159-161.

8. The nucleic acid of claim 1, wherein the heavy chain variable region and the light chain variable region are separated by a linker, wherein the linker is between 6 and 100 amino acids in length.

9. The nucleic acid of claim 8, wherein the linker comprises the amino acid sequence of any one of SEQ ID NOs: 53-55.

10. The nucleic acid of claim 1, wherein the chimeric antigen receptor further comprises a stalk domain and a co-stimulatory domain, and wherein the chimeric antigen receptor comprises from amino terminus to carboxy terminus, the ASTR, the stalk domain, the transmembrane domain, the co-stimulatory domain, and the intracellular activating domain.

11. The nucleic acid of claim 10, wherein the stalk domain comprises a CD8 stalk domain or a CD28 stalk domain, and wherein the co-stimulatory domain comprises a CD137 co-stimulatory domain, an ICA co-stimulatory domain comprising proline-to-alanine mutations corresponding to residues 29, 32, and 33 of SEQ ID NO:2, a CD28 co-stimulatory domain, or comprises both the ICA co-stimulatory domain and the CD137 co-stimulatory domain.

12. The nucleic acid of claim 11, wherein the stalk domain comprises the CD28 stalk domain, wherein the transmembrane domain comprises a CD28 transmembrane domain, and wherein the co-stimulatory domain comprises the ICA co-stimulatory domain.

13. The nucleic acid of claim 1, wherein the transmembrane domain comprises a CD8 transmembrane domain or a CD28 transmembrane domain, and wherein the intracellular activating domain comprises a CD3Z activating domain.

14. The nucleic acid of claim 1, wherein the ASTR is an antibody selected from an scFv, an Fab fragment, an Fab' fragment, an (Fab') 2 fragment, an Fv fragment, and a divalent single-chain antibody or a diabody.

15. The nucleic acid of claim 1, wherein the ASTR is a single-chain variable fragment.

16. An isolated recombinant T cell, comprising a genome comprising the nucleic acid of claim 1, wherein the nucleic acid is operably linked to a promoter active in T cells.

17. The isolated recombinant T cell of claim 16, wherein the nucleic acid further encodes an elimination domain, wherein the nucleic acid sequence encoding the elimination domain is separated from the nucleic acid sequence encoding the chimeric antigen receptor by a ribosomal skip sequence.

18. A vector, comprising the nucleic acid of claim 1, wherein the nucleic acid is operably linked to a promoter active in T cells.

19. The vector of claim 18, wherein the nucleic acid further encodes an elimination domain, wherein the nucleic acid sequence encoding the elimination domain is separated from the nucleic acid sequence encoding the chimeric antigen receptor by a ribosomal skip sequence.

20. The vector of claim 19, wherein the elimination domain is recognized by a regulatory authority-approved antibody.

21. The vector of claim 18, wherein the vector is a replication incompetent retroviral particle.

22. The vector of claim 18, wherein the vector is a lentiviral vector.

* * * * *